(12) United States Patent
Keiser et al.

(10) Patent No.: US 8,000,904 B2
(45) Date of Patent: Aug. 16, 2011

(54) METHODS AND PRODUCTS RELATED TO THE IMPROVED ANALYSIS OF CARBOHYDRATES

(75) Inventors: Nishla Keiser, Arlington, MA (US); Carlos Bosques, Arlington, MA (US); Ram Sasisekharan, Bedford, MA (US); Pankaj Gandhe, Sayreville, NJ (US); Sasi Raguram, Hillsborough, NJ (US); Aravind Srinivasan, Cambridge, MA (US)

(73) Assignees: Momenta Pharmaceuticals, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/574,161

(22) Filed: Oct. 6, 2009

(65) Prior Publication Data

US 2010/0136599 A1    Jun. 3, 2010

Related U.S. Application Data

(62) Division of application No. 11/107,982, filed on Apr. 15, 2005, now abandoned.

(60) Provisional application No. 60/562,874, filed on Apr. 15, 2004.

(51) Int. Cl.
*G01N 31/00* (2006.01)

(52) U.S. Cl. .................. 702/22; 702/30; 506/6

(58) Field of Classification Search .......... None
See application file for complete search history.

(56) References Cited

U.S. PATENT DOCUMENTS

| | | |
|---|---|---|
| 4,455,380 A | 6/1984 | Adachi |
| 5,605,807 A | 2/1997 | Dennis |
| 5,607,859 A | 3/1997 | Biemann et al. |
| 6,217,863 B1 | 4/2001 | Godavarti et al. |
| 6,228,654 B1 | 5/2001 | Chait et al. |
| 6,319,680 B1 | 11/2001 | Yasuno et al. |
| 6,597,996 B1 | 7/2003 | Venkataraman et al. |
| 6,610,484 B1 | 8/2003 | Hung |
| 6,730,485 B2 | 5/2004 | Griffey et al. |
| 6,844,166 B1 | 1/2005 | Wolf |

(Continued)

FOREIGN PATENT DOCUMENTS

EP    0747705 A1    12/1996

(Continued)

OTHER PUBLICATIONS

Papac et al. (Anal. Chem. 1996, 68, p. 3215-3223).*

(Continued)

*Primary Examiner* — Karlheinz R Skowronek
(74) *Attorney, Agent, or Firm* — Choate Hall & Stewart LLP; Brenda Herschbach Jarrell; Jessica Russell Colantonio

(57) ABSTRACT

The invention relates, in part, to the improved analysis of carbohydrates. In particular, the invention relates to the analysis of carbohydrates, such as N-glycans and O-glycans found on proteins. Improved methods, therefore, for the study of glycosylation patterns on cells, tissue and body fluids are also provided. Information regarding the analysis of glycans, such as the glycosylation patterns on cells, tissues and in body fluids, can be used in diagnostic and treatment methods as well as for facilitating the study of the effects of glycosylation/altered glycosylation on protein function. Such methods are also provided. Methods are also provided to assess protein production processes, to assess the purity of proteins produced, and to select proteins with the desired glycosylation.

22 Claims, 60 Drawing Sheets

U.S. PATENT DOCUMENTS

| | | | |
|---|---|---|---|
| 6,869,789 B2 | 3/2005 | Liu et al. |
| 6,962,699 B2 | 11/2005 | Pojasek et al. |
| 7,056,504 B1 | 6/2006 | Sasisekharan et al. |
| 7,083,937 B2 | 8/2006 | Sasisekharan et al. |
| 7,105,334 B2 | 9/2006 | Pojasek et al. |
| 7,110,889 B2 | 9/2006 | Venkataraman et al. |
| 7,117,100 B2 | 10/2006 | Venkataraman et al. |
| 7,129,335 B2 | 10/2006 | Pojasek et al. |
| 7,139,666 B2 | 11/2006 | Venkataraman et al. |
| 7,247,445 B2 | 7/2007 | Sasisekharan et al. |
| 7,270,815 B2 | 9/2007 | Sasisekharan et al. |
| 2002/0122793 A1 | 9/2002 | Liu et al. |
| 2002/0128225 A1 | 9/2002 | Liu et al. |
| 2002/0169143 A1 | 11/2002 | Sasisekharan et al. |
| 2003/0008820 A1 | 1/2003 | Kwan et al. |
| 2003/0099628 A1 | 5/2003 | Liu et al. |
| 2003/0148462 A1 | 8/2003 | Kirschner et al. |
| 2003/0191587 A1 | 10/2003 | Venkataraman et al. |
| 2004/0091471 A1 | 5/2004 | Myette et al. |
| 2004/0091472 A1 | 5/2004 | Pojasek et al. |
| 2004/0092037 A1 | 5/2004 | Sasisekharan et al. |
| 2004/0132118 A1 | 7/2004 | Furukawa et al. |
| 2004/0132131 A1 | 7/2004 | Markman et al. |
| 2004/0147033 A1 | 7/2004 | Shriver et al. |
| 2004/0197933 A1 | 10/2004 | Venkataraman et al. |
| 2004/0204869 A1 | 10/2004 | Venkataraman et al. |
| 2004/0248317 A1 | 12/2004 | Swamy et al. |
| 2004/0253651 A1 | 12/2004 | Saarinen et al. |
| 2005/0037376 A1 | 2/2005 | Sasisekharan et al. |
| 2005/0065738 A1 | 3/2005 | Raguram |
| 2005/0227320 A1 | 10/2005 | Pojasek et al. |
| 2005/0233402 A1 | 10/2005 | Liu et al. |
| 2005/0233419 A1 | 10/2005 | Pojasek et al. |
| 2006/0024664 A1 | 2/2006 | Sasisekharan et al. |
| 2006/0057638 A1 | 3/2006 | Bosques et al. |
| 2006/0067927 A1 | 3/2006 | Chandrasekaran et al. |
| 2006/0067928 A1 | 3/2006 | Liu et al. |
| 2006/0078959 A1 | 4/2006 | Prabhakar et al. |
| 2006/0083711 A1 | 4/2006 | Berry et al. |
| 2006/0105430 A1 | 5/2006 | Sasisekharan et al. |
| 2006/0127950 A1 | 6/2006 | Bosques et al. |
| 2006/0154894 A1 | 7/2006 | Berry et al. |
| 2006/0177885 A1 | 8/2006 | Myette et al. |
| 2006/0177910 A1 | 8/2006 | Myette et al. |
| 2006/0177911 A1 | 8/2006 | Myette et al. |
| 2006/0182734 A1 | 8/2006 | Liu et al. |
| 2006/0183713 A1 | 8/2006 | Liu et al. |
| 2006/0183891 A1 | 8/2006 | Myette et al. |
| 2006/0292130 A1 | 12/2006 | Sasisekharan et al. |
| 2006/0292655 A1 | 12/2006 | Sasisekharan et al. |
| 2006/0292673 A1 | 12/2006 | Sasisekharan et al. |
| 2007/0004012 A1 | 1/2007 | Sasisekharan et al. |
| 2007/0020243 A1 | 1/2007 | Sengupta et al. |
| 2007/0065424 A1 | 3/2007 | Pojasek et al. |
| 2007/0065921 A1 | 3/2007 | Sasisekharan et al. |
| 2007/0066769 A1 | 3/2007 | Venkataraman et al. |
| 2007/0148157 A1 | 6/2007 | Prabhakar et al. |
| 2007/0148158 A1 | 6/2007 | Sasisekharan et al. |
| 2007/0148740 A1 | 6/2007 | Prabhakar et al. |
| 2007/0161073 A1 | 7/2007 | Sasisekharan et al. |
| 2007/0202563 A1 | 8/2007 | Prabhakar et al. |
| 2007/0224670 A1 | 9/2007 | Prabhakar et al. |

FOREIGN PATENT DOCUMENTS

| | | | |
|---|---|---|---|
| WO | WO-96/28169 A1 | 9/1996 |
| WO | WO-9716556 A1 | 5/1997 |
| WO | WO-0012726 A2 | 3/2000 |
| WO | WO-0065521 A2 | 11/2000 |
| WO | WO-0166772 A2 | 9/2001 |
| WO | WO-0192890 A1 | 12/2001 |
| WO | WO-0223190 A2 | 3/2002 |
| WO | WO-0232406 A2 | 4/2002 |
| WO | WO-02077199 A2 | 10/2002 |
| WO | WO-03052120 A2 | 6/2003 |
| WO | WO-03087833 A2 | 10/2003 |
| WO | WO-03102160 A2 | 12/2003 |
| WO | WO-2004019040 A1 | 3/2004 |
| WO | WO-2004055491 A2 | 7/2004 |
| WO | WO-2004062592 A2 | 7/2004 |
| WO | WO-2004069152 A2 | 8/2004 |
| WO | WO-2005087920 A2 | 9/2005 |
| WO | WO-2005110438 A2 | 11/2005 |
| WO | WO-2005111627 A2 | 11/2005 |
| WO | WO-2006076627 A2 | 7/2006 |
| WO | WO-2006083328 | 8/2006 |
| WO | WO-2006088491 A2 | 8/2006 |
| WO | WO-2006105313 A2 | 10/2006 |
| WO | WO-2006105315 A2 | 10/2006 |
| WO | WO-2007044471 A2 | 4/2007 |
| WO | WO-2007/120478 A2 | 10/2007 |

OTHER PUBLICATIONS

Abushoufa et al. "The development of a sialic acid specific lectin-immunoassay for the measurement of human chorionic gonadotrophin glycoforms in serum and its application in normal and Down's syndrome pregnancies", *Clinical endocrinology*, vol. 52, No. 4, (Apr. 2000) 499-508. Abstract only.

Adam et al., Serum protein fingerprinting coupled with a pattern-matching algorithm distinguishes prostate cancer from benign prostate hyperplasia and healthy men. Cancer Res. Jul. 2002;62(13):3609-14.

An et al. "Determination of N-glycosylation sites and site heterogeneity in glycoproteins", *Anal. Chem.*, vol. 75, No. 20 (Oct. 15, 2003) 5628-5637.

An et al., Profiling of glycans in serum for the discovery of potential biomarkers for ovarian cancer. J Proteome Res. Jul. 2006;5(7):1626-35.

Andersen et al. "Monosaccharide and oligosaccharide analysis of isoelectric focusing-separated and blotted granulocyte colony-stimulating factor glycoforms using high-pH anion-exchange chromatography with pulsed amperometric detection", *Glycobiology*, vol. 4, No. 4, (1994) 459-67, Abstract only.

Anon "Analysis of human serum transferrin glycoforms", LC-GC, vol. 15, No. 4 (1997) 370. Abstract only.

Apffel et al. "Application of new analytical technology to the production of a well-characterized biological", *Developments in biological standardization*, vol. 96 (1998) 11-25. Abstract only.

Asao et al., Tumor cells as the origin of elevated serum alpha1,3fucosyltransferase in association with malignancy. Clin Exp Metastasis. 2000;18(7):605-10.

Bai et al. (Rapid Communications in Mass Spectrometry, vol. 9, 1172-1176, 1995).

Bateman et al. "Characterization of protein glycoforms by capillary-zone electrophoresis-nanoelectrospray mass spectrometry", *J. of Chromatography*, A, vol. 794, No. 1+2 (1998) 327-344. Abstract only.

Belanger et al. "Molecular mass and carbohydrate structure of prostate specific antigen: studies for establishment of an international PSA standard", *Prostate*, Oct. 1995; 27(4):187-97.

Bergen et al. (*Analytical Chemistry*, vol. 296, p. 122-129, 2001).

Bergstroem et al. "Lectin affinity capillary electrophoresis in glycoform analysis applying the partial filling technique", *J. of Chromatography, B: Anal. Technologies in the Biomedical and Life Sciences*, vol. 809, No. 2 (2004) 323-329. Abstract only.

Bihoreau et al. "Combination of capillary electrophoresis and matrix-assisted laser desorption ionization mass spectrometry for glycosylation analysis of a human monoclonal anti-Rhesus(D) antibody", *J Chromatogr B Biomed Sci Appl.*, Sep. 12, 1997; 697(1-2):123-33.

Bonneil et al. "Probing genetic variation and glycoform distribution in lectins of the Erythrina genus by mass spectrometry", *Archives of Biochemistry and Biophysics*, vol. 426, No. 2(2004) 241-249. Abstract only.

Brawer et al., Prostate-specific antigen: current status. CA Cancer J Clin, Sep. Oct. 1999;49(5):264-81.

Brockhausen, "Pathways of O-glycan biosynthesis in cancer cells", *Biochimica et Biophysica Acta* 1473 (1999) 67-95.

Burchell et al. "O-linked glycosylation in the mammary gland: changes that occur during malignancy", *J Mammary Gland Biol Neoplasia.*, Jul. 2001; 6(3):355-64.

Burlingame "Characterization of protein glycosylation by mass spectrometry", *Current Opinion in Biotech.*, vol. 7, No. 1(1996) 4-10. Abstract only.
Butler et al. "Detailed glycan analysis of serum glycoproteins of patients with congenital disorders of glycosylation indicates the specific defective glycan processing step and provides an insight into pathogenesis", *Glycobiology*, vol. 13 No. 9(2003) 601-622.
Butters et al. "Structural characterization of the N-linked oligosaccharides derived from HIV gp120 expressed in lepidopteran cells", *Glycoconjugate J*, vol. 15, No. 1(1998) 83-88. Abstract only.
Callewaert et al. "Increased fucosylation and reduced branching of serum glycoprotein N-glycans in all known subtypes of congenital disorder of glycosylation I", *Glycobiology*, vol. 13, No. 5 (2003) 367-375.
Callewaert et al. "Noninvasive diagnosis of liver cirrhosis using DNA sequencer-based total serum protein glycomics", *Nature Med.* vol. 10, No. 4 (Apr. 2004) 429-434.
Callewaert et al. "Total serum N-glycome profiling on a capillary electrophoresis-microfluidic platform", *Electrophoresis*, vol. 25 (2004) 3128-3131.
Callewaert et al. "Ultrasensitive profiling and sequencing of N-linked oligosaccharides using standard DNA-sequencing equipment", *Glycobiology*, vol. 11, No. 4 (2001) 275-281.
Carlson et al., Biosynthesis of abnormally glycosylated alpha 1-antitrypsin by a human hepatoma cell line. Hepatology. Mar.-Apr. 1984;4(2):235-41.
Catalona et al., Measurement of prostate-specific antigen in serum as a screening test for prostate cancer. N Engl J Med. Apr. 25, 1991;324(17):1156-61.
Chen "Capillary electrophoretic analysis of glycoform of glycoproteins", *Fushun Shiyou Xueyuan Xuebao*, vol. 16, No. 3 (1996) 68-69. Abstract only.
Cifuentes et al. "Capillary isoelectric focusing of erythropoietin glycoforms and its comparison with flat-bed isoelectric focusing and capillary zone electrophoresis", *J. of Chromatography*, A, vol. 830, No. 2 (1999) 453-463. Abstract only.
Clogston et al. "Glycosidase digestion, electrophoresis and chromatographic analysis of recombinant human granulocyte colony-stimulating factor glycoforms produced in Chinese hamster ovary cells", *J. of Chromatography.*, vol. 637, No. 1(1993) 55-62. Abstract only.
Coco-Martin et al. "Analysis of glycoforms present in two mouse IgG2a monoclonal antibody preparations", *J. of Immunol. Methods*, vol. 155, No. 2 (1995) 241-8. Abstract only.
Cointe et al. "Unusual N-glycosylation of a recombinant human erythropoietin expressed in a human lymphoblastoid cell line does not alter its biological properties", *Glycobiology*, vol. 10, No. 5 (2000) 511-519.
Concato et al., The effectiveness of screening for prostate cancer: a nested case-control study. Arch Intern Med. Jan. 9, 2006;166(1):38-43.
Conrads et al. "Cancer diagnosis using proteomic patterns", *Expert Rev. Mol Diagn.*, vol. 3, No. 4 (2003) 411-420.
Cooper at al. "GlycoMod—a software tool for determining glycosylation compositions from mass spectro-metric data", *Proteomics*, vol. 1, (2001) 340-349.
Cooper et al. (Nucleic acids research, vol. 29, No. 1, p. 332-335, 2001).
Cooper et al., "GlycoSuiteDB: a curated relational database of glycoprotein glycan structures and their biological sources. 2003 update", *Nuc. Acid Res.* vol. 31, No. 1 (2003) 511-513.
De Reggi et al. "The glycan moiety of human pancreatic lithostathine. Structure characterization and possible pathophysiological implications", *European J. of Biochem.*, vol. 230, No. 2 (1995) 503-10. Abstract only.
Dennis et al. "Glycoprotein glycosylation and cancer progression", *Biochim Biophys Acta.*, Dec. 6, 1999; 1473(1):21-34.
Dennis et al., Beta 1-6 branching of Asn-linked oligosaccharides is directly associated with metastasis. Science. May 1, 1987;236(4800:582-5.
Diamandis et al., Analysis of serum proteomic patterns for early cancer diagnosis: drawing attention to potential problems. J Natl Cancer Inst. Mar. 3, 2004;96(5):353-6.
Djavan et al., New serum and urinary markers for prostate cancer detection in the new millenium. Eur Urol Suppl. 2004;3:25-32.
Djavan et al., PSA, PSA density, PSA density of transition zone, free/total PSA ratio, and PSA velocity for early detection of prostate cancer in men with serum PSA 2,5 to 4.0 ng/mL. Urology. Sep. 1999;54(3):517-22.
Domyslawska et al. "The analysis of the heterogeneity of acid glycoprotein at the patients with arthritis", *Polski Merkuriusz Lekarski, organ Polskiego Towarzystwa Lekarskiego*, vol. 17, No. 100 (Oct. 2004), 349-52. Abstract only.
Dube et al., Glycans in cancer and inflammation-potential for therapeutics and diagnostics. Nat Rev Drug Discov. Jun. 2005;4(6):477-88.
Duffin et al. "Identification and oligosaccharide structure analysis of rhodopsin glycoforms containing galactose and sialic acid", *Glycobiology*, vol. 3, No. 4 (1993) 365-380. Abstract only.
Ernst et al. "Direct evidence for a predominantly exolytic processive mechanism for depolymerization of heparin-like glycosaminoglycans by heparinse I", *Proc. Natl Acad. ScL USA*, vol. 95 (Apr. 1998) 4182-7.
Ethier et al. "Application of the StrOligo algorithm for the automated structure assignment of complex N-linked glycans from glycoproteins using tandem mass spectrometry", *Rapid Commun. Mass Spectrom*, vol. 17 (2003) 2713-2720.
Ethier et al. "Automated structural assignment of derivatized complex N-linked oligosaccharides from tandem mass spectra", *Rapid Commun. Mass Spectrom*, vol. 16 (2002) 1743-1754.
Ferens-Sieczkowska et al. "Haptoglobin glycoforms in a case of carbohydrate-deficient glycoprotein syndrome", *Glycoconjugale J.*, Oct. 1999; 16(10):573-7.
Fernandes et al. "Beta 1-6 branched oligosaccharides as a marker of tumor progression in human breast and colon neoplasia", *Cancer Res.*, Jan. 15, 1991; 51(2):718-23.
Forno et al., N- and O-linked carbohydrates and glycosylation site occupancy in recombinant human granulocyte-macrophage colony-stimulating factor secreted by a Chinese hamster ovary cell line. Eur J Biochem. Mar. 2004; 271(5): 907-19.
Fukazawa et al. "Sugar chain alterations of glycoproteins in spent culture media of human hepatocellular carcinoma cell lines analyzed by lectin-affinity electrophoresis", *Okayama Igakkai Zasshi*, vol. 110, No. 1-6 (1998) 53-60. Abstract only.
Fuster et al., The sweet and sour of cancer: glycans as novel therapeutic targets. Nat Rev Cancer. Jul. 2005;5(7):526-42.
Garbis et al., Limitations of current proteomics technologies. J Chromatogr A. Jun. 3, 2005;1077(1):1-18.
Gaucher et al. "STAT: A saccharide topology analysis tool used in combination with tandem mass spectrometry", *Anal. Chem.*, vol. 72 (2000) 2331-2336.
Gerber at al. "Absolutely quantification of proteins and phosphoproteins from cell lysates by tandem MS", *PNAS*, Jun. 10, 2003; 100(12):6940-5.
Gerwig et al. "Analysis of glycoprotein-derived glycopeptides", *Proteomics in Functional Genomics*, EXS, Birkhaeuser Verlag 2000; 88:159-86.
Geyer (Analytical Chemistry, vol. 71, No. 2, Jan. 15, 1999).
Ghosh et al., Regulated secretion of glycosylated human ferritin from hepatocytes. Blood. Mar. 15, 2004;103(6):2369-76. Epub Nov. 13, 2003.
Girnita et al., Inhibition of N-linked glycosylation down-regulates insulin-like growth factor-I receptor at the cell surface and kills Ewing's sarcoma cells: therapeutic implications. Drug Des. Feb. 2000; 15(1):67-72. Anticancer.
Glick et al. "Activity of fucosyltransferases and altered glycosylation in cystic fibrosis airway epithelial cells", *Biochimie.*, Aug. 2001; 83(8):743-7.
Goldberg et al. "Automatic annotation of MALDI N-glycan spectra", *Proteomics*, vol. 5, No. 4 (Mar. 2005) 865-75.
Goldman et al. "Monitoring recombinant human interferon-gamma N-glycosylation during perfused fluidized-bed and stirred-tank batch culture of CHO cells", *Biotechnology and Bioengineering*, vol. 60, No. 5 (1998)596-607. Abstract only.

Guerrini et al. "A novel computational approach to integrate NMR spectroscopy and capillary electrophoresis for structure assignment of heparin and heparan sulfate oligosaccharides", *Glycobiology*, vol. 12, No. 11 (2002) 713-719.

Guo et al., Aberrant N-glycosylation of beta] integrin causes reduced alpha5beta1 integrin clustering and stimulates cell migration. Cancer Res, Dec. 1, 2002;62(23):6837-45.

Hahn et al., Growth-associated glycosylation of transferrin secreted by HepG2 cells. J Biol Chem. Nov. 25, 1992;267(33):23982-7.

Hanisch et al. "MUC1 glycoforms in breast cancer cell line T47D as a model for carcinoma-associated alterations of O-glycosylation", *European Journal of Biochemistry*, vol. 236, No. 1, (1996) 318-27. Abstract only.

Hanley et al., Biosynthesis and processing of rat haptoglobin. J Biol Chem. Jun. 25, 1993;258(12):7858-69.

Hansen et al. (Nucleic acids research, vol. 24, No. 1, p. 248-252, 1996).

Harazono et al. "Site-specific glycosylation analysis of human apolipoprotein B100 using LC/ESI MS/MS", *Glycobiology*, vol. 15, No. 5 (May 2005) 447-62. Epub Dec. 22, 2004.

Harvey "Identification of cleaved oligosaccharides by matrix-assisted laser desorption/ionization", *Methods Mol Biol.*, vol. 61 (1996) 243-53.

Harvey "Identification of sites of glycosylation", *Methods Mol, Biol.*, vol. 211 (2003)371-83.

Harvey "Matrix-assisted laser desorption/ionization mass spectrometry of carbohydrates and glycoconjugates", *Int'L J. of Mass Spect.*, vol. 226 (2003) 1-35.

Harvey (Mass Spectrometry Reviews, vol. 18, p. 349-451, 1999).

Harvey et al. "Composition of N-linked carbohydrates from ovalbumin and co-purified glycoproteins", *J. Am. Soc. Mass Spectrom.*, Jun. 2000; 11(6):564-71.

Harvey, "Quantitative aspects of the matrix-assisted laser desorption mass spectrometry of complex oligosaccharides", *Rapid Commun Mass Spectrom*, vol. 7, No. 7 (Jul. 1993)614-9.

Hashimoto et al. "Alpha1-acid glycoprotein fucosylation as a marker of carcinoma progression and prognosis", *Cancer*, vol. 101, No. 12 (2004) 2825-36. Abstract only.

Hefta et al. "Sequence and glycosylation site identity of two distinct glycoforms of nonspecific cross-reacting antigen as demonstrated by sequence analysis and fast atom bombardment mass spectrometry", *J. of Biol. Chem.*, vol. 265, No. 15 (1990) 8618-26. Abstract only.

Hoffman et al. "Molecular characterization of b-trace protein in human serum and urine: a potential diagnostic marker for renal diseases", *Glycobiology*, vol. 7, No. 4 (1997) 499-506. Abstract only.

Holland et al. "Analysis of O-glycosylation site occupancy in bovine kappa-casein glycoforms separated by two-dimensional gel electrophoresis", *Proteomics*, vol. 5, No. 4 (Mar. 2005) 990-1002. Abstract only.

Holland et al. "Proteomic analysis of kappa-casein micro-heterogeneity", *Proteomics*, vol. 4, No. 3 (2004) 743-52. Abstract only.

Honda "Application of capillary electrophoresis to the analyses of carbohydrates and glycoproteins", *Seibutsu Butsuri Kagaku*, vol. 40, No. 3 (1996) 147-154. Abstract only.

Hooker et al. "High resolution glycoform analysis of recombinant human interferon-gamma during batch cultures of Chinese hamster ovary cells", *Animal Cell Technology Basic & Applied Aspects, Proceeding of the Annual Meeting of the Japanese Assoc. for Animal Cell Tech., 8'th Fukuoka*, (Nov. 6-10, 1995) 315-321. Abstract only.

Hooker et al. "Identification of sites of glycosylation", *Methods Mol. Biol.*, vol. 211 (2003) 371-83. Abstract only.

Hsu et al. "Differential N-glycan patterns of secreted and intracellular IgG produced in Trichoplusia ni cells", *J. of Biol Chem.*, vol. 272, No. 14 (1997) 9062-9070. Abstract only.

Hui et al. Identification of glycan structure and glycosylation sites in cellobiohydrolase II and endoglucanases I and II from *Trichoderma reeser*, *Glycobiology*, vol. 12, No. 12 (2002) 837-849.

Hyuga et al. "Analysis of site-specific glycosylation in recombinant human follistatin expressed in Chinese hamster ovary cells", *Biologicals*, vol. 32, No. 2 (Jun. 2004) 70-7. Abstract only.

International Search Report for PCT/US2005/013107, mailed on Jan. 2, 2006.

Iourin et al, "The identification of abnormal glycoforms of serum transferrin in carbohydrate deficient glycoprotein syndrome type I by capillary zone electrophoresis", *Glycoconjugate J.*, vol. 13, No. 6(1996) 1031-1042. Abstract only.

Itoh et al. "Study on evaluating methods for the quality control of glycoprotein products. (III)—erythropoietin products. Part 3". *Kokuritsu Iyakuhin Shokuhin Eisei Kenkyusho Hokoku*, vol. 119 (2001) 65-9. Abstract only.

Iwase "Analysis of the microheterogeneity of the IgA1 hinge glycopeptide having multiple O-linked oligosaccharides by capillary electrophoresis", *Analytical Biochem.*, vol. 288, No. 1 (Jan. 1, 2001) 22-7. Abstract only.

Iwase et al. "Abundance of Galbl,3GalNAc in O-linked oligosaccharide on hinge region of polymerized IgA1 and heat-aggregated IgA1 from normal human serum", *J. of Biochem. Tokyo*, vol. 120, No. 1(1996) 92-97. Abstract only.

Iwase et al. "Analysis of glycoform of O-glycan from human myeloma immunoglobulin A1 by gas-phase hydrazinolysis following pyridylamination of oligosaccharides", *Analytical Biochem.*, vol. 206, No. 1 (1992) 202-5. Abstract only.

Iwase et al. "Application of matrix-assisted laser desorption ionization time-of-flight mass spectrometry to the analysis of glycopeptide-containing multiple O-linked oligosaccharides", *Journal of Chromatography, B, Biomedical sciences and applications*, vol. 709, No. I (May 8, 1998), 145-9. Abstract only.

Iwase et al. "Estimation of the number of O-linked oligosaccharides per heavy chain of human serum IgA1 by matrix-assisted laser desorption ionization time-of-flight mass spectrometry (MALDI-TOFMS) analysis of the hinge glycopeptide", *J. of Biochem. Tokyo*, vol. 120, No. 2 (1996) 393-397. Abstract only.

Jacobs et al. "Enhancement of the quality of MALDI mass spectra of highly acidic oligosaccharides by using a nafion-coated probe", *Anal. Chem.* vol. 73, No. 3 (Feb. 1, 2001) 405-410.

Jacobs et al., Progress and challenges in screening for early detection of ovarian cancer. Mol Cell Proteomics. Apr. 2004;3(4):355-66.

Jacoby et al. "Determination of the glycoforms of human chorionic gonadotropin beta-core fragment by matrix-assisted laser desorption/ionization time-of-flight mass spectrometry", *Clinical Chem.* vol. 46, No. 11 (Nov. 2000) 1796-803. Abstract only.

Janska et al. "The lower molecular weight acid phosphatase from the frog liver: isolation of homogeneous AcPase III and IV representing glycoforms with different bioactivity", *Comparative Biochem. and Phys.: Part B: Biochem. & Mol. Bio.*, vol. 92B, No. 2 (1989) 341-6. Abstract only.

Jenkins "Monitoring and control of recombinant glycoprotein heterogeneity in animal cell cultures", *Biochem. Soc. Transactions*, vol. 23, No. 1(1995) 171-5. Abstract only.

Jiang et al. "Enhanced detection of sulfated glycosylation sites in glycoproteins", *J. of Am. Soc. for Mass Spectrometry*, vol. 16, No. 3 (2005) 340-348. Abstract only.

Joao et al. "Effects of glycosylation on protein structure and dynamics in ribonuclease B and some of its individual glycoforms," *Eur. J. Biochem.*, Nov. 15, 1993; 218(1):239-44.

Jorgensen et al., Up-regulation of the oligosaccharide sialyl LewisX: a new prognostic parameter in metastatic prostate cancer. Cancer Res. May 1, 1995;55(9):1817-9.

Joshi et al. "Development of a mass fingerprinting tool for automated interpretation of oligosaccharide framentation data", *Proteomics*, vol. 4(2004) 1650-1664.

Juhasz et al. "Utility of non-covalent complexes in the matrix-assisted laser desorption ionization mass spectrometry of heparin-derived oligosaccharides", *Carbohydr Res.*, Apr. 30, 1995; 270(2):131-47.

Juhasz et al., "Mass spectrometric molecular-weight determination of highly acidic compounds of biological significance via their complexes with basic polypeptides", *Proc. Natl. Acad. Sci. USA*, May 1994; 91:4333-7.

Kaji et al. "Lectin affinity capture, isotope-coded tagging and mass spectrometry to identify N linked glycoproteins", Nat. Biotech., vol. 21, No. 6 (Jun. 2003) 667-672.

Kakehi et al. "Analysis of glycoproteins and the oligosaccharides thereof by high-performance capillary electrophoresis-significance in regulatory studies on biopharmaceutical products", Biomed. Chromatography: BMC, vol. 16, No. 2 (Apr. 2002) 103-15. Abstract only.

Kakehi et al. "Analysis of glycoproteins, glycopeptides and glycoprotein-derived oligosaccharides by high-performance capillary electrophoresis" J. of Chromatography, A, vol. 720, No. (1+2) (1996) 377-93. Abstract only.

Kakehi et al. "Basic studies on validation of glycoprotein pharmaceuticals using carbohydrate chains as markers", Igakuhin Kenkyu, vol. 34, No. 10 (2003) 639-648. Abstract only.

Kannagi et al,, Molecular mechanism for cancer-associated induction of sialyl Lewis X and sialyl Lewis A expression—The Warburg effect revisited. Glycoconj J. 2004;20(5):353-64.

Kannagi et al., Carbohydrate-mediated cell adhesion involved in hematogenous metastasis of cancer. Glycoconj J. Aug. 1997;14(5):577-84.

Karlsson et al. "The glycosylation of rat intestinal Muc2 mucin varies between rat strains and the small and large intestine. A study of O-linked oligosaccharides by a mass spectrometric approach", J. of Biological Chem., vol. 272, No. 43 (1997) 27025-27034. Abstract only.

Keiser "Development of novel analytical tools for complex carbohydrates", Massachusetts Institute of Technology, Jul. 22, 2004, thesis defense presented Apr. 15, 2004.

Kelly et al. "Development of electrophoretic conditions for the characterization of protein glycoforms by capillary electrophoresis-electrospray mass spectrometry", J. of Chromatography, A, vol. 720 (1+2) (1996) 409-427. Abstract only.

Kim et al., Perspectives on the significance of altered glycosylation of glycoproteins in cancer. Glycoconj J. Aug. 1997;14(5):569-76.

Kinoshita "Comparative studies on the analysis of glycosylation heterogeneity of sialic acid containing glycoproteins using capillary electrophoresis", Journal of Chromatography, A, vol. 866, No. 2, (Jan. 14, 2000) 261-71. Abstract only.

Kirmiz et al., A serum glycomics approach to breast cancer biomarkers. Mal Cell Proteomies, Jan. 2007;6(1):43-55.

Klausen et al. "Analysis of the glycoforms of human recombinant factor VIIa by capillary electrophoresis and high-performance liquid chromatography", J. of Chromatography, vol. 718, No. 1 (1995) 195-202. Abstract only.

Kleindienst et al. "Capillary electrophoresis peptides and proteins in fused-silica capillaries coated with derivatized polystyrene nanoparticles", Electrophoresis, vol. 19, No. 2 (1998) 262-269. Abstract only.

Kobata and Amano, Altered glycosylation of proteins produced by malignant cells, and application for the diagnosis and immunotherapy of tumours. Immunol Cell Biol. Aug. 2005;83(4):429-39. Review.

Krapp et al. "Structural analysis of human IgG-Fc glycoforms reveals a correlation between glycosylation and structural integrity", J. Mol. Biol., Jan. 31, 2003; 325(5):979-89.

Krokhin et al. "Site-specific N-glycosylation analysis: Matrix-assisted laser desorption/ionization quadrupole-quadrupole time-of-flight tandem mass spectral signatures for recognition and identification of glycopeptides", Rapid Comm. in Mass Spectrometry, vol. 18, No. 18 (2004) 2020-2030. Abstract only.

Kui Wong et al., Characterization of the oligosaccharides associated with the human ovarian tumor marker CAI25. J Biol Chem. Aug. I, 2003 ;278(31):28619-34.

Kunkel et al. "Comparisons of the glycosylation of a monoclonal antibody produced under nominally identical cell culture conditions in two different bioreactors", Biotechnol. Prog. May-Jun. 2000; 16(3): 462-70.

Kuster et al., 18O-labeling of N-glycosylation sites to improve the identification of gel-separated glycoproteins using peptide mass mapping and database searching. Anal Chem. Apr. 1, 1999; 71(7): 1431-40.

Lacko et al. Characterization of recombinant human plasma lecithin: cholesterol acyltransferase (LCAT): N-linked carbohydrate structures and catalytic properties, J Lipid Res., Apr. 1998; 39(4):807-20.

Landberg et al., Carbohydrate composition of serum transferrin isoforms from patients with high alcohol consumption. Biochem Biophys Res Commun. May 16, 1995; 210(2): 267-74.

Landberg et al., Changes in glycosylation of human bile-salt-stimulated lipase during lactation. Arch Biochem Biophys. May 15, 2000; 377(2): 246-54.

Lapadula et al. "Congruent strategies for carbohydrate sequencing. 3. OSCAR: an algorithm for assigning oligosaccharide topology from MS data", Anal. Chem., vol. 77, No. 19 (Oct. 1, 2005) 6271-9.

Legaz et al. "Effect of polyamines on the separation of ovalbumin glycoforms by capillary electrophoresis", J. of Chromatography, A, vol. 719, No. 1(1996) 159-70. Abstract only.

Lin et al. "Cell surface alpha 2,6 sialylation affects adhesion of breast carcinoma cells", Exp Cell Res., May 15, 2002; 276(1): 101-10.

Liu et al. "Capillary electrophoresis-electrospray mass spectrometry for the characterization of high-mannose-type N-glycosylation and differential oxidation in glycoproteins by charge reversal and protease/glycosidase digestion", Analytical Chem, vol. 73, No. 24 (Dec. 15, 2001) 5875-85. Abstract only.

Lopez et al. "Microheterogeneity of the oligosaccharides carried by the recombinant bovine lactoferrin expressed in Mamestra brassicae cells", Glycobiology, vol. 7, No. 5 (1997) 635-651.

Lopez-Soto-Yarritu et al. "Improved capillary isoelectric focusing method for recombinant erythropoietin analysis", J. of Chromatography, vol. 968, No. (1-2) (Aug. 30, 2002) 221-8. Abstract only.

Ma et al., "Carbohydrate analysis of a chimeric recombinant monoclonal antibody by capillary electrophoresis with laser-induced fluorescence detection", Anal. Chem., vol. 71, (1999) 5185-5192.

Mackiewicz et al. "Glycoformas of al-acid glycoprotein as disease markers", Acute Phase Proteins (1993) 651-61. Abstract only.

Mackiewicz et al. "Glycoforms of serum al-acid glycoprotein as markers of inflammation and cancer", Glycoconjugate J, vol. 12, No. 3(1995) 241-7. Abstract only.

Manzi et al. "Exploring the glycan repertoire of genetically modified mice by isolation and profiling of the major glycan classes and nano-NMR analysis of glycan mixtures", Glycobiology, vol. 10, No. 7(2000) 669-689.

Matsuura et al. "Human a-galactosidase A: characterization of the N-linked oligosaccharides on the intracellular and secreted glycoforms overexpressed by Chinese hamster ovary cells", Glycobiology, vol. 8, No. 4, (1998) 329-339.

Mechref et al., Structural investigations of glycoconjugates at high sensitivity. Chem Rev. Feb. 2000; 102(2): 321-69.

Medzihradszky et al. "Characterization of protein N-glycosylation by reversed-phase microbore liquid chromatography/electrospray mass spectrometry, complementary mobile phases, and sequential exoglycosidase digestion", J. of Am. Soc. for Mass Spectro., vol. 5, No. 5(1994) 350-8. Abstract only.

Merry, "Current techniques in protein glycosylation analysis. A guide to their application", Acta Biochimica Polonica, 1999; 46(2):303-14.

Mills et al. "Mass spectrometric analysis of glycans in elucidating the pathogenesis of CDG type IIx" J Inherit. Metab. Dis., vol. 26 (2003) 119-134.

Moran et al. "A systematic approach to the validation of process control parameters for monoclonal antibody production in fed-batch culture of a murine myeloma", Biotechnology and bioengineering, vol. 69, No. 3, (Aug. 5, 2000) 242-55. Abstract only.

Morelle et al., Glycomics and mass spectrometry. Curr Pharm Des. 2005; 11(20): 2615-45.

Morris et al. "Gender-specific glycosylation of human glycodelin affects its contraceptive activity", J. of Biological Chem, vol. 271, No. 50 (1996) 32159-32167. Abstract only.

Mueller et al. "Characterization and direct glycoform profiling of a hybrid plasminogen activator by matrix-assisted laser desorption and electrospray mass spectrometry: correlation with high-performance liquid chromatographic and nuclear magnetic resonance analyses of the released glycans", Biol. Mass Spectrom., vol. 23, No. 6 (1994)330-8. Abstract only.

Murata et al., Expression of N-acetylglucosaminyltransferase V in colorectal cancer correlates with metastasis and poor prognosis. Clin Cancer Res. May 2000;6(5):1772-7.

Muthing et al., "Effects of buffering conditions and culture pH on production rates and glycosylation of clinical phase I anti-melanoma mouse IgG3 monoclonal antibody R24", *Biotechnol. Bioeng.*, Aug. 5, 2003; 83(3):321-34.

Nagy et al. "Electrospray ionization fourier transform ion cyclotron resonance mass spectrometry of human alpha-1-acid glycoprotein", *Analytical Chem.*, vol. 76, No. 17 (Sep. 1, 2004) 4998-5005. Abstract only.

Nemeth et al. "Characterization of the glycosylation sites in cyclooxygenase-2 using mass spectrometry" *Biochem.* vol. 40, No. 10 (Mar. 13, 2001) 3109-16. Abstract only.

Nemoto-Sasaki et al., "Correlation between the sialylation of cell surface Thomsen Friedenreich antigen and the metastatic potential of colon carcinoma cells in a mouse model", *Glycoconj J.*, Nov.-Dec. 2001; 18(11-12):895-906.

Nimtz "Structural characterization of the oligosaccharide chains of native and crystallized boar seminal plasma spermadhesin PSP-I and PSP-II glycoforms", *European journal of biochemistry/FEBS*, vol. 265, No. 2 (Oct. 1999) 703-18.

Norgard-Sumnicht et al. "Exploring the outcome of genetic modifications of glycosylation in cultured cell lines by concurrent isolation of the major classes of vertebrate glycans", *Glycobiology*, vol. 10, No. 7(2000) 691-700.

Novotny "Capillary electrophoresis of carbohydrates", *Chemical Analysis*, (146 High Performance Capillary Electrophoresis), (1998) 729-765. Abstract only.

O'Hare et al. "Glycoforms of human serum proteins identified by *Ricinus communis* lectin", *Biochem. Soc. Trans.* vol. 18, No. 2(1990) 323. Abstract only.

Oda et al. "Capillary electrophoresis-based separation of transferrin sialoforms in patients with carbohydrate-deficient glycoprotein syndrome", *Electrophoresis*, vol. 18, No. 10 (1997) 1819-1826. Abstract only.

Odani "Direct evidence for decreased sialylation and galactosylation of human serum IgA1 Fc O-glycosylated hinge peptides in IgA nephropathy by mass spectrometry", *Biochemical and Biophysical Research Communications*, vol. 271, No. 1, (Apr. 29, 2000) 268-74. Abstract only.

Ogonah et al. "Analysis of human interferon-g glycoforms produced in baculovirus infected insect cells by matrix assisted laser desorption spectrometry", *Biochem. Soc. Transactions*, vol. 23, No. 1(1995) 100s. Abstract only.

Ogonah et al. "Characterization and analysis of human interferon-g glycoforms produced in baculovirus infected *Spodoptera frugiperda* (Sf9) and *Estigmena acrea* (Ea) cell lines", *Animal Cell Tech: Dev. towards the 21" Century*, [*Proceedings of the Meeting*] Veldhoven, Neth. Sep. 11-16, 1994 (1995) Meeting Date 1994, 427-430. Abstract only.

Ohyama et al. "Carbohydrate structure and differential binding of prostate specific antigen to *Maackia amurensis* lectin between prostate cancer and benign prostate hypertrophy", *Glycobiology*, vol. 14, No. 8(2004) 671-679.

Orntoft et al., "Clinical aspects of altered glycosylation of glycoproteins in cancer", *Electrophoresis*, Feb. 1999; 20(2):362-71.

Packer et al. "Analyzing glycoproteins separated by two-dimensional gel electrophoresis", *Electrophoresis*, vol. 19, No. 6(1998) 981-988. Abstract only.

Packer et al. "Proteome analysis of glycoforms: a review of strategies for the microcharacterization of glycoproteins separated by two-dimension polyacrylamide gel electrophoresis", *Electrophoresis*, vol. 18, No. 3-4 (1997) 452-460. Abstract only.

Pannek et al., The role of PSA and percent free PSA for staging and prognosis prediction in clinically localized prostate cancer. Semin Urol Oncol. Aug. 1998; I 6(3):100-5.

Pantazaki et al. "Recent advances in the capillary electrophoresis of recombinant glycoproteins", *Analytical Chimica Acta*, vol. 383, No. 1-2 (1999) 137-156. Abstract only.

Papac et al., A high-throughput microscale method to release N-linked oligosaccharides from glycoproteins for matrix-assisted laser desorption/ionization time-of-flight mass spectrometric analysis. Glycobiology. May 1998;8(5):445-54.

Parekh "Glycoform analysis of glycoproteins", *Methods in Enzymology (Guide to Techniques)*, vol. 230 (1994) 340-8. Abstract only.

Pedersen et al. "Characterization of proteinase A glycoforms from recombinant *Saccharomyces cerevisiae*", *Biotech. and Applied Biochem.*, vol. 18, No. 3. (1993) 377-88. Abstract only.

Peracaula et al. "Altered glycosylation pattern allows the distinction between prostate-specific antigen (PSA) from normal and tumor origins", *Glycobiology*, vol. 13, No. 6 (2003) 457-470.

Peter-Katalinic "Methods in Enzymology: *O*-Glycosylation of Proteins", *Methods in Enzymology*, 2005; 405:139-71.

Petricoin et al., SELDI-TOF-based serum proteomic pattern diagnostics for early detection of cancer. Curr Opin Biotechnol. Feb. 2004;15(1):24-30.

Petricoin III et al. "Use of proteomic patterns in serum to identify ovarian cancer", *Lancet*, vol. 359 (Feb. 16, 2002) 572-577.

Pierce et al., Regulation of N-acetylglucosaminyltransferase V and Asn-linked oligosaccharide beta(I,6) branching by a growth factor signaling pathway and effects on cell adhesion and metastatic potential. Glycoconj J. Aug. 1997;14(5):623-30.

Pili et al., The alpha-glucosidase I inhibitor castanospermine alters endothelial cell glycosylation, prevents angiogenesis, and inhibits tumor growth. Cancer Res. Jul. 1, 1995;55(13):2920-6.

Pirie-Shepherd et al. "Sialic acid content of plasminogen 2 glycoforms as a regulator of fibrinolytic activity. Isolation, carbohydrate analysis, and kinetic characterization of six glycoforms of plasminogen 2", *J. of Biol. Chem.*, vol. 270, No. 11 (1995)5877-81. Abstract only.

Polascik et al., Prostate specific antigen: a decade of discovery—what we have learned and where we are going. J Urol. Aug. 1999;162(2):293-306.

Powell et al. "Natural ligands of the B cell adhesion molecule CD2213 carry N-linked oligosaccharides with α-2,6-linked sialic acids that are required for recognition", *J. Biol. Chem.*, Apr. 5, 1993; 268(10):7019-27.

Prakash et al., "Glycotyping of prostate specific antigen", *Glycobiology*, Feb. 2000; 10(2):173-6.

Protein Aqua®, Aqua Peptides http://www.sigmaaldrich.com/Area__of __Interest/LifeScience/Proteomics__and __Protein__Exp... (date printed Jul. 8, 2005).

Przybylo et al. "Different glycosylation of cadherins from human bladder non-malignant and cancer cell lines", *Cancer Cell Int.*, Jun. 18, 2002; 2:6.; printed Jul. 8, 2005).

Qu et al., Boosted decision tree analysis of surface-enhanced laser desorption/ionization mass spectral serum profiles discriminates prostate cancer from noncancer patients, Clin Oct;48(10):1835-43. Chem. 2002.

Race et al. "Comparison of abnormal prion protein glycoform patterns from transmissible spongiform encephalopathy agent-infected deer, elk, sheep, and cattle", *J. of Virol.*, vol. 76, No. 23 (Dec. 2002) 12365-8. Abstract only.

Rahbek-Nielsen et al. "Glycopeptide profiling of human urinary erythropoietin by matrix assisted laser desorption/ionization mass spectrometry", *J. of Mass. Spectrometry*, vol. 32 (1997) 948-958.

Raju et al., "Species-specific variation in glycosylation of IgG: evidence for the species-specific sialylation and branch-specific galactosylation and importance for engineering recombinant glycoprotein therapeutics", *Glycobiology*, May 2000; 10(5):477-86.

Ray et al., Glycoprotein Glycan Analysis: A new USP General Chapter. Slides of a lecture presented at the USP Conference on Biological and Biotechnological Drug Substances and Products. Crystal City, Virginia. Nov. 20, 2003.

Rhomberg et al. "Mass spectrometric and capillary electrophoretic investigation of the enzymatic degradation of heparin-lilce glycosaminoglycans", *Proc Natl Acad Sci U S A.*, Apr. 14, 1998;95(8):4176-81.

Rhomberg et al. "Mass spectrometric evidence for the enzymatic mechanism of the depolymerization of heparin-like glycosaminoglycans by heparinase II", *Proc Natl Acad Sci U S A.*, Oct. 13, 1998;95(21):12232-7.

Roberts et al. "An Integrated Strategy for Structural Characterization of the Protein and Carbohydrate Components of Monoclonal Antibodies: Application to Anti-Respiratory Syncytial Virus Mab", *Analytical Chem.*, vol. 67, No. 20 (1995) 3613-25. Abstract only.

Rohovec et al., "The structure of the sugar residue in glycated human serum albumin and its molecular recognition by phenylboronate", *Chem. Eur. J*, May 23, 2003; 9(10):2193-9.

Routier et al. "Quantitation of the different oligosaccharides of human serum IgG from patients with rheumatoid arthritis: a critical evaluation of different methods", *J. of ImmunoL Methods*, vol. 213, No. 2 (1998)113-130. Abstract only.

Royle et al. "An analytical and structural database provides a strategy for sequencing O-glycans from microgram quantities of glycoproteins", *Anal. Biochem.*, vol. 304 (2002) 70-90.

Rudd et al. "Glycoforms modify the dynamic stability and functional activity of an enzyme", *Biochem.*, vol. 33, No. 1(1994) 17-22. Abstract only.

Rudd et al. "Separation and analysis of the glycoform populations of ribonuclease B using capillary electrophoresis", *Glycoconjugate J*, vol. 9, No. 2(1992) 86-91. Abstract only.

Rush et al. "Microheterogeneity of erythropoietin carbohydrate structure", *Anal. Chem.*, vol. 67 (1995) 1442-1452.

Rush et al. "Peptide mapping and evaluation of glycopeptide microheterogeneity derived from endoproteinase digestion of erythropoietin by affinity high-performance capillary electrophoresis", *Anal. Chem.* vol. 65, (1993) 1834-1842.

Sakai et al. "18O-labeling quantitative proteomics using an ion trap mass spectrometer", *Proteomics*, vol. 5, No. 1 (Jan. 2005) 16-23. Abstract only.

Sanz-Nebot "Characterization of human transferrin glycoforms by capillary electrophoresis and electrospray ionization mass spectrometry", *J. of Chromatography, B: Analytical Tech. in the Biomedical and Life Sc.*, vol. 798, No. 1 (2003), 1-7. Abstract only.

Sanz-Nebot, "Separation of recombinant human erythropoietin glycoforms by capillary electrophoresis using volatile electrolytes: assessment of mass spectrometry for the characterization of erythropoietin glycoforms", *Analytical Chem.*, vol. 75, No. 19 (2003) 5220-5229. Abstract only.

Sasaki et al. "Site-specific glycosylation of human recombinant erythropoietin: analysis of glycopeptides or peptides at each glycosylation site by fast atom bombardment mass spectrometry", *Biochem.*, vol. 27 (1988) 8618-8626.

Satomi et al. "Site-specific carbohydrate profiling of human transferrin by nano-flow liquid chromatography/electrospray ionization mass spectrometry", *Rapid Commun. Mass. Spectrom* vol. 18, No. 24 (2004) 2938-8. Abstract only.

Scanlin et al., "Terminal glycosylation and disease: influence on cancer and cystic fibrosis", *Glycoconj J.*, Jul.-Sep. 2000; 17(7-9):617-26.

Schilow et al. "Charge analysis of N-glycans from human recombinant coagulation factor VIII and human FVIII standards", *Thrombosis and Haemostasis*, vol. 92, No. 2(2004) 427-428. Abstract only.

Seelentag et al., Expression of CD44 isoforms and beta 1,6-branched oligosaccharides in human malignant melanoma is correlated with tumor progression but not with metastatic potential. J Cutan Pathol. Apr. 1997;24(4):206-11.

Sei et al. "Collection of alpha1-acid glycoprotein molecular species by capillary electrophoresis and the analysis of their molecular masses and carbohydrate chains", *J. of Chromatography*, vol. 958, No. 1-2, (Jun. 7, 2002) 273-81. Abstract only.

Seidenfaden et al., Polysialic acid directs tumor cell growth by controlling heterophilic neural cell adhesion molecule interactions. Mol Cell Biol. Aug. 2003;23(16):5908-18.

Senger et al. "Effect of shear stress on intrinsic CHO culture state and glycosylation of recombinant tissue-type plasminogen activator protein", *Biotechnol. Prog.*, Jul.-Aug. 2003; 19(4):1199-209.

Senger et al. "Neural-Network-Based Identification of Tissue-Type Plasminogen Activator Protein Production and Glycosylation in CHO Cell Culture under Shear Environment", *Biotechnology Progress*, vol. 19, No. 6(2003) 1828-1836. Abstract only.

Shimodaira et al. "Carcinoma-associated expression of core 2 beta-1,6-N acetylglucosaminyltransferase gene in human colorectal cancer: role of 0-glycans in tumor progression", Cancer Res., Dec. 1, 1997; 57(23):5201-6.

Society et al., http://www.cancer.org/docroot/STT/sU_O.asp. 2005.

Stemmann et al. "Dual inhibition of sister chromatid separation at metaphase", *Cell*, vol. 107 (Dec. 14, 2001) 715-726.

Tabares et al., Different glycan structures in prostate-specific antigen from prostate cancer sera in relation to seminal plasma PSA. Glycobiology. Feb. 2006;16(2):132-45.

Tagliaro et al. "Comments on 'Capillary zone electrophoresis for determination of carbohydrate-deficient transferrin in human serum'", *Electrophoresis*, vol. 25, No. 10-11 (2004) 1723-1725. Abstract only.

Taketa "Characterization of sugar chain structures of human alpha-fetoprotein by lectin affinity electrophoresis", ibarahp@oka.urban.ne.jp., *Electrophoresis*, vol. 19, No. 15, (Nov. 1998) 2592-602. Abstract only.

Taniguchi et al., Implication of GnT-V in cancer metastasis: a glycomic approach for identification of a target protein and its unique function as an angiogenic cofactor. Glycoconj J. Nov.-Dec. 2001;18(11-12):859-65.

Taverna, et al. "Electrophoretic methods for process monitoring and the quality assessment of recombinant glycoproteins", *Electrophoresis*, vol. 19, No. 15, (1998) 2572-2594. Abstract only.

Thompson et al., Prevalence of prostate cancer among men with a prostate-specific antigen level 54.0 ng per milliliter. N Engl J Med. May 27, 2004;350(22):2239-46.

Thornton et al. "Respiratory mucins: identification of core proteins and glycoforms", *Biochem. J.*, vol. 316, No. 3 (1996) 967-975. Abstract only.

Tran, et al. "Routine O-glycan characterization in nutritional supplements-a comparison of analytical methods for the monitoring of the bovine kappa-casein macropeptide glycosylation", *J. of Chromatography*, vol. 929, No. 1-2 (Sep. 21, 2001) 151-63. Abstract only.

Treuheit et al. "Analysis of the five glycosylation sites of human α1-acid glycoprotein", *Biochem. J*, vol. 283, No. 1(1992) 105-12. Abstract only.

Tseng et al "Profiling with structural elucidation of the neutral and anionic O-linked oligosaccharides in the egg jelly coat of *Xenopus laevis* by Fourier transform mass spectrometry", *Glycoconjugate J*, vol. 18 (2001) 309-320.

Tseng et al. "Catalog-library approach for the rapid and sensitive structural elucidation of oligosaccharides", *Anal. Chem.* vol. 71 (1999) 3747-3754.

Van Der Linden et al. "Preparative affinity electrophoresis of different glycoforms of serum glycoproteins: Application for the study of inflammation-induced expression of sialyl-Lewisx groups on al-acid glycoprotein (orosomucoid)", *Glycosylation & Disease*, vol. 1, No. 1(1994) 45-52. Abstract only.

Van Dijk et al. "α1-Acid glycoprotein (orosomucoid): pathophysiological changes in glycosylation in relation to its function", *Glycoconjugate J.*, vol. 12, No. 3(1995) 227-33. Abstract only.

Van Dijk et al. "Glycosylation of α1-acid glycoprotein (orosomucoid) in health and disease: occurrence, regulation and possible functional implications", *Trends in Glycoscience and Glycotechnology*, vol. 10, No. 53 (1998) 235-245. Abstract only.

Venkataraman et al. "Sequencing complex polysaccharides", *Science*, vol. 286 (Oct. 15, 1999) 537-542.

Vorberg et al. "Molecular basis of scrapie strain glycoform variation", *J. of Biol. Chem.*, vol. 277, No. 39 (Sep. 27, 2002) 36775-81. Abstract only.

Wan et al. "Rapid method for monitoring galactosylation levels during recombinant antibody production by electrospray mass spectrometry with selective-ion monitoring", *J. of Chromatography.*, vol. 913, No. 1-2 (Apr. 13, 2001) 437-46. Abstract only.

Wang et al. "Mass spectrometric characterization and glycosylation profile of bovine pancreatic bile salt-activated lipase", *Protein Expression and Purification*, vol. 12, No. 2 (1998) 259-268. Abstract only.

Watt et al. "Site-specific glycosylation of an aglycosylated human IgG1-Fc antibody protein generates neoglycoproteins with enhanced function", *Chem & Biol.*, Sep. 2003; 10(9):807-14.

Weiss et al., Optimized rule induction. IEEE Expert Journal. 1993;8:61-69.

Written Opinion for PCT/US2005/03107, mailed on Jan. 2, 2006.

Wu et al. "Characterization of neutralization epitopes in the V2 region of human immunodeficiency virus type 1 gp120 and the role of glycosylation in the correct folding of the V1/V2 domain", *J. Virology*. vol. 69, No. 4 (1995) 2271-8. Abstract only.

Wulfkuhle et al. "Proteomic applications for the early detection of cancer", *Nat Rev Cancer*, Apr. 2003; 3(4):267-75.

Xie et al. "Method for the comparative glycomic analyses of O-linked, mucin-type oligosaccharides", *Analytical Chem.*, Sep. 1, 2004; 76(17):5186-97.

Yamada et al. "Structural changes of immunoglobulin G oligosaccharides with age in healthy human serum", *Glycoconjugate J.*, vol. 14, No. 3(1997) 401-405. Abstract only.

Yang et al. "Capillary isoelectric focusing-electrospray ionization mass spectrometry for transferrin glycoforms analysis", *Analytical biochemistry*, vol. 243, No. 1, (1996) 140-9. Abstract only.

Yang et al., Approach to the comprehensive analysis of glycoproteins isolated from human serum using a multi-lectin affinity column. J Chromatogr A. Oct. 22, 2004;1053(1-2):79-88.

Yang et al., Glycosylation in human thyroglobulin: location of th N-linked oligosaccharide unites and comparison with bovine thryoglobulin. Arch Biochem Biophys. Mar. 1, 1996; 327(1): 61-70.

Yim et al. "Capillary zone electrophoresis resolution of recombinant human bone morphogenetic protein 2 glycoforms. An investigation into the separation mechanisms for an exquisite separation", *J. of Chromatograraphy*, vol. 716, No. 1-2, (Nov. 17, 1995) 401-12. Abstract only.

Yim, "Fractionation of the human recombinant tissue plasminogen activator (rtPA) glycoforms by high-performance capillary zone electrophoresis and capillary isoelectric focusing", *J. of. Chromatography*, vol. 559, No. 1-2, (1991) 401-10. Abstract only.

Yousefi et al., Increased UDP-GlcNAc:Galbetal-3GalNAc-R (GlcNAc to GalNAc) beta-1,6-N-acerylglucosaminyltransferase activity in metastatic murine tumor cell lines. Control of polylactosamine synthesis. J Biol Chem. Jan. 25, 1991;266(3):1772-82.

Zamfir et al. "Capillary electrophoresis-mass spectrometry for glycoscreening in biomedical research", *Electrophoresis*, vol. 25, No. 13 (2004) 1949-1963. Abstract only.

Zeng et al. "Characterization and analysis of a novel glycoprotein from snake venom using liquid chromatography-electrospray mass spectrometry and Edman degradation", *European J. of Biochem./FEBS*, vol. 266, No. 2 (Dec. 1999) 352-8. Abstract only.

Zhang et al. "Identification and quantification of N-linked glycoproteins using hydrazide chemistry, stable isotope labeling and mass spectrometry", *Nature Biotech.*, vol. 21, No. 6 (Jun. 2003) 660-666.

Zhang et al. "Quantitative analysis and process monitoring of site-specific glycosylation microheterogeneity in recombinant human interferon-g from Chinese hamster ovary cell culture by hydrophilic interaction chromatography", *J. of Chromatography, B:Biomedical Sciences and Applications*, vol. 712, No. 1+2, (1998) 73-82. Abstract only.

Zhang et al. "The effect of dissolved oxygen (DO) concentration on the glycosylation of recombinant protein produced by the insect cell-baculovirus expression system", *Biotechnol. Bioeng.*, Jan. 20, 2002; 77(2):219-24.

Zhao et al. "Rapid, sensitive structure analysis of oligosaccharides", *Proc. Natl. Acad. Sci. USA*, vol. 94 (Mar. 1997) 1629-1633.

Zhou et al. "Application of capillary electrophoresis, liquid chromatography, electrospray-mass spectrometry, and matrix-assisted laser desorption/ionization—time of flight—mass spectrometry to the characterization of recombinant human erythropoietin", *Electrophoresis*, vol. 19, No. 13 (1998) 2348-2355. Abstract only.

Zhou et al., Uroplakin Ia is the urothelial receptor for uropathogenic *Escherichia coli*: evidence from in vitro FimH binding. J Cell Sci. Nov. 2001; 114(Pt 22): 4095-103.

Zhu et al. (Biochemistry, vol. 39, p. 11194-11204, 2000).

* cited by examiner

High Mannose Type

Complex Type

Hybrid Type

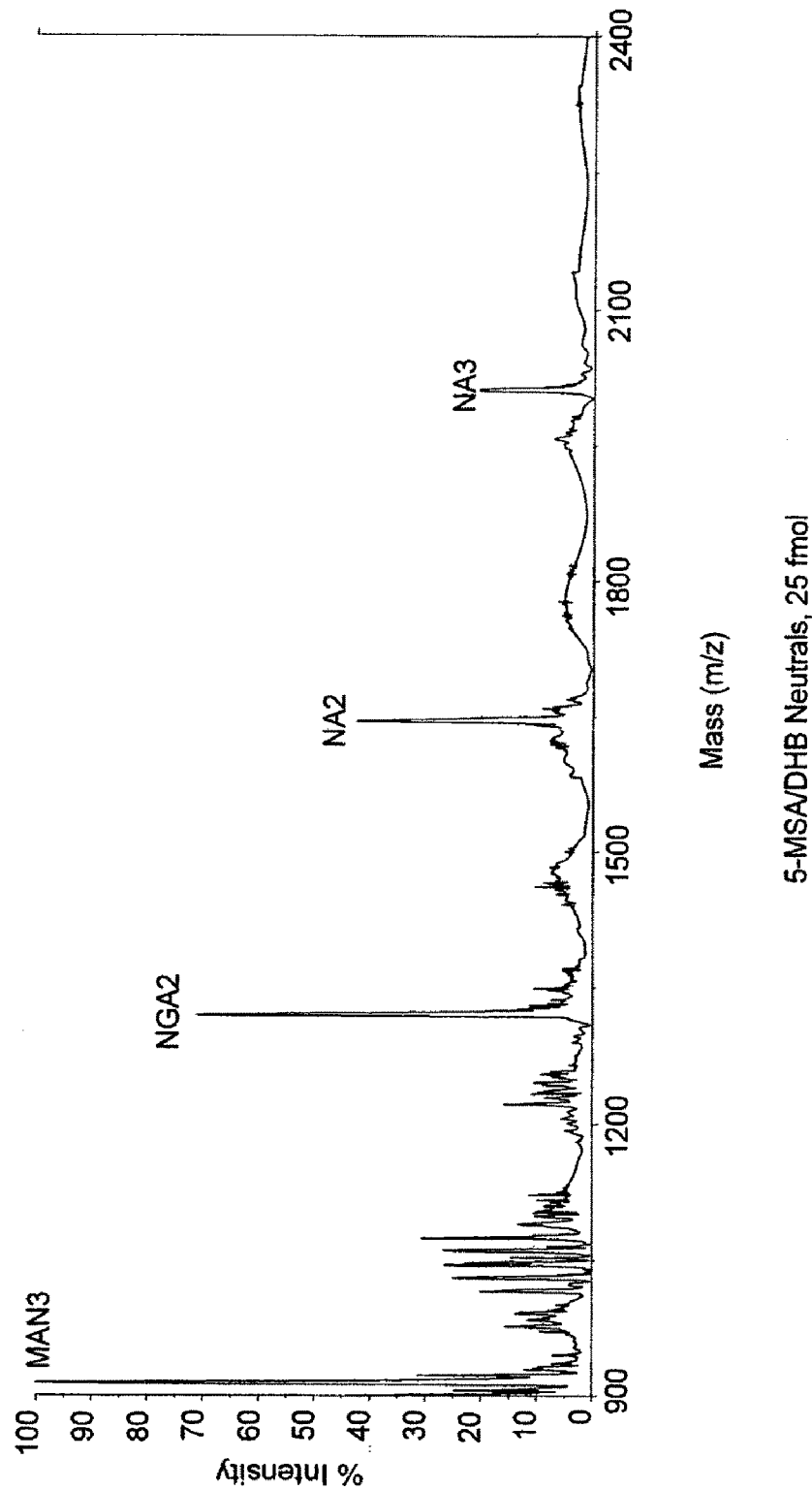

| Glycans in Spot | Man3 Intens. | NGA2 Intens. | NA2 Intens. | NGA3 Intens. |
|---|---|---|---|---|
| Man3 | 5.9e3 | — | — | — |
| Man3 NGA2 | 6.5e3 | 4.4e3 | — | — |
| Man3 NGA2 NA2 | 6.4e3 | 4.5e3 | 2.0e3 | — |
| Man3 NGA2 NA2 | 8.4e3 | 4.8e3 | 2.3e3 | — |

*FIG. 21C*

| Glycans in Spot | A1 Intens. | A2F Intens. | A3 Intens. | SC1840 Intens. | SC2132 Intens. |
|---|---|---|---|---|---|
| A1 | 2.2e3 | — | — | — | — |
| A1 A2F | 4.6e3 | 2.3e3 | — | — | — |
| A1 A2F A3 | 2.6e3 | 1.2e3 | 3.6e3 | — | — |
| A1 A2F A3 SC1840 | 3.2e3 | 2.0e3 | 5.1e3 | 3.5e3 | — |
| A1 A2F A3 SC1840 SC2132 | 2.8e3 | 1.6e3 | 3.9e3 | 2.0e3 | 2.5e3 |

*FIG. 21D*

SEQUENCE LISTING

<160> NUMBER OF SEQ ID NOS: 10

<210> SEQ ID NO 1
<211> LENGTH: 17
<212> TYPE: PRT
<213> ORGANISM: Artificial Sequence
<220> FEATURE:
<223> OTHER INFORMATION: synthetic glycoprotein fragment

<400> SEQUENCE: 1

Tyr Cys Asn Ile Ser Gln Lys Met Met Ser Arg Asn Leu Thr Lys Asp
1               5                   10                  15

Arg

<210> SEQ ID NO 2
<211> LENGTH: 4
<212> TYPE: PRT
<213> ORGANISM: Artificial Sequence
<220> FEATURE:
<223> OTHER INFORMATION: synthetic peptide fragment glycosylation site

<400> SEQUENCE: 2

Cys Asn Ile Ser
1

<210> SEQ ID NO 3
<211> LENGTH: 4
<212> TYPE: PRT
<213> ORGANISM: Artificial Sequence
<220> FEATURE:
<223> OTHER INFORMATION: synthetic peptide fragment glycosylation site

<400> SEQUENCE: 3

Phe Asn Leu Thr
1

<210> SEQ ID NO 4
<211> LENGTH: 4
<212> TYPE: PRT
<213> ORGANISM: Artificial Sequence
<220> FEATURE:
<223> OTHER INFORMATION: synthetic trypsin peptide fragment

<400> SEQUENCE: 4

Asn Leu Thr Lys
1

<210> SEQ ID NO 5
<211> LENGTH: 4
<212> TYPE: PRT
<213> ORGANISM: Artificial Sequence
<220> FEATURE:
<223> OTHER INFORMATION: synthetic trypsin peptide fragment

<400> SEQUENCE: 5

Met Met Ser Arg
1

<210> SEQ ID NO 6
<211> LENGTH: 7
<212> TYPE: PRT
<213> ORGANISM: Artificial Sequence
<220> FEATURE:
<223> OTHER INFORMATION: synthetic trypsin peptide fragment

<400> SEQUENCE: 6

```
Tyr Cys Asn Ile Ser Gln Lys
1               5

<210> SEQ ID NO 7
<211> LENGTH: 17
<212> TYPE: PRT
<213> ORGANISM: Artificial Sequence
<220> FEATURE:
<223> OTHER INFORMATION: glycopeptide fragment
<220> FEATURE:
<221> NAME/KEY: CARBOHYD
<222> LOCATION: (3)..(3)
<223> OTHER INFORMATION: Glycan site 1
<220> FEATURE:
<221> NAME/KEY: CARBOHYD
<222> LOCATION: (13)..(13)
<223> OTHER INFORMATION: Glycan site 2

<400> SEQUENCE: 7

Tyr Cys Asn Ile Ser Gln Lys Met Met Ser Arg Asn Leu Thr Lys Asp
1               5                   10                  15

Arg

<210> SEQ ID NO 8
<211> LENGTH: 150
<212> TYPE: PRT
<213> ORGANISM: Artificial Sequence
<220> FEATURE:
<223> OTHER INFORMATION: synthetic ovalbumin glycoprotein
<220> FEATURE:
<221> NAME/KEY: CARBOHYD
<222> LOCATION: (65)..(65)
<223> OTHER INFORMATION: glycosylation site

<400> SEQUENCE: 8

Met Ala Leu Lys Ser Leu Val Leu Leu Ser Leu Val Leu Val Leu Leu
1               5                   10                  15

Leu Leu Val Arg Val Gln Pro Ser Leu Gly Lys Glu Thr Ala Ala Ala
                20                  25                  30

Lys Phe Glu Arg Gln His Met Asp Ser Ser Thr Ser Ala Ala Ser Ser
            35                  40                  45

Ser Asn Tyr Cys Asn Gln Met Met Lys Ser Arg Asn Leu Thr Lys Asp
        50                  55                  60

Arg Cys Lys Pro Val Asn Thr Phe Val His Glu Ser Leu Ala Asp Val
65                  70                  75                  80

Gln Ala Val Cys Ser Gln Lys Asn Val Ala Cys Lys Asn Gly Gln Thr
                85                  90                  95

Asn Cys Tyr Gln Ser Tyr Ser Thr Met Ser Ile Thr Asp Cys Arg Glu
            100                 105                 110

Thr Gly Ser Ser Lys Tyr Pro Asn Cys Ala Tyr Lys Thr Thr Gln Ala
        115                 120                 125

Asn Lys His Ile Ile Val Ala Cys Glu Gly Asn Pro Tyr Val Pro Val
    130                 135                 140

His Phe Asp Ala Ser Val
145                 150

<210> SEQ ID NO 9
<211> LENGTH: 4
<212> TYPE: PRT
<213> ORGANISM: Artificial Sequence
<220> FEATURE:
<223> OTHER INFORMATION: synthetic peptide glycosylation site

<400> SEQUENCE: 9
```

```
Ser Asn Leu Thr
1

<210> SEQ ID NO 10
<211> LENGTH: 12
<212> TYPE: PRT
<213> ORGANISM: Artificial Sequence
<220> FEATURE:
<223> OTHER INFORMATION: synthetic glycopeptide

<400> SEQUENCE: 10

Lys Leu Glu Glu Gln Arg Pro Glu Arg Val Lys Gly
1               5                   10
```

METHODS AND PRODUCTS RELATED TO THE IMPROVED ANALYSIS OF CARBOHYDRATES

RELATED APPLICATIONS

This application is a Divisional of U.S. patent application Ser. No. 11/107,982, filed Apr. 15, 2005, which claims priority under 35 U.S.C. §119 from U.S. provisional application Ser. No. 60/562,874, filed Apr. 15, 2004, the entire contents of each of which is herein incorporated by reference.

GOVERNMENT SUPPORT

Aspects of the invention may have been made using funding from National Institutes of Health Grant number GM 57073. Accordingly, the Government may have rights in the invention.

FIELD OF THE INVENTION

The invention relates to the improved analysis of carbohydrates. In particular, the invention relates to the analysis of carbohydrates, such as N-glycans and O-glycans found on proteins and lipids. The invention also relates to the analysis of glycoconjugates, such as glycoproteins, glycolipids and proteoglycans. Methods for the study of glycosylation patterns on cells, tissues and in body fluid, such as serum, are also provided. Information regarding the glycosylation patterns on cells can be used in diagnostic and treatment methods as well as for facilitating the study of the effects of glycosylation/altered glycosylation on diseases, protein or lipid function and function of medical treatments. Information regarding the glycosylation of glycoconjugates can also be used in the quality control analysis of glycoconjugate production and/or therapeutics.

BACKGROUND OF THE INVENTION

Asparagine-linked glycosylation (N-glycosylation) is the most common co-translational modification found in eukaryotic proteins. As proteins are synthesized by the ribosome, the polypeptide enters the endoplasmic reticulum, where oligosaccharyl transferase (OT) attaches a branched carbohydrate (N-glycan) to the side chain of certain asparagine residues [Hirschberg, C. B., Snider, M. D. (1987) Topography of glycosylation in the rough endoplasmic reticulum and Golgi apparatus. *Annu Rev Biochem* 56, 63-87.] This process requires an Asn-X-Ser/Thr consensus sequence in the peptide substrate, where X is any amino acid except proline [Bause, E. (1983) Structural requirements of N-glycosylation of proteins. Studies with proline peptides as conformational probes. *Biochem J* 209, 331-6; Marshall, R. D. (1972) Glycoproteins. *Annu Rev Biochem* 41, 673-702.] After the attachment of the glycans, the carbohydrate moiety is extensively modified by a complex array of glycosidases and glycosyl transferases in the ER and golgi apparatus. The attached N-glycans are very important in protein folding, as well as directing the protein to the appropriate location within the cell [Dwek, R. A. (1996) Glycobiology: Toward Understanding the Function of Sugars. *Chem. Rev* 96, 683-720; O'Connor, S. E., Imperiali, B. (1996) Modulation of protein structure and function by asparagine-linked glycosylation. *Chem Biol* 3, 803-12.] Outside the cell, the sugars aid in protein-protein interactions, often modulating the activity of the protein to which they are attached. Depending on the glycan composition, they can also protect against or facilitate protein degradation in circulation, as well as target the protein to a specific organ [Crocker, P. R., Varki, A. (2001) Siglecs in the immune system. *Immunology* 103, 137-45; Helenius, A., Aebi, M. (2001) Intracellular functions of N-linked glycans. *Science* 291, 2364-9; Imperiali, B., O'Connor, S. E. (1999) Effect of N-linked glycosylation on glycopeptide and glycoprotein structure. *Curr Opin Chem Biol* 3, 643-9.]

N-glycans also have an essential role in normal biology, as evidenced by the high lethality in cases of defective glycosylation. In mouse knockout models, disrupting even one of the biosynthetic enzymes can lead to enormous multisystemic disorders, and several result in embryonic lethality [Furukawa, K., Takamiya, K., Okada, M., Inoue, M., Fukumoto, S. (2001) Novel functions of complex carbohydrates elucidated by the mutant mice of glycosyltransferase genes. *Biochim Biophys Acta* 1525, 1-12.] There are currently six recognized human congenital disorders of glycosylation (CDGs), all resulting in patients with multiple organ abnormalities, developmental delay and immune problems, among others [Jaeken, J., Matthijs, G. (2001) Congenital disorders of glycosylation. *Annu Rev Genomics Hum Genet.* 2, 129-51; Freeze, H. H., Aebi, M. (1999) Molecular basis of carbohydrate-deficient glycoprotein syndromes type I with normal phosphomannomutase activity. *Biochim Biophys Acta* 1455, 167-78; Carchon, H., Van Schaftingen, E., Matthijs, G., Jaeken, J. (1999) Carbohydrate-deficient glycoprotein syndrome type IA (phosphomannomutase-deficiency). *Biochim Biophys Acta* 1455, 155-65.] In fact, the immune system is one of the most commonly studied systems where N-glycans have been shown to play an important physiological role. For example, specific carbohydrate structures are recognized by selectins, a family of proteins expressed on endothelial cells or lymphocytes that can trigger the immune system upon activation [Powell, L. D., Sgroi, D., Sjoberg, E. R., Stamenkovic, I., Varki, A. (1993) Natural ligands of the B cell adhesion molecule CD22 beta carry N-linked oligosaccharides with alpha-2,6-linked sialic acids that are required for recognition. *J Biol Chem* 268, 7019-27; Sgroi, D., Varki, A., Braesch-Andersen, S., Stamenkovic, I. (1993) CD22, a B cell-specific immunoglobulin superfamily member, is a sialic acid-binding lectin. *J Biol Chem* 268, 7011-8.] The same class of structures that are necessary for proper immune function can also provide a binding site for certain viruses, bacteria or tumor cells in the body [Karlsson, K. A. (1998) Meaning and therapeutic potential of microbial recognition of host glycoconjugates. *Mol Microbiol* 29, 1-11; Pritchett, T. J., Brossmer, R., Rose, U., Paulson, J. C. (1987) Recognition of monovalent sialosides by influenza virus H3 hemagglutinin. *Virology* 160, 502-6.]

Viral infection is mediated by the interaction of viral proteins with N-glycans on the cell surfaces of the host [Van Eijk, M., White, M. R., Batenburg, J. J., Vaandrager, A. B., Van Golde, L. M., Haagsman, H. P., Hartshorn, K. L. (2003) Interactions of Influenza A virus with Sialic Acids present on Porcine Surfactant Protein D. *Am J Respir Cell Mol. Biol.*] Despite the increasing evidence associating glycans to different pathogenic conditions, in multiple instances it is unclear whether changes in N-glycan structure are a cause or a symptom of the disorder. In cystic fibrosis, increased antennary fucosylation ($\alpha$1-3 linked to GlcNAc) is observed on surface membrane glycoproteins of airway epithelial cells [Glick, M. C., Kothari, V. A., Liu, A., Stoykova, L. I., Scanlin, T. F. (2001) Activity of fucosyltransferases and altered glycosylation in cystic fibrosis airway epithelial cells. *Biochimie* 83, 743-7; Scanlin, T. F., Glick, M. C. (2000) Terminal glycosylation and disease: influence on cancer and cystic fibrosis. *Glycoconj J* 17, 617-26.]

There have also been many reports of alterations in N-glycan composition on cancer cell proteins. For example, there are indications that prostate cancer cells produce prostate specific antigen (PSA) with more glycan branching than non-cancer cells [Peracaula, R., Tabares, G., Royle, L., Harvey, D. J., Dwek, R. A., Rudd, P. M., de Llorens, R. (2003) Altered glycosylation pattern allows the distinction between prostate-specific antigen. (PSA) from normal and tumor origins. *Glycobiology* 13, 457-70; Belanger, A., van Halbeek, H., Graves, H. C., Grandbois, K., Stamey, T. A., Huang, L., Poppe, I., Labrie, F. (1995) Molecular mass and carbohydrate structure of prostate specific antigen: studies for establishment of an international PSA standard. *Prostate* 27, 187-97; Prakash, S., Robbins, P. W. (2000) Glycotyping of prostate specific antigen. Glycobiology 10, 173-6.] Melanoma and bladder cancer cells produce proteins with highly branched glycans due to an overexpression of the biosynthetic enzyme β1,6-N-acetylglucosaminyltransferase V (GnT-V) [Chakraborty, A. K., Pawelek, J., Ikeda, Y., Miyoshi, E., Kolesnikova, N., Funasaka, Y., Ichihashi, M., Taniguchi, N. (2001) Fusion hybrids with macrophage and melanoma cells up-regulate N-acetylglucosaminyltransferase V, beta1-6 branching, and metastasis. *Cell Growth Differ* 12, 623-30; Przybylo, M., Hoja-Lukowicz, D., Litynska, A., Laidler, P. (2002) Different glycosylation of cadherins from human bladder non-malignant and cancer cell lines. *Cancer Cell Int* 2, 6.] Increased sialylation and additional branching have also been observed in cells from human breast and colon neoplasia [Lin, S., Kemmner, W., Grigull, S., Schlag, P. M. (2002) Cell surface alpha 2,6 sialylation affects adhesion of breast carcinoma cells. *Exp Cell Res* 276, 101-10; Nemoto-Sasaki, Y., Mitsuki, M., Morimoto-Tomita, M., Maeda, A., Tsuiji, M., Irimura, T. (2001) Correlation between the sialylation of cell surface Thomsen-Friedenreich antigen and the metastatic potential of colon carcinoma cells in a mouse model. *Glycoconj J* 18, 895-906; Dennis, J. W., Granovsky, M., Warren, C. E. (1999) Glycoprotein glycosylation and cancer progression. *Biochim Biophys Acta* 1473, 21-34; Fernandes, B., Sagman, U., Auger, M., Demetrio, M., Dennis, J. W. (1991) Beta 1-6 branched oligosaccharides as a marker of tumor progression in human breast and colon neoplasia. *Cancer Res* 51, 718-23.]

SUMMARY OF THE INVENTION

This invention provides, in part, methods related to the analysis of carbohydrates. In particular, the invention relates to the analysis of carbohydrates, such as N-glycans and O-glycans found on proteins and lipids. The invention also relates to the analysis of glycoconjugates, such as glycoproteins, glycolipids and proteoglycans.

In an aspect of the invention, methods of analyzing a sample containing glycoconjugates are provided. The methods include (a) separating the carbohydrates (e.g., glycans) from the sample containing the glycoconjugates, (b) determining the glycosylation site and/or occupancy of the glycoconjugates, (c) analyzing the carbohydrates (e.g., glycans) for characterization and/or quantification, and (d) determining the glycoforms and/or glycan profile of the glycoconjugates in the sample with the results obtained from steps (b) and (c) with a computational approach. In certain embodiments, the methods also include determining the occupancy of each glycan at each glycosylation site.

In an embodiment of the invention, step (a) includes denaturing the glycoconjugates. In a second embodiment, glycoconjugates are denatured with a denaturing agent. In another embodiment, the denaturing agent is detergent, urea, guanidium hydrochloride or heat. In a further embodiment, the glycoconjugates are reduced following their denaturation. In yet another embodiment, the glycoconjugates are reduced with a reducing agent. The reducing agent in certain embodiments is DTT, β-mercaptoethanol or TCEP. In a further embodiment, the glycoconjugates are alkylated with an alkylating agent following their reduction. The alkylating agent in certain embodiments is iodoacetic acid or iodoacetamide.

In certain embodiments of the foregoing methods, the step of determining the glycosylation sites and/or glycosylation site occupancy includes analyzing the glycoconjugates, preferably with 2D-NMR. In one embodiment, the step of determining the glycosylation site and glycosylation site occupancy includes cleaving the peptide backbone of the glycoconjugates (and optionally analyzing the cleaved fragments), cleaving and labeling with a first label the glycoconjugates at their glycosylation sites of a first portion of the sample, cleaving the glycoconjugates at their glycosylation sites of a second portion of the sample, analyzing the first and second portions of the sample of glycoconjugates, and quantifying the results. The analysis of the first and second portions of the sample can be performed separately or mixed in any ratio.

In one embodiment, the glycoconjugates of the first portion are labeled with a label. Preferably the label is an isotope of C, N, H, S or O. More preferably, the label is $O^{18}$. In another embodiment, the glycoconjugates of the second portion are unlabeled. In a further embodiment, the glycoconjugates of the second portion are labeled. In yet another embodiment, the first and second portions of the sample of glycoconjugates are analyzed separately. In still another embodiment, the first and second portions of the sample of glycoconjugates are analyzed as a mixture. In another embodiment, the glycosylation site occupancy is quantified from ratios of the masses of cleaved glycoconjugates of the first and second portions of the sample.

In a further embodiment, the first and second portions of the sample are analyzed with a mass spectrometric method. Preferably, the mass spectrometric method is LC-MS, LC-MS/-MS, MALDI-MS, MALDI-TOF, TANDEM-MS or FTMS.

In still another embodiment, the step further includes generating a list of possible glycoconjugates and/or and peptides, e.g., using databases. In a second embodiment, the step further includes generating a list of possible glycans.

The step of analyzing the glycans includes, in certain embodiments, analyzing the glycans with a mass spectrometric method, an electrophoretic method, NMR, a chromatographic method or a combination thereof. In a further embodiment, the mass spectrometric method is LC-MS, LC-MS/MS, MALDI-MS, MALDI-TOF, TANDEM- MS or FTMS. Preferably, the mass spectrometric method is a quantitative MALDI-MS or MALDI-FTMS using optimized conditions. In yet another embodiment, the MALDI-MS is MALDI-MS optimized with a mixture of 6-aza-2-thiothymine (ATT) and NAFION® (a perfluorinated ion-exchange compound) coating. In still another embodiment, the electrophoretic method is CE-LIF.

In additional embodiments, the step further includes contacting the glycans with one or more glycan-degrading enzymes. In another embodiment, the one or more glycan-degrading enzymes is sialidase, galactosidase, mannosidase, N-acetylglucosaminidase or a combination thereof. In yet another embodiment, the step of analyzing the glycans includes quantifying the glycans using calibration curves of known glycan standards. In still another embodiment, the method further includes determining a peptide sequence of the glycoconjugate.

In further embodiments of the foregoing methods, low abundance species are detected due to the low detection limits, which preferably extend to lower than about 5 fmol. Low abundance species include, but are not limited to, fucoses, sialic acids, galactoses, mannoses and sulfate groups.

According to another aspect of the invention, methods of analyzing a sample containing glycoconjugates are provided. The methods include separating glycans from the sample containing the glycoconjugates, determining the glycosylation sites and glycosylation site occupancy of the glycoconjugates, and analyzing the glycans to characterize and/or quantify the glycans. Determining the glycosylation sites and glycosylation site occupancy includes cleaving and labeling with a first label the glycoconjugates of a first portion of the sample at their glycosylation sites, cleaving the glycoconjugates of a second portion of the sample at their glycosylation sites, analyzing the first and second portions of the sample of glycoconjugates, and quantifying the results.

In an embodiment, the glycoconjugates of the first portion are labeled. In a second embodiment, the glycoconjugates of the second portion are unlabeled. In another embodiment, the glycoconjugates of the second portion are labeled. In yet another embodiment, the first and second portions of the sample of glycoconjugates are analyzed with a mass spectrometric method. Preferably, the mass spectrometric method is LC-MS, LC-MS/MS, MALDI-MS, MALDI-TOF, TANDEM-MS or FTMS.

In certain embodiments, determining the glycosylation sites and glycosylation site occupancy further includes generating a list of possible glycoconjugates. In other embodiments, the step of separating the glycans from the sample includes denaturing the glycoconjugates with a denaturing agent. Preferably, the glycoconjugates are reduced with a reducing agent following their denaturation. More preferably, the glycoconjugates are alkylated with an alkylating agent following their reduction.

In further embodiments, the step of analyzing the glycans includes analyzing the glycans with a mass spectrometric method, an electrophoretic method, NMR, a chromatographic method or a combination thereof. The mass spectrometric method preferably is LC-MS, LC-MS/MS, MALDI-MS, MALDI-TOF, TANDEM-MS or FTMS. The electrophoretic method preferably is CE-LIF. In still further embodiments, the step further includes contacting the glycans with one or more glycan-degrading enzymes. Preferably the one or more glycan-degrading enzymes is sialidase, galactosidase, mannosidase, N-acetylglucosaminidase or a combination thereof. In another embodiment, the method further includes determining a peptide sequence of the glycoconjugate.

According to still another aspect of the invention, methods of determining the glycosylation site occupancy of glycoconjugates in a sample are provided. The methods include cleaving and labeling with a first label the glycoconjugates at their glycosylation sites of a first portion of the sample, cleaving the glycoconjugates at their glycosylation sites of a second portion of the sample, analyzing the first and second portions of the sample of glycoconjugates, and quantifying the results. In an embodiment, the method further includes determining the possible fragments of the glycoconjugate.

In other embodiments, the glycoconjugates of the first portion are labeled with an isotope of C, N, H, S or O. Preferably the label is $O^{18}$. In a further embodiment, the glycoconjugates of the second portion are unlabeled. In another embodiment, the glycoconjugates of the second portion are labeled. In a further embodiment, the first and second portions of the sample of glycoconjugates are analyzed with a mass spectrometric method. In yet a further embodiment, the mass spectrometric method is LC-MS, LC-MS/MS, MALDI-MS, MALDI-TOF, TANDEM-MS or FTMS.

In further embodiments of the foregoing methods, low abundance species are detected due to the low detection limits, which preferably extend to lower than about 5 fmol. Low abundance species include, but are not limited to, fucoses, sialic acids, galactoses, mannoses and sulfate groups.

According to yet another aspect of the invention, methods of analyzing a sample containing glycans are provided. The methods include separating neutral from charged glycans, and analyzing the neutral and charged glycans separately to analyze the glycan. In preferred embodiments, the analysis of the glycans is performed with MALDI-MS.

In a further aspect of the invention, methods of analyzing a glycan are provided. The methods include analyzing the glycan in the presence of NAFION® (a perfluorinated ion-exchange compound) and 6-aza-2-thiothymine (ATT).

Certain embodiments of the foregoing methods are methods of analyzing the purity of a sample containing glycans. Other embodiments of the foregoing methods are methods of analyzing the glycans of a sample of a cell, a group of cells, a tissue or serum or other body fluid from a subject. Still other embodiments of the foregoing methods are high-throughput methods, in which more than one sample of glycoconjugates is analyzed. In some preferred embodiments, the more than one sample of glycoconjugates are in a 96-well plate. In other preferred embodiments, the more than one sample of glycoconjugates are on a membrane.

In other embodiments of the high-throughput methods, carbohydrate cleavage is performed using enzymes such as PNGase F, endoglycosydase H, or endoglycosydase F, or chemical methods such as hydrazinolisis or alkali borohydrate cleavage. Preferably, cleavage is performed in a high-throughput manner in 96-well plates or in solution. In certain other embodiments, purification is performed using solid phase extraction cartridges such as graphitized carbon columns and C-18 columns. Preferably, purification is performed in a high-throughput manner in 96-well plates. All of the foregoing steps, particularly the step of separation, can be performed with the use of robotics.

According to another aspect of the invention, methods of generating a glycoconjugate, (preferably glycopeptide) library are provided. The methods include cleaving the backbone of the glycoconjugate (preferably the peptides of the glycopeptides) in a sample and labeling the fragments generated with a first labeling agent, and cleaving the glycans in the sample and labeling the fragments generated in the sample with a second labeling agent. Preferably the library represents all possible glycoform fragments of the sample containing the glycoconjugates. The glycoconjugates preferably are glycopeptides, glycolipids or proteoglycans.

In certain embodiments, the first and second labeling agent is the same labeling agent. In other embodiments, the labeling agent is an isotope of C, N, H, S or O, preferably $O^{18}$. In still other embodiments, the method further includes characterizing the fragments generated from the cleavage of the glycopeptides. In some embodiments, the characterization is performed with LC-MS, LC-MS/MS, MALDI-MS, MALDI-TOF, TANDEM-MS or FTMS. In further embodiments, the characterizing includes characterizing the glycosylation sites, characterizing the peptides of the glycopeptides and/or characterizing the glycans.

According to a further aspect of the invention, a library of glycopeptides generated with the foregoing methods is generated.

The library can be used as an internal standard to analyze new batches of glycoconjugates by direct comparison to each labeled standard from the library. For example, the backbones of new batches of glycoconjugates can be cleaved and mixed with the labeled fragments from the library to characterize all the glycoforms present in the new batch from the ratios of labeled and unlabeled fragments. Thus, in a further aspect of the invention, methods of analyzing a sample of glycopeptides are provided. The methods include analyzing the glycopeptides, and comparing the analyzed glycopeptides with the foregoing library of glycopeptides of the foregoing embodiments. In certain embodiments, it is preferred that comparative characterization is performed using LC-MS, LC-MS/MS, MALDI-MS, MALDI-TOF, TANDEM-MS or FTMS.

According to another aspect of the invention, methods of generating a list of glycoconjugate properties are provided. The methods include measuring two or more properties of the glycoconjugate, and recording a value for the two or more properties of the glycoconjugate to generate a list, wherein the value of the two or more properties is recorded in a computer-generated data structure. In some embodiments, one of the two or more properties of the glycoconjugates is the number of one or more types of monosaccharides of the glycoconjugate. In other embodiments, one of the two or more properties of the glycoconjugates is the total mass of the glycans of the glycoconjugate. In still other embodiments, the glycoconjugate is a glycoprotein or proteoglycan, and one of the two or more properties of the glycoconjugate is the mass of the peptide of the glycoconjugate. In yet other embodiments, the glycoconjugate is a glycolipid, and one of the two or more properties of the glycoconjugate is the mass of the lipid of the glycoconjugate. In further embodiments, one of the two or more properties of the glycoconjugate is the mass of the glycoconjugate. In other embodiments, one of the two or more properties of the glycoconjugate is the mass of permethylated glycans.

In a further aspect of the invention, a database, tangibly embodied in a computer-readable medium, for storing information descriptive of one or more glycoconjugates is provided. The database includes one or more data units corresponding to the one or more glycoconjugates, each of the data units including an identifier that includes two or more fields, each field for storing a value corresponding to one or more properties of the glycoconjugates.

According to still another aspect of the invention, methods of analyzing the total glycome of a sample of body fluid, cells or tissues are provided. The methods include (a) analyzing all the glycans of the sample, and (b) determining a profile of the glycans of the sample. In some embodiments, the sample is optionally fractionated and/or the glycans are separated from the glycoconjugates. The cleavage, fractionation, purification and/or separation steps described elsewhere herein are optionally included in the methods.

In certain embodiments, the method further includes performing a pattern analysis on the results from (a) using computational tools. The pattern can be described as (but is not limited to) relative amounts of the components of the pattern, absolute amounts of the components of the pattern, ratios between the components of the pattern, combinations of different components of the pattern, presence or absence of any of the components of the pattern or combination of the above. In certain embodiments, the identification of the glycome pattern and the pattern analysis can be performed using computational methods. Preferably this includes an iterative process, which optionally includes one of more of the following: incorporation of all experimental data sets from the glycome analysis and other glycan characterization, generation of theoretical glycan structures, incorporation of glycan composition, incorporation of structure and property information from databases, incorporation of glycan biosynthetic pathway information, incorporation of patient (or sample origin) information such as patient history and demographics, extract features from the experimental data sets, generation of data sets with specific features, submitting the combined information to data mining analysis, establishing relationship rules and validating the patterns.

In other embodiments, step (a) includes quantifying the glycans using calibration curves of known glycan standards. In another embodiment, the method further includes recording the pattern in a computer-generated data structure. In yet another embodiment, the method is a method for diagnostic or prognostic purposes. In a further embodiment, the method is a method for assessing the purity of the sample. In yet another embodiment, the sample is a sample of serum, plasma, blood, urine, saliva, sputum, tears, CSF, seminal fluid, feces, tissues or cells.

According to another aspect of the invention, methods of analysis are provided. The methods include (a) analyzing all of the glycans of a sample of body fluid, cells and/or tissues and (b) comparing the results from (a) with a known pattern. In an embodiment, the sample is a sample of serum, plasma, blood, urine, saliva, sputum, tears, CSF, seminal fluid, feces, tissues or cells.

In some embodiments, the methods are methods of diagnosis and the pattern is associated with a diseased state. In one preferred embodiment, the pattern associated with a diseased state is a pattern associated with cancer, such as prostate cancer, melanoma, bladder cancer, breast cancer, lymphoma, ovarian cancer, lung cancer, colorectal cancer or head and neck cancer. In other preferred embodiments, the pattern associated with a diseased state is a pattern associated with an immunological disorder; a neurodegenerative disease, such as a transmissible spongiform encephalopathy, Alzheimer's disease or neuropathy; inflammation; rheumatoid arthritis; cystic fibrosis; or an infection, preferably viral or bacterial infection. In other embodiments, the method is a method of monitoring prognosis and the known pattern is associated with the prognosis of a disease. In yet another embodiment, the method is a method of monitoring drug treatment and the known pattern is associated with the drug treatment. In particular, the methods (e.g., analysis of glycome profiles) are used for the selection of population-oriented drug treatments and/or in prospective studies for selection of dosing, for activity monitoring and/or for determining efficacy endpoints.

In another aspect of the invention, methods of determining the purity of a sample are provided. The methods include (a) analyzing total glycans of the sample, (b) identifying the glycan pattern of the sample, and (c) comparing the pattern with a known pattern to assess the purity of the sample. Similar methods are provided in which glycoconjugates in sample are analyzed.

In an aspect of the invention, a method of generating the complete glycan pattern of a body fluid, cells and/or tissue is provided. The method includes, (a) analyzing the glycans in a sample of the body fluid, cells and/or tissue, and (b) identifying the complete glycan pattern of the sample. In an embodiment, neutral, charged, N-linked and O-linked glycans are included in the pattern. In other embodiments, glycosaminoglycans and glycolipids are included in the pattern. In a second embodiment, the sample is a sample of serum, plasma, blood, urine, saliva, sputum, tears, CSF, seminal fluid, feces, tissues or cells.

In a further aspect of the invention, methods of analyzing the total glycome of a sample are provided. The methods include determining the glycosylation site and glycosylation site occupancy of all glycoconjugates in the sample, characterizing components of the glycoconjugates and all glycans of the glycome in the sample, and matching specific glycans to glycoconjugates with a computational method.

According to another aspect of the invention, methods of analyzing a sample of glycoconjugates are provided. The methods include analyzing the glycans of the sample with an analytical method, and determining the glycoforms of the sample with a computational method. In certain embodiments of the foregoing methods, the methods include generating constraints from the experimental analysis and solving them.

A further method for matching each carbohydrate in the glycome to its glycoconjugate includes characterization of glycosylation sites and occupancy of all glycoconjugates from body fluids, determination of possible glycans at each site by comparing unlabeled, glycoconjugate fragments to labeled, deglycosylated fragments, characterization of the entire glycome from body fluids, and combination of the different datasets into the iterative computational analysis to match the glycans to the glycoconjugates.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE FIGURES

FIG. 7 provides results from a study of N-glycans from antibody samples. FIG. 7C represents the results for DO controlled, pH uncontrolled, and NaOH in the media, while FIG. 7D represents the results with NaHCO$_3$ in the media instead of NaOH. The results shown in FIG. 7E are for DO uncontrolled with pH=7.

DETAILED DESCRIPTION

Figure 1:
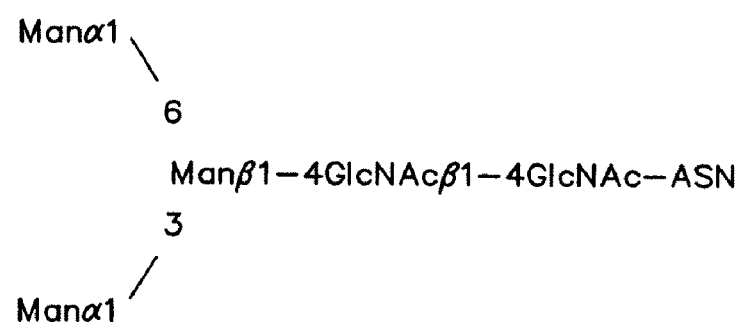
FIG. 1 shows the conserved N-glycan pentasaccharide core.

It has been recognized that carbohydrates play a significant role in a variety of biological and pathological processes. However, information regarding which carbohydrates are important and how they affect biological functions is limited. Therefore, additional methods for analyzing carbohydrates are desirable. Some of the methods provided herein provide better limits of detection of glycans and/or glycoconjugates that, in some examples, can extend to lower than 5 fmol.

Methods are provided herein which are directed to improved methods of analyzing carbohydrates. As used herein, the term "carbohydrate" is intended to include any of a class of aldehyde or ketone derivatives of polyhydric alcohols. Therefore, carbohydrates include starches, celluloses, gums and saccharides. Although, for illustration, the term "saccharide" or "glycan" is used below, this is not intended to be limiting. It is intended that the methods provided herein can be directed to any carbohydrate, and the use of a specific carbohydrate is not meant to be limiting to that carbohydrate only.

As used herein, the term "saccharide" refers to a polymer comprising one or more monosaccharide groups. Saccharides, therefore, include mono-, di-, tri- and polysaccharides (or glycan). Glycans can be branched or branched. Glycans can be found covalently linked to non-saccharide moieties, such as lipids or proteins (as a glycoconjugate). These covalent conjugates include glycoproteins, glycopeptides, peptidoglycans, proteoglycans, glycolipids and lipopolysaccharides. The use of any one of these terms also is not intended to be limiting as the description is provided for illustrative purposes. In addition to the glycans being found as part of a glycoconjugate, the glycans can also be in free form (i.e., separate from and not associated with another moiety). The use of the term peptide is not intended to be limiting. The method provided herein are also intended to include proteins where "peptide" is recited.

The methods, therefore, provided can be used to analyze glycans that are found as part of a glyconjugate or are found in free form. The methods provided are also directed to the analysis of the total glycome of a sample. The sample can be of a cell, group of cells, tissue or serum. The "total glycome" refers to all of the glycans that can found in a sample. For instance, the glycans can be in free form or they can be part of one or more glycoconjugates in the sample. The total glycome, therefore, represents all of the glycans (in free form, as part of glycoconjugates or both) in the sample. Likewise the use of the phrase "a sample of glycans" or the like is intended to include a sample containing free glycans and/or glycans as part of glycoconjugates. The sample can be, for instance, a sample of body fluid. Samples of body fluid include serum, plasma, blood, urine, saliva, sputum, tears, CSF, seminal fluid, feces, etc. The sample, can also be, as an example, a sample of a cell, group of cells or tissue.

Figure 2A:
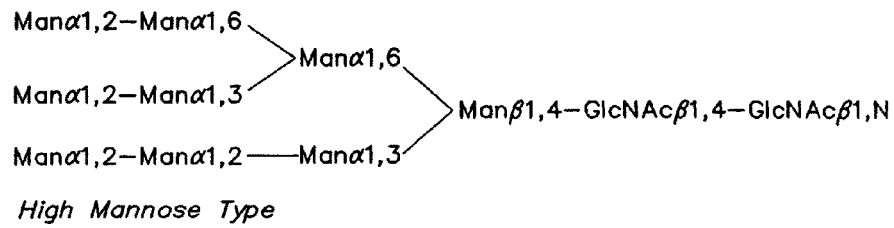
FIG. 2 illustrates classes of N-linked glycans. High-mannose structures contain up to 9 mannose residues (FIG. 2A). Complex type glycans are modified with hexosamines, galactoses, sialic acids and/or fucose, among other residues (FIG. 2B). Complex type chains can occur as mono-, bi-, tri-, and tetra-antennary structures. Also, the amount and type of sialylation differs. Hybrid structures contain characteristics of both high-mannose and complex types (FIG. 2C). Zone Name: B1,AMD FIG. 3 provides the detailed pathway of N-glycan biosynthesis (www.genome.ad.jp/kegg/pathway/map/map00510.html).
Figure 2B:
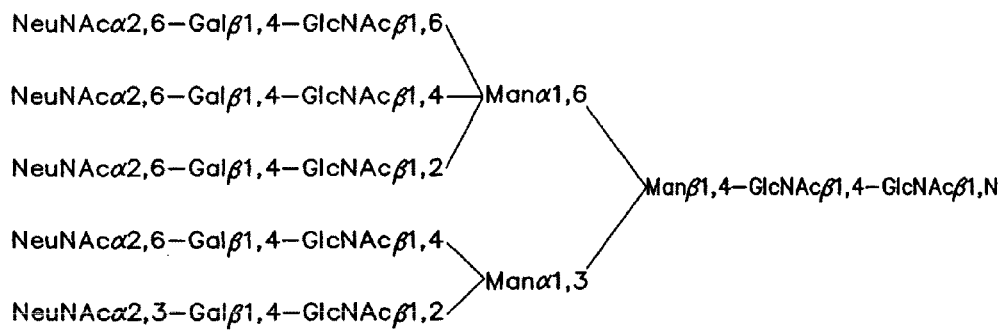
Figure 2C:
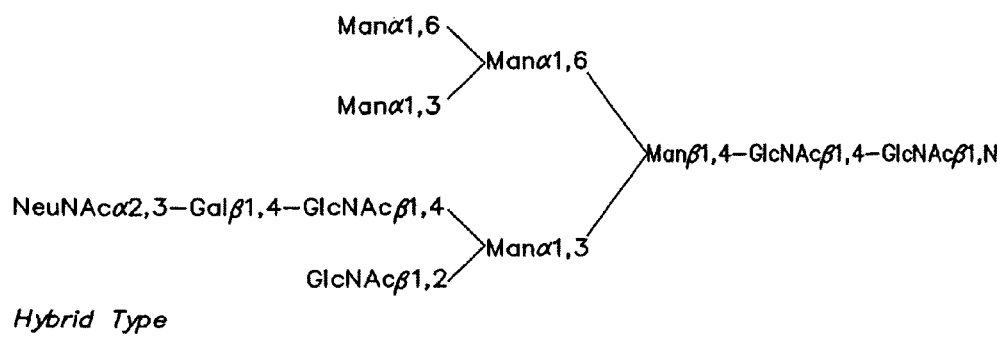
Figure 3A:
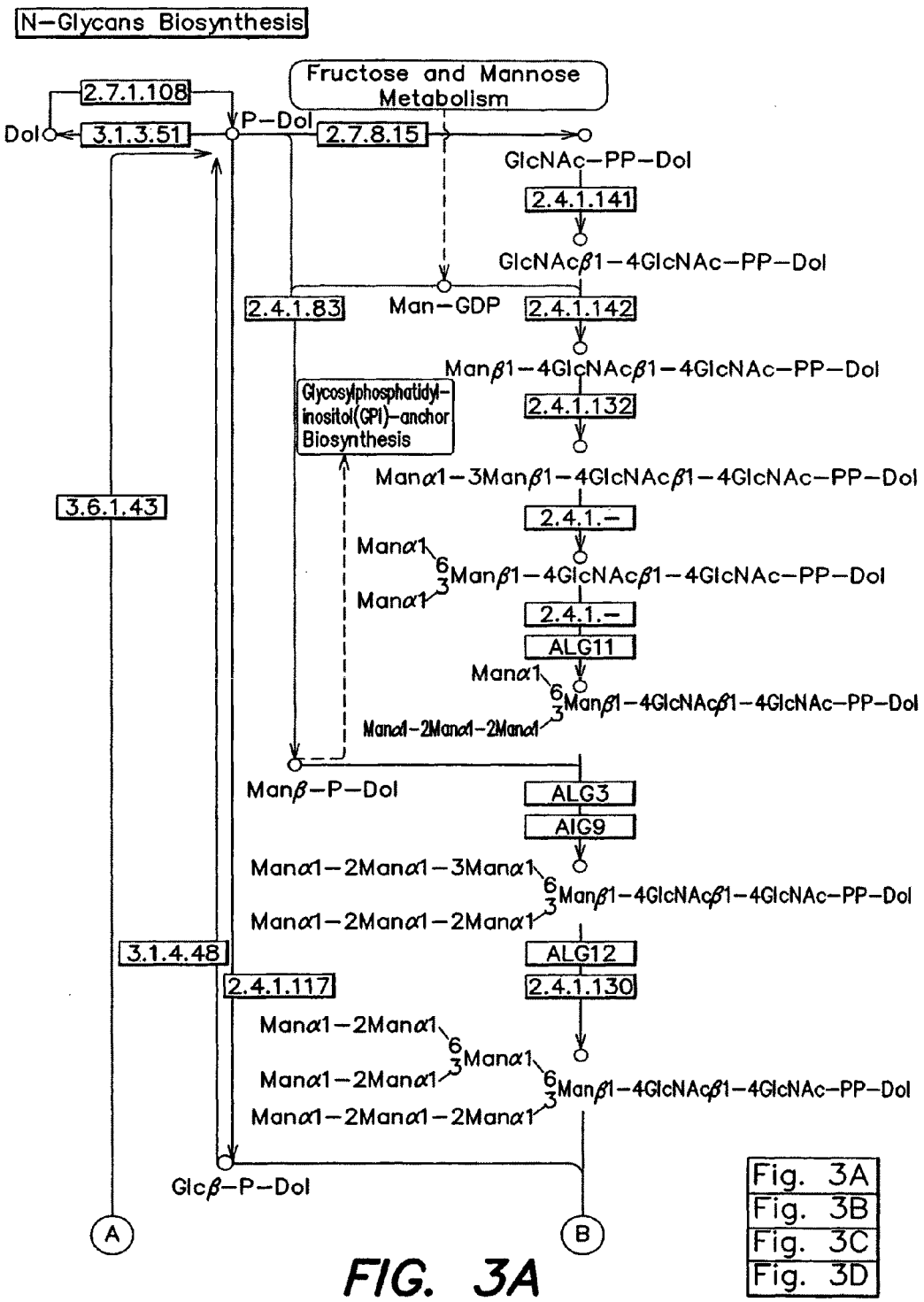
Figure 3B:
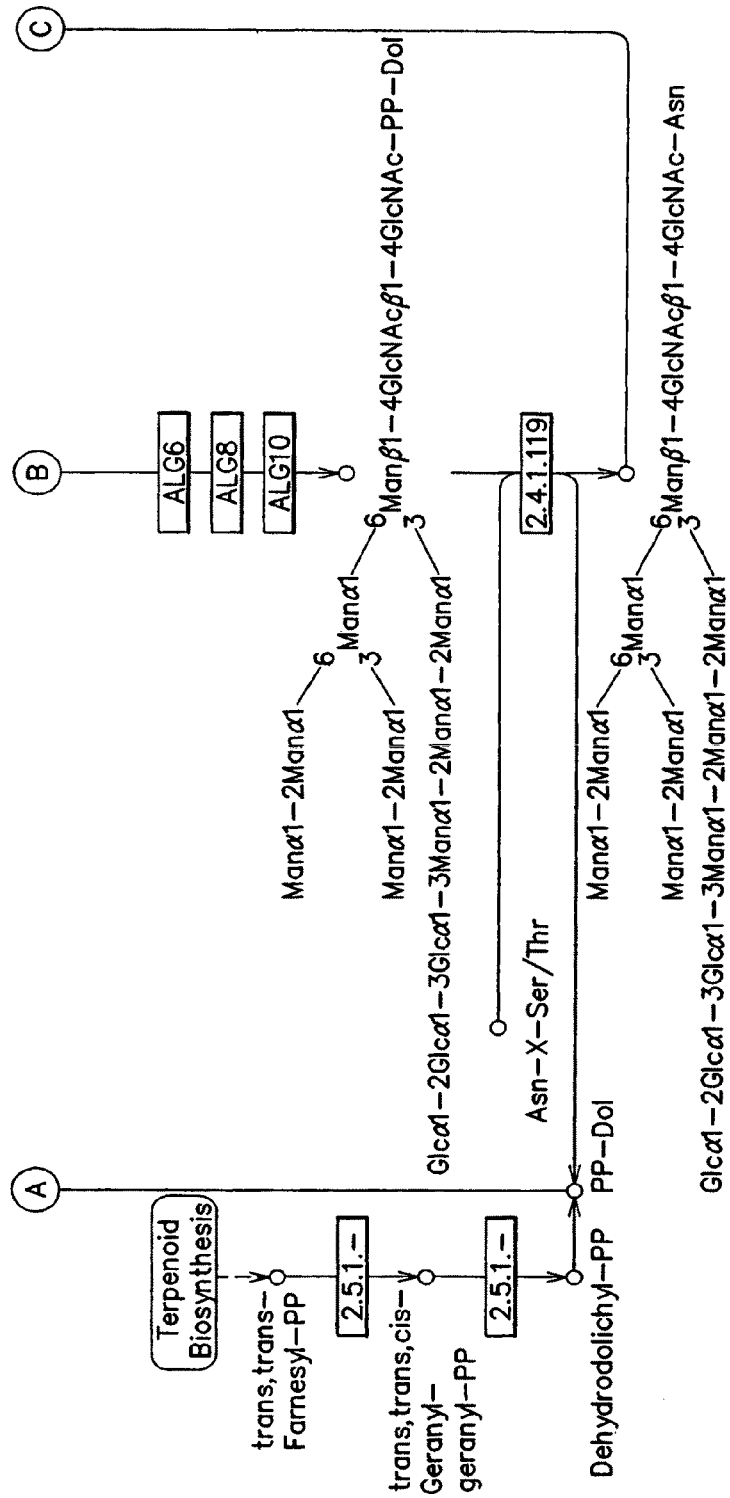
Figure 3C:
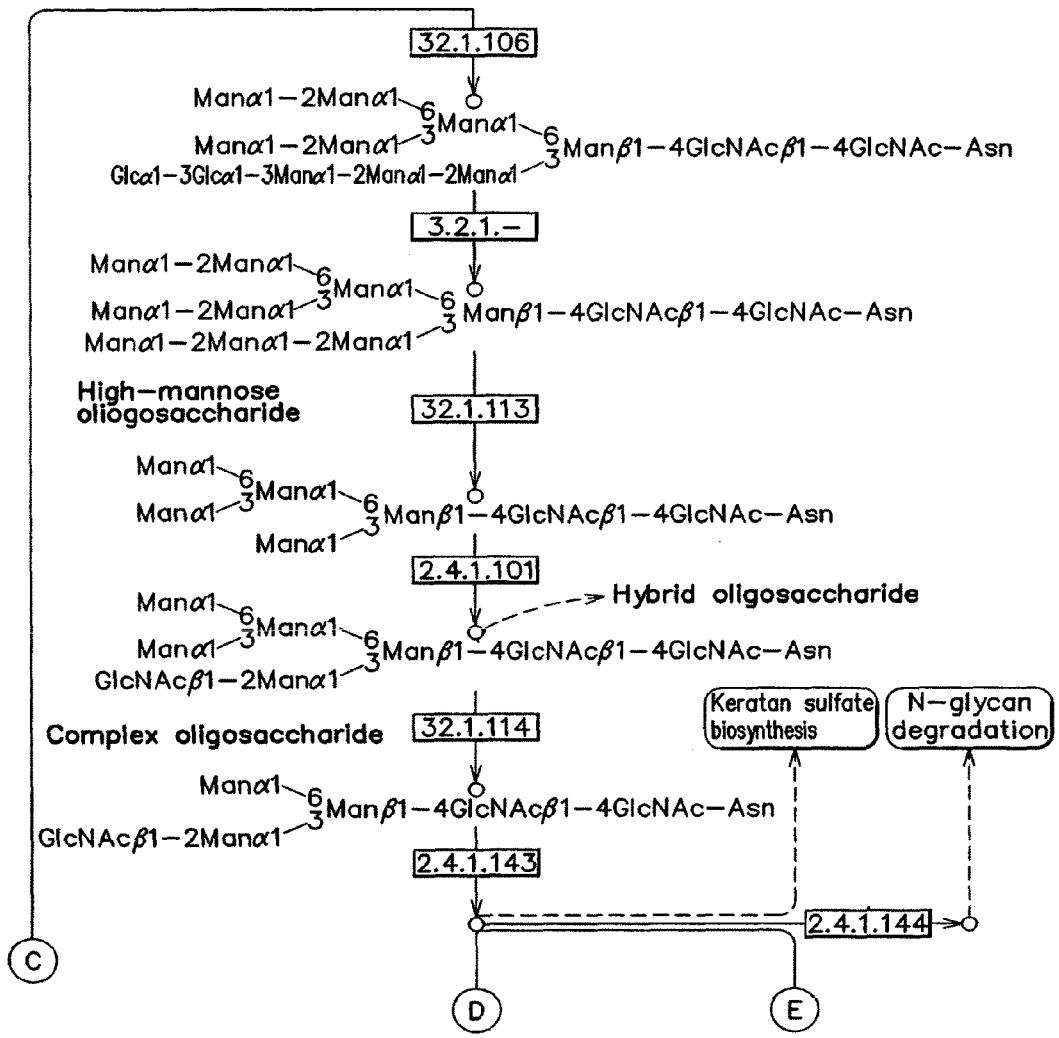
Figure 3D:
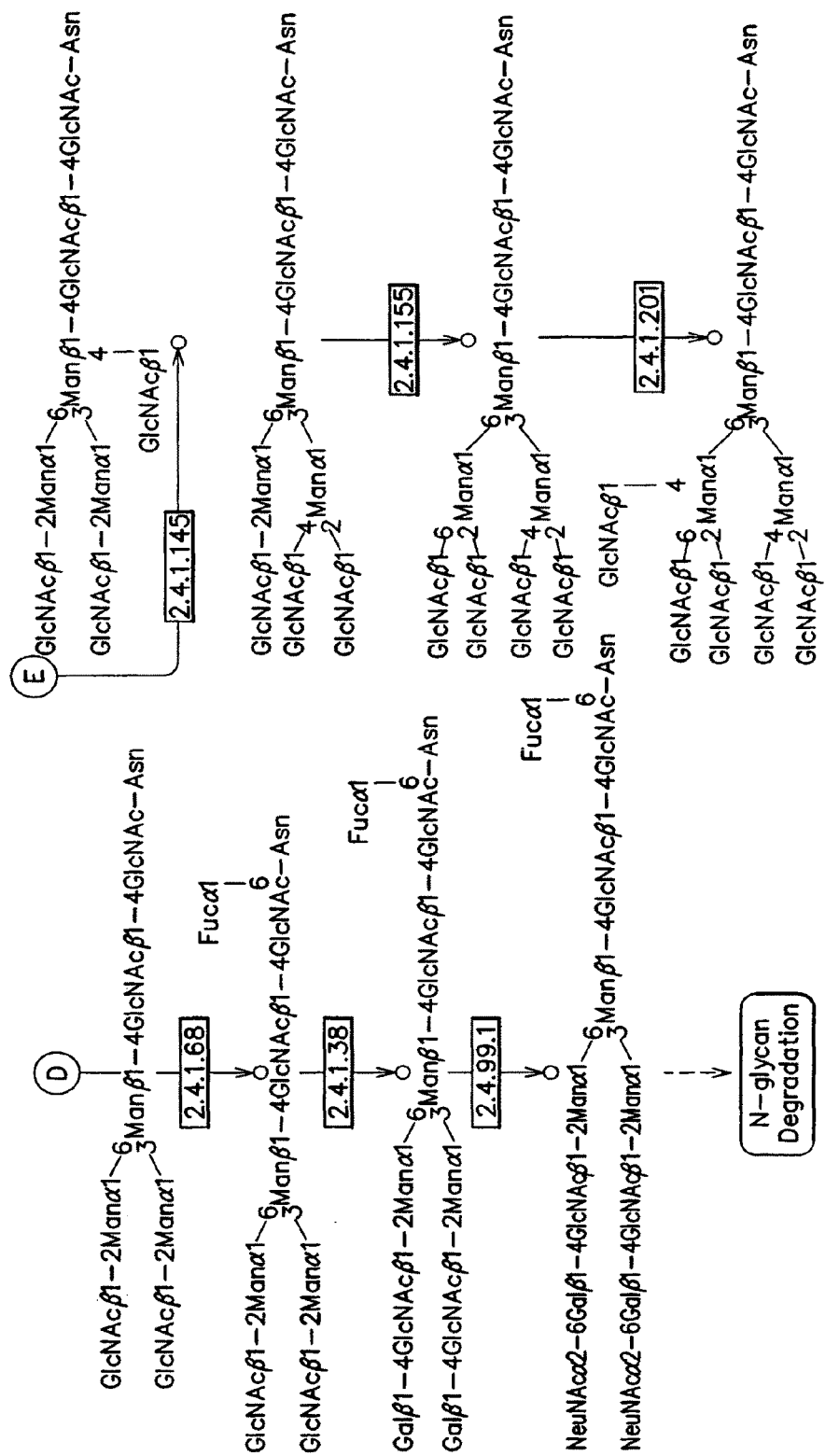
Figure 4:
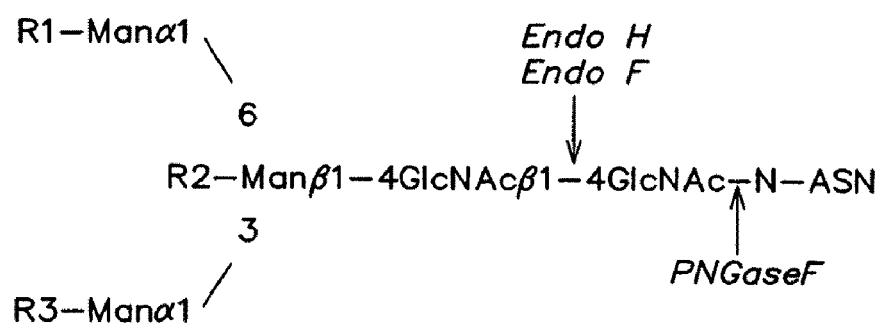
FIG. 4 shows the cleavage sites of EndoH, EndoF and PNGaseF. EndoH can only act on high mannose and hybrid structures, while EndoF is effective at cleaving all classes of N-glycans. PNGaseF also cleaves all mammalian N-glycan structures.
Figure 5A:
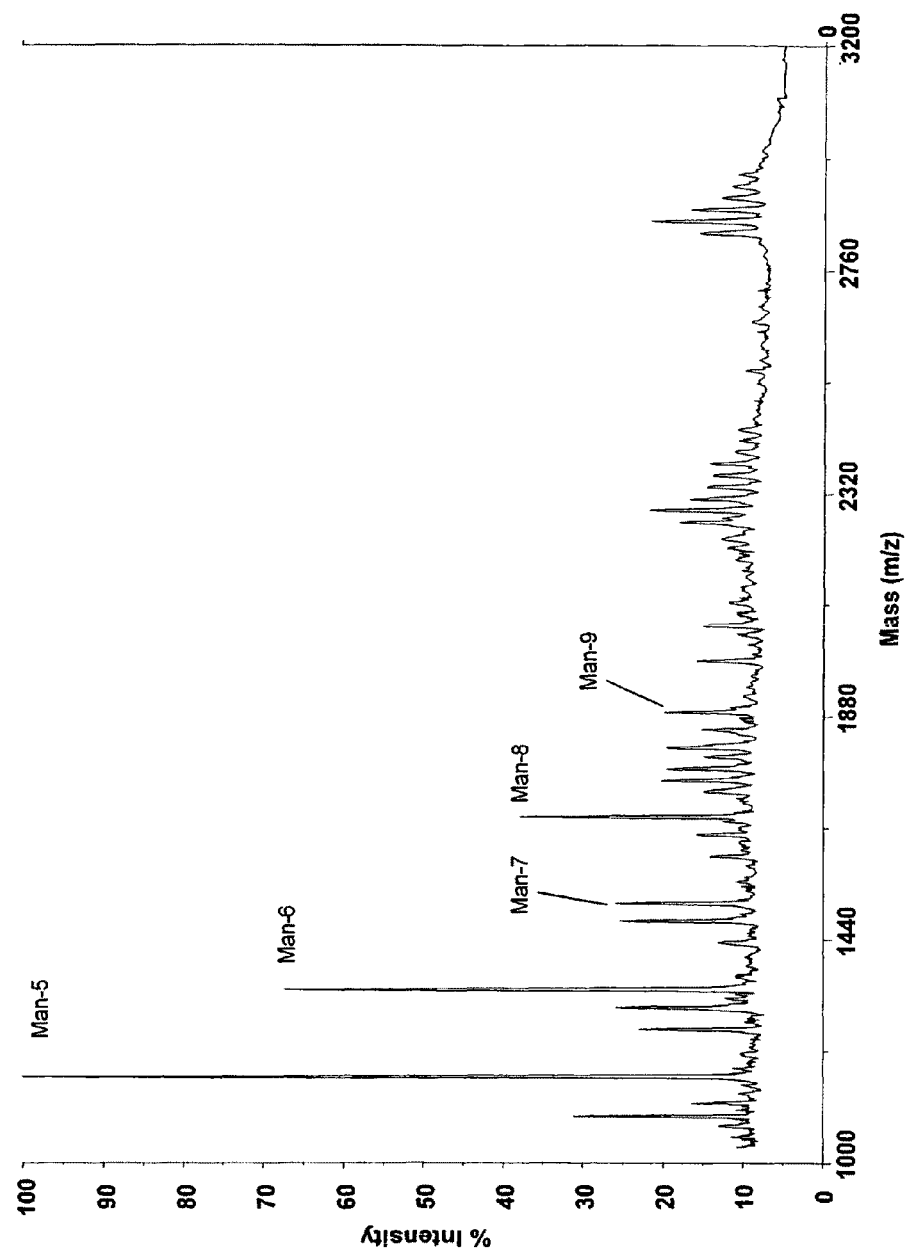
FIG. 5 provides the MALDI-MS spectra of N-glycans from RNaseB samples prepared by various methods. Glycans after GlycoClean S (Table 2, Sample 12), with the expected high mannose peaks and significant contamination of unknown identity (FIG. 5A). A small amount of sample (10 µg) was prepared using a 25 mg GlycoClean H column (Table 2, Sample 17), which showed only detergent peaks (FIG. 5B). A larger amount of protein (50 µg) was prepared (Table 2, Sample 18), yielding the expected glycan peaks but still containing detergent contamination (FIG. 5C). Using a 200 mg GlycoClean H column to purify N-glycans from 150 µg of RNaseB (Table 2, Sample 20), only the high mannose saccharides were observed (FIG. 5D).
Figure 5B:
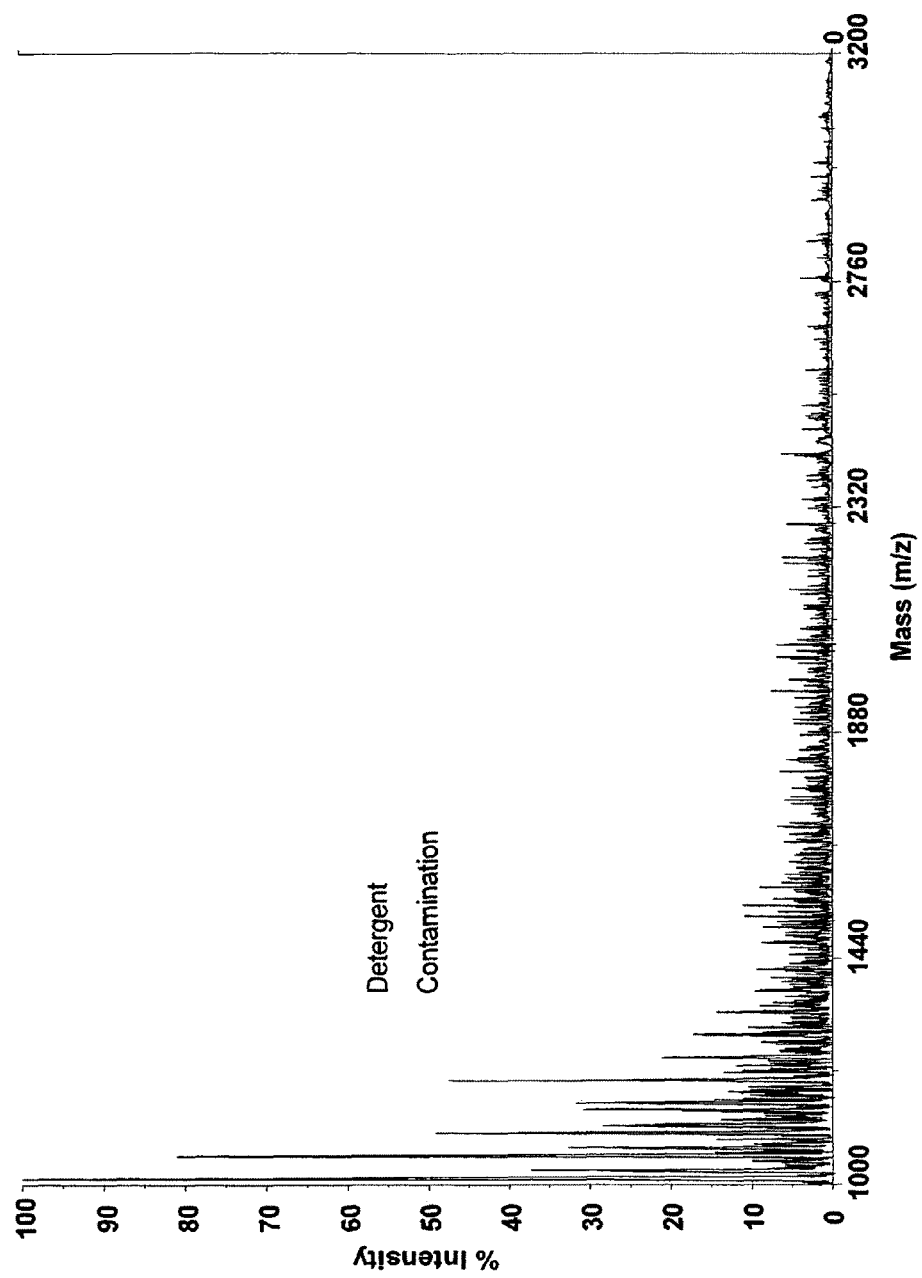
Figure 5C:
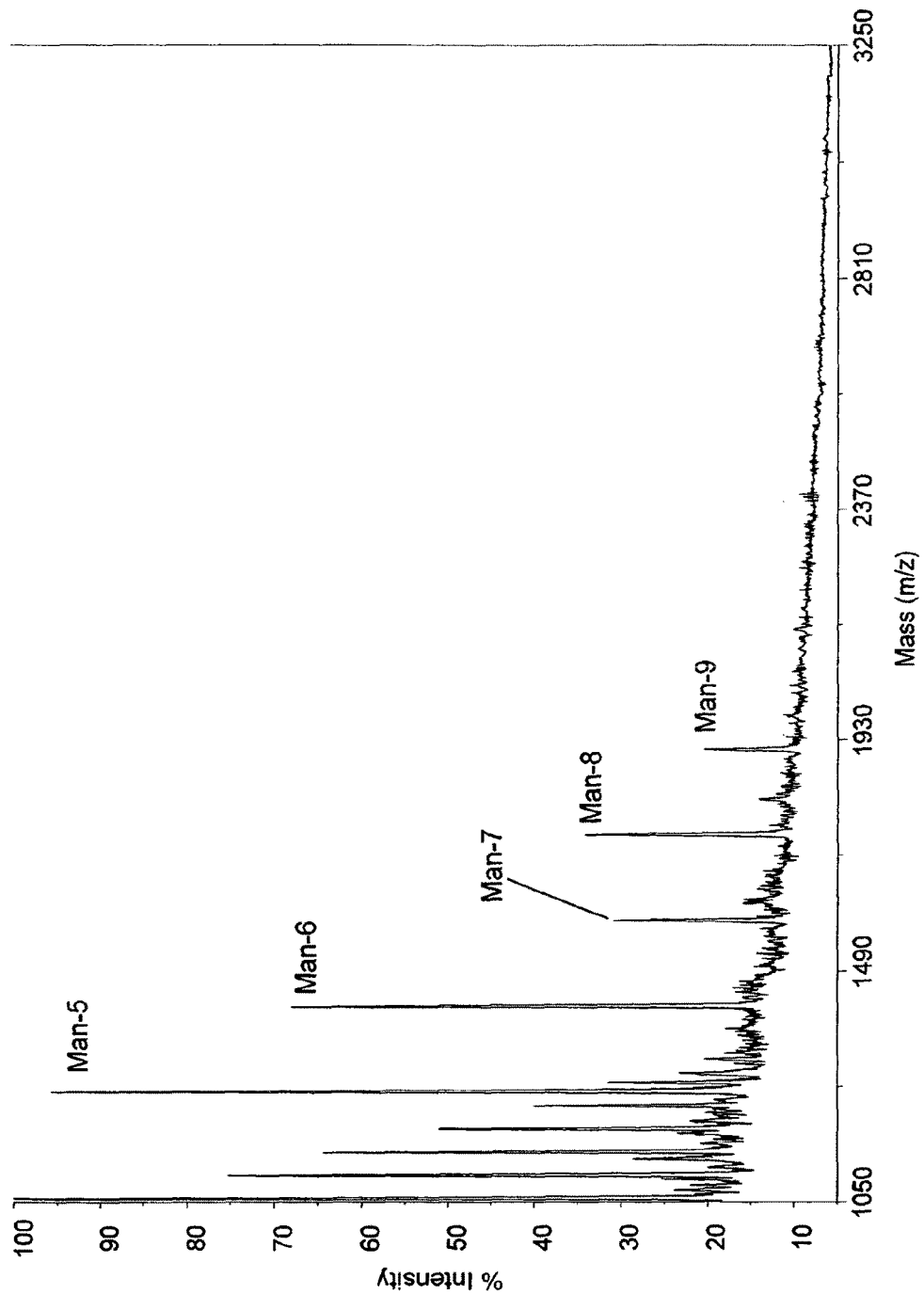
Figure 5D:
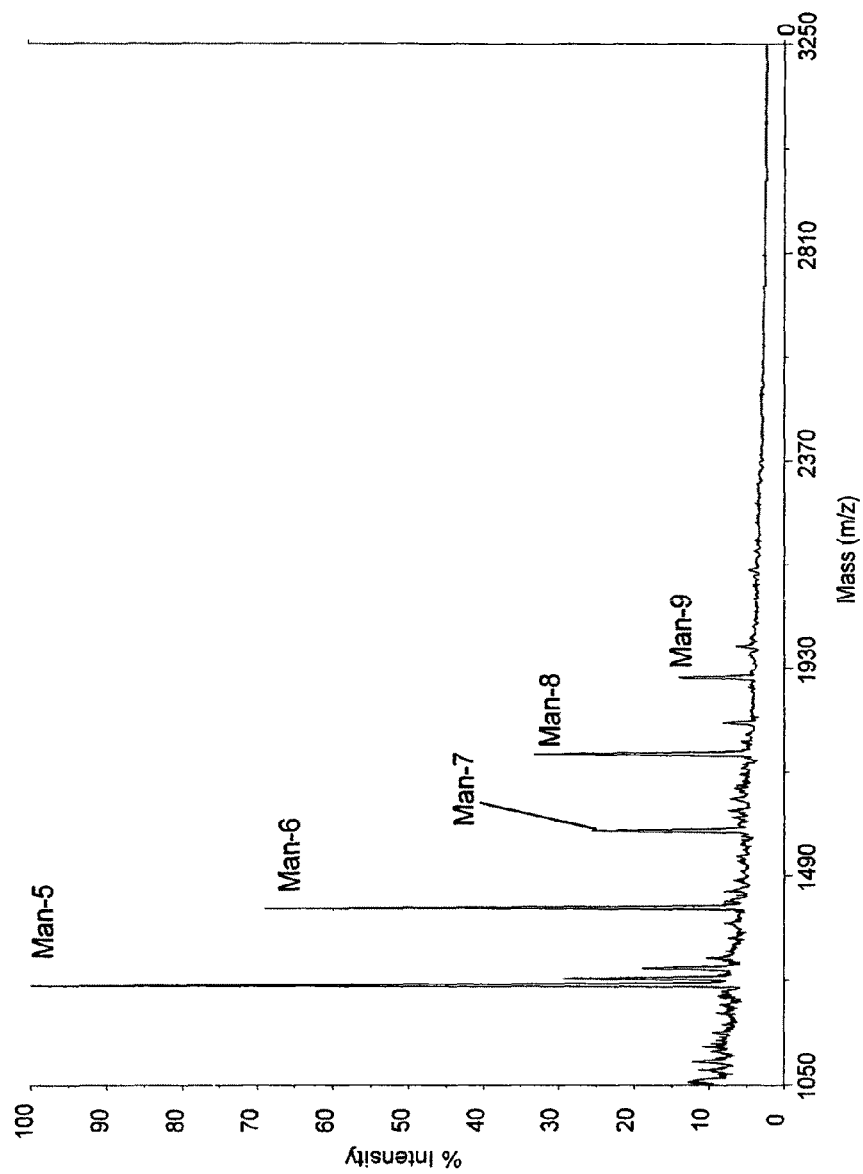

Glycans include N- and O-glycans. For illustration, but not intended to be limiting, N-glycans are classified into three types based on their structure: high mannose, hybrid and complex [Sears, P., Wong, C. H. (1998) Enzyme action in glycoprotein synthesis. *Cell Mol Life Sci* 54, 223-52.] All N-glycans contain a conserved pentasaccharide core composed of two N-acetylglucosamine residues followed by three mannose saccharides (FIG. 1). High mannose structures contain up to six more mannoses on both branches (FIG. 2A), while complex structures have no additional mannoses on either arm (FIG. 2B). Instead, they are composed of additional hexosamines and/or galactose. Hybrid structures are mixes of both high mannose and complex structures (FIG. 2C). Additionally, branch termini can be capped with sialic acid (a charged monosaccharide), and the core or branches can be fucosylated. Many other rare modifications exist, including sulfate, phosphate and xylose, but these are typically not found in humans. As provided herein, the methods of analyzing glycans may include the analysis of any glycan including glycans with any of the structures described herein. The term "glycan" is also intended to include glycans that are intact (i.e., as they were originally found in a sample) or have been digested (i.e., fragment of the original glycan).

Glycans can be analyzed with a number of different methods that include different steps and different experimental techniques. The glycans can be, for example, those displayed on proteins or lipids, on the surface of cells or any of the glycans that are present in a body fluid. In general, when the glycans in a sample are part of a glycoconjugate, the sample of glycoconjugates can be first denatured with a denaturing agent.

A "denaturing agent" is an agent that alters the structure of a molecule, such as a protein. Denaturing agents, therefore, include agents that cause a molecule, such as a protein to unfold. Denaturing can be accomplished with any of a number of methods that are known in the art. Denaturing can be accomplished, for instance, with heat, with heat denaturation in the presence of β-mercaptoethanol and/or SDS, by reduction followed by carboxymethylation (or alkylation), etc. Reduction can be accomplished with reducing agent, such as, dithiothreitol (DTT). Carboxymethylation or alkylation can be accomplished with, for example, iodoacetic acid or iodoacetamide. Denaturation can, for example, be accomplished by reducing with DTT, β-mercaptoethanol or tri(2-carboxyethyl)phosphine (TCEP) followed by carboxymethylation with iodoacetic acid. When the glycoconjugate sample is a sample of a body fluid, such as serum, the denaturation can be accomplished with EndoF. The glycoconjugates can also be denatured with denaturing agents, such as detergent, urea or guanidium hydrochloride.

In some methods following denaturation the sample of glycoconjugates is reduced with a reducing agent. As provided above, reducing agents include DTT, β-mercaptoethanol and tri(2-carboxyethyl)phosphine (TCEP). In other methods the sample of glycoconjugates is alkylated after being reduced, such as, for example, with iodoacetic acid or iodoacetamide.

Methods of analyzing glycans of glycoconjugates can also include cleaving the glycans from the non-saccharide moiety using any chemical or enzymatic methods or combinations thereof that are known in the art. An example of a chemical method for cleaving glycans from glycoconjugates is hydrazinolysis or alkali borohydrate. Enyzmatic methods include methods that are specific to N- or O-linked sugars. These enzymatic methods include the use of Endoglycosidase H (Endo H), Endoglycosidase F (EndoF), N-Glycanase F (PNGaseF) or combinations thereof. In some preferred embodiments, PNGaseF is used when the release of N-glycans is desired. When PNGaseF is used for glycan release the proteins is, for example, first unfolded prior to the use of the enzyme. The unfolding of the protein can be accomplished with any of the denaturing agents provided above.

The glycans analyzed by the methods provided herein can also be contacted with a glycan-degrading enzyme. Examples of glycan-degrading enzymes are known in the art and include sialidase, galactosidase, mannosidase, N-acetylglucosaminidase or a combination thereof. The methods provided herein also include the use of a carbohydrate-degrading enzyme. As used herein "carbohydrate-degrading enzymes" or "glycan-degrading enzymes" are enzymes that can modify a carbohydrate or glycan in some way. Some examples of glycan-degrading enzymes include sialidase, galactosidase, mannosidase, N-acetylglucosaminidase or some combination thereof.

After the release of the glycan from the protein core, or when the glycans were already in free form (not part of a glycoconjugate), the sample can be purified, for instance, by precipitating the proteins with ethanol and removing the supernatant containing the glycans. Other experimental methods for removing the proteins, detergent (from a denaturing step) and salts include any methods known in the art. These methods include dialysis, chromatographic methods, etc. In one example, the purification is accomplished with a porous graphite column. In some preferred embodiments, everything but the glycans are removed from the sample. Samples can also be purified with commercially available resins and cartridges for clean-up after chemical cleavage or enzymatic digestion used to separate glycans from protein. Such resins and cartridges include ion exchange resins and purification columns, such as GlycoClean H, S, and R cartridges. Preferably, in some embodiments GlycoClean H is used for purification.

Purification can also include the removal of high abundance proteins, such as the removal of albumin and/or antibodies, from a sample containing glycans. In some methods the purification can also include the removal of unglycosylated molecules, such as unglycosylated proteins. Removal of high abundance proteins can be a desirable step for some methods, such as some high-throughput methods described elsewhere herein. In some embodiments of the methods provided, abundant proteins, such as albumin or antibodies, can be removed from the samples prior to the final composition analysis.

Prior to the analysis of a sample of glycans as provided herein the sample of glycans can also be fractionated. The sample can be fractionated so as to obtain a sample of glycans with specific subgroups of molecules. "Subgroups of molecules" include molecules of specific properties, such as charge, molecular weight, size, binding properties to other molecules or materials, acidity, basicity, pI, hydrophobicity, hydrophilicity, etc. In one embodiment the subgroup of molecules of a sample is the low abundance species, and it is the low abundance species that are analyzed with the methods. The low abundance species can contain fucoses, sialic acids, galactoses, mannoses or sulfate groups.

The fractionation can be performed using any methods known in the art. Such methods include using solid supports with immobilized proteins, organic molecules, inorganic molecules, lipids, carbohydrates, nucleic acids, etc. The fractionation can also be performed with filters, such as molecular weight cutoff filters, resins, such as cation or anion exchange resins, etc. Therefore, the method provided herein can be used for the analysis of the glycans of a subgroup of molecules.

Glycans can be charged or uncharged. They can be acidic, basic or neutral. It has now been found that separately analyzing charged and uncharged glycans of a sample can provide an improvement in the analysis of glycans. Therefore, the charged and uncharged glycans can be separated prior to the analysis of the glycans, such as with an analytic method. As described further in the Examples provided below, such a method has now been found to clearly discriminate the glycans present in the sample. Therefore, any of the methods provided herein can include a step of separating neutral and charged glycans, such as acidic glycans. Such separation can be achieved using purification methods. For instance, in a preferred embodiment, the separation is accomplished with a porous carbon purification cartridge by eluting glycan pools with different concentrations of acetonitrile. Other methods will be known to those of skill in the art. Analysis of these separate glycan pools can then be undertaken. For instance, when using MALDI-MS, the acidic glycans can be analyzed in negative ion mode, while the neutral glycans are analyzed in positive ion mode.

In other embodiments, the glycans can be modified to improve ionization of the glycans, particularly when MALDI-MS is used for analysis. Such modifications include permethylation. An other method to increase glycan ionization is to conjugate the glycan to a peptide. Examples of the methods are described further in the Examples below. In other embodiments, spot methods can be employed to improve signal intensity.

Any analytic method for analyzing the glycans so as to characterize them can be performed on any sample of glycans, such analytic methods include those described herein. As used herein, to "characterize" a glycan or other molecule means to obtain data that can be used to determine its identity, structure, composition or quantity. When the term is used in reference to a glycoconjugate, it can also include determining the glycosylation sites, the glycosylation site occupancy, the identity, structure, composition or quantity of the glycan and/or non-saccharide moiety of the glycoconjugate as well as the identity and quantity of the specific glycoform. These methods include, for example, mass spectrometry, NMR (e.g., 2D-NMR), electrophoresis and chromatographic methods. Examples of mass spectrometic methods include FAB-MS, LC-MS, LC-MS/-MS, MALDI-MS, MALDI-TOF, TANDEM-MS, FTMS, etc. NMR methods can include, for example, COSY, TOCSY, NOESY. Electrophoresis can include, for example, CE-LIF. In one embodiment the glycans can be quantified using calibration curves of known glycan standards. More details regarding examples of these methods are provide below in the Examples.

Other methods that can be used to analyze the saccharide composition of the glycans once released from the protein include procedures involving the labeling of the saccharides with chemical or fluorescent tags. Such methods include fluorescence assisted carbohydrate electrophoresis (FACE), HPLC or capillary electrophoresis (CE). A method for the compositional analysis of oligosaccharides using CE has been described (Rhomberg, A. J., Ernst, S., Sasisekharan, R. & Biemann, K. (1998) Proc Natl Acad Sci USA 95, 4176-81).

In some embodiments, the analytic method for the characterization of the glycans includes the use of MALDI-MS. Matrix-assisted laser desorption ionization mass spectrometry (MALDI-MS) techniques for the analysis of oligosaccharides have also been described (Juhasz, P. & Biemann, K. (1995) Carbohydr Res 270, 131-47 and Juhasz, P. & Biemann, K. (1994) Proc Natl Acad Sci USA 91, 4333-7; Venkataraman, G., Shriver, Z., Raman, R. & Sasisekharan, R. (1999) Science 286, 537-42; Rhomberg, A. J., Shriver, Z., Biemann, K. & Sasisekharan, R. (1998) Proc Natl Acad Sci USA 95, 12232-7; Ernst, S., Rhomberg, A. J., Biemann, K. & Sasisekharan, R. (1998) Proc Natl Acad Sci USA 95, 4182-7; and Rhomberg, A. J., Ernst, S., Sasisekharan, R. & Biemann, K. (1998) Proc Natl Acad Sci USA 95, 4176-81). Optimized MALDI-MS analytic methods are also provided herein.

Analytic methods can also comprise the use of carbohydrate- or glycan-degrading enzymes. Following enzymatic degradation the sample of degraded glycans can be further analyzed with an analytic method as described above or otherwise known in the art.

The characterization of one or more glycoconjugates with an analytic method can also include determining the identity, structure or sequence of the non-saccharide moiety of the glycoconjugate. As an example, the characterization with an analytic method can include determining the peptide (or lipid) sequence of a glycopeptide (or glycolipid). Such methods are known in the art and examples are provided in the Examples section below.

In some methods, such as with MALDI-MS, the matrix in which the sample of glycans is suspended may affect the quality of compositional analysis. In some embodiments the matrix preparation is caffeic acid with or without spermine. In other embodiments, the matrix preparation is DHB with or without spermine. In preferred embodiments the matrix preparation is spermine with DHB. The spermine, for example, can be in the matrix preparation at a concentration of 300 mM. The matrix preparation can also be a combination of DHB, spermine and acetonitrile. MALDI-MS can also be performed in the presence of NAFION® (a perfluorinated ion-exchange compound) and ATT. Additionally, when using MALDI-MS to analyze the samples, instrument parameters can also be modified. These parameters may include guide wire voltage, accelerating voltage, grid values and negative versus positive mode.

The samples of glycans can be analyzed separately or they can be analyzed as a mixture. The methods provided include methods for the analysis of glycosylation of a single protein (or lipid) in a sample or a mixture of proteins (or lipids or a mixture of proteins and lipids). Such mixtures can contain glycosylated and non-glycosylated proteins and/or lipids.

A glycoconjugate, such as a glycoprotein, can exist in many glycoforms; that is, each glycosylation site may (or may not) be occupied by a specific glycan all the time. The methods provided comprise or consist of steps for determining the glycosylation site occupancy of the glycoconjugates of a sample. As used herein, the term "glycosylation site occupancy" refers to the frequency (percentage) in which one or more specific glycosylation sites on a lipid, protein or peptide is occupied by a glycan. The glycosylation site can be determined using the methods provided below in the Examples as well as methods that are known in the art. In one embodiment the glycosylation site occupancy is the "total glycosylation site occupancy", which refers to the frequencies in which all of the specific glycosylation sites on a lipid, protein or peptide are occupied by a glycan. The specific glycans that occupy each specific glycosylation site can also be characterized using one or more analytic techniques.

2D-NMR provides a reliable method for the identification of N-linked and O-linked glycan site occupancy. A combination of COSY, TOCSY, NOESY experiments are first conducted on a specific quantity of a glycoprotein. Using COSY and TOCSY data, all the spin systems (amino acids) are assigned. NOESY experiments are subsequently used to determine the specific amino acid sequence. This information allows the specific identification of all the asparagines (Asn) and serine (Ser) or threonine (Thr) residues in the sample. More importantly, since NOES between the protons of the Asn, Ser or Thr side chains and proximal carbohydrate residues can be easily monitored, this allows the monitoring and quantification of site glycan occupancy at each glycosylation site. This is particularly useful for high abundance glycosylation sites.

Figure 24A:
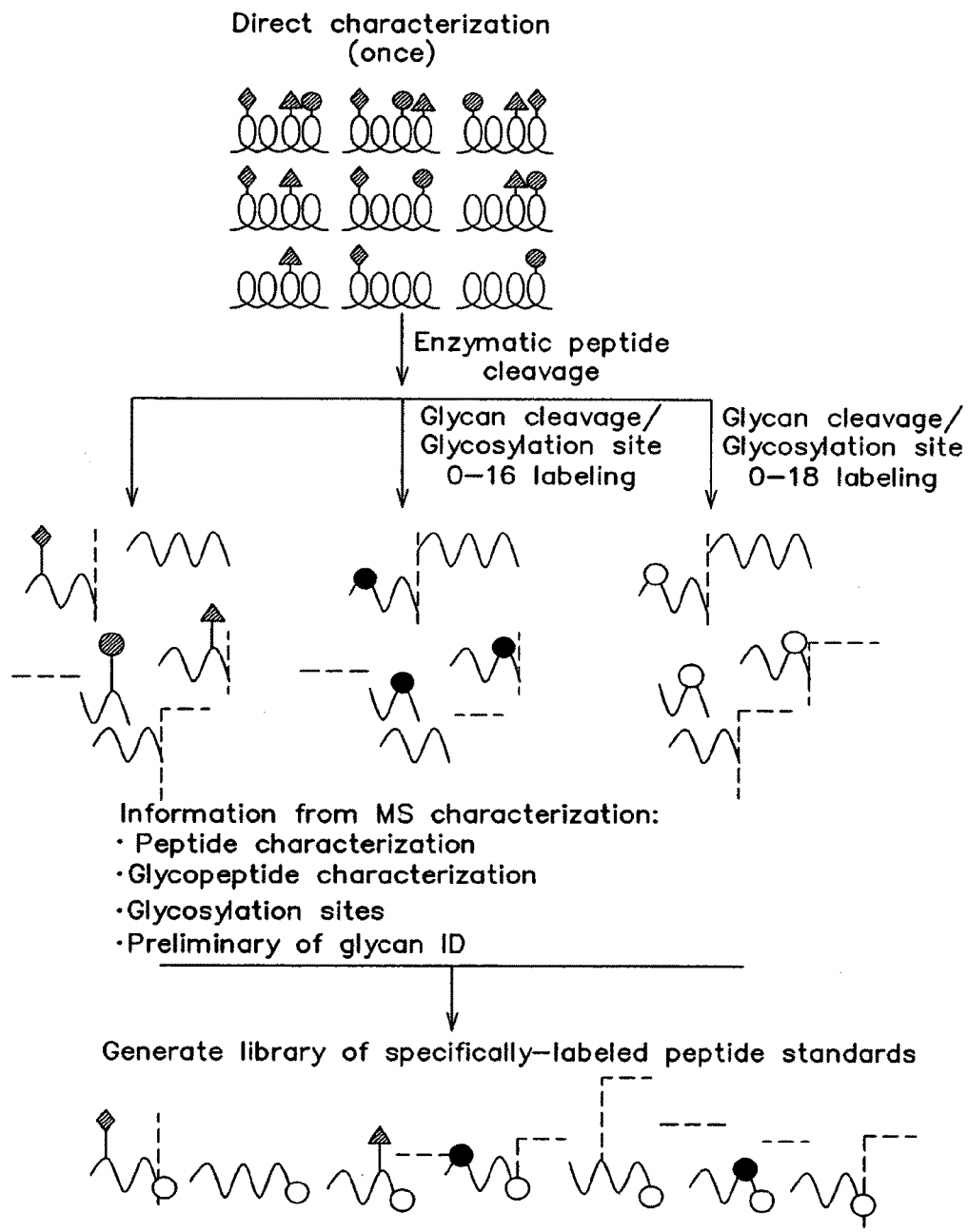
FIG. 24 provides a scheme for an exemplary method for glycoprotein analysis-glycan site occupancy analysis.
Figure 24B:
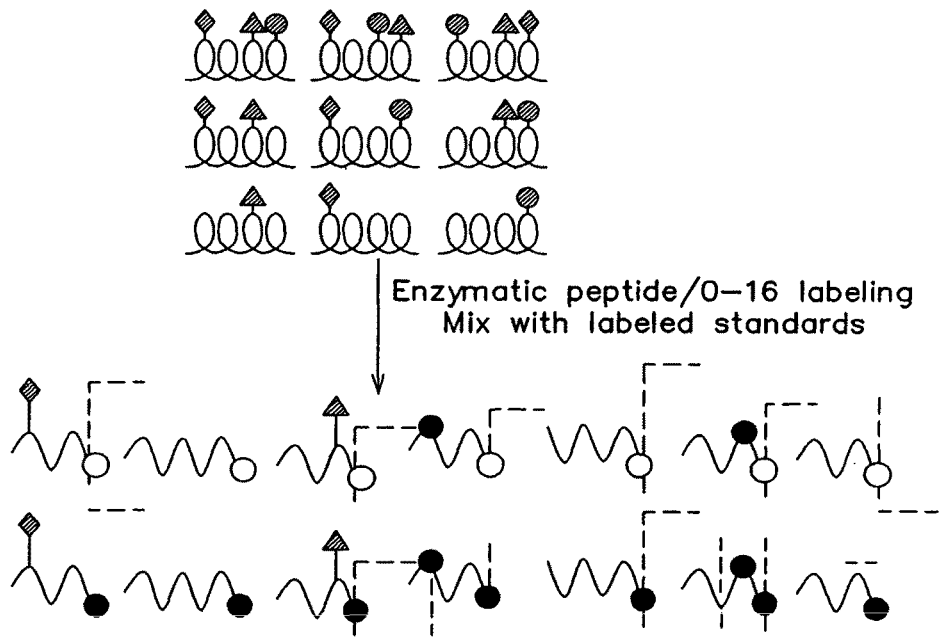

Also provided in one aspect of the invention is a method for determining glycosylation site occupancy of a glycoconjugate. For the determination of the glycan site occupancy, such as for lower abundance glycoforms, concepts from phosphoproteomics were adapted. FIG. 24 provides one embodiment of a method for determining glycosylation site occupancy. Briefly, a well characterized batch of the glycoprotein under study is used to generate a library of labeled peptides and glycopeptides by trypsin digest. In order to order to facilitate the determination of the glycosylation sites, each glycosylated amino acid is differentially labeled. The labels that can be used include isotopes of C, N, H, S, or O. In one embodiment the glycosylated amino acids are labeled with $O^{18}$ and $O^{16}$ using methods known in the art. [Kaji, 2003]. After the labeling, the samples can be further analyzed. In one embodiment the glycan site occupancy is quantified from the ratios of the masses of the labeled and unlabeled fragments. In one examples, determining the glycosylation site and its occupancy can include cleaving and labeling with a first label the glycoconjugates at the glycosylation sites of a portion of the sample, cleaving the glycoconjugates at the glycosylation sites of another portion of the sample and analyzing the portion of the sample. The portions of the sample can be analyzed separately or as a mixture in any ratio. First instance, when there are two portions of the sample, the two portions can be mixed in a 1:1, 1:2, 1:3, 1:4, or 1:5 ratio. The glycosylation site occupancy method can be used to determine the identity and number of glycoforms in the sample. Therefore, a method of determining the identity and number of glycoforms in a sample comprising determining the glycosylation site occupancy of a glycoconjugate and analysis to characterize the glycoconjugates so as to determine the identity and number of glycoforms is also provided.

As illustrated in the Examples below, the fragment containing the partner peak with a molecular weight 2 Da heavier is identified as the peptide containing the glycosylation site. By comparing the data between the glycosylated and deglycosylated samples, a preliminary identification all the peptides (or lipids when the glycoconjugate is a glycolipid) and glycopeptides (or glycolipid) are identified and a preliminary identification of the glycans is obtained. This quantitative information can be combined with a glycan analysis and used as constraints in a computational analysis, such as the one described below, to arrive at the complete characterization of the glycoprotein.

"Constraints" as used herein are one or more values or relationships to which results obtained from an analysis of a sample containing glycans can be compared to or evaluated. The constraints can, for example, be one or more mathematical equations that can be solved with the data obtained from an analysis of a sample containing glycans and/or other data obtained from other sources, such as databases or with other analytical tools. The constraints can, for example, be generated from the one or more of the results obtained from an analysis of a sample of glycans and/or with other glycan/glycoconjugate information, such as the information regarding glycan synthesis or from databases.

The labels that can be used in any of the methods provided include isotopes of C, N, H, S, or O. In one embodiment the glycosylated amino acids are labeled with $O^{18}$.

Also provided is a method of generating a library. The library consists of labeled glycoconjugates and fragments of the glycoconjugates, the fragments being the non-saccharide portions of the glycoconjugates. In one example, a library is generated by cleaving the backbone of the glycoconjugate and labeling the non-saccharide fragments and the non-saccharide portions of the glycoconjugates that result with a labeling agent. This example also includes the step of cleaving the glycans from the glycoconjugate. The glycans can then be removed from the sample. The libraries so produced can be analyzed with the methods provided herein. The libraries can also be used as a standard once characterized and methods of using such libraries are also provided. In one example, a method of analyzing a sample with glycoconjugates includes cleaving the glycoconjugates, enzymatically removing the glycans from the glycoconjugates and mixing the sample with a standard. The sample mixed with the standard can then be analyzed. In one embodiment, the amounts of the glycoconjugates and non-saccharide moieties of the sample and standard are compared. In one aspect of the invention the standards are also provided.

The methods provided can also comprise or consist of the steps of generating a list of glycan properties. One example of such a method includes measuring 1, 2, 3, 4, 5, 6, 7, 8, 9, 10 or more properties of the glycan, recording a value for the one or more properties to generate a list of the glycan properties. The method also is intended to refer to generating a list of glycoconjugate properties. A "property" as used herein is a characteristic (e.g., structural characteristic) of the glycan or glycoconjugate that provides information (e.g., structural information) about the glycan or glycoconjugate. Examples of properties include charge, chirality, nature of substituents, quantity of substituents, molecular weight, molecular length, compositional ratios of substituents or units, type of basic building blocks (saccharide, amino acid, lipid constituents), hydrophobicity, enzymatic sensitivity, hydrophilicity, secondary structure and conformation, ratio of one set of modifications to another set of modifications, etc. In one embodiment the list comprises the number of one or more types of monosaccharides. The list can also include the total mass of the glycan or glycoconjugate, the mass of the non-saccharide moiety of a glycoconjugate, the mass of one and/or more modified glycans, etc. The list in one embodiment can be a data structure tangibly embodied in a computer-readable medium, such as computer hard drive, floppy disk, CD-ROM, etc. Table 6 represents an examples for such a data structure. The data structure of Table 6 has a plurality of entries, where each entry encodes a value of a property. The values encoded can be encoded by any kind of value, for example, as single-bit values, single-digit hexadecimal values, or decimal values.

Therefore, also provided is a database, tangibly embodied in a computer-readable medium, wherein the database stores information descriptive of one or more glycans and/or glycoconjugates. The database comprises data units that correspond to the glycan and/or glycoconjugate. The data units include an identifier that includes one or more fields, each field storing a value corresponding to one or more properties of the glycans and/or glycoconjugates. In one embodiment the identifier includes 2, 3, 4, 5, 6, 7, 8, 9, 10 or more fields. The database, for example, can be a database of all possible glycoconjugates, glycans or can be a database of values representing a glycome profile or pattern for one or more samples. Methods of analyzing and characterizing a glycome profile or pattern is described further below.

Herein, improved methods for analyzing samples containing glycans are provided, which include a combined analytical-computational platform to achieve a thorough characterization of glycans. Therefore, any of the methods provided can be combined with computational methods. Non-limiting examples of the computational methods that can be used are illustrated in detail in the Examples. Briefly, the diverse information gathered from the different experimental techniques can be used to generate constraints. This can be done in combination with a panel of proteomics and glycomics based bioinformatics tools and databases for the efficient characterization (glycosylation site occupancy, quantification, glycan structure, etc.) of the glycan/glycoconjugate mixture of interest. The databases can be those known in the art or can be generated with the methods provided. As an example, a method of analyzing glycans with the combined analytic and computational techniques can include the steps of performing an experiment on a sample containing glycans, analyzing the results of the experiment, generating constraints and solving them. The constraints can be generated and/or solved with the data obtained from experimental results as well as other known information, such as information from databases that contain information about glycans or glycoconjugates and with other tools that analyze the properties of glycans, glycoconjugates or the non-saccharide moieties thereof, such as mass and enzyme action.

The constraints can be generated using, for instance, what is known of the biosythetic pathway of glycan synthesis.

Unlike DNA or protein synthesis, which are template-driven processes, glycan biosynthesis is a complex process involving a multitude of enzymes. A detailed scheme of N-glycan biosynthesis is shown in FIG. 3 and the biosynthetic enzymes and their EC numbers are listed in Table 1. The process is initiated in the cytoplasm, with the nascent sugar attached to the ER membrane through a lipid anchor. After a glycan core of two glucosamines followed by five mannose residues is constructed, the orientation of the growing glycan is flipped to face the lumen of the ER. There, four more mannose residues are added by α-mannosyltransferase, and one branch is capped with three glucoses. At this point, oligosaccharyl transferase catalyzes the removal of the naïve glycan from its lipid anchor, and attaches it to a glycosylation site on a protein undergoing synthesis in the ER [Varki, A. (1999) *Essentials of glycobiology*. Cold Spring Harbor Laboratory Press, Cold Spring Harbor, N.Y.]

To ensure that the glycan can play its proper role in protein folding and transport, the three terminal glucose residues and one mannose are removed. This trimming is required for the glycan to interact with the chaperone proteins calnexin and calreticulin [Helenius, A., Aebi, M. (2001) Intracellular functions of N-linked glycans. *Science* 291, 2364-9; Parodi, A. J. (2000) Protein glucosylation and its role in protein folding. *Annu Rev Biochem* 69, 69-93.] As the correctly folded protein passes through the Golgi on its way either to secretion or the cell membrane, further glycan modifications can take place. Specifically, mannosidases can trim more mannoses off the core sugar, while a host of glycosyltransferases can add further GlcNAc, fucose, galactose, and sialic acid moieties, among others [Sears, P., Wong, C. H. (1998) Enzyme action in glycoprotein synthesis. *Cell Mol Life Sci* 54, 223-52.]

TABLE 1

Common enzymes involved in N-glycan biosynthesis

| EC # | Enzyme name |
|---|---|
| 2.4.1.— | Hexosyltransferases (ALG 6, 8, 10, 11) |
| 2.4.1.38 | Glycoprotein β-galactosyltransferase |
| 2.4.1.68 | Glycoprotein 6-α-L-fucosyltransferase |
| 2.4.1.83 | Dolichyl phosphate mannose transferase |
| 2.4.1.101 | α-1,3-mannosyl-glycoprotein 2-β-N-acetylglucosaminyl transferase |
| 2.4.1.117 | Dolichyl phosphate β-glucosyltransferase |
| 2.4.1.119 | Oligomannosyl transferase |
| 2.4.1.130 | Oligomannosyl synthase (ALG 3, 9, 12) |
| 2.4.1.132 | Glycolipid 3-α-mannosyltransferase |
| 2.4.1.141 | N,N'-diacetylchitobiosyl pyrophosphoryldolichol synthase |
| 2.4.1.142 | chitobiosyldiphosphodolichol β-mannosyltransferase |
| 2.4.1.143 | α-1,6-mannosyl-glycoprotein 2-β-N-acetylglucosaminyl transferase |
| 2.4.1.144 | β-1,4-mannosyl-glycoprotein 4-β-N-acetylglucosaminyl transferase |
| 2.4.1.145 | α-1,3-mannosyl-glycoprotein 4-β-N-acetylglucosaminyl transferase |
| 2.4.1.155 | α-1,6-mannosyl-glycoprotein 6-β-N-acetylglucosaminyl transferase |

TABLE 1-continued

Common enzymes involved in N-glycan biosynthesis

| EC # | Enzyme name |
|---|---|
| 2.4.1.201 | β-1,6-mannosyl-glycoprotein 4-β-N-acetylglucosaminyl transferase |
| 2.4.99.1 | β-galactoside α-2,6-sialyltransferase |
| 2.5.1.— | Transferring alkyl or aryl groups, other than methyl groups |
| 2.7.1.108 | Dolichol kinase |
| 2.7.8.15 | Chitobiosylpyrophosphoryl dolichol synthase |
| 3.1.3.51 | Dolichyl-phosphatase |
| 3.1.4.48 | dolichylphosphate-glucose phosphodiesterase |
| 3.2.1.— | Hydrolyzing O- and S-glycosyl compounds |
| 3.2.1.106 | Mannosyl-oligosaccharide glucosidase |
| 3.2.1.113 | mannosyl-oligosaccharide 1,2-α-mannosidase |
| 3.2.1.114 | mannosyl-oligosaccharide 1,3-1,6-α-mannosidase |
| 3.6.1.43 | Dolichol diphosphatase |

The constraints are solved using mathematical and heuristic approaches known to art such as linear programming and search techniques. A more detailed illustration of one embodiment of an analytical and computational method is provided in FIG. 23. One of skill in the art will appreciate, however, that there are a number of ways in which experimental analytic methods can be combined with computational methods to achieve the desired characterization. It is the combination which provides more efficient analysis of samples of glycans. The examples provided are not intended to be limiting in any way.

In some embodiments, the methods provided herein also include generating a list of the possible compositions of glycans and their theoretical masses. The list can be based on the biosynthetic pathways for glycosylation (FIG. 3). An example of such a list is provided herein. The list can also be recorded in a computer-readable medium. The list can be generated with other means, such as with the results from the use of any of the methods provided herein or known in the art. In one embodiment, the method can include the use of exoenzymes to cleave the glycans in order to analyze the composition of the glycans. The list can be used in any of the methods provided in order to characterize glycans. Methods that include the use of a list are also provided herein.

Protein glycosylation can affect the function of proteins or be indicative of a cause or symptom of a disease state. For many proteins, N- and O-linked glycans are an important factor for determining proper folding, stability and resistance to degradation (which affects the half-life of the protein). In some proteins, N- and O-linked glycans play a role in the activity and/or function of the protein. In some proteins, N- and O-linked glycans are indicative of a normal or disease state. Therefore, methods are provided herein to analyze the glycosylation of a protein for a variety of reasons. The methods, therefore, provided above can be used in diagnosis.

Also provided is the method described below, which can also be used for diagnostic or prognostic purposes. In this method the total profile of carbohydrates from body fluids or tissues can be examined, and in some embodiments this can be done in a high-throughput format. The examination of total glycan profiles are now exceedingly accessible thanks to the recent advances in proteomic pattern diagnostics. This approach should be useful in sensing susceptible physiological alterations to the body's natural homeostasis. This method should not only serve as a fast diagnostic tool but should also help to understand the function of specific carbohydrate modifications in some diseases.

Before developing a method to study N-glycans from body fluids, it was important to understand the types of molecules present. For example, proteins comprise an enormous portion of serum, approximately 7% of the total wet weight [Vander, 2001]. Of this amount, over half is albumin (~50 mg/ml), a protein that can be non-enzymatically glycosylated, but not N-glycosylated [Rohovec, 2003]. Although the overwhelming amounts of albumin can obscure analysis for proteomics, it may not interfere with N-glycan profiling. There are also large amounts of glycosylated antibodies, which have a number of glycan structures [Bihoreau, 1997; Watt, 2003]. However, simple methods exist to separate these abundant antibodies from the less abundant glycoproteins.

When working with serum, there are several issues to consider that are not relevant for single protein systems. Because the proteins in the sample are so concentrated, they can easily precipitate out of solution. Also, even though albumin does not have N-linked sugars, the sheer quantity present may interfere with glycan release or purification. There are several other major proteins in serum (i.e. immunoglobulins) that are N-glycosylated, which may overshadow the signals from less abundant proteins. However, alterations in immunoglobulin glycosylation may also be correlated with changes in physiological state. To determine the contributions and/or interference from major serum proteins, several options for separating serum proteins into fractions before analysis were explored.

Identifying glycan structures with complex protein mixtures can be somewhat difficult. By generating a master list of all possible compositions and their theoretical masses based on biosynthetic pathways for glycosylation, all possible monosaccharide composition was assigned to each peak observed in a MALDI-MS spectrum. Such lists and databases comprising these lists are provided herein. In most cases, each mass peak corresponds uniquely to a monosaccharide assignment. However, in some instances there can be more than one potential composition. If necessary, the correct composition can be determined by coupling different separation and characterization techniques with commercially available exoenzymes that cleave the glycans only at particular linkages.

The method provided allows fast and sensitive spectrometric analysis of patterns for the total composition of glycans in body fluids such as serum, saliva, urine, tears, seminal fluid, feces, etc. Specifically the use of the analysis of these patterns can be extended for the purpose of diagnosis, prognosis and monitoring the effects of therapeutics. Using optimized methods described above, the total content of serum, saliva and urine glycome was analyzed and it was shown that specific and reproducible MALDI-MS patterns which are dependent on the source (patient) of the sample and state could be obtained. Since every signal inside the pattern corresponds to specific glycans, the alteration of these patterns are easily determined and correlated with the expression levels of the carbohydrates. These alterations can be easily determined manually or more efficiently with the help of computational analysis. Since specific alterations in these glycan patterns are associated with disease state, this method serve as reliable platform for diagnosis, prognosis and the analysis associated with therapeutics. The methods provided can also be used to profile populations to aid the development and application of patient-oriented treatments.

Methods, therefore, are provided for the determining the glycome profile of a sample. The total glycome and/or patterns deduced therefrom can be used for studying the effects of glycosylation on protein activity and/or function as in the case of glycoprotein therapeutics. Likewise, the total glycome and/or patterns deduced therefrom can also be used in methods for diagnosis, assessing prognosis and assessing drug treatment, etc.

A "glycome profile" refers to the number and kind of glycans found in a sample. The sample can contain one or more glycans and/or one or more glycoconjugates. The glycome profile can be, for example, the number and kind of a specific type of glycan (e.g., N-glycan, O-glycan, etc.). Each component of a glycome profile can correspond to a glycan or fragment thereof or a glycoconjugate or fragment thereof. The number refers to the amount and can be an actual or a relative amount. The "total glycome profile" as used herein the absolute or relative number and kind of all glycans in a sample. The sample can be a sample of cells, tissue or body fluid.

To assess the glycome profile of a sample any analytic methods can be used. Some of these methods are described above; others are known in the art. For example, the analytic method can be MALDI-MS, LC-MS, LC-MS/MS, MALDI-TOF, TANDEM-MS, FTMS, NMR, HPLC, electrophoresis, capillary electrophoresis, microfluidic devices or nanofluidic devices. In a preferred embodiment the glycome profile is determined using a quantitative MALDI-MS or MALDI-FTMS in the presence of ATT and NAFION® (a perfluorinated ion-exchange compound) coating. To quantify the glycans, in one example, calibration curves of known glycan standards can be used.

Prior to analyzing the glycans of the sample, the sample can be fractionated. The sample can be fractionated based on properties of the glycans and/or glycoconjugates, such as but not limited to, charge, size, molecular weight, binding properties to other molecules or materials, acidity, basicity, pI, hydrophobicity and hydrophilicity. As an example, the fractionation can be performed using solid supports with immobilized proteins, organic molecules, inorganic molecules, lipids, carbohydrates, nucleic acids, etc. As a further example, the fractionation can be performed using filters, such as molecular weight cutoff filters. The fractionation can also be performed using resins, such as, cation or anion exchange resins. Any method of fractionation known in the art can be used. In one embodiment, however, the sample is not fractionated before it is analyzed.

Prior to analysis the sample, the sample can also be degraded with a chemical or enzymatic method to cleave the glycans from any glycoconjugates in the sample. Examples of enzymatic methods are provided above and include, for example, the use of PNGase F, endoglycosydase H and endoglycosydase F or combinations thereof. Chemical methods have also been described above and include hydrazinolisis or alkali borohydrate.

After chemical or enzymatic degradation the sample can then be performed in some embodiments. Purification methods were also provided above. Examples of particular purification methods include using solid phase extraction cartridges, such as graphitized carbon columns and C-18 columns.

Once a glycome profile is determined, a glycome pattern can be identified. As used herein "glycome pattern" refers to a glycome profile or subset of the profile that has been associated with a certain function (of a lipid or protein), cellular state, or pathological condition (i.e., a disease condition). A glycome pattern can be identified using a computational method. An glycome pattern, like, the profile, can be represented by the relative or absolute amounts of components of the pattern or ratios between the components of the pattern. The glycome pattern can also be represented by combinations of different components or the presence or absence of a component. The pattern can also be any combination of representations, such as those provided herein.

The pattern can be determined using a computational method. Examples of such computational methods are provided herein in the Examples. The computational method can, for example, incorporate one or more of the following to determine a glycome pattern: experimental data from analytic methods of glycome and/or glycan analysis; theoretical glycan structures; glycan composition, structure, property information from databases, glycan biosynthetic pathway information, patient or sample origin information, such as patient history, demographics; extracting features from the experimental data sets, generating all possible data sets with specific features, submitting the combined information to a data mining analysis, establish the relationship rules and validating the pattern. The computational method can be an iterative process. One detailed example is provided in FIG. 3.

The patterns that are ultimately validated can be recorded in a computer-generated data structure. A database of validated glycome patterns is, therefore, also provided herein.

The patterns can be subsequently used for, for example, diagnostic and prognostic purposes and for determining the purity of a sample.

The methods provided herein include methods for determining the glycosylation of a protein and its effects on the protein's activity and/or function. The protein glycosylation can be studied with the methods provided to determine the proper folding of the protein or to determined the influence of the protein's glycosylation on the stability/and or degradation resistance of the protein (indicative of the protein's half-life). Changing the composition or the degree of glycosylation of a protein can greatly influence its half-life in circulation, as well as its activity [Chang, G. D., Chen, C. J., Lin, C. Y., Chen, H. C., Chen, H. (2003) Improvement of glycosylation in insect cells with mammalian glycosyltransferases. *J Biotechnol* 102, 61-71; Perlman, S., van den Hazel, B., Christiansen, J., Gram-Nielsen, S., Jeppesen, C. B., Andersen, K. V., Halkier, T., Okkels, S., Schambye, H. T. (2003) Glycosylation of an N-terminal extension prolongs the half-life and increases the in vivo activity of follicle stimulating hormone. *J Clin Endocrinol Metab* 88, 3227-35.] For example, erythropoietin (EPO) is a glycoprotein that has been developed as a therapeutic due to its ability to stimulate red blood cell production in the bone marrow. It has been determined that increased sialylation of EPO greatly increases its half-life in circulation[Darling, R. J., Kuchibhotla, U., Glaesner, W., Micanovic, R., Witcher, D. R., Beals, J. M. (2002) Glycosylation of erythropoietin affects receptor binding kinetics: role of electrostatic interactions. *Biochemistry* 41, 14524-31.] Thus, by understanding the role of EPO glycosylation, it is possible to manufacture a more potent drug.

Similarly, methods are provided for identifying glycosylated proteins with a desired activity and/or function. In immunoglobulins, glycosylation plays an important role in the structure of the Fc region, which is important for activation of leukocytes expressing Fc receptors. When glycans on the IgG Fc region are truncated, the resulting conformational changes reduce the ability of the IgG to bind to the Fc receptor [Krapp, S., Mimura, Y., Jefferis, R., Huber, R., Sondermann, P. (2003) Structural analysis of human IgG-Fc glycoforms reveals a correlation between glycosylation and structural integrity. *J Mol Biol* 325, 979-89.] In addition, IgG glycosylation is species specific, making it essential to choose the appropriate production method for protein therapeutics [Raju, T. S., Briggs, J. B., Borge, S. M., Jones, A. J. (2000) Species-specific variation in glycosylation of IgG: evidence for the species-specific sialylation and branch-specific galactosylation and importance for engineering recombinant glycoprotein therapeutics. *Glycobiology* 10, 477-86.] For example, a human protein produced in a mouse cell line may not have the necessary glycans for optimal function in human patients. Therefore, the immune recognition of an antibody can be assessed with the methods of analysis provided herein.

One of the major challenges during the production of glycoprotein therapeutics is to control the generation of a specific glycoform and the subsequent characterization for quality control of the product. Therefore, methods that can efficiently characterize new batches of glycoprotein therapeutics are of great value to the pharmaceutical industry. For a complete characterization of glycoprotein therapeutics, information such as glycan site occupancy, carbohydrate composition and structure at each site and quantity of each carbohydrate is required.

As described below in the Examples, the methods for analyzing glycans found on proteins, which can include antibodies, can be used to assess the quality and variability of protein production. With the recently increased focus on protein-based therapeutics by pharmaceutical companies and research laboratories, it has become important to understand how glycosylation composition is influenced by protein production methods. In the field of bioprocess engineering, there are many different types of bioreactors available for protein production. Depending on the model, parameters such as pH and dissolved oxygen (DO) can be controlled in several ways, and agitation methods can result in wide variations in shear stress. In addition, the cell-feeding process during fermentation can be altered to change the cell growth profile. All of these variables can affect protein glycosylation—even using identical conditions in two different bioreactors causes changes in glycan patterns [Kunkel, J. P., Jan, D. C., Butler, M., Jamieson, J. C. (2000) Comparisons of the glycosylation of a monoclonal antibody produced under nominally identical cell culture conditions in two different bioreactors. *Biotechnol Prog* 16, 462-70; Zhang, F., Saarinen, M. A., Itle, L. J., Lang, S. C., Murhammer, D. W., Linhardt, R. J. (2002) The effect of dissolved oxygen (DO) concentration on the glycosylation of recombinant protein produced by the insect cell-baculovirus expression system. *Biotechnol Bioeng* 77, 219-24; Senger, R. S., Karim, M. N. (2003) Effect of Shear Stress on Intrinsic CHO Culture State and Glycosylation of Recombinant Tissue-Type Plasminogen Activator Protein. *Biotechnol Prog* 19, 1199-209; Muthing, J., Kemminer, S. E., Conradt, H. S., Sagi, D., Nimtz, M., Karst, U., Peter-Katalinic, J. (2003) Effects of buffering conditions and culture pH on production rates and glycosylation of clinical phase I anti-melanoma mouse IgG3 monoclonal antibody R24. *Biotechnol Bioeng* 83, 321-34.] Therefore, provided herein are methods for analyzing the glycosylation of proteins to assess protein production methods and to determine the purity or homogeneity of glycosylated proteins produced.

Therefore, methods are provided for the direct characterization of subsequent samples of the proteins under study (as in the cases of new batches of glycoprotein therapeutics). Examples of this is described herein. One example is as follows. A well characterized batch of the glycoprotein under study is used to generate a library of backbone-labeled peptides and glycopeptides by enzymatic digest using methods know in the art [Gehrmann, 2004; Yao, 2003; Reynolds, 2002; Yao, 2001]. Trypsin proteolytic digest cleavage can be employed before and after glycan cleavage in order to expand the peptide library. Peptide labeling can be performed using methods know to experts in the art. Each characterized and quantified peptide and glycopeptide can be used to generate calibration curves using LC-MS or LC-MS/MS techniques. These peptides and glycopeptides can then be mixed (in known concentrations) with the peptide/glycopeptide mixture resulting from the trypsin proteolytic cleavage digest of the new sample batch under study. The co-elution of the labeled peptides with the unknown peptides followed by the co-detection (the ratio between labeled and unlabeled peptides) using mass spectrometry allows the quantification of each peptide (and therefore the different glycoforms) in the unknown sample. In addition to the peptide/glycopeptide analysis, by splitting the flow from LC column (before entering the electrospray source) to a collection plate, the respective glycans from the eluted glycopeptides can be analyzed using the methods described herein. The use of other well established methods (e.g., hydrazide column, peptide) for the determination of glycan site occupancy can also be used [Cointe, 2000, Hui, 2002, An, 2003].

The methods provided, where the amount or type of glycans on proteins can be determined, can be used to analyze the purity of a protein sample. As used herein the term "purity" refers to the proportion of a protein sample that contains a particular glycan or a particular glycosylation pattern. In some embodiments, the protein sample is determined to be at least 10%, 20%, 30%, 40%, 50%, 60%, 70%, 80%, 90% or more pure. In some embodiments the method is used to assess the amount of a particular glycan in a protein sample. In some instances, it may be desired that the proteins are selected depending on the particular glycosylation pattern they exhibit. As used herein, "glycosylation" is meant to include the pattern or a subset or even one particular glycan, while "glycosylation pattern" refers to the number and kind of glycans present on the protein. In other aspects of the invention the methods provided herein can be used to evaluate a process of producing proteins and/or compare a process with another to evaluate the types of proteins produced. The "types of proteins produced" includes not only the protein itself but also its glycosylation pattern.

As stated above, the glycosylation of a protein may be indicative of a normal or a disease state. Therefore, methods are provided for diagnostic purposes based on the analysis of the glycosylation of a protein or set of proteins, such as the total glycome. The methods provided herein can be used for the diagnosis of any disease or condition that is caused or results in changes in protein glycosylation. For example, the methods provided can be used in the diagnosis of cancer, inflammatory disease, benign prostatic hyperplasia (BPH), etc.

The diagnosis can be carried out in a person with or thought to have a disease or condition. The diagnosis can also be carried out in a person thought to be at risk for a disease or condition. "A person at risk" is one that has either a genetic predisposition to have the disease or condition or is one that has been exposed to a factor that could increase his/her risk of developing the disease or condition. In some embodiments, the person can have, be thought to have or is at risk of cancer, cystic fibrosis, mad cow disease, etc.

Detection of cancers at an early stage is crucial for its efficient treatment. Despite advances in diagnostic technologies, many cases of cancer are not diagnosed and treated until the malignant cells have invaded the surrounding tissue or metastasized throughout the body. Although current diagnostic approaches have significantly contributed to the detection of cancer, they still present problems in sensitivity and specificity.

Cancers or tumors also include but are not limited to adrenal gland cancer, biliary tract cancer; bladder cancer, brain cancer; breast cancer; cervical cancer; choriocarcinoma; colon cancer; endometrial cancer; esophageal cancer; extrahepatic bile duct cancer; gastric cancer; head and neck cancer; intraepithelial neoplasms; kidney cancer; leukemia; lymphomas; liver cancer; lung cancer (e.g. small cell and non-small cell); melanoma; multiple myeloma; neuroblastomas; oral cancer; ovarian cancer; pancreas cancer; prostate cancer; rectal cancer; sarcomas; skin cancer; small intestine cancer; testicular cancer; thyroid cancer; uterine cancer; urethral cancer and renal cancer, as well as other carcinomas and sarcomas.

Protein samples, therefore, may include samples from a subject. The samples can, for example, be serum or saliva samples.

The methods can also be used to determine whether or not cells are undergoing dramatic change or are "stressed cells". Stressed cells are cells that are undergoing a stress response that alters the cell's protein production. The stress response can be any change that causes altered protein production or causes the cell to deviate from its normal state. Stressed cells can be identified by analyzing the glycans exhibited by the proteins on the cell's surface. Such glycans can be found in, for example, a glycoprotein. In some embodiments, the methods provided are used to detect changes in glycosylation that occur under growth conditions or inflammation.

In other aspects of the invention methods for analyzing blood type antigens are also provided.

In other aspects of the invention methods are provided for therapeutics. The glycosylation of proteins can be assessed to evaluate treatment regimens and/or to select specific therapies.

A subject is any human or non-human vertebrate, e.g., dog, cat, horse, cow, pig. A sample includes any sample obtained from any of these subjects.

High-throughput methods are also provided. "High-throughput" methods refer to the ability to process and/or analyze multiple samples at one time. High-throughput methods provided herein can include the use of a membrane-based method, such as a PVDF membrane in a 96-well plate, for high throughput sample processing (i.e., digestion and/or denaturation steps, etc.) In some preferred embodiments membrane based high-throughput methods may also include the removal of abundant proteins such as albumin. In one aspect of the invention, therefore, the methods of analysis provided are high-throughput methods. Any step or steps of any of the methods provided herein can be performed as a high: throughput step. For instance purification, degradation, etc. can be performed in a high-throughput manner in some embodiments.

Robotics can be used in one or more steps of the methods provided herein. In one embodiment robotics is used for separation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

N-Glycan Analysis

Materials and Methods
PNGaseF Digest of N-Glycans from Protein Cores

Between 10 and 100 μg of protein was denatured for 10 minutes at 90° C. with 0.5% SDS and 1% β-mercaptoethanol. Since SDS (and other ionic detergents) inhibits enzyme activity, 1% NP-40 was added to counteract these effects. The enzyme reaction was performed overnight with 2 μl of PNGaseF at 37° C. in a 50 mM sodium phosphate buffer, pH 7.5.

Purification of Released N-Glycans

Proteins were precipitated with a 3× volume of 100% ethanol on ice for 1 hour. After centrifugation to remove the proteins, the supernatant containing the N-glycans was evaporated by vacuum (SpeedVac, TeleChem International, Inc., Sunnyvale, Calif.). Dried glycans were resuspended in 50 μl of water.

Samples were desalted using 1 ml ion exchange column of AG50W X-8 beads (Bio-Rad, Hercules, Calif.). The resin was charged with 150 mM acetic acid and washed with water. Glycan samples were loaded onto the column in water and washed through with 3 ml $H_2O$. This flow through was collected and lyophilized to obtain the desalted sugars.

GlycoClean R and S cartridges were purchased from Prozyme (San Leandro, Calif.; formerly Glyko). GlycoClean R cartridges were primed with 3 ml of 5% acetic acid, and the samples were loaded in water. Sugars were eluted with 3 ml of water passed through the column. For GlycoClean S, the membrane was primed with 1 ml water and 1 ml 30% acetic acid, followed by 1 ml acetonitrile. The glycan sample was loaded (in a maximum volume of 10 μl) onto the disc, and the glycans were allowed to adsorb for 15 minutes. After washing the disc with 1 ml of 100% acetonitrile and 5×1 ml of 96% acetonitrile, glycans were eluted with 3×0.5 ml water.

GlycoClean H cartridges were purchased from Prozyme (200 mg bed) or ThermoHypersil (25 mg bed). To prepare the GlycoClean H cartridge, the column (containing 200 mg of matrix) was washed with 3 ml of 1M NaOH, 3 ml $H_2O$, 3 ml 30% acetic acid, and 3 ml $H_2O$ to remove impurities. The matrix was primed with 3 ml 50% acetonitrile with 0.1% TFA (Solvent A) followed by 3 ml 5% acetonitrile with 0.1% TFA (Solvent B). After loading the sample in water, the column was washed with 3 ml $H_2O$ and 3 ml Solvent B. Finally, the sugars were eluted using 4×0.5 ml of Solvent A. GlycoClean H cartridges can be reused after washing with 100% acetonitrile and re-priming with 3 ml of Solvent A followed by 3 ml of Solvent B. For the 25 mg cartridge, wash volumes were reduced to 0.5 ml. Eluted fractions were lyophilized and the isolated glycans were resuspended in 10-40 μl $H_2O$.

MALDI-MS of N-Glycans

Several MALDI-MS matrix compounds were tested in this study. First, caffeic acid was added to 30% acetonitrile to make a saturated solution, with or without 300 mM spermine. Alternatively, a saturated solution of dihydroxybenzoic acid (DHB) in water was used with or without 300 mM spermine. To prepare the sample spots, three methods were used. For the crushed spot method, 1 μl of matrix was spotted on the stainless steel MALDI-MS sample plate and allowed to dry. After crushing the spot with a glass slide, 1 μl of matrix mixed 1:1 with sample was spotted on the seed crystals and allowed to dry. Alternatively, 1 μl of matrix was applied followed by 1 μl of sample, or vice versa. All spectra were taken with the following instrument parameters: accelerating voltage 22000V, grid voltage 93%, guide wire 0.15% and extraction delay time of 150 nsec (unless otherwise noted). All N-glycans were detected in linear mode with delayed type extraction and positive polarity.

Results

With an IgG-producing mouse hybridoma cell line, the effects of DO and pH control on cell metabolism and growth kinetics using two different reactor types was investigated. It was determined whether the IgG glycan profile was altered by the different reactor conditions. For a complete glycan analysis, the procedure for glycan isolation was optimized. The purification and analysis was performed using two known N-glycosylated standards with different properties, ribonuclease B (RNaseB), a glycoprotein that only contains high mannose structures [29], and ovalbumin, which contains both hybrid and complex glycan structures at just one glycosylation site [30]. After finding the best methods for glycan analysis, the procedure was applied to samples (Hamel laboratory, MIT Bioprocess Engineering Center, Cambridge, Mass.) produced under various conditions.

There are several required steps for N-glycan analysis from proteins. While it is possible to study both the intact glycoprotein and glycopeptides from digested proteins, these types of analysis make it difficult to determine the exact composition of the glycan structures. Therefore, the intact glycan was removed from the core protein. Then, the sugar structures were separated from the protein core, purified and analyzed using methods that can provide specific saccharide compositions in an accurate manner.

Release and Purification of N-Glycans from Protein Standards

There are several methods, both enzymatic and chemical, to separate glycans from their protein cores. Of the chemical methods, hydrazinolysis provides the most efficient release of glycans [31]. However, both N- and O-linked glycans are released using this method, and must be separated afterwards. The sample must be very clean, with no residual salts, and the reaction does not proceed efficiently in air or water, making hydrazinolysis somewhat undesirable as a quick measure of quality control.

Several enzymatic methods are available that are specific to N-linked sugars. Endoglycosidases H and F (EndoH and EndoF) cleave between the two interior GlcNAc residues of the glycan core, while protein N-glycanase F (PNGaseF) cleaves between the interior GlcNAc and the asparagine side chain of the protein core [32-34].

EndoH only acts on high mannose or hybrid structures, while EndoF can cleave complex glycans. With EndoH and EndoF, information about fucosylation on the reducing end GlcNAc is lost since this residue remains attached to the protein core. On the other hand, PNGaseF releases the entire glycans and can cleave all classes of N-glycans, making it a tool of choice for N-glycan release.

For optimal enzyme activity, proteins should be unfolded prior to digestion with PNGaseF. Typically, a protein sample can be denatured by heating in the presence of β-mercaptoethanol and/or SDS. After PNGaseF cleavage, samples contain a mixture of free glycans, protein, detergent (from the denaturing step), and salts. In some instance it is preferred that everything except the glycans are removed from the sample. To achieve this, the proteins were first precipitated with ethanol and the supernatant containing the glycans was then dried under vacuum (SpeedVac) and resuspended in water. At this point, the most difficult component to get rid of was the detergent, which interferes with some types of analytical techniques.

There are several commercially available resins and cartridges for N-glycan clean-up after PNGaseF digest. In addition to an ion exchange resin (AG50W X-8 from Bio-Rad), three types of purification columns from Prozyme (formerly Glyko) were tested—the GlycoClean H, S and R cartridges (Glyco H, S and R). Glyco R contains a reverse phase material that allows glycans to flow through, while retaining peptides and detergents. Glyco S is a small membrane that adsorbs the sugars in >90% acetonitrile, while hydrophobic molecules are washed away. The glycans can then be eluted with water. Glyco H, on the other hand, is a porous graphitic carbon matrix which retains both neutral and charged sugars, while allowing salts to be washed away with a low concentration of acetonitrile. The sugars can then be eluted with higher acetonitrile concentrations. Proteins and detergents typically remain on the Glyco H column. Overall, the Glyco H cartridge yielded the best results in these studies (Table 2).

Glycan Analysis by MALDI-MS

Numerous analytical techniques have been applied to study N-glycans, including mass spectrometry, NMR, electrophoresis, and chromatographic methods. NMR, for instance, can provide detailed structural information in a single experiment. Due to the lack of natural chromophores in N-linked carbohydrates, many of the procedures require the labeling of saccharides with chemical tags or fluorescent labels to facilitate detection. In fluorescence assisted carbohydrate electrophoresis (FACE), glycans are fluorescently labeled and run on a polyacrylamide gel [35]. Glycan bands can then be excised for further structural analysis. Similar methods use HPLC or capillary electrophoresis (CE) for greater sensitivity and better separation. However, these techniques merely yield migration times of a sample's components, giving limited structural information.

One of the simplest and most sensitive glycan analysis methods is MALDI-MS, which has detection limits in the femto- to picomole range. In addition, many samples can be analyzed in a single experiment within minutes. MALDI-MS is a soft ionization technique that utilizes an organic matrix to absorb and transfer the ionizing energy from the laser. This technique is useful for many applications, from small molecules to large proteins over 100 kDa. However, sample ionization is sensitive to instrument conditions as well as sample preparation.

In particular, the matrix used to suspend the sample is important for good ionization. The efficiency of a particular matrix can vary widely, depending on the nature of the sample. Multiple matrix preparations were tested, namely caffeic acid (saturated solution in 30% acetonitrile) with or without spermine, and DHB (saturated solution in water) with or without spermine. In addition, several spotting methods were evaluated: spotting 1 µl of sample followed by 1 µl of matrix, spotting matrix followed by sample, or mixing the two before spotting. Whether using the crushed spot method to promote matrix crystallization would improve signal intensity [36] was also investigated. When acquiring the MALDI-MS data, the data collection was optimized by varying instrument parameters such as guide wire voltage, accelerating voltage, grid values, as well as negative vs. positive mode.

To evaluate the MALDI-MS conditions and calibrate the masses, commercially available N-glycan standards (NGA2 and NGA3) were used. In addition, we used RNaseB and ovalbumin as model glycoproteins to determine the effects of sample preparation on spectra quality and to optimize glycan release.

MALDI conditions for N-glycan analysis were optimized using the matrix and sample preparation conditions shown in Table 2. Among the matrix preparations used, DHB with spermine displayed the best results. Typically, spermine is used to allow glycans to be detected in negative mode, but it enhanced the glycan signals even in positive mode. The neutral glycans had poor signals in negative mode. Using the crushed spot method did not make a significant difference in signal intensity.

TABLE 2

Optimization of conditions for MALDI-MS and N-glycan clean-up.

| | Sample | Matrix | Sample info | Results and comments |
|---|---|---|---|---|
| 1. | NGA2, NGA3 | DHB, saturated solution in $H_2O$, 300 mM spermine | 1 µl matrix on plate, add 1 µl sample | Signal okay. Not too much noise |
| 2. | NGA2, NGA3 | DHB, saturated solution in $H_2O$, 300 mM spermine | 1 µl sample on plate, add 1 µl matrix | Better signal than Sample 1 or 3. This method used in all subsequent samples unless otherwise noted. |
| 3. | NGA2, NGA3 | DHB, saturated solution in $H_2O$, 300 mM spermine | Mix sample and matrix, spot 1 µl. | Lower signal than Sample 1 |
| 4. | NGA3 | Caffeic acid, 30% ACN, saturated solution | | Good signal intensity but significant unidentified adduct |
| 5. | NGA3 | Caffeic acid, 30% ACN, 300 mM spermine | | Large unidentified contamination peak |
| 6. | NGA3 | Caffeic acid, 30% ACN | Crushed spot method | Good signal intensity but also more noise than Sample 2 |
| 7. | NGA3 | DHB, saturated solution in $H_2O$ | | Low signal intensity compared to Sample 2 or 5 |
| 8. | NGA3 | DHB, saturated solution in $H_2O$ | Acc voltage 18000, guide wire 0.1%. | Comparable to Sample 7 |
| 9. | NGA3 | DHB, saturated solution in $H_2O$, 300 mM spermine | | Good signal |
| 10. | NGA3 | DHB, saturated solution in $H_2O$, 300 mM spermine | Acc voltage 18000, guide wire 0.1%. | |

TABLE 2-continued

Optimization of conditions for MALDI-MS and N-glycan clean-up.

| | Sample | Matrix | Sample info | Results and comments |
|---|---|---|---|---|
| 11. | NGA3 | DHB, saturated solution in H$_2$O, 300 mM spermine | Negative mode | Very low signal, almost undetectable |
| 12. | 500 µg RNaseB | DHB, saturated solution in H$_2$O, 300 mM spermine | GlycoS | Some high mannose peaks, many unidentified peaks |
| 13. | 500 µg RNaseB | DHB, saturated solution in H$_2$O, 300 mM spermine | AG50W X-8 Column and batch mode | Both spots spread a lot, no signal |
| 14. | 500 µg RNaseB | DHB, saturated solution in H$_2$O, 300 mM spermine | Glyco R | Spot does not dry properly |
| 15. | 500 µg RNaseB | DHB, saturated solution in H$_2$O, 300 mM spermine | Glyco H (200 mg) | Good signal, Man-5 through Man-9 |
| 16. | 500 µg Ovalbumin | DHB, saturated solution in H$_2$O, 300 mM spermine | Glyco H (200 mg) | Good signal, 30 peaks that match published reports |
| 17. | 10 µg RNaseB or ovalbumin | DHB, saturated solution in H$_2$O, 300 mM spermine | Glyco H (25 mg) | Spots spread, mostly contamination peaks in 1000-1300 Da range. Probably detergent. |
| 18. | 50 µg RNaseB | DHB, saturated solution in H$_2$O, 300 mM spermine | Glyco H (25 mg) | Spot spreads a lot, significant detergent contamination peaks. |
| 19. | 15 µg RNaseB | DHB, saturated solution in H$_2$O, 300 mM spermine | Glyco H (200 mg) | Good signal, very slight contamination that does not interfere with signal. GlycoH column used for future experiments. |
| 20. | 150 µg RNaseB | DHB, saturated solution in H$_2$O, 300 mM spermine | Glyco H (200 mg) | Good signal, very clean |

Using commercially available glycans and known protein standards, it was determined that the optimal method for purifying glycans after PNGaseF release was to use Glyco-Clean H cartridges containing 200 mg of the stationary material. This method allowed resulted in MALDI-MS spectra of N-glycans from RNaseB and ovalbumin that were consistent with published reports. The ion exchange resin did not remove all the detergents from the sample, causing the sample spots to spread on the MALDI-MS target and not crystallize properly. GlycoClean R, on the other hand, removed detergents but did not completely remove salt, which subsequently interfered with matrix crystallization and spectra quality. GlycoClean S yielded acceptable sample spots on the MALDI-MS target, but failed to remove all contamination.

FIG. 5 shows spectra of some of the representative RNaseB samples from Table 2, with glycans purified under different conditions. In the cleanest samples, all glycan masses correspond with high mannose structures (Man-5 through Man-9).

Figure 6:
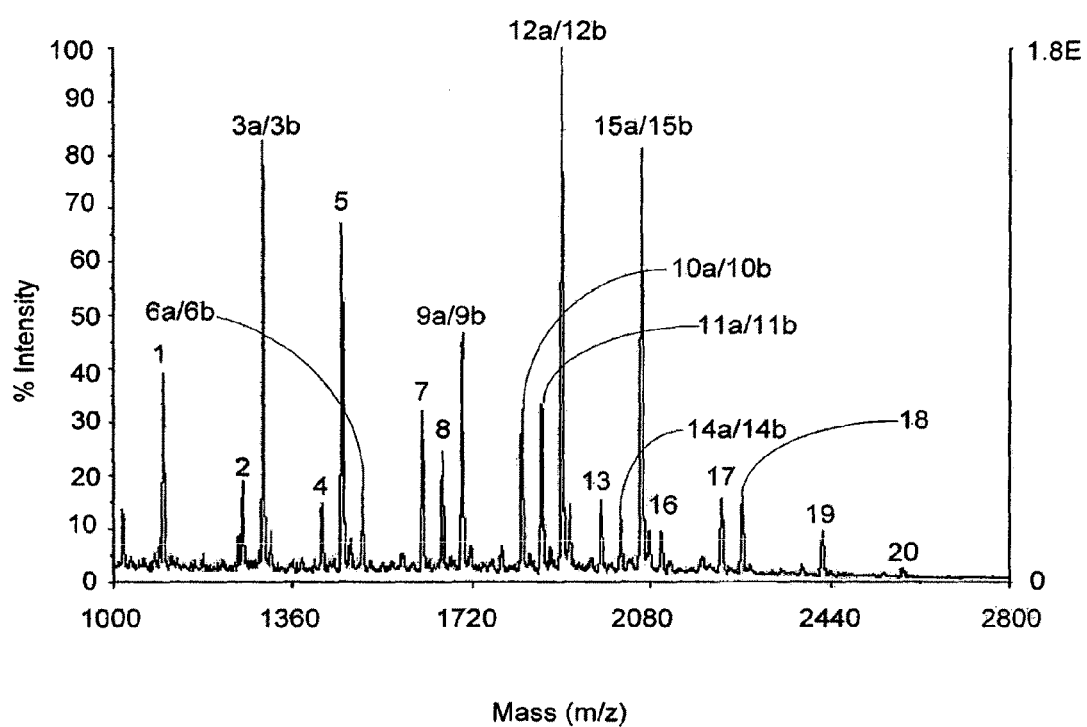
FIG. 6 shows the spectra from MALDI-MS of N-glycans from ovalbumin. Each labeled peak corresponds to a previously reported structure listed in Table 3.
Figure 7A:
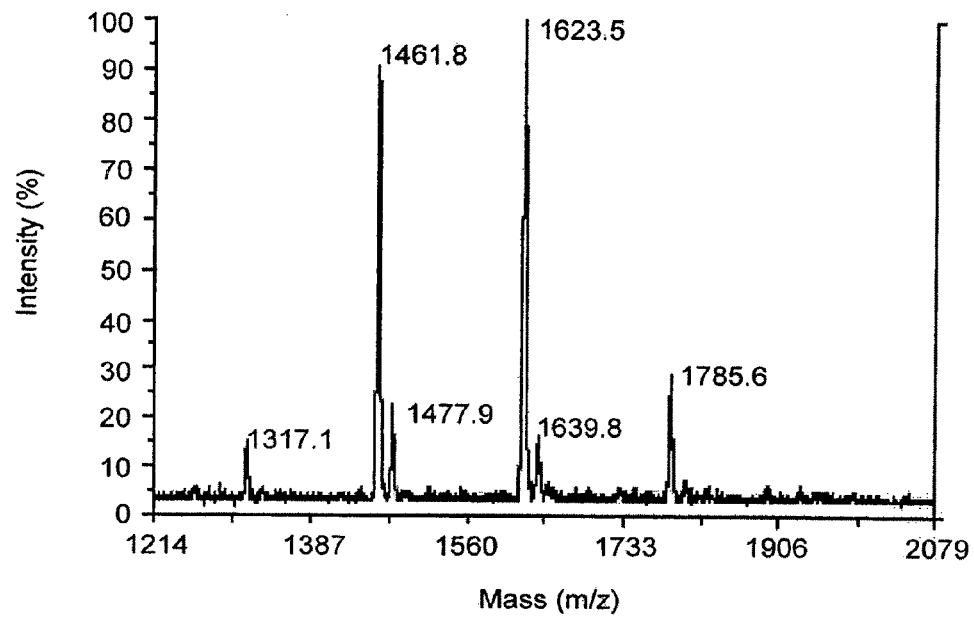
FIGS. 7A and 7B are for samples from Applikon bioreactors, with DO=50%, pH=7 and DO=90%, pH uncontrolled, respectively.
Figure 7B:
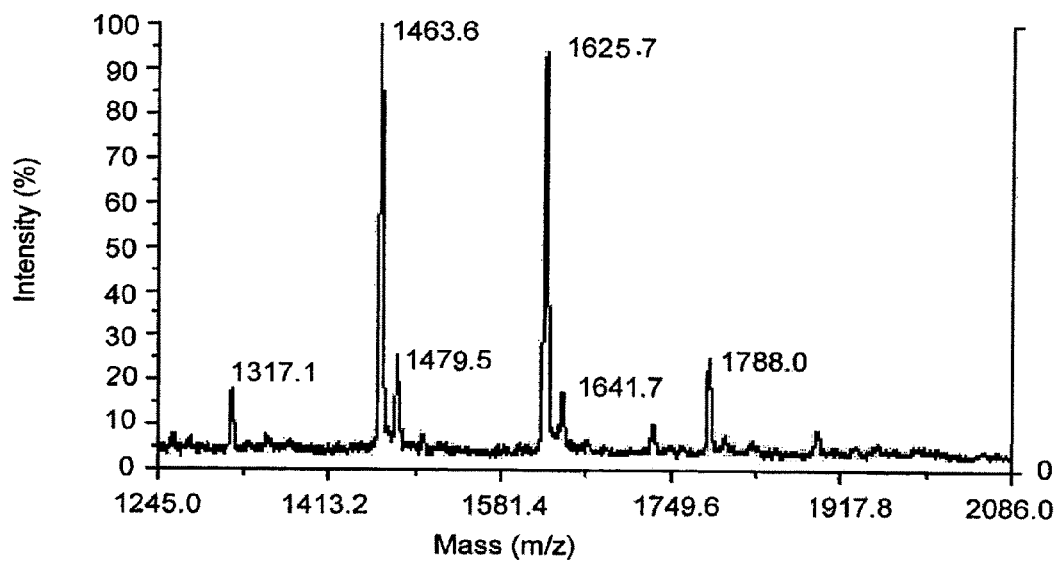
Figure 7C:
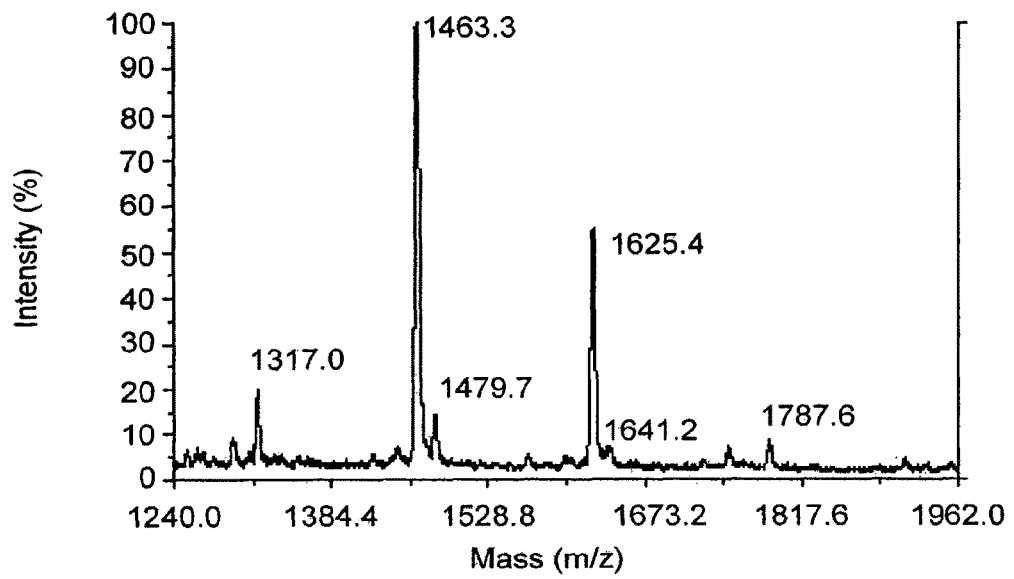
FIGS. 7C-7E are for samples from Wave reactors.
Figure 7D:
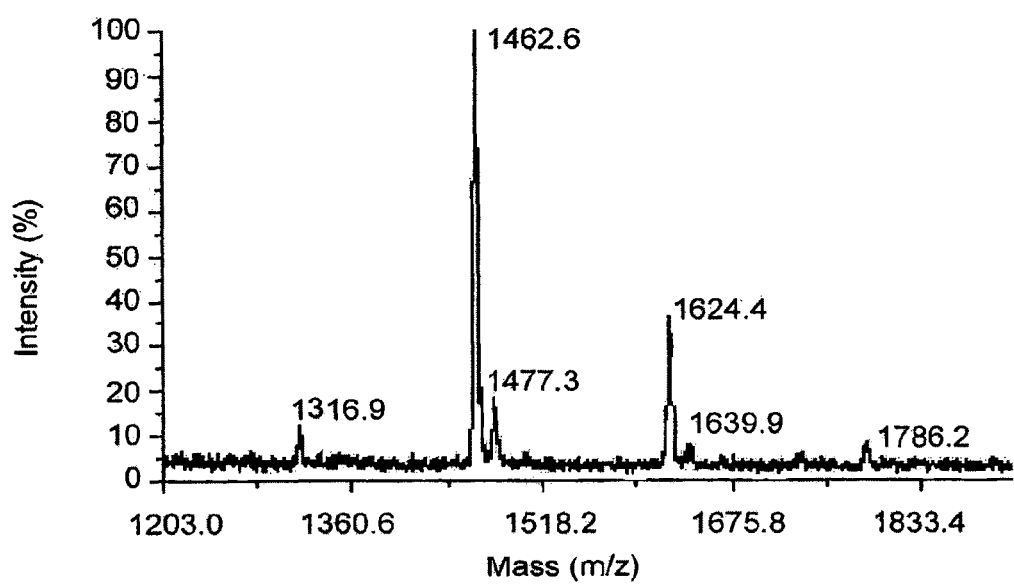
Figure 7E:
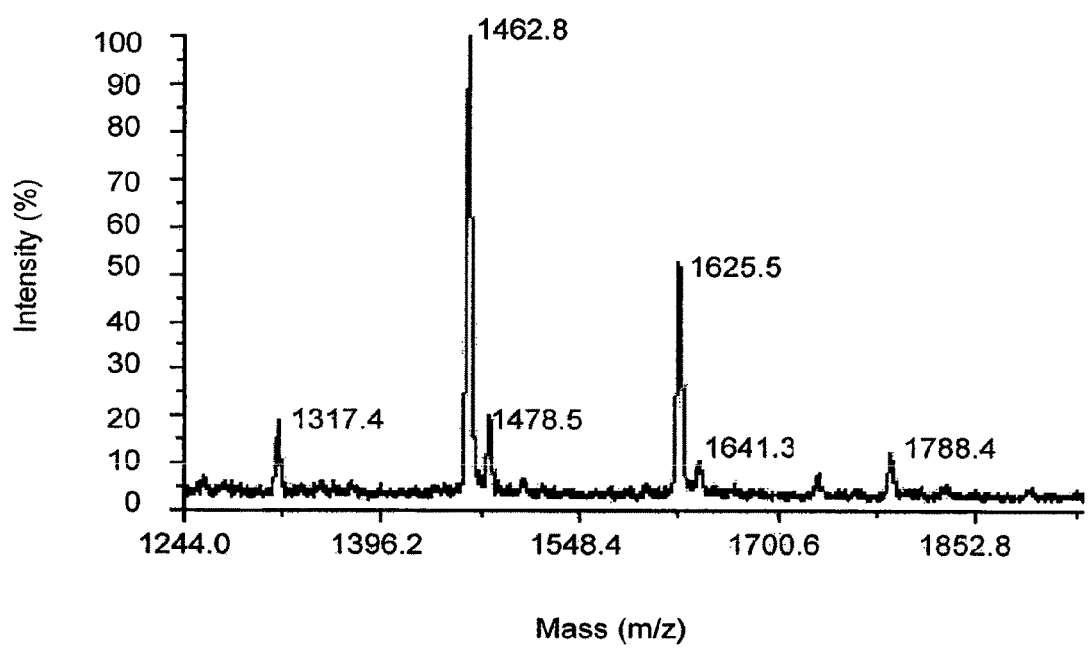

To validate the reproducibility of the method, ovalbumin was used as a protein standard with complex type N-glycans. Optimized purification and MALDI-MS conditions were used (Glyco H 200 mg, DHB matrix with spermine). The MALDI-MS data displayed results comparable to previously published reports [30]. FIG. 6 shows the MALDI-MS spectrum of ovalbumin glycans, and Table 3 lists the observed peaks and their structures.

TABLE 3

N-glycan structures from ovalbumin (Harvey et al, 2000)

| Peak | Structure | Theoretical Mass |
|---|---|---|
| 1 | GlcNAcβ1——?——[Manα1→6, Manα1→3]Manβ1——4GlcNAcβ1——4GlcNAc | 1136.4 |
| 2 | Manα1——3(6)Manα1→6Manβ1——4GlcNAcβ1——4GlcNAc; GlcNAcβ1——2Manα1→3 | 1298.5 |
| 3a | Manα1→6[GlcNAcβ1——4]Manβ1——4GlcNAcβ1——4GlcNAc; GlcNAcβ1——2Manα1→3 | 1339.5 |

TABLE 3-continued

N-glycan structures from ovalbumin (Harvey et al, 2000)

| Peak | Structure | Theoretical Mass |
|---|---|---|
| 3b | GlcNAcβ1——2Manα1\ <br>　　　　　　　　　＼6 <br>　　　　GlcNAcβ1——4Manβ1——4GlcNAcβ1——4GlcNAc <br>　　　　　　　　　／3 <br>　　　　　　　Manα1 | 1339.5 |
| 4 | Manα1\ <br>　　　＼6 <br>　　　　Manα1\ <br>Manα1／3　　＼6 <br>　　　　　　　Manβ1——4GlcNAcβ1——4GlcNAc <br>　　　　　　／3 <br>GlcNAcβ1——2Manα1 | 1460.5 |
| 5 | GlcNAcβ1——3Manα1\ <br>　　　　　　　　　＼6 <br>　　　　GlcNAcβ1——4Manβ1——4GlcNAcβ1——4GlcNAc <br>　　　　　　　　　／3 <br>GlcNAcβ1——2Manα1 | 1501.5 |
| 6a | 　　　　　　　Manα1\ <br>　　　　　　　　　＼6 <br>GlcNAcβ1\GlcNAcβ1——4Manβ1——4GlcNAcβ1——4GlcNAc <br>　　　　4　　　　　／3 <br>　　　　　Manα1 <br>　　　　／2 <br>GlcNAcβ1 | 1542.6 |
| 6b | GlcNAcβ1——2Manα1\ <br>　　　　　　　　　＼6 <br>　　　　GlcNAcβ1——4Manβ1——4GlcNAcβ1——4GlcNAc <br>　　　　　　　　　／3 <br>GlcNAcβ1——2Manα1 | 1542.6 |
| 7 | Manα1\ <br>　　　＼6 <br>　　　　Manα1\ <br>Manα1／　GlcNAcβ1——4Manβ1——4GlcNAcβ1——4GlcNAc <br>　　　　　　　　　／3 <br>GlcNAcβ1——2Manα1 | 1663.6 |
| 8 | 　　Manα1——3Manα1\ <br>　　　　　　　　　＼6 <br>GlcNAcβ1\GlcNAcβ1——4Manβ1——4GlcNAcβ1——4GlcNAc <br>　　　　4　　　　　／3 <br>　　　　　Manα1 <br>　　　　／2 <br>GlcNAcβ1 | 1704.6 |
| 9a | GlcNAcβ1——2Manα1\ <br>　　　　　　　　　＼6 <br>GlcNAcβ1\GlcNAcβ1——4Manβ1——4GlcNAcβ1——4GlcNAc <br>　　　　4　　　　　／3 <br>　　　　　Manα1 <br>　　　　／2 <br>GlcNAcβ1 | 1745.6 |
| 9b | GlcNAcβ1\ <br>　　　　＼6 <br>　　　　　Manα1\ <br>　　　　／2　　＼6 <br>GlcNAcβ1／GlcNAcβ1——4Manβ1——4GlcNAcβ1——4GlcNAc <br>　　　　　　　　　／3 <br>GlcNAcβ1——2Manα1 | 1745.6 |

TABLE 3-continued

N-glycan structures from ovalbumin (Harvey et al, 2000)

| Peak | Structure | Theoretical Mass |
|---|---|---|
| 10a | Manα1→6Manα1, Manα1→3, GlcNAcβ1→6Manβ1→4GlcNAcβ1→4GlcNAc, GlcNAcβ1→4Manα1, GlcNAcβ1→2 | 1866.7 |
| 10b | Manα1→3Manα1→6Manβ1→4GlcNAcβ1→4GlcNAc, Galβ1→4GlcNAcβ1→GlcNAcβ1→4Manα1, GlcNAcβ1→2 | 1866.7 |
| 11a | Galβ1→4 [GlcNAcβ1→6Manα1, GlcNAcβ1→GlcNAcβ1→4Manβ1→4GlcNAcβ1→4GlcNAc, GlcNAcβ1→2Manα1] | 1907.7 |
| 11b | Galβ1→4 [GlcNAcβ1→2Manα1→6Manβ1→4GlcNAcβ1→4GlcNAc, GlcNAcβ1→GlcNAcβ1→4Manα1, GlcNAcβ1→2] | 1907.7 |
| 12a | GlcNAcβ1→6Manα1, GlcNAcβ1→4, GlcNAcβ1→2, GlcNAcβ1→GlcNAcβ1→4Manβ1→4GlcNAcβ1→4GlcNAc, GlcNAcβ1→2Manα1→3 | 1948.7 |
| 12b | GlcNAcβ1→4,6 Manα1, GlcNAcβ1→2, GlcNAcβ1→4Manβ1→4GlcNAcβ1→4GlcNAc, GlcNAcβ1→4Manα1, GlcNAcβ1→2 | 1948.7 |
| 13 | Manα1→6Manα1, Manα1→3, GlcNAcβ1→4Manβ1→4GlcNAcβ1→4GlcNAc, Galβ1→4GlcNAcβ1→4Manα1, GlcNAcβ1→2 | 2028.7 |

TABLE 3-continued
N-glycan structures from ovalbumin (Harvey et al, 2000)
| Peak | Structure | Theoretical Mass |
|---|---|---|
| 14a | 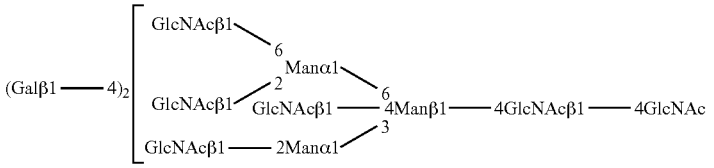 | 2069.7 |
| 14b | 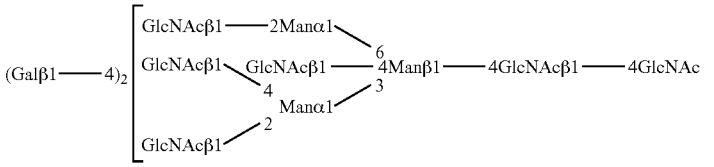 | 2069.7 |
| 15a | 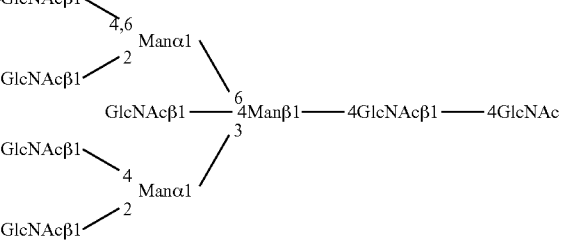 | 2110.8 |
| 15b | 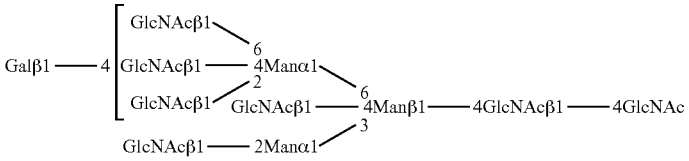 | 2110.8 |
| 16 | 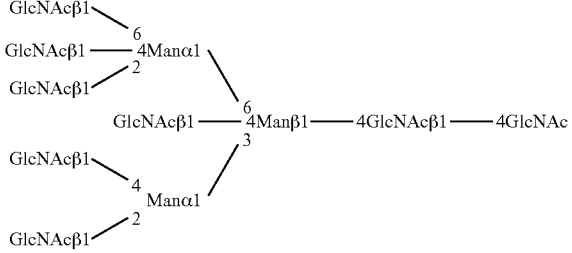 | 2151.8 |
| 17 | 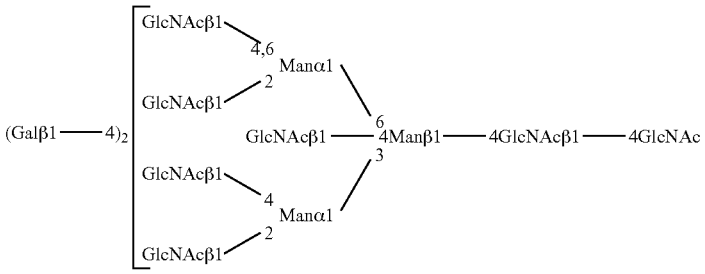 | 2272.8 |

TABLE 3-continued

N-glycan structures from ovalbumin (Harvey et al, 2000)

| Peak | Structure | Theoretical Mass |
|---|---|---|
| 18 | 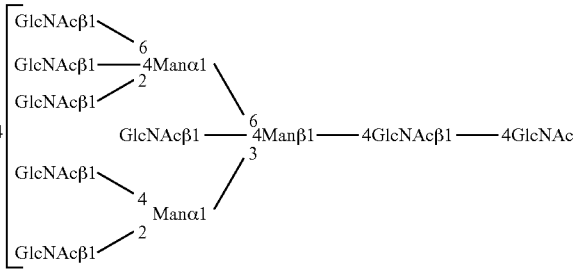 | 2313.9 |
| 19 | 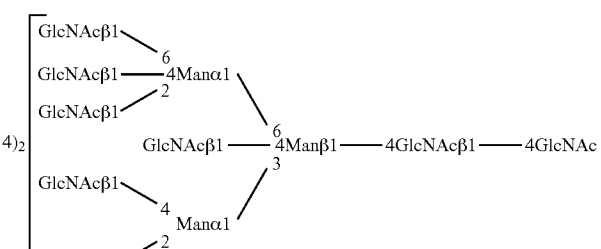 | 2475.9 |
| 20 | 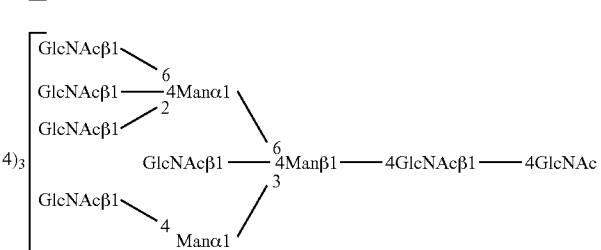 | 2638.0 |

MALDI-MS Analysis of N-Glycans from Antibodies Produced in Applikon and Wave Reactors Two antibody samples produced by mouse-mouse hybridoma cells (Biokit S A, Barcelona, Spain) grown in an Applikon stirred tank reactor (STR) were analyzed, along with three samples produced in Wave reactors. The reactor conditions used are shown in Table 4.

TABLE 4

Reactor conditions used to produce antibody samples.

| Sample | Reactor Type | DO | pH | Other |
|---|---|---|---|---|
| 1 | Applikon STR | 50% | 7 | |
| 2 | Applikon STR | 90% | Not controlled | |
| 3 | Wave | Controlled | Not controlled | |
| 4 | Wave | Controlled | 7 | NaHCO$_3$ for pH control |
| 5 | Wave | Not controlled | 7 | Fresh media for pH control |

In the Applikon STR reactor, pH can be controlled automatically by the instrument, which dispenses $CO_2$, $NaHCO_3$ and $O_2$ as needed. In the Wave reactor, however, measurements must be taken manually and pH adjusted by hand. The pH in this reactor can be controlled by either adding fresh media as the cells grow, or adding $NaHCO_3$ for increased buffering capacity, and $CO_2$ as needed. The main difference between the reactor types is the mode of agitation. In the Applikon STR, a blade stirrer keeps the cell suspension in motion, while a sparger introduces oxygen to the system in a controlled manner. In the Wave reactor, a rocking motion generates waves that mix the components of the system and aids the transfer of oxygen and other gases into the system.

Figure 8:
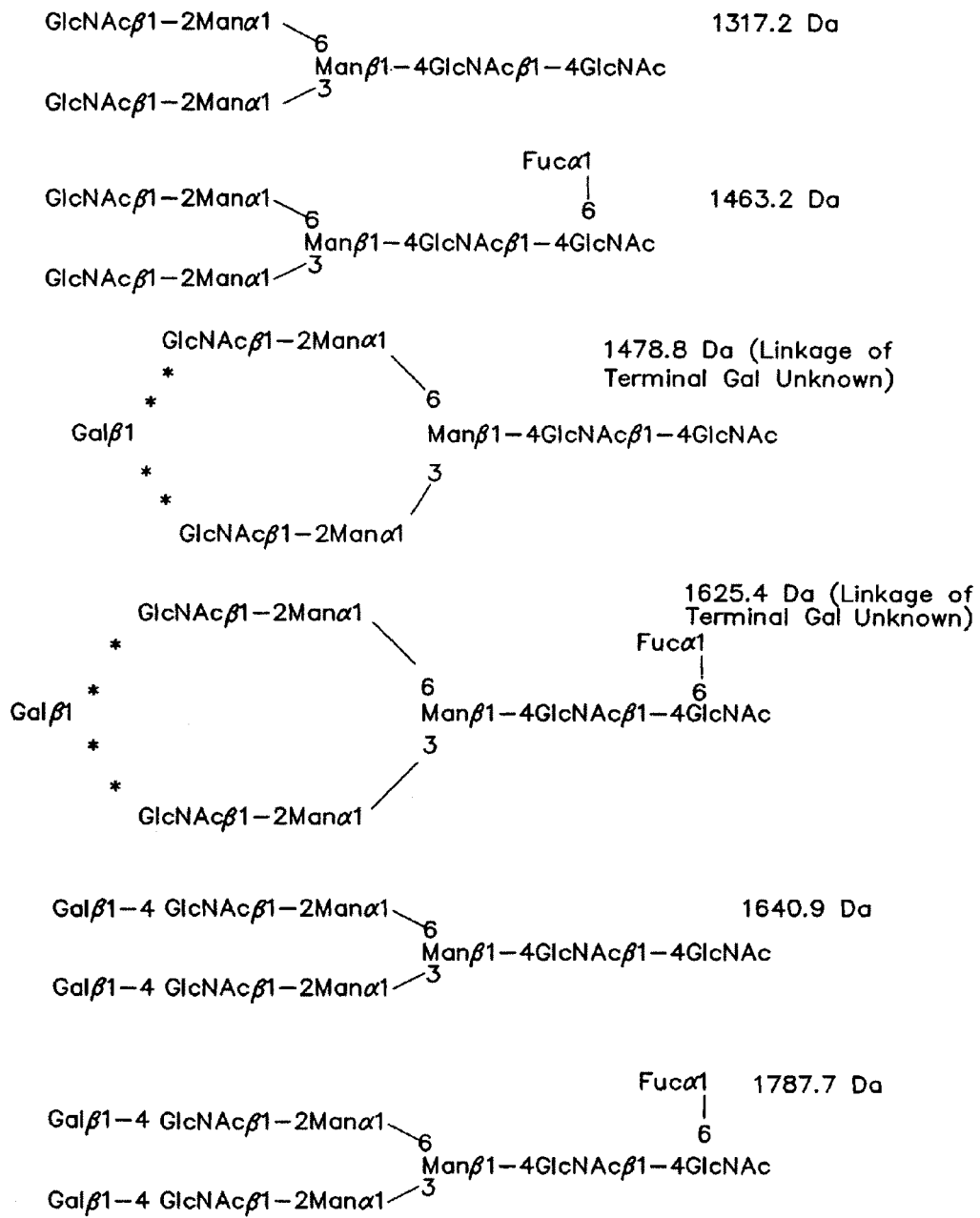
FIG. 8 shows the structures and theoretical masses of N-glycans released from antibodies.

The purified antibodies were processed according to the optimized method described above. For each sample, 100 μg of protein was used as the starting material. Both positive and negative ion modes were used in the MALDI-MS to determine whether there were charged sugars present. No signal was observed in the negative mode, indicating that only neutral sugars were obtained from the antibodies. The positive ion mode MALDI-MS data of the five antibody samples are shown in FIG. 7. Glycoproteins produced using different conditions are shown in Table 4. All fractions contained the same six glycans at 1317 Da, 1463 Da, 1478 Da, 1625 Da, 1641 Da and 1787 Da. The structures corresponding to these peaks are shown in FIG. 8 with their theoretical masses.

These results indicate that the production method did not significantly alter the occurrence of the glycans; rather, the ratios between glycans seemed to be affected. Notably, samples prepared in the Wave reactor had a lower amount of the 1625.4 Da glycan with respect to the other glycans, as well as significant reductions in the relative peak heights at 1640.9 and 1787.7 Da. Altering the culture conditions within a reactor type did not affect the relative abundance of the N-glycans.

While the exact mechanisms for producing these changes are not known, it is interesting that the largest changes occurred due to reactor type, not reactor conditions such as pH, DO or media composition. In previous studies, pH above 7.2 was shown to affect glycosylation composition [28]. However, for the two samples in this study with pH uncontrolled, the pH was between 6.8 and 7.2 throughout the culture period. Studies of DO effects on glycosylation demonstrated the largest differences at extremes (10% or 190%) [26], while the samples studied here were produced under moderate DO conditions (between 50% and 90%). Because the Applikon STR and the Wave reactors differ most in their method of agitation, reactor configuration is therefore the most likely source of glycan variation.

Differences in protein glycosylation have been linked to shear stress, as can be generated by the stirring blade or the gas sparger in an STR reactor. However, the turbulence created in the Wave reactor also generates shear stress. One hypothesis for the shear stress effect is that cells must increase their overall protein production in response to membrane and/or cytoskeletal damage. As a consequence, the biosynthetic enzymes for glycosylation are diverted away from the protein of interest [27].

Although most observed parameters, including total antibody production, were similar in Applikon STR and Wave cultures, cells from the Wave reactor had slight increases in metabolic rates. Changes in cell metabolism may yield effects similar to those caused by shear stress, as all glycoproteins synthesized in the cell must compete for the same machinery in the ER and golgi.

Example 1

References

1. Hirschberg, C. B., Snider, M. D. (1987) Topography of glycosylation in the rough endoplasmic reticulum and Golgi apparatus. *Annu Rev Biochem* 56, 63-87.
2. Bause, E. (1983) Structural requirements of N-glycosylation of proteins. Studies with proline peptides as conformational probes. *Biochem J* 209, 331-6.
3. Marshall, R. D. (1972) Glycoproteins. *Annu Rev Biochem* 41, 673-702.
4. Dwek, R. A. (1996) Glycobiology: Toward Understanding the Function of Sugars. *Chem. Rev* 96, 683-720.
5. O'Connor, S. E., Imperiali, B. (1996) Modulation of protein structure and function by asparagine-linked glycosylation. *Chem Biol* 3, 803-12.
6. Crocker, P. R., Varki, A. (2001) Siglecs in the immune system. *Immunology* 103, 137-45.
7. Helenius, A., Aebi, M. (2001) Intracellular functions of N-linked glycans. *Science* 291, 2364-9.
8. Imperiali, B., O'Connor, S. E. (1999) Effect of N-linked glycosylation on glycopeptide and glycoprotein structure. *Curr Opin Chem Biol* 3, 643-9.
9. Furukawa, K., Takamiya, K., Okada, M., Inoue, M., Fukumoto, S. (2001) Novel functions of complex carbohydrates elucidated by the mutant mice of glycosyltransferase genes. *Biochim Biophys Acta* 1525, 1-12.
10. Jaeken, J., Matthijs, G. (2001) Congenital disorders of glycosylation. *Annu Rev Genomics Hum Genet.* 2, 129-51.
11. Freeze, H. H., Aebi, M. (1999) Molecular basis of carbohydrate-deficient glycoprotein syndromes type I with normal phosphomannomutase activity. *Biochim Biophys Acta* 1455, 167-78.
12. Carchon, H., Van Schaftingen, E., Matthijs, G., Jaeken, J. (1999) Carbohydrate-deficient glycoprotein syndrome type IA (phosphomannomutase-deficiency). *Biochim Biophys Acta* 1455, 155-65.
13. Powell, L. D., Sgroi, D., Sjoberg, E. R., Stamenkovic, I., Varki, A. (1993) Natural ligands of the B cell adhesion molecule CD22 beta carry N-linked oligosaccharides with alpha-2,6-linked sialic acids that are required for recognition. *J Biol Chem* 268, 7019-27.
14. Sgroi, D., Varki, A., Braesch-Andersen, S., Stamenkovic, I. (1993) CD22, a B cell-specific immunoglobulin superfamily member, is a sialic acid-binding lectin. *J Biol Chem* 268, 7011-8.
15. Karlsson, K. A. (1998) Meaning and therapeutic potential of microbial recognition of host glycoconjugates. *Mol Microbiol* 29, 1-11.
16. Pritchett, T. J., Brossmer, R., Rose, U., Paulson, J. C. (1987) Recognition of monovalent sialosides by influenza virus H3 hemagglutinin. *Virology* 160, 502-6.
17. Sears, P., Wong, C. H. (1998) Enzyme action in glycoprotein synthesis. *Cell Mol Life Sci* 54, 223-52.
18. Varki, A. (1999) *Essentials of glycobiology*. Cold Spring Harbor Laboratory Press, Cold Spring Harbor, N.Y.
19. Parodi, A. J. (2000) Protein glucosylation and its role in protein folding. *Annu Rev Biochem* 69, 69-93.
20. Chang, G. D., Chen, C. J., Lin, C. Y., Chen, H. C., Chen, H. (2003) Improvement of glycosylation in insect cells with mammalian glycosyltransferases. *J Biotechnol* 102, 61-71.
21. Perlman, S., van den Hazel, B., Christiansen, J., Gram-Nielsen, S., Jeppesen, C. B., Andersen, K. V., Halkier, T., Okkels, S., Schambye, H. T. (2003) Glycosylation of an N-terminal extension prolongs the half-life and increases the in vivo activity of follicle stimulating hormone. *J Clin Endocrinol Metab* 88, 3227-35.
22. Darling, R. J., Kuchibhotla, U., Glaesner, W., Micanovic, R., Witcher, D. R., Beals, J. M. (2002) Glycosylation of erythropoietin affects receptor binding kinetics: role of electrostatic interactions. *Biochemistry* 41, 14524-31.
23. Krapp, S., Mimura, Y., Jefferis, R., Huber, R., Sondermann, P. (2003) Structural analysis of human IgG-Fc glycoforms reveals a correlation between glycosylation and structural integrity. *J Mol Biol* 325, 979-89.
24. Raju, T. S., Briggs, J. B., Borge, S. M., Jones, A. J. (2000) Species-specific variation in glycosylation of IgG: evidence for the species-specific sialylation and branch-specific galactosylation and importance for engineering recombinant glycoprotein therapeutics. *Glycobiology* 10, 477-86.
25. Kunkel, J. P., Jan, D. C., Butler, M., Jamieson, J. C. (2000) Comparisons of the glycosylation of a monoclonal antibody produced under nominally identical cell culture conditions in two different bioreactors. *Biotechnol Prog* 16, 462-70.
26. Zhang, F., Saarinen, M. A., Itle, L. J., Lang, S. C., Murhammer, D. W., Linhardt, R. J. (2002) The effect of dissolved oxygen (DO) concentration on the glycosylation of recombinant protein produced by the insect cell-baculovirus expression system. *Biotechnol Bioeng* 77, 219-24.
27. Senger, R. S., Karim, M. N. (2003) Effect of Shear Stress on Intrinsic CHO Culture State and Glycosylation of Recombinant Tissue-Type Plasminogen Activator Protein. *Biotechnol Prog* 19, 1199-209.

28. Muthing, J., Kemminer, S. E., Conradt, H. S., Sagi, D., Nimtz, M., Karst, U., Peter-Katalinic, J. (2003) Effects of buffering conditions and culture pH on production rates and glycosylation of clinical phase I anti-melanoma mouse IgG3 monoclonal antibody R24. *Biotechnol Bioeng* 83, 321-34.
29. Joao, H. C., Dwek, R. A. (1993) Effects of glycosylation on protein structure and dynamics in ribonuclease B and some of its individual glycoforms. *Eur J Biochem* 218, 239-44.
30. Harvey, D. J., Wing, D. R., Kuster, B., Wilson, I. B. (2000) Composition of N-linked carbohydrates from ovalbumin and co-purified glycoproteins. *J Am Soc Mass Spectrom* 11, 564-71.
31. Patel, T., Bruce, J., Merry, A., Bigge, C., Wormald, M., Jaques, A., Parekh, R. (1993) Use of hydrazine to release in intact and unreduced form both N- and O-linked oligosaccharides from glycoproteins. *Biochemistry* 32, 679-93.
32. Tarentino, A. L., Plummer, T. H., Jr., Maley, F. (1974) The release of intact oligosaccharides from specific glycoproteins by endo-beta-N-acetylglucosaminidase H. *J Biol Chem* 249, 818-24.
33. Tarentino, A. L., Maley, F. (1974) Purification and properties of an endo-beta-N-acetylglucosaminidase from *Streptomyces griseus*. *J Biol Chem* 249, 811-7.
34. Tarentino, A. L., Gomez, C. M., Plummer, T. H., Jr. (1985) Deglycosylation of asparagine-linked glycans by peptide: N-glycosidase F. *Biochemistry* 24, 4665-71.
35. Hu, G. F. (1995) Fluorophore-assisted carbohydrate electrophoresis technology and applications. *J Chromatogr A* 705, 89-103.
36. Rhomberg, A. J., Ernst, S., Sasisekharan, R., Biemann, K. (1998) Mass spectrometric and capillary electrophoretic investigation of the enzymatic degradation of heparin-like glycosaminoglycans. *Proc Natl Acad Sci USA* 95, 4176-81.

Example 2

Profiling of N-Glycans from Human Serum

Materials and Methods
Cleavage of N-Glycans from Serum Glycoproteins (Reduction/Carboxymethylation Method)

Human male normal serum samples were obtained from IMPATH (Franklin, Mass.) and Biomedical Resources (Hatboro, Pa.), and stored at −85° C. For each experiment, 50 µl of serum was used to harvest N-glycans. Serum samples were first diluted 1:4 with water, then DTT was added to a final concentration of 80 mM. After incubation for 30 minutes at 37° C., iodoacetic acid was added to a final concentration of 400 mM and incubated for 1 hour more at 37° C. The sample was dialyzed against 10 mM Tris acetate pH 8.3 overnight and concentrated to ~200 µl in a spin column with a 3000 Da MWCO filter. To cleave the sugars from the protein, 5 µl (1,000 U) of PNGaseF (New England Biolabs, Beverly, Mass.) was added and allowed to react overnight at 37° C.
Purification of N-Glycans After glycans were cleaved from the protein, the sample was dialyzed against water to remove excess salts and glycerol (from PNGaseF formulation). Samples were then spun for 5 minutes at 6000×g to remove most proteins and the supernatant lyophilized to <500 µl. A C18 cartridge (Waters Corporation, Milford, Mass.) was primed with 3 ml methanol, then 3 ml water, and 3 ml 5% acetonitrile with 0.1% TFA. The supernatant from the spun down sample was applied to the cartridge, and 3 ml of 5% acetonitrile with 0.1% TFA was added to elute the glycans, while unwanted proteins were retained on the column.

GlycoClean H cartridges (Prozyme, formerly Glyko) were first primed with 3 ml 1M NaOH, 3 ml $H_2O$, 3 ml 30% acetic acid, and 3 ml $H_2O$ to clean the column of any impurities. Then the cartridges were washed with 3 ml Solution A (50% acetonitrile, 0.1% TFA), 6 ml Solution B (5% acetonitrile, 0.1% TFA), and 3 ml of water. Glycan samples were loaded in a minimal volume of water (<100 µl), and the column was washed with 3 ml $H_2O$ followed by 3 ml Solution B. Neutral glycans were eluted with 3 ml of 15% acetonitrile, 0.1% TFA, and acidic glycans were eluted with 3 ml of Solution A. For the trials with glycan standards, the six glycans listed in Table 5 were mixed in equimolar amounts (1 µl of 100 µM each), and the mixture was applied to the GlycoClean H cartridge and processed as described above. Each fraction was dried, then redissolved in 40 µl $H_2O$ for MALDI-MS analysis. All MALDI-MS spectra were calibrated using the six glycan standards in Table 5. Separate calibration files were used for positive and negative modes.
Fractionation of Serum Proteins Concanavalin A-agarose beads were purchased from Vector Laboratories (Burlingame, Calif.). To prepare the column, 3 ml ConA-agarose slurry was washed with ConA buffer (20 mM Tris, 1 mM $MgCl_2$, 1 mM $CaCl_2$, 500 mM NaCl, pH 7.4). Before loading, 500 µl of serum was mixed with 150 µl of 5×ConA buffer. After washing with 3 ml ConA buffer, glycoproteins were eluted with 2 ml of 500 mM α-methyl-mannoside and dialyzed against 10 mM phosphate pH 7.2 overnight at 4° C.

Protein A-agarose beads were purchased from Calbiochem (La Jolla, Calif.). Before use, 1 ml beads were washed 3× with PBS. To separate IgG from other serum proteins, samples were diluted 1:4 with PBS and incubated with protein A-agarose overnight at 4° C. Non-IgGs were collected by loading the slurry into a column and washing with 2 ml PBS. IgGs were eluted with 2 ml of 0.2M glycine pH 2.5 and neutralized in 200 µl Tris-HCl, pH 6.3.
SDS-PAGE and Glycoblotting of Serum Samples Protein samples were prepared for SDS-PAGE by diluting 1:1 with 2× denaturing buffer (40 µg/ml SDS, 20% glycerol, 30 µg/ml DTT and 10 µg/ml bromophenol blue in 125 mM Tris, pH 6.8), and boiling for 2 min. Pre-cast Nu-PAGE 10% Bis-Tris protein gels were obtained from Invitrogen (Carlsbad, Calif.). Each lane was loaded with a maximum of 10 µl of sample, and run for 50 min at 200V. After electrophoresis was complete, the gel was stained with Invitrogen SafeStain (1 hour in staining solution, then washed overnight with water).

The GlycoTrack glycoprotein detection kit was obtained from Prozyme (formerly Glyko). All reagents except buffers were supplied with the kit. Two methods were attempted—either biotinylating glycoproteins after blotting (a) or before blotting (b). For both methods, samples were first diluted 1:1 with 200 mM sodium acetate buffer, pH 5.5. The membrane was blocked by incubating overnight at 4° C. with blocking reagent, then washed 3×10 minutes with TBS.

For method (a), samples were denatured with SDS sample buffer, and subjected to SDS-PAGE and blotting to nitrocellulose. After washing the membrane with PBS, the proteins were oxidized with 10 ml of 10 mM sodium periodate in the dark at room temperature for 20 minutes. The membrane was washed 3 times with PBS, and 2 µl of biotin-hydrazide reagent was added in 10 ml of 100 mM sodium acetate, 2 mg/ml EDTA for 60 minutes at room temperature. After 3 washes with TBS, the membrane was blocked overnight at 4°

C. with blocking reagent. Before adding 5 µl of streptavidin-alkaline phosphatase (S-AP) conjugate, the membrane was washed again with TBS. The S-AP was allowed to incubate for 60 minutes at room temperature, and excess was washed off with TBS. To develop the blot, 50 µl of nitro blue tetrazolium (50 mg/ml) and 37.5 µl of 5-bromo-4-chloro-3-indolyl phosphate p-toluidine (50 mg/ml) were added in 10 ml TBS, 10 mg/ml $MgCl_2$. After 60 minutes, the blot was washed with distilled water and allowed to air dry.

In method (b), 20 µl of sample was mixed with 10 µl of 10 mM periodate in 100 mM sodium acetate, 2 mg/ml EDTA and incubated in the dark at room temperature for 20 minutes.

To destroy excess periodate 10 µl of a 12.5 mg/ml sodium bisulfite solution in 200 mM NaOAc, pH 5.5 was added for 5 minutes at room temperature. Biotinylation was performed by adding 5 µl of biotin amidocaproyl hydrazide solution in DMF. After incubating at room temperature for 60 minutes, the sample was mixed with SDS denaturing buffer and boiled for 2 minutes. Samples were run on SDS-PAGE gels as described above, then transferred to a nitrocellulose membrane (2 hrs, 30V). At this point, blocking and developing steps were identical to method (a).

Chemical Modification of N-Glycans

For permethylation, glycans in water were placed in a round-bottomed flask and lyophilized overnight. A slurry of NaOH in DMSO (0.5 ml) was added to the glycan sample, along with 0.5 ml methyl iodide and incubated for 15 minutes. The sample was then diluted with water and extracted 2× with $CHCl_3$, collecting the organic phase. After drying the organic phase with $MgSO_4$, it was filtered through glass wool and dried under vacuum. Samples were then redissolved in methanol for MALDI-MS analysis.

To conjugate N-glycans to synthetic aminooxyacetyl peptide, glycans were dried and resuspended in aqueous peptide solution (240 µM). After adding 1 µl of 500 mM NaOAc pH 5.5 and 20 µl of acetonitrile, the sample was incubated overnight at 40° C. Before MALDI-MS analysis, glycopeptides were purified by C18, 0.6 µl bed ZipTip (Millipore, Billerica, Mass.). Specifically, the tip was washed with 50 of 100% acetonitrile, followed by water and 5% acetonitrile, 0.1% TFA. To load the sample, 2 µl of sample was drawn into the tip, and discarded after 5 seconds. After washing 3× with 5 µl $H_2O$, glycopeptides were eluted with 10% acetonitrile.

PNGaseF Digestion on PVDF Membrane

PVDF-coated wells in a 96-well plate were washed with 200 µl MeOH, 3×200 µl $H_2O$ and 200 µl RCM buffer (8M urea, 360 mM Tris, 3.2 mM EDTA, pH 8.3). The protein samples (50 µl) were then loaded in the wells along with 300 µl RCM buffer. After washing with wells two times with fresh RCM buffer, 500 µl of 0.1M DTT in RCM buffer was added for 1 hr at 37° C. To remove the excess DTT, the wells were washed three times with $H_2O$. For the carboxymethylation, 500 µl of 0.1M iodoacetic acid in RCM buffer was added for 30 minutes at 37° C. in the dark. The wells were washed again with water, then the membrane was blocked with 1 ml polyvinylpyrrolidone (360,000 AMW, 1% solution in $H_2O$) for 1 hr at room temperature. Before adding the PNGaseF, the wells were washed again with water. To release the glycans, 4 µl of PNGaseF was added in 3000 of 50 mM Tris, pH 7.5 and incubated overnight at 37° C. Released glycans were pipetted from the wells and purified by C18 and GlycoClean H as described above.

Results

Building on the work with single protein systems, the purpose of this study was to isolate and purify N-glycans from human serum, generating a total N-glycan profile. Serum was chosen as the diagnostic medium because many disease markers are released into circulation[16, 17], and obtaining serum is a relatively simple procedure.

Before being able to develop a method to study N-glycans from serum, it was important to understand the types of molecules present. Proteins comprise an enormous portion of serum, approximately 7% of the total wet weight [18]. Of this amount, over half is albumin (~50 mg/ml), a protein that can be non-enzymatically glycosylated, but not N-glycosylated [19]. Although the overwhelming amounts of albumin can obscure analysis for proteomics, it may not interfere with N-glycan profiling. There are also large amounts of glycosylated antibodies, which have a number of glycan structures [20, 21]. However, simple methods exist to separate these abundant antibodies from the less abundant glycoproteins.

When working with serum, there are several issues to consider that are not relevant for single protein systems. Because the proteins in the sample are so concentrated, they can easily precipitate out of solution. Also, even though albumin does not have N-linked sugars, the sheer quantity present may interfere with glycan release or purification. There are several other major proteins in serum (i.e. immunoglobulins) that are N-glycosylated, which may overshadow the signals from less abundant proteins. However, alterations in immunoglobulin glycosylation may also be correlated with changes in physiological state. To determine the contributions and/or interference from major serum proteins, several options for separating serum proteins into fractions before analysis were explored.

There are both neutral and charged sugars on serum glycoproteins. Acidic glycans generally do not ionize well in the positive ion mode of MALDI-MS, and also suffer loss of sialic acids. On the other hand, neutral sugars ionize extremely poorly in negative mode, which is commonly used for charged glycans. Therefore, a method where the neutral and acidic structures were assayed separately was compared to two chemical modification methods that allow the glycans to ionize more uniformly.

Identifying glycan structures with complex protein mixtures can be rather difficult. By generating a master list of all possible compositions and their theoretical masses based on biosynthetic pathways for glycosylation, all possible monosaccharide composition was assigned to each peak observed in a MALDI-MS spectrum. In most cases, each mass peak corresponds uniquely to a monosaccharide assignment. However, in some instances there can be more than one potential composition. If necessary, the correct composition can be determined by using commercially available exoenzymes that cleave the glycans only at particular linkages.

Sample Preparation

Figure 9A:
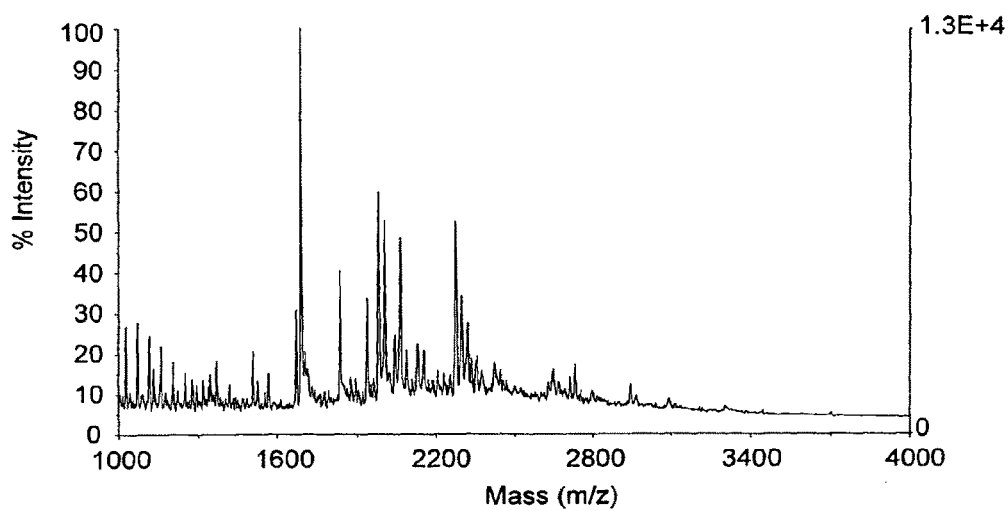
FIG. 9 MALDI-MS spectra of glycans released from serum proteins using PNGaseF and EndoF. Serum samples were treated with PNGaseF (FIG. 9A) or EndoF (FIG. 9B) and purified. While glycans were observed, the samples did not produce clean results. The peak cluster indicated by an arrow represents detergent contamination.
Figure 9B:
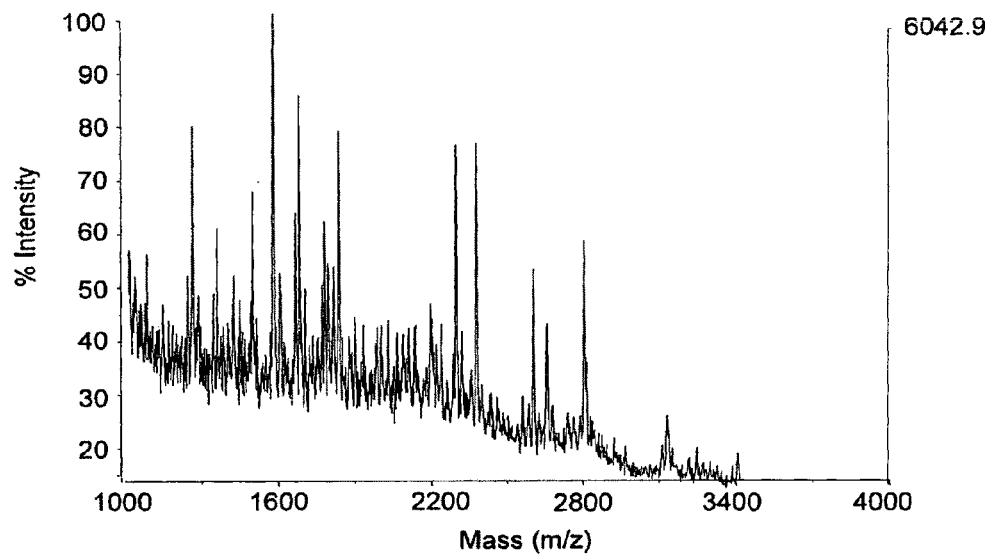

Serum samples generally contained upwards of 120 mg/ml of protein, making heat denaturing less ideal. Even when diluted, the proteins in these samples precipitated rapidly, giving the sample a gel-like consistency. This could prevent the PNGaseF from accessing all the N-glycan sites on the proteins. One set of samples was processed using the traditional heat-denaturation method after diluting the serum samples 1:10 in water (FIG. 9A). A number of glycan peaks were observed in the MALDI-MS spectrum, but there clearly was residual detergent contamination from the denaturing step. On a separate sample, EndoF was used since the enzyme can act on folded proteins (FIG. 9B).

However, as discussed above, EndoF cleaves between the first and second GlcNAc on the glycan core, causing a loss of information on core fucosylation. After EndoF digestion the samples were purified as usual. As shown in FIG. 9, glycans could indeed be obtained using both methods. EndoF spectra had a relatively high level of baseline noise, and signal intensities were relatively low (~1000), leaving room for improvement.

As an alternative to heat denaturation, the proteins were reduced with dithiothreitol (DTT) followed by carboxymethylation with iodoacetic acid to denature the proteins [22]. Reduction disrupts the disulfide bonds in proteins, while carboxymethylation prevents the proteins from re-folding. After dialysis to remove excess iodoacetic acid and DTT, PNGaseF was added to the denatured proteins for overnight cleavage. An additional advantage to this method over the regular SDS/β-mercaptoethanol heat-denaturation method was that the absence of detergents facilitated purification. After the glycans were cleaved from the core protein, the sample was dialyzed against water overnight and lyophilized. Exchanging the sample into water prepared it to be passed through a C18 cartridge (Waters Corporation) to remove remaining protein. At this stage, both neutral and acidic sugars were present in the same sample, potentially complicating the assignment of glycan peaks in the MALDI-MS spectrum.

Because serum contains proteins with a wide variety of neutral and charged N-glycans, analysis was facilitated by separating the neutral sugars from the acidic carbohydrates. This allowed each pool to be analyzed using methods particularly suited to the chemical properties of neutral vs. charged molecules. The GlycoClean H purification cartridge (Prozyme) was used for this purpose by eluting glycan pools with different concentrations of acetonitrile. Neutral sugars were eluted with 15% acetonitrile, 0.1% TFA, while acidic sugars were eluted with 50% acetonitrile, 0.1% TFA. To test the separation of neutral and acidic sugars, six known glycan standards were used (Table 5).

TABLE 5

Glycan standards used to test GlycoClean H separation of neutral and acidic sugars.

| Commercial name | Structure description | Mass | Charge state (# sialic acids) |
|---|---|---|---|
| NGA2 | Asialo, agalacto biantennary | 1317.2 | 0 |
| NA2 | Asialo, galactosylated, biantennary | 1641.5 | 0 |
| NA3 | Asialo, galactosylated, triantennary | 2006.0 | 0 |
| SC1223 | Disialylated, galactosylated, fucosylated biantennary | 2370.2 | 2 |
| A3 | Trisialylated, galactosylated, triantennary | 2879.9 | 3 |
| SC1840 | Tetrasialylated, galactosylated, tetrantennary | 3683.4 | 4 |

Figure 10A:
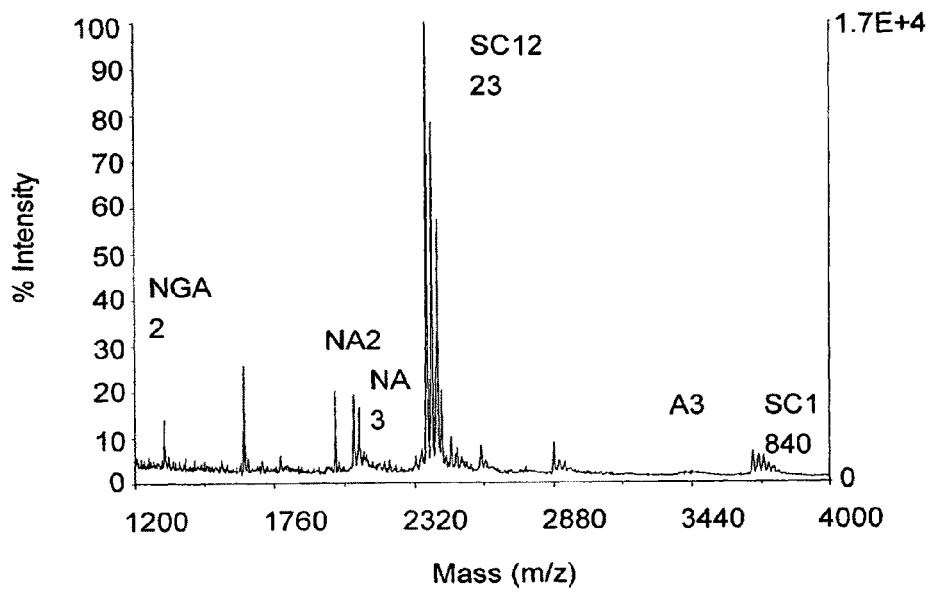
FIG. 10 shows a separation of neutral and acidic glycans using GlycoClean H cartridge. (a) The original mix of standards is shown in positive mode. A3 and SC1840 are additional highly charged, and do not ionize well. (b) Neutral glycans eluted off the GlycoH cartridge ionize well in positive mode, while only the charged sugars are present in (c), allowing them to be observed in negative mode. The multiple peaks in (c) arise from sodium adducts, typically one adduct per sialic acid residue.
Figure 10B:
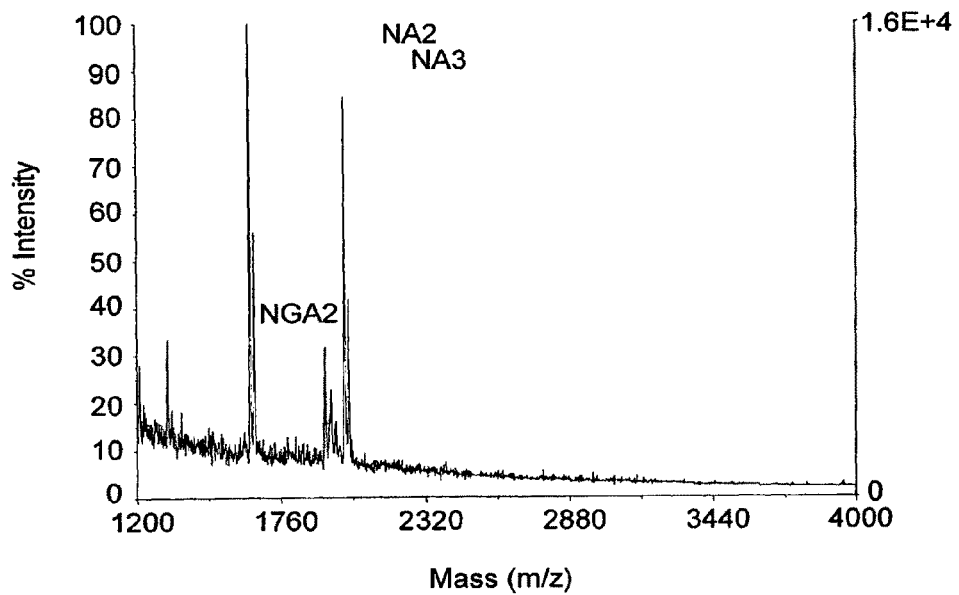
Figure 10C:
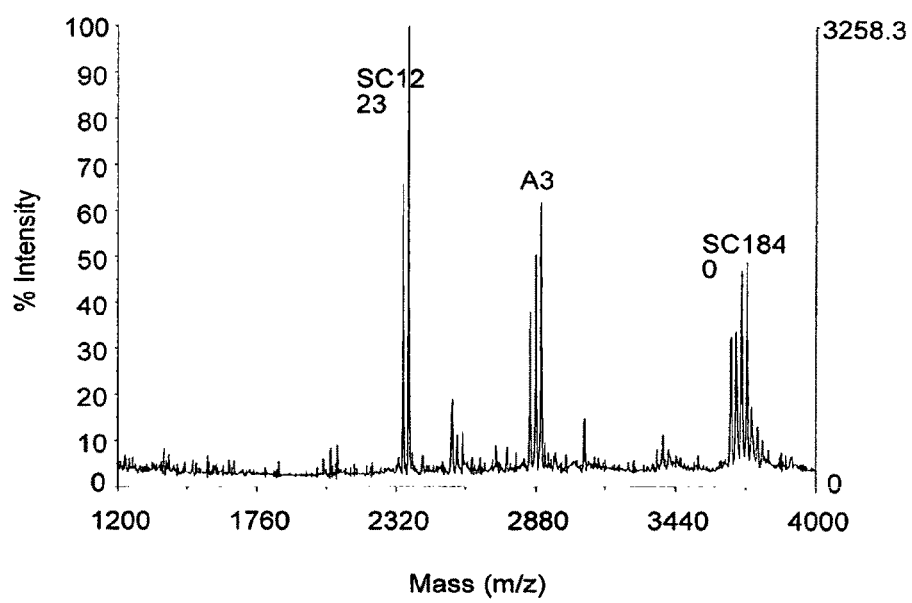
Figures 11A, 11B:
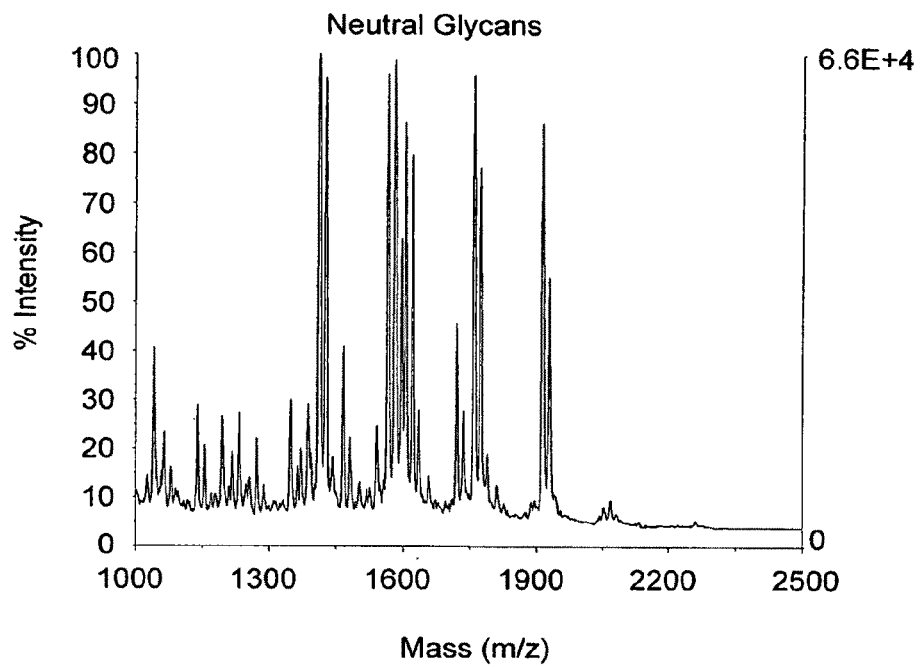
FIG. 11 provides the results from MALDI-MS of N-glycans from human serum in neutral (left) and acidic (right) fractions. (a) and (b) represent neutral glycans prepared from two different IMPATH normal male human serum samples, while (d) and (e) show the acidic fraction. (c) and (f) are the neutral and acidic fractions of a normal human sample from Biomedical Resources.
Figure 11C:
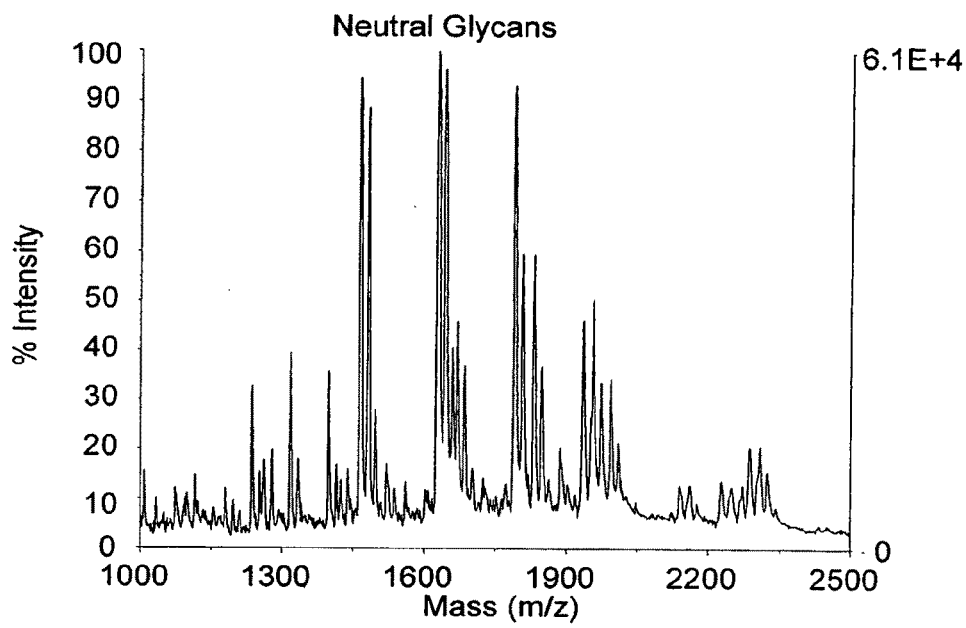
Figure 11D:
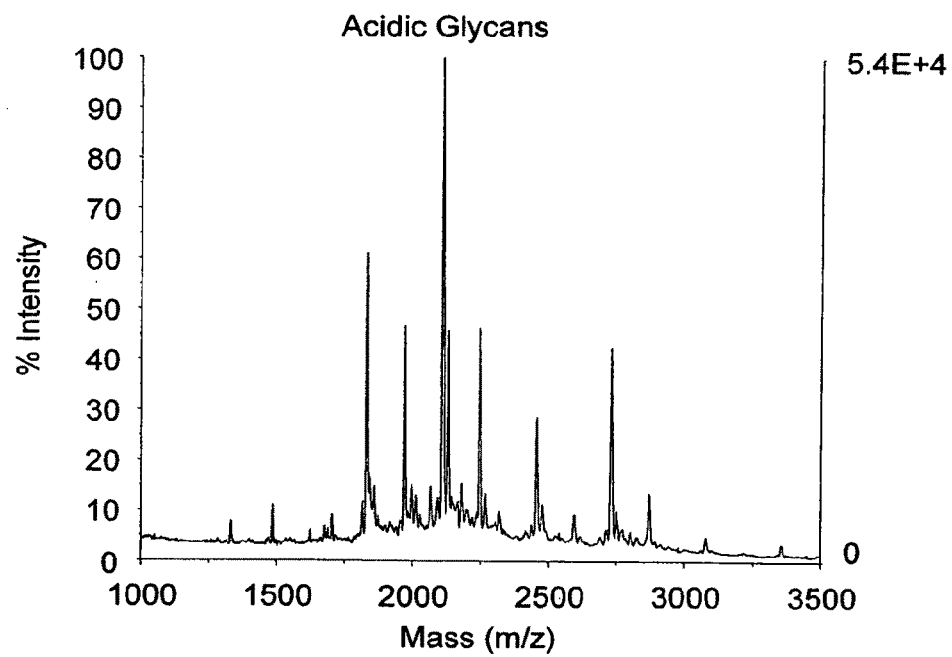
Figure 11E:
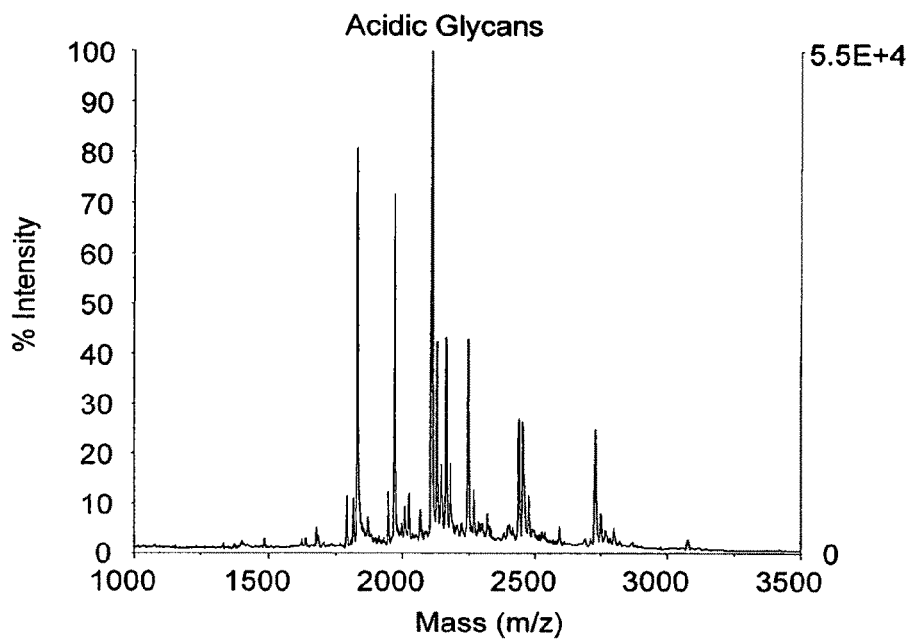
Figure 11F:
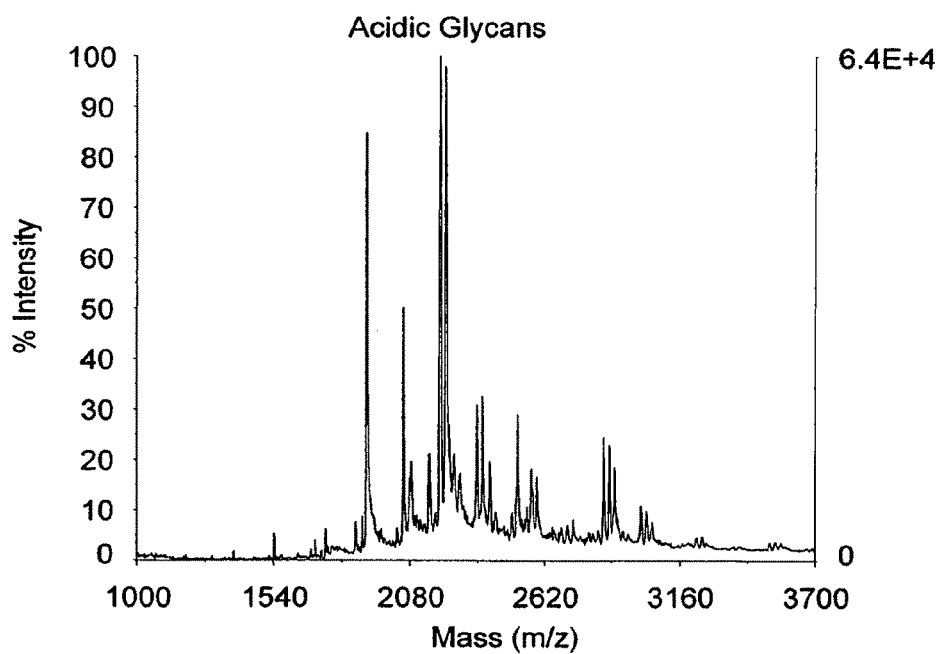

The neutral sugars were analyzed in positive ion mode in the MALDI-MS, while acidic sugars were examined in negative mode (FIG. 10). To confirm that no neutral sugars were present in the acidic glycan sample, the positive mode spectrum was checked for charged glycans. When this method was applied to human serum N-glycans, the spectra appeared much cleaner than those obtained from a mixed sample, since each group of sugars could be analyzed under optimal conditions (FIG. 11).

This process was repeated multiple times with the same serum sample to ensure reproducibility (three aliquots were purified in parallel on one day, and another two on two different days). In addition, multiple normal serum samples were processed by this method to determine the degree of glycan variation between serum samples. Five normal male human samples from each of two different sources (IMPATH tissue bank and Biomedical Resources) were used to assess whether observed glycan profiles were consistent across suppliers. As expected, there was some variation in the spectra from different normal samples in both the neutral and acidic fraction (FIG. 11), while aliquots from the same serum sample appeared very similar even when they were purified on different days. The samples from different serum banks showed similar profiles and major peak clusters.

Most Abundant Proteins

Although serum samples can be analyzed with all proteins present, including non-glycosylated species, it was determined whether better results could be obtained by removing proteins such as albumin. Concanavalin A (ConA) is a lectin that binds to α-linked mannose, as contained in all N-glycans [23]. A serum sample was passed through a column of agarose-bound ConA. Proteins containing N-glycans bound to the column while non-glycosylated proteins were washed off (this sample was collected as the ConA flow through). The glycoproteins were then eluted with a 500 mM α-methylmannoside solution, which competes for the ConA binding sites.

Figure 12A:
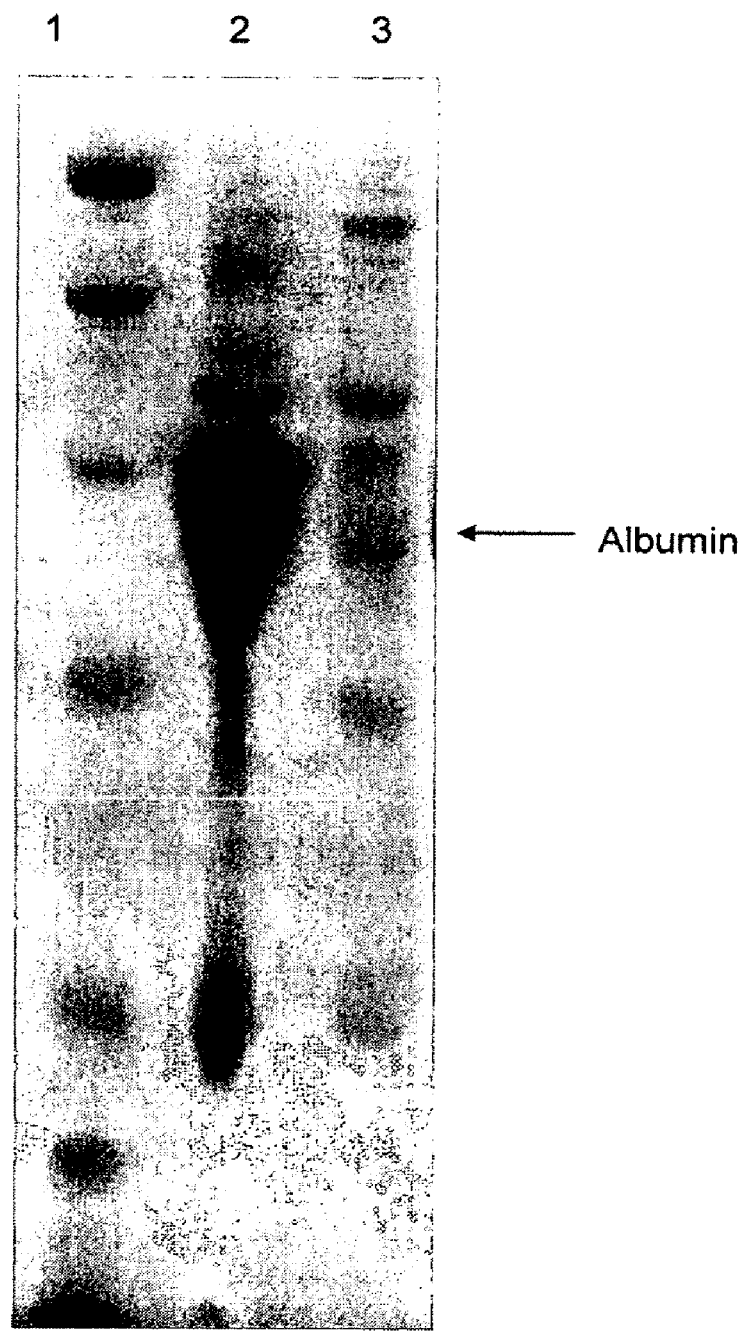
FIG. 12 provides the results of serum glycans separated by ConA. (a) SDS-PAGE of ConA flow through (Lane 2) and elution (Lane 3). vLane 1 shows molecular weight standards. vMALDI-MS of (b) neutral and (c) acidic sugars obtained from ConA elution.
Figure 12B:
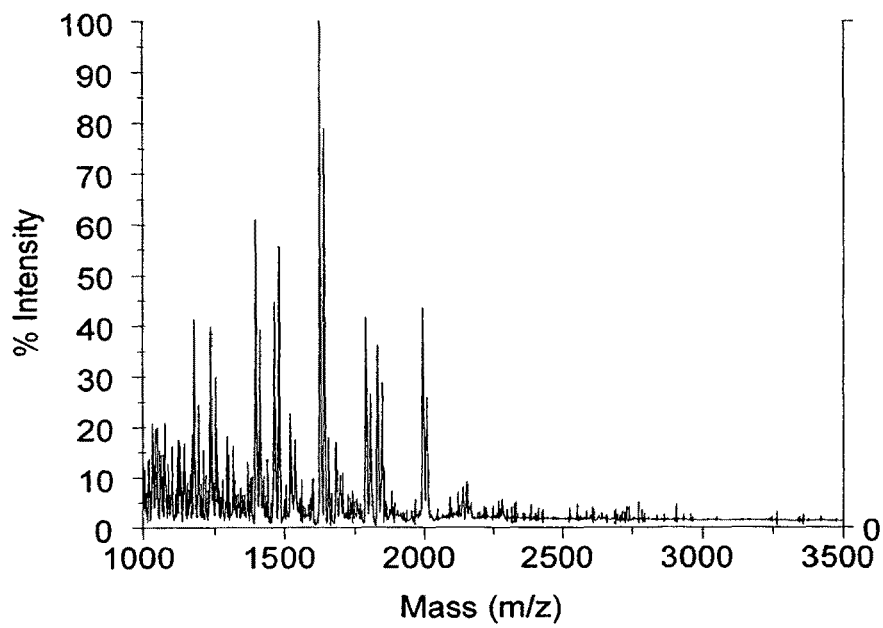
Figure 12C:
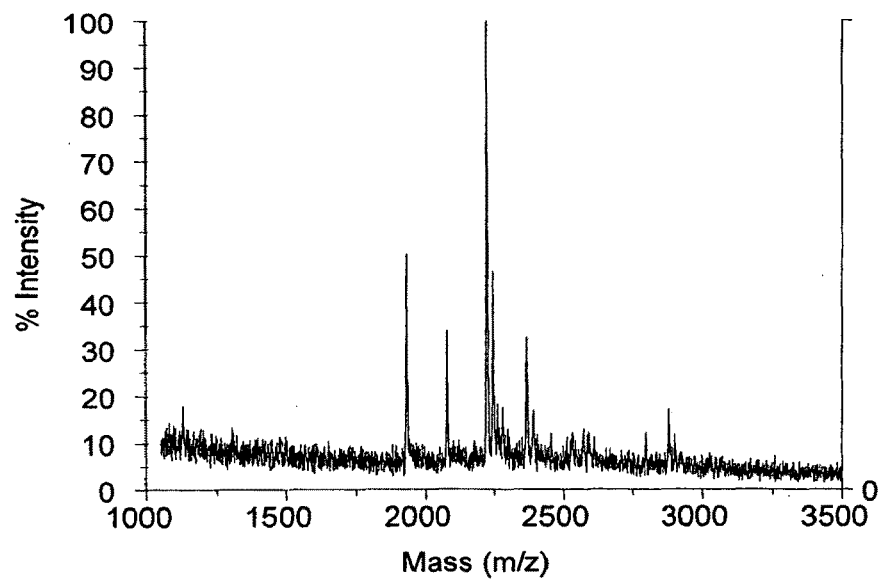

To evaluate the separation of the serum sample into glycosylated and non-glycosylated proteins, the ConA flow through and elution samples were run on an SDS-PAGE gel (FIG. 12A). In the gel, the albumin fraction is clearly visible in the flow through from the ConA column, while multiple bands in the elution lane represent glycoproteins. In addition, the glycan profiles of both the flow through and the elution fraction were analyzed. After dialyzing the samples against 10 mM phosphate buffer, they were processed with PNGaseF and purified by C18 cartridge and GlycoH as described above. There were no observable glycans present in the flow-through fraction, while neutral and acidic sugars from the elution fraction are shown in FIGS. 12B and 12C. The results from total serum digests, however, yield MALDI-MS data with signal-to-noise ratio and signal intensity that are as good as or better than from ConA elution. Therefore, in some cases there will be little to no advantage to removing non-glycosylated proteins before analysis.

Figure 13A:
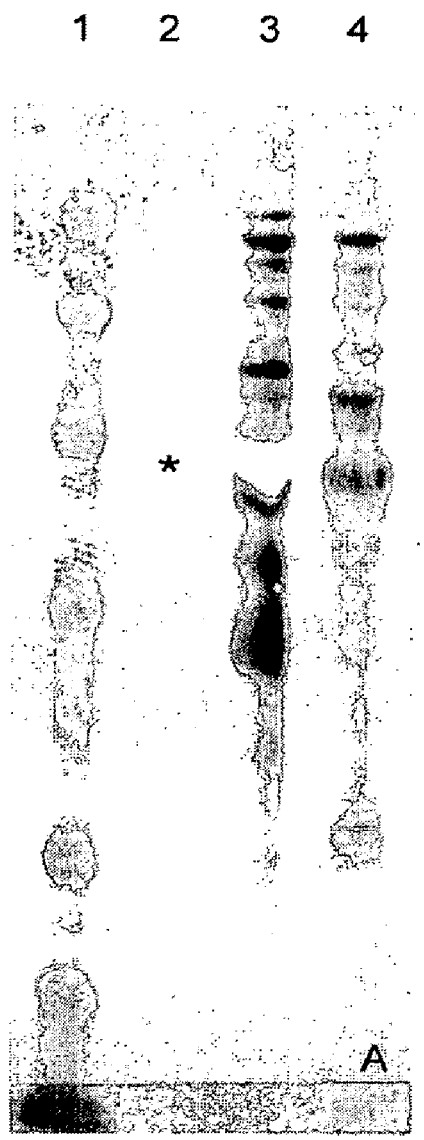
FIG. 13 provides the results from protein A separation of IgG from serum. (a) Glycoblot of Protein A flow-through (Lane 3) and elution (Lane 4). Lane 1 contains protein standards, while Lane 2 (negative control) contains human serum albumin (* marks where albumin would run on an SDS-PAGE gel). Only glycosylated proteins are observed in the glycoblot, so the albumin does not stain. MALDI-MS of glycans harvested from the elution fraction are shown in (b) neutral and (c) acidic. Total serum glycans are pictured in (d) neutral and (e) acidic.
Figure 13B:
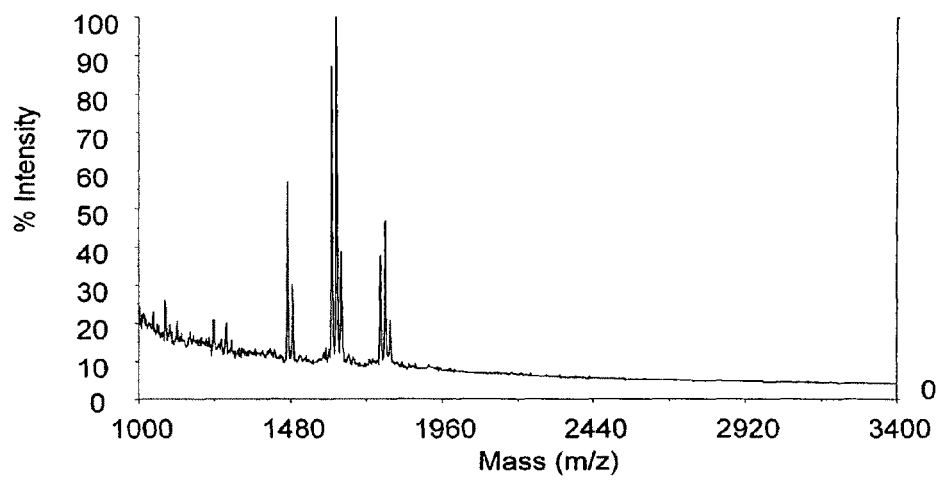
Figure 13C:
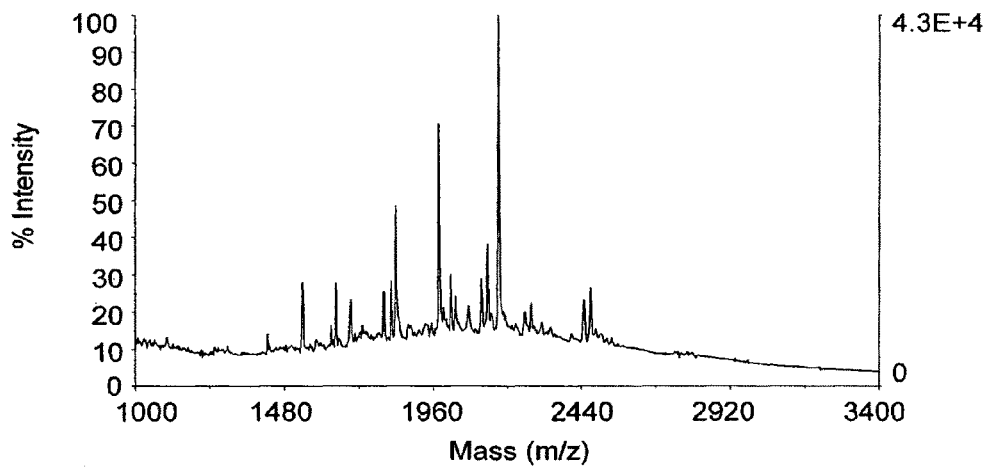
Figure 13D:
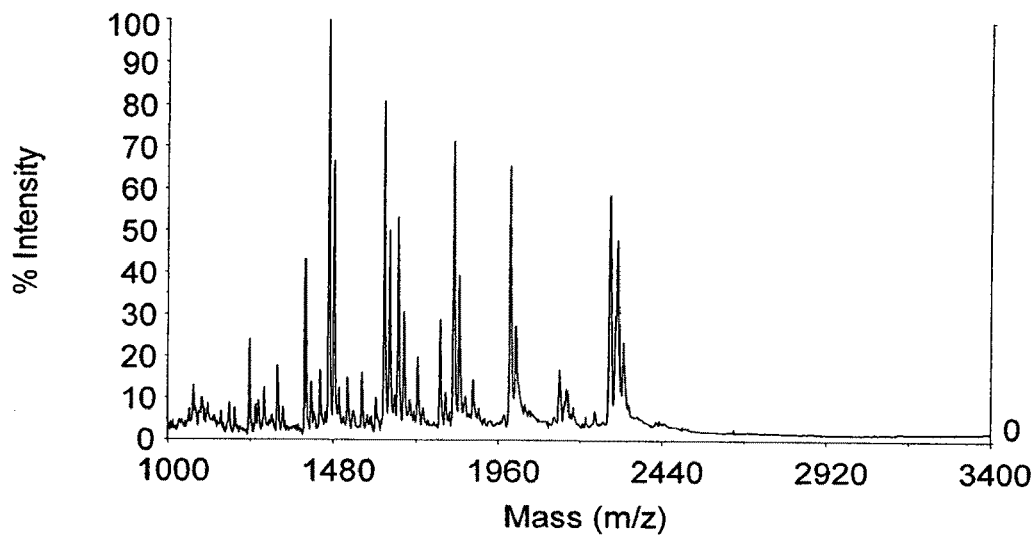
Figure 13E:
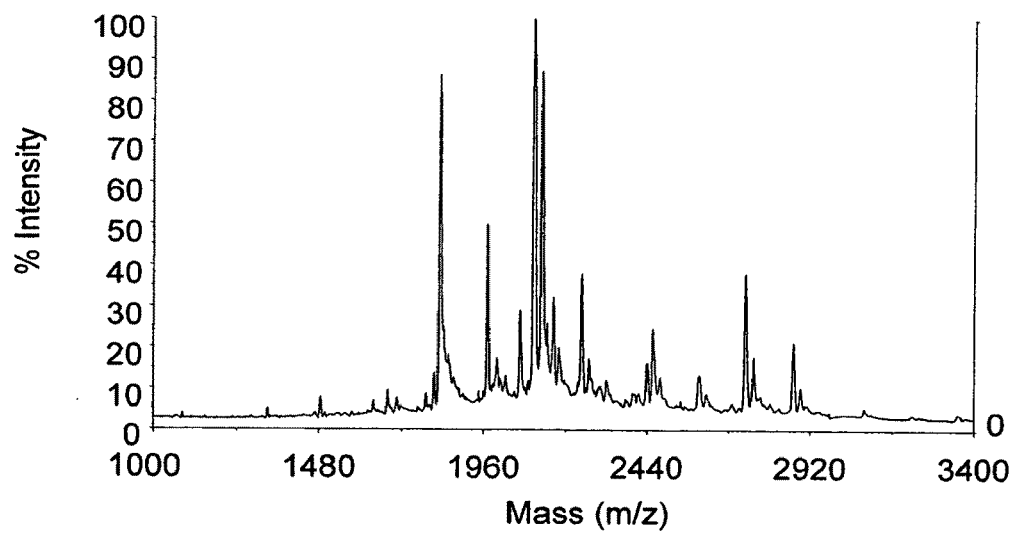

Serum samples were also depleted of antibodies through a Protein A column to determine how many major peaks in the final spectra came from IgG. The presence of glycoproteins in both the flow through and elution fractions were determined by GlycoTrack glycoprotein detection kit (Prozyme/Glyko) (FIG. 13A). The Protein A elution fraction containing IgGs was treated with PNGaseF and purified as described above. FIGS. 13B-13E show a comparison of the glycans from IgG (Protein A elution) to the total glycan profile. Although several of the major peaks in the spectra indeed come from this antibody population, they do not appear for these samples to be in large enough quantities to interfere with the signals from other glycans.

MALDI-MS Analysis of Serum N-Glycans

Neutral and acidic sugars require different treatment when being analyzed by MALDI-MS. In particular, neutral sugars ionize well in the positive ion mode, but not well in negative mode, while the opposite is true for charged sugars. Three different matrix formulations were tested to determine the best one for these samples. All formulations contained DHB and spermine, as this had yielded the best results with single-protein studies. The three matrix preparations were 1) saturated DHB in water with 300 mM spermine, 2) 20 mg/ml DHB in acetonitrile and 25 mM spermine in water in a 1:1 ratio and 3) 20 mg/ml DHB in methanol and 25 mM spermine in water in a 1:1 ratio. Preparation 2 yielded MALDI-MS spectra with the highest signal-to-noise ratio in both positive and negative mode, and was used for all experiments.

There are several reported methods for increasing the sensitivity and ionization efficiency of mass spectrometry data in the analysis of glycans. With these methods, it is sometimes possible to analyze glycan pools as a mixture of neutral and acidic glycans, as the chemical properties of the glycans are modified to allow for more uniform ionization. Two types of chemical modifications were tested to determine whether the MALDI-MS results could be improved upon.

Figure 14:
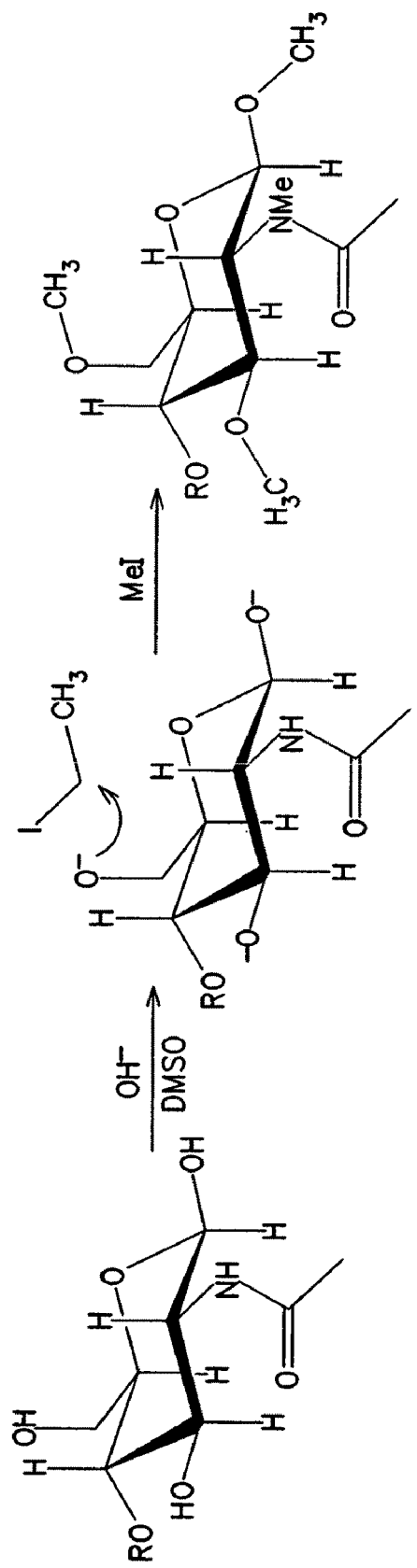
FIG. 14 shows the permethylation of N-glycans. All OH and NH groups can be permethylated. For complete reaction, it is essential that the reaction vessel is free of air and water.
Figure 15A:
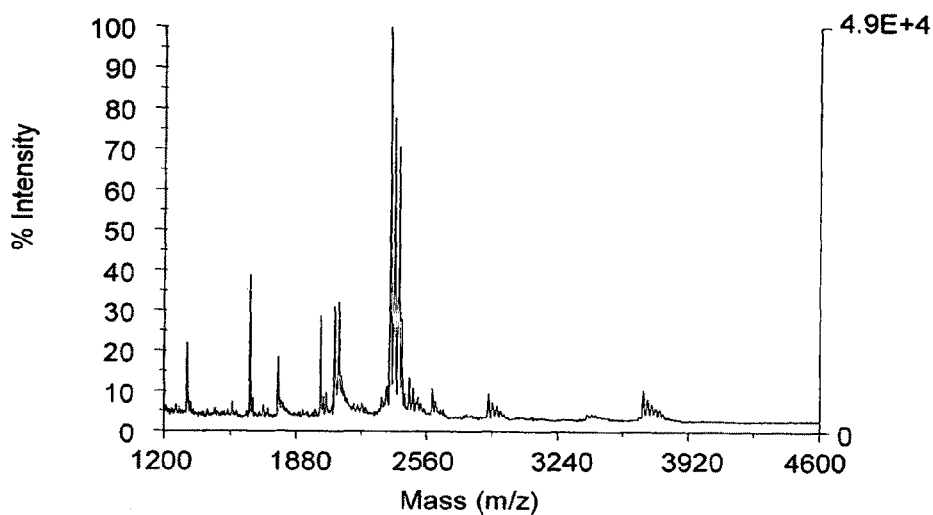
FIG. 15 shows the results of MALDI-MS of permethylated glycan standards. (a) Unmodified standards ionized unevenly. Permethylated standards (b) showed more uniform ionization, but generally did not have higher signal-to-noise ratios.
Figure 15B:
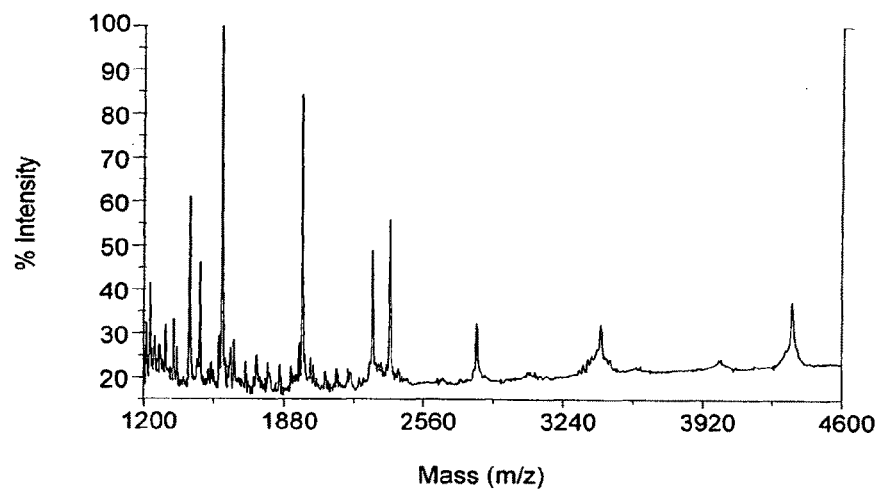

N-glycan samples are commonly permethylated to protect each OH and $NH_2$ or amide group in the carbohydrate [24]. This is particularly useful for MS techniques such as fast atom bombardment (FAB-MS), since permethylated glycans fragment in a much more predictable manner than underivatized glycans. Permethylation can also increase sensitivity in electrospray (ES-MS) and MALDI-MS. The schematic of the permethylation reaction is shown in FIG. 14. Some drawbacks to permethylation are that the sample has to be extremely clean for the reaction to go to completion, and the sample requires clean-up after the reaction. In the current study, although this method slightly improved the ionization of N-glycan standards in MALDI-MS over non-modified glycans, the increase in signal-to-noise ratio was not significant (FIG. 15).

Figure 16:
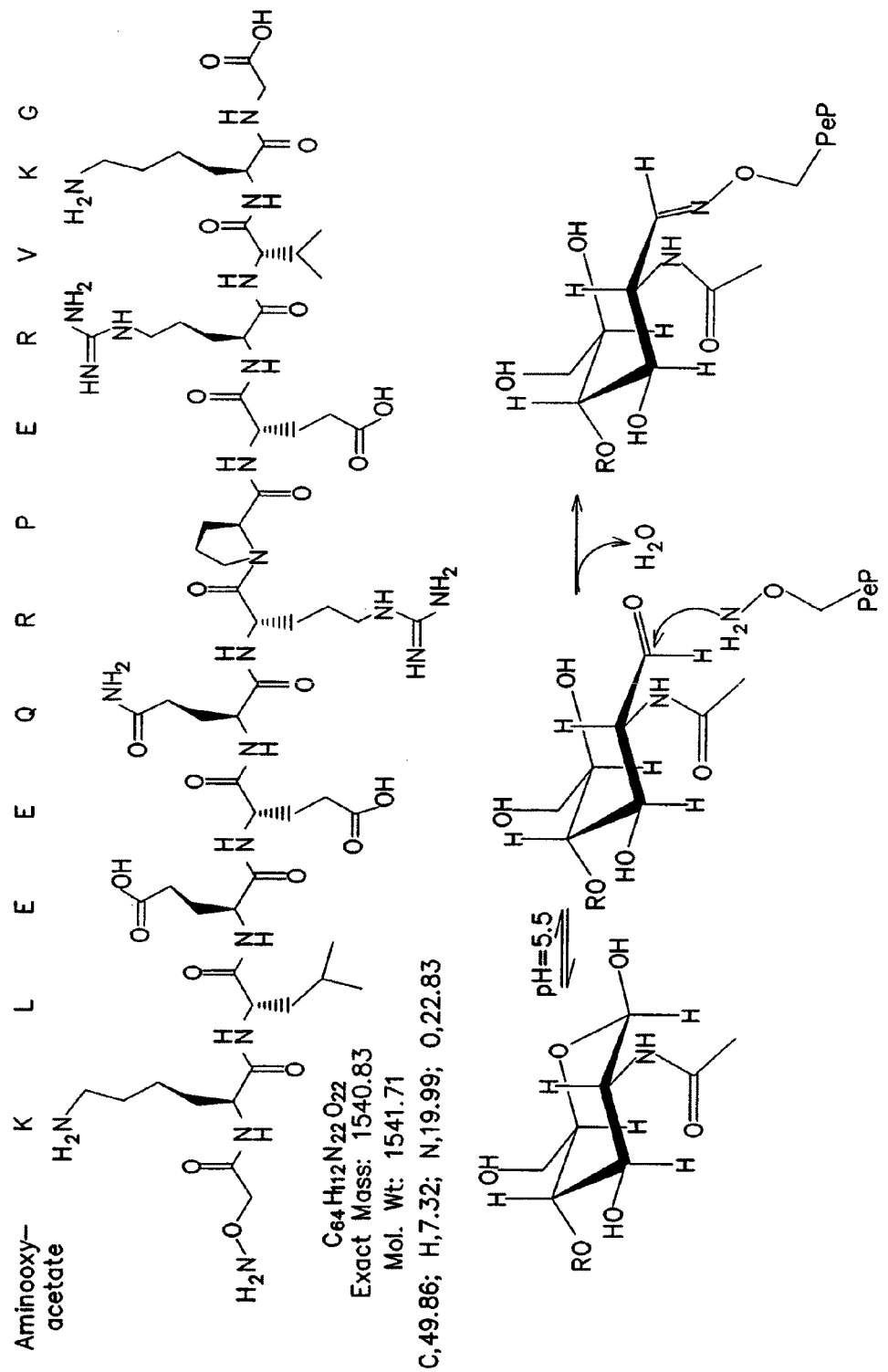
FIG. 16 shows the aminooxyacetyl peptide and its conjugation to N-glycans. The aminooxyacetate end of the synthetic peptide (top) reacts with the open form of the reducing end GlcNAc of N-glycans (bottom).
Figure 17A:
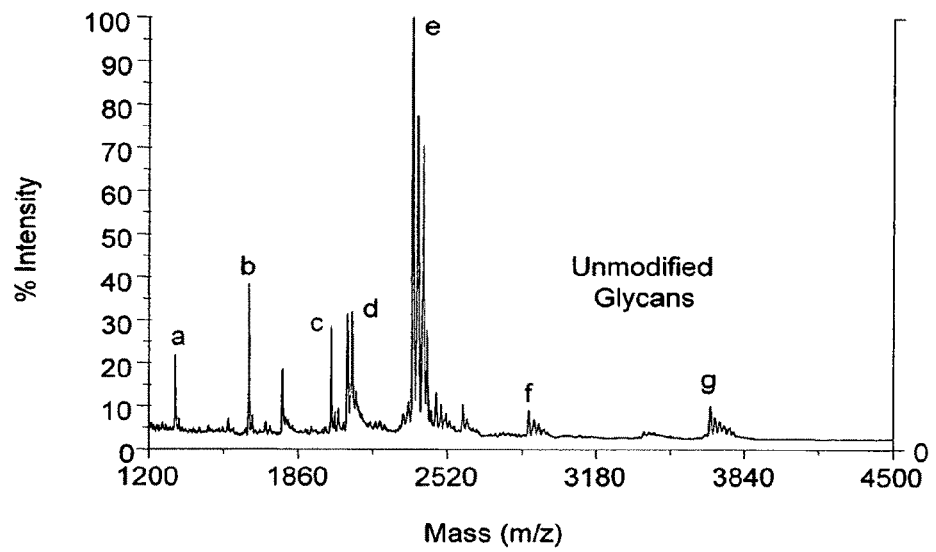
FIG. 17 shows the results of MALDI-MS of peptide-conjugated N-linked standards. (a) Unmodified glycans ionize unevenly, especially charged glycans f and g. After conjugation with aminooxyacetyl peptide (b), ionization is much more uniform.
Figure 17B:
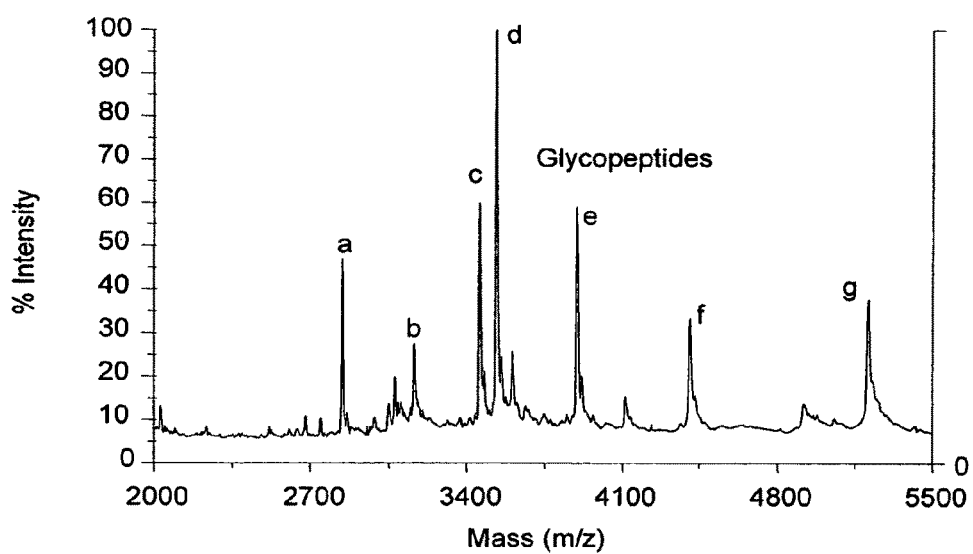

A newer method for increasing N-glycan ionization, as well as allowing the glycans to ionize more uniformly across species is to conjugate it to a peptide [25]. The structure of the peptide and its glycan conjugation reaction are shown in FIG. 16. Before MALDI-MS, it was necessary to clean up the reaction mixture using a C18 ZipTip in order to eliminate the buffer (NaOAc) used in the reaction. The ZipTip flowthrough, water wash and 10% acetonitrile elution were all spotted on the plate. The glycopeptide conjugates (in the 10% elution fraction) were readily observed in the MALDI-MS, and neutral and acidic sugars ionized more evenly in the positive mode as compared to unmodified glycans (FIG. 17). While the glycan-peptide conjugation reaction is simple, the free peptide is particularly unstable. Specifically, the peptide's active hydroxylamine group readily reacts with any aldehydes or ketones present, thus preventing it from conjugating to the glycans. Although the reaction with glycan standards displayed promising results, it was difficult to obtain a complete reaction with serum samples. Even after several attempts to label serum glycans with varying amounts of peptide, free glycan peaks in the spectra were observed from flow-through and water wash spots. Because there may be excess aldehydes or ketones remaining in serum samples, peptide conjugation was not used, and the samples were analyzed as separate neutral and acidic fractions.

Identifying Composition of Glycans from MALDI-MS Data

In a MALDI-MS spectrum, the main information obtained is mass of the parent ion. With just this data, it was indeed possible to deduce the monosaccharide composition of each peak (number of hexNAc, hexose, fucose and sialic acid residues). Using our knowledge of biosynthetic rules, as well as whether each glycan is charged or uncharged, we can significantly limit the number of possible structures for each mass peak observed. A spreadsheet to use as a lookup table for unknown peaks was created. In addition to unmodified masses, entries for permethylated masses were included as well as peptide-conjugated glycans, according to the following equations:

$n = Hex$NAc $\quad h =$ hexose $\quad f =$ fucose $\quad s =$ sialic acid $MW$-$H_2O$ = 203.1 $\quad$ 162.1 $\quad$ 146.1 $\quad$ 291.3

Unmodified Glycans mass=$203.1n+162.1h+146.1f+291.3s+18$

Permethylated Glycans perm=mass+51+14[3($n+h$)+2$f$+5$s$]

Peptide-Conjugated Glycans peptide=mass+1527.1

Using this table, regardless of the analytical methods, MALDI-MS peaks can be associated with specific monosaccharide compositions. Sample entries from this database are shown in Table 6.

TABLE 6

Table of sample entries for identifying N-glycan composition from MALDI-MS data.

| HexNAc | Hexose | Fucose | Sialic Acid | mass | perm | peptide |
|---|---|---|---|---|---|---|
| 2 | 3 | 1 | 0 | 1056.6 | 1345.6 | 2583.7 |
| 2 | 4 | 0 | 0 | 1072.6 | 1375.6 | 2599.7 |
| 3 | 3 | 0 | 1 | 1404.9 | 1777.9 | 2932 |
| 4 | 3 | 0 | 1 | 1608 | 2023 | 3135.1 |
| 4 | 3 | 2 | 0 | 1608.9 | 2009.9 | 3136 |
| 5 | 3 | 1 | 0 | 1665.9 | 2080.9 | 3193 |
| 6 | 3 | 0 | 0 | 1722.9 | 2151.9 | 3250 |
| 3 | 6 | 1 | 0 | 1746 | 2203 | 3273.1 |
| 4 | 3 | 1 | 1 | 1754.1 | 2197.1 | 3281.2 |
| 4 | 3 | 0 | 2 | 1899.3 | 2384.3 | 3426.4 |
| 4 | 3 | 2 | 1 | 1900.2 | 2371.2 | 3427.3 |

Figure 18A:
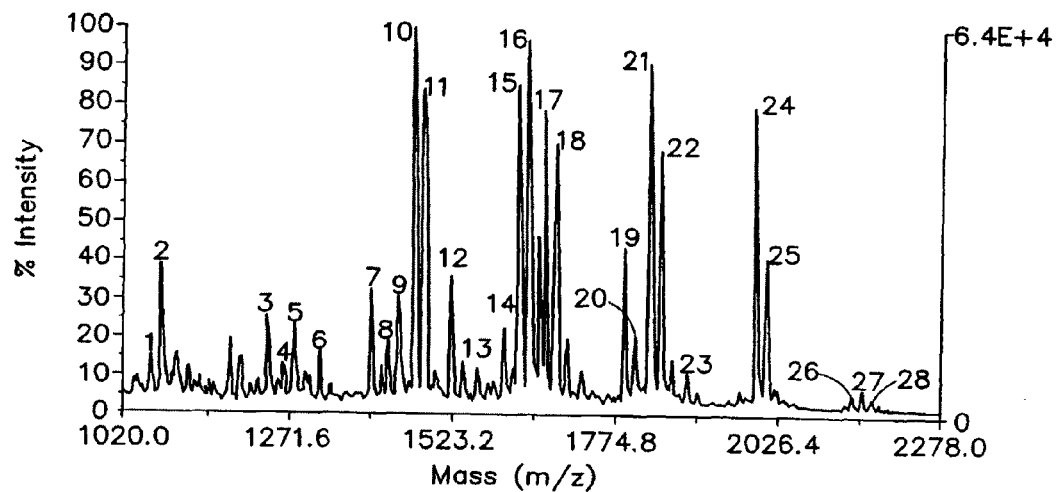
FIG. 18 shows the identification of serum N-glycans from MALDI-MS spectra. (a) shows neutral glycans, while (b) shows acidic glycans. Labeled peak numbers correspond to entries in Table 7.
Figure 18B:
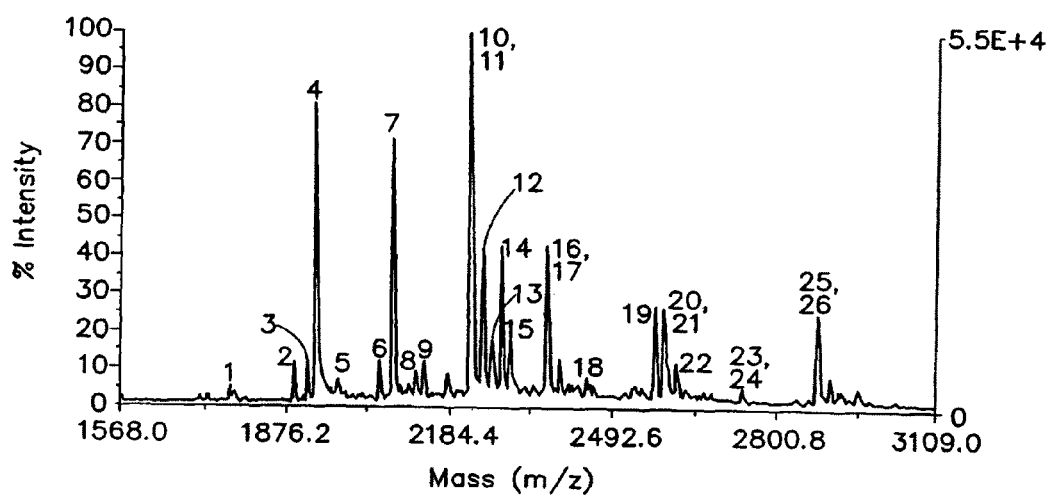

Using the table almost all the peaks in MALDI-MS serum profiles could be identified as glycans of known composition (FIG. 18). Many of the unidentified peaks are ammonium or sodium adducts. The composition and mass of each labeled peak are listed in Table 7. A few peaks in the acidic glycan spectrum correspond to more than one composition. This is more common in the higher mass range since there are a larger number of possible monosaccharide compositions. Many of the glycans observed in these spectra were also present in other serum samples; there are typically between 25-30 neutral glycans as well as 25-30 acidic glycans present in a given sample.

TABLE 7

Composition and mass of serum glycans observed in FIG. 18

| Peak | HexNAc | Hexose | Fucose | Sialic Acid | Mass |
|---|---|---|---|---|---|
| Neutral glycans (FIG. 18A) | | | | | |
| 1 | 2 | 3 | 1 | 0 | 1056.6 |
| 2 | 2 | 4 | 0 | 0 | 1072.6 |
| 3 | 2 | 5 | 0 | 0 | 1234.7 |
| 4 | 3 | 3 | 1 | 0 | 1259.7 |
| 5 | 3 | 4 | 0 | 0 | 1275.5 |
| 6 | 4 | 3 | 0 | 0 | 1316.7 |
| 7 | 2 | 6 | 0 | 0 | 1396.8 |
| 8 | 3 | 4 | 1 | 0 | 1421.8 |
| 9 | 3 | 5 | 0 | 0 | 1437.8 |
| 10 | 4 | 3 | 1 | 0 | 1642.8 |
| 11 | 4 | 4 | 0 | 0 | 1478.8 |
| 12 | 5 | 3 | 0 | 0 | 1519.8 |
| 13 | 2 | 7 | 0 | 0 | 1558.9 |
| 14 | 3 | 6 | 0 | 0 | 1599.9 |
| 15 | 4 | 4 | 1 | 0 | 1624.9 |
| 16 | 4 | 5 | 0 | 0 | 1640.9 |
| 17 | 5 | 3 | 1 | 0 | 1665.9 |
| 18 | 5 | 4 | 0 | 0 | 1681.9 |
| 19 | 4 | 5 | 1 | 0 | 1787.0 |
| 20 | 4 | 6 | 0 | 0 | 1803.0 |
| 21 | 5 | 4 | 1 | 0 | 1828.0 |
| 22 | 5 | 5 | 0 | 0 | 1844.0 |
| 23 | 2 | 9 | 0 | 0 | 1883.1 |
| 24 | 5 | 5 | 1 | 0 | 1990.1 |

TABLE 7-continued

Composition and mass of serum glycans observed in FIG. 18

| Peak | HexNAc | Hexose | Fucose | Sialic Acid | Mass |
|---|---|---|---|---|---|
| 25 | 5 | 6 | 0 | 0 | 2006.1 |
| 26 | 5 | 5 | 2 | 0 | 2136.2 |
| 27 | 5 | 6 | 1 | 0 | 2152.2 |
| 28 | 5 | 7 | 0 | 0 | 2168.2 |
| Acidic glycans (FIG. 18B) | | | | | |
| 1 | 4 | 4 | 0 | 1 | 1770.1 |
| 2 | 3 | 6 | 0 | 1 | 1891.2 |
| 3 | 4 | 4 | 1 | 1 | 1916.2 |
| 4 | 4 | 5 | 0 | 1 | 1932.2 |
| 5 | 5 | 4 | 0 | 1 | 1973.2 |
| 6 | 3 | 7 | 0 | 1 | 2053.3 |
| 7 | 4 | 5 | 1 | 1 | 2078.3 |
| 8 | 5 | 4 | 1 | 1 | 2119.3 |
| 9 | 5 | 5 | 0 | 1 | 2135.3 |
| 10 | 4 | 5 | 0 | 2 | 2223.5 |
| 11 | 4 | 5 | 2 | 1 | 2224.4 |
| 12 | 5 | 3 | 1 | 2 | 2248.5 |
| 13 | 5 | 4 | 0 | 2 | 2264.5 |
| 14 | 5 | 5 | 1 | 1 | 2281.4 |
| 15 | 5 | 6 | 0 | 1 | 2297.4 |
| 16 | 4 | 5 | 1 | 2 | 2369.6 |
| 17 | 4 | 5 | 3 | 1 | 2370.5 |
| 18 | 5 | 6 | 1 | 1 | 2443.5 |
| 19 | 5 | 5 | 1 | 2 | 2572.7 |
| 20 | 5 | 6 | 0 | 2 | 2588.7 |
| 21 | 5 | 6 | 2 | 1 | 2589.6 |
| 22 | 6 | 4 | 1 | 2 | 2613.7 |
| 23 | 5 | 6 | 1 | 2 | 2734.8 |
| 24 | 5 | 6 | 3 | 1 | 2735.7 |
| 25 | 5 | 6 | 2 | 2 | 2880.9 |
| 26 | 5 | 6 | 4 | 1 | 2881.8 |

Alternative Sample Preparation Methods

Figure 19:
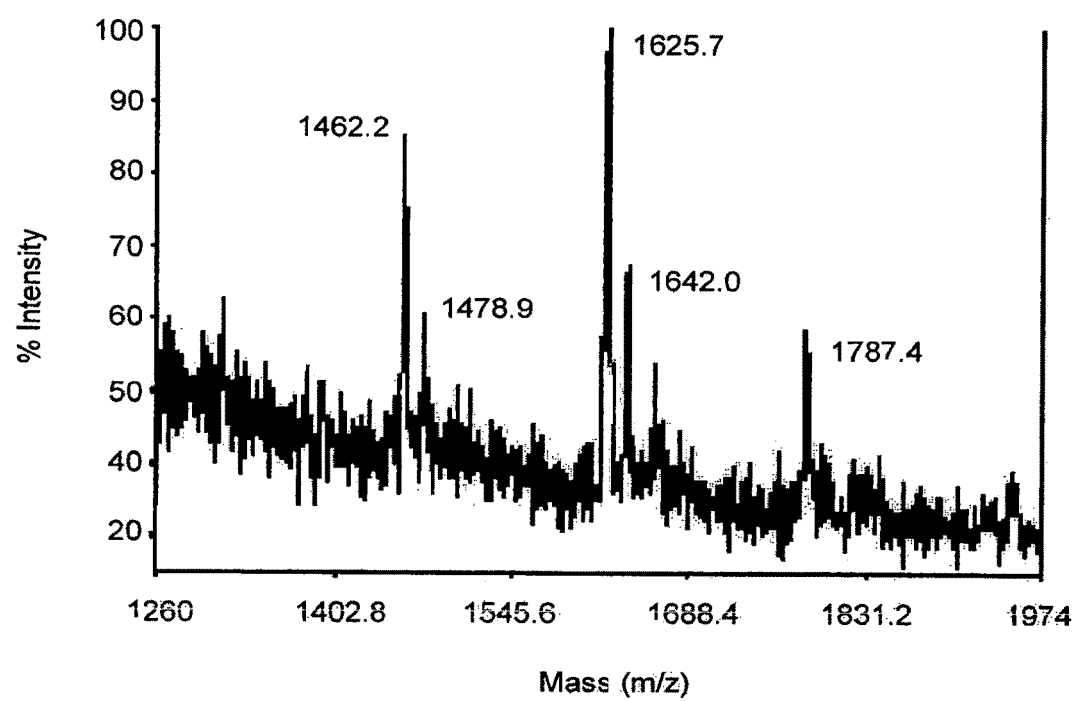
FIG. 19 shows the results of neutral N-glycans from PVDF digest. Only the most abundant glycans are observed.

Besides performing PNGaseF digests in solution, a membrane-based method was tested with the potential for high throughput sample processing. Proteins were adsorbed onto a PVDF membrane in a 96-well plate, followed by reduction, carboxymethylation and digestion in the wells[26]. While this method works well with single glycoproteins, very few glycans were observed when serum was used. An explanation for this result is that albumin most likely saturated the membrane binding capacity, and most of the glycoproteins were washed away before the PNGaseF was added. Without removing albumin, only a few glycans were observed in the neutral fraction, and no acidic glycans were present (FIG. 19). Although time saved by performing the experiment in a 96-well format may be negated by the extra steps required to remove albumin, using the PVDF membrane as a platform for digestion may be extremely useful for the development of a high-throughput glycomics methodology for serum samples. All samples in this study were, however, processed with the PNGaseF digest in solution.

It has been demonstrated that a complete N-glycan profile from human serum proteins can be obtained. By separating glycans into neutral and acidic pools, it was possible to clearly identify glycans directly from MALDI-MS without chemical modification. In addition, it was shown that albumin and IgGs do not need to be removed from serum samples prior to analysis. With the ability to profile all glycans from serum, it becomes possible to apply bioinformatics approaches to search for patterns that define normal or disease states.

Furthermore, a glycomics approach may be even more sensitive than what can be achieved with proteomics. Even in cases where protein expression does not change, the types of N-glycans present on these proteins can indicate a change in physiological condition. Already, proteomics technologies are being explored as diagnostic tools. Examining glycosylation patterns may enable more precise characterization of certain disease states, such as the differentiation between benign and malignant tumors. Thus, in combination with a bioinformatics platform, serum glycan profiling could advance the utility of glycomics data for the early diagnosis of currently undetectable disease states.

Example 2

References

1. Jaeken, J., Matthijs, G. (2001) Congenital disorders of glycosylation. *Annu Rev Genomics Hum Genet.* 2, 129-51.
2. Freeze, H. H., Aebi, M. (1999) Molecular basis of carbohydrate-deficient glycoprotein syndromes type I with normal phosphomannomutase activity. *Biochim Biophys Acta* 1455, 167-78.
3. Van Eijk, M., White, M. R., Batenburg, J. J., Vaandrager, A. B., Van Golde, L. M., Haagsman, H. P., Hartshorn, K. L. (2003) Interactions of Influenza A virus with Sialic Acids present on Porcine Surfactant Protein D. *Am J Respir Cell Mol Biol.*
4. Glick, M. C., Kothari, V. A., Liu, A., Stoykova, L. I., Scanlin, T. F. (2001) Activity of fucosyltransferases and altered glycosylation in cystic fibrosis airway epithelial cells. *Biochimie* 83, 743-7.
5. Scanlin, T. F., Glick, M. C. (2000) Terminal glycosylation and disease: influence on cancer and cystic fibrosis. *Glycoconj J* 17, 617-26.
6. Peracaula, R., Tabares, G., Royle, L., Harvey, D. J., Dwek, R. A., Rudd, P. M., de Llorens, R. (2003) Altered glycosylation pattern allows the distinction between prostate-specific antigen (PSA) from normal and tumor origins. *Glycobiology* 13, 457-70.
7. Belanger, A., van Halbeek, H., Graves, H. C., Grandbois, K., Stamey, T. A., Huang, L., Poppe, I., Labrie, F. (1995) Molecular mass and carbohydrate structure of prostate specific antigen: studies for establishment of an international PSA standard. *Prostate* 27, 187-97.
8. Prakash, S., Robbins, P. W. (2000) Glycotyping of prostate specific antigen. *Glycobiology* 10, 173-6.
9. Chakraborty, A. K., Pawelek, J., Ikeda, Y., Miyoshi, E., Kolesnikova, N., Funasaka, Y., Ichihashi, M., Taniguchi, N. (2001) Fusion hybrids with macrophage and melanoma cells up-regulate N-acetylglucosaminyltransferase V, beta1-6 branching, and metastasis. *Cell Growth Differ* 12, 623-30.
10. Przybylo, M., Hoja-Lukowicz, D., Litynska, A., Laidler, P. (2002) Different glycosylation of cadherins from human bladder non-malignant and cancer cell lines. *Cancer Cell Int* 2, 6.
11. Lin, S., Kemmner, W., Grigull, S., Schlag, P. M. (2002) Cell surface alpha 2,6 sialylation affects adhesion of breast carcinoma cells. *Exp Cell Res* 276, 101-10.
12. Nemoto-Sasaki, Y., Mitsuki, M., Morimoto-Tomita, M., Maeda, A., Tsuiji, M., Irimura, T. (2001) Correlation between the sialylation of cell surface Thomsen-Friedenreich antigen and the metastatic potential of colon carcinoma cells in a mouse model. *Glycoconj J* 18, 895-906.
13. Dennis, J. W., Granovsky, M., Warren, C. E. (1999) Glycoprotein glycosylation and cancer progression. *Biochim Biophys Acta* 1473, 21-34.
14. Fernandes, B., Sagman, U., Auger, M., Demetrio, M., Dennis, J. W. (1991) Beta 1-6 branched oligosaccharides as a marker of tumor progression in human breast and colon neoplasia. *Cancer Res* 51, 718-23.

15. Petricoin, E. F., Ardekani, A. M., Hitt, B. A., Levine, P. J., Fusaro, V. A., Steinberg, S. M., Mills, G. B., Simone, C., Fishman, D. A., Kohn, E. C., Liotta, L. A. (2002) Use of proteomic patterns in serum to identify ovarian cancer. *Lancet* 359, 572-7.
16. Pujol, J. L., Quantin, X., Jacot, W., Boher, J. M., Grenier, J., Lamy, P. J. (2003) Neuroendocrine and cytokeratin serum markers as prognostic determinants of small cell lung cancer. *Lung Cancer* 39, 131-8.
17. Gadducci, A., Cosio, S., Carpi, A., Nicolini, A., Genazzani, A. R. (2004) Serum tumor markers in the management of ovarian, endometrial and cervical cancer. *Biomed Pharmacother* 58, 24-38.
18. Vander, A. J., Sherman, J. H., Luciano, D. S. (2001) *Human physiology: the mechanisms of body function.* McGraw-Hill, Boston, Mass.
19. Rohovec, J., Maschmeyer, T., Aime, S., Peters, J. A. (2003) The structure of the sugar residue in glycated human serum albumin and its molecular recognition by phenylboronate. *Chemistry* 9, 2193-9.
20. Bihoreau, N., Ramon, C., Lazard, M., Schmitter, J. M. (1997) Combination of capillary electrophoresis and matrix-assisted laser desorption ionization mass spectrometry for glycosylation analysis of a human monoclonal anti-Rhesus(D) antibody. *J Chromatogr B Biomed Sci Appl* 697, 123-33.
21. Watt, G. M., Lund, J., Levens, M., Kolli, V. S., Jefferis, R., Boons, G. J. (2003) Site-specific glycosylation of an aglycosylated human IgG1-Fc antibody protein generates neoglycoproteins with enhanced function. *Chem Biol* 10, 807-14.
22. Lacko, A. G., Reason, A. J., Nuckolls, C., Kudchodkar, B. J., Nair, M. P., Sundarraj an, G., Pritchard, P. H., Morris, H. R., Dell, A. (1998) Characterization of recombinant human plasma lecithin: cholesterol acyltransferase (LCAT): N-linked carbohydrate structures and catalytic properties. *J Lipid Res* 39, 807-20.
23. Bryce, R. A., Hillier, I. H., Naismith, J. H. (2001) Carbohydrate-protein recognition: molecular dynamics simulations and free energy analysis of oligosaccharide binding to concanavalin A. *Biophys J* 81, 1373-88.
24. Fukuda, M., Kobata, A. (1993) *Glycobiology: a practical approach.* IRL Press at Oxford University Press, Oxford; N.Y.
25. Zhao, Y., Kent, S. B., Chait, B. T. (1997) Rapid, sensitive structure analysis of oligosaccharides. *Proc Natl Acad Sci USA* 94, 1629-33.
26. Papac, D. I., Briggs, J. B., Chin, E. T., Jones, A. J. (1998) A high-throughput microscale method to release N-linked oligosaccharides from glycoproteins for matrix-assisted laser desorption/ionization time-of-flight mass spectrometric analysis. *Glycobiology* 8, 445-54.

Example 3

Glycan Analysis

Release of Glycans from Proteins

Several methods were used to cleave the carbohydrates from proteins:

A) Glycoproteins were denatured with 0.5% SDS and 1% β-mercaptoethanol. Since SDS (and other ionic detergents) inhibits enzyme activity, 1% NP-40 was added to counteract these effects. The enzymatic cleavage was performed overnight with PNGaseF (New England Biolabs, Beverly, Mass.) at 37° C. in sodium phosphate buffer, pH 7.5 or Tris acetate buffer pH 8.3.

B) Samples were reduced with DTT followed by alkylation with either iodoacetic acid or iodoacetamide. The sample was dialyzed against phosphate buffer, pH 7.5 or Tris acetate pH 8.3 overnight and concentrated to ~200 μl in a spin column with a 3000 Da MWCO filter. To cleave the sugars from the protein between 100 and 2,000 U of PNGaseF (New England Biolabs, Beverly, Mass.) were used.

C) Glycoproteins were denatured using a buffer containing 8M urea, 3.2 mM EDTA and 360 mM Tris, pH 8.6 [Papac, 1998]. Reduction and carboxymethylation of the glycoproteins was then achieved using DTT and iodoacetic acid (or iodoacetamide), respectively. After removal of denaturing, reducing and alkylating reagents, N-glycans were selectively released from the glycoproteins by incubation with PNGase F.

D) The steps for protein denaturing, protein alkylation and glycan release were also performed with the proteins bound to a solid support [Papac, 1998]. PVDF-coated wells in a 96-well plate were washed with 200 μl MeOH, 3×200 μl $H_2O$ and 200 μl RCM buffer (8M urea, 360 mM Tris, 3.2 mM EDTA, pH 8.3). The protein samples (10 to 50 μl) were then loaded in the wells along with 300 μl RCM buffer. After washing with wells two times with fresh RCM buffer, 300 μl of 0.1M DTT in RCM buffer was added for 1 hr at 37° C. To remove the excess DTT, the wells were washed three times with $H_2O$. For the carboxymethylation, 300 μl of 0.1M iodoacetic acid in RCM buffer was added for 30 minutes at 37° C. in the dark. The wells were washed again with water, the membrane was then blocked with 1 ml polyvinylpyrrolidone (360,000 AMW, 1% solution in $H_2O$) for 1 hr at room temperature. Before adding the PNGaseF, the wells were washed again with water. To release the glycans, 100 to 1,000 U of PNGaseF were added in 300 μl of 50 mM Tris, pH 7.5 and incubated overnight at 37° C. Released glycans were pipetted from the wells and purified.

E) Alternatively, after the proteins were denatured, EndoH or Endo F (instead of PNGASE F) was used to release the glycans.

F) Chemical methods, such as hydrazinolysis and reductive β-elimination were also used.

G) The denaturing, reduction, alkylation and glycan cleavage steps were also performed in a semi-high-throughput fashion either in solution or by binding the proteins to solid supports in plates with hydrophobic membranes [Papac, 1998].

Purification of Released N-Glycans

Several methods were used to isolate and purify the released carbohydrates. These methods were used either individually and some were used in combination.

A) Proteins were precipitated with a 3× volume of cold ethanol. After centrifugation to remove the proteins, the supernatant containing the N-glycans was evaporated by vacuum (SpeedVac, TeleChem International, Inc., Sunnyvale, Calif.). Dried glycans were resuspended in water.

B) Concomitant protein and salt removal was achieved using cation exchange column of AG50W X-8 beads (Bio-Rad, Hercules, Calif.). The resin was charged with 150 mM acetic acid and washed with water. Glycan samples were loaded onto the column in water, and washed through with 3 ml $H_2O$. The flow through was collected and lyophilized to obtain the desalted sugars.

C) GlycoClean R cartridges (Prozyme, San Leandro, Calif.; formerly Glyko) were primed with 3 ml of 5% acetic acid, and the samples were loaded in water. Sugars were eluted with 3 ml of water passed through the column.

D) GlycoClean S cartridges (Prozyme, San Leandro, Calif.; formerly Glyko), were primed with 1 ml water and 1 ml 30% acetic acid, followed by 1 ml acetonitrile. The glycan sample was loaded (in a maximum volume of 10 µl) onto the disc, and the glycans were allowed to adsorb for 15 minutes. After washing the disc with 1 ml of 100% acetonitrile and 5×1 ml of 96% acetonitrile, glycans were eluted with 3×0.5 ml water.

E) GlycoClean H cartridges (Prozyme; 200 mg bed) were washed with 3 ml of 1M NaOH, 3 ml $H_2O$, 3 ml 30% acetic acid, and 3 ml $H_2O$ to remove impurities. The matrix was primed with 3 ml 50% acetonitrile with 0.1% TFA (Solvent A) followed by 3 ml 5% acetonitrile with 0.1% TFA (Solvent B). After loading the sample in water, the column was washed with 3 ml $H_2O$ and 3 ml Solvent B. Finally, the sugars were eluted using 4×0.5 ml of Solvent A. GlycoClean H cartridges can be reused after washing with 100% acetonitrile and re-priming with 3 ml of Solvent A followed by 3 ml of Solvent B. For the 25 mg cartridge, wash volumes were reduced to 0.5 ml. Eluted fractions were lyophilized and the isolated glycans were resuspended in 10-40 µl $H_2O$.

F) Hypercarb SPE cartridges (Thermo) were washed with 3 ml of 1M NaOH, 3 ml $H_2O$, 3 ml 30% acetic acid, and 3 ml $H_2O$ to remove impurities. The matrix was primed with 3 ml 5% acetonitrile with 0.05% TFA (Solvent B). After loading the sample in water, the column was washed with 3 ml $H_2O$ and 3 ml Solvent B. Finally, the neutral sugars were eluted using 15% acetonitrile 0.05% TFA and acidic glycans were eluted using 50% acetonitrile 0.05% TFA.

G) Non-porous graphitic carbon SPE cartridges (SU-PELCO) were primed with 3 ml 5% acetonitrile and 0.05% TFA (Solvent B). After loading the sample in water, the column was washed with 3 ml $H_2O$ and 3 ml Solvent B. Finally, the neutral sugars were eluted using 15% acetonitrile 0.05% TFA and acidic glycans were eluted using 50% acetonitrile 0.05% TFA.

H) The glycan purification step was also performed in a high-throughput format by using columns in 96-well plates. This process was facilitated by the use of a TECAN robot. This protocol allowed the processing of more than 90 samples at the same time.

Chemical Modification of N-Glycans

Several derivatization methods are currently used to increase the sensitivity and ionization efficiency of mass spectrometry data in the analysis of glycans. With these methods, it is often possible to analyze glycan pools as a mixture of neutral and acidic glycans, as the chemical properties of the glycans are modified to allow for more uniform ionization. N-glycan samples are commonly permethylated to protect each OH and $NH_2$ or amide group in the carbohydrate. This is particularly useful for MS techniques such as fast atom bombardment (FAB-MS), since permethylated glycans fragment in a more predictable manner than underivatized glycans. Permethylation can also increase sensitivity in electrospray (ES-MS) and MALDI-MS.

For permethylation, glycans in water were placed in a round-bottomed flask and lyophilized overnight. A slurry of NaOH in DMSO (0.5 ml) was added to the glycan sample, along with 0.5 ml methyl iodide and incubated for 15 minutes. The sample was then diluted with water and extracted 2× with $CHCl_3$, collecting the organic phase. After drying the organic phase with $MgSO_4$, it was filtered through glass wool and dried under vacuum. Samples were then redissolved in methanol for MALDI-MS analysis. Some drawbacks to per-methylation are that the sample has to be extremely clean for the reaction to go to completion and requires additional purification after the reaction. Although this method slightly improved the ionization of N-glycan standards in MALDI-MS over unmodified glycans, many species corresponding to incomplete modification were detected.

To conjugate N-glycans to the synthetic aminooxyacetyl peptide, glycans were dried and resuspended in aqueous peptide solution (240 µM). After adding 1 µl of 500 mM NaOAc pH 5.5 and 20 µl of acetonitrile, the sample was incubated overnight at 40° C. Before MALDI-MS analysis, glycopeptides were purified by C18, 0.6 µl bed ZipTip (Millipore, Billerica, Mass.). Specifically, the tip was washed with 5 µl of 100% acetonitrile, followed by water and 5% acetonitrile, 0.1% TFA. To load the sample, 2 µl of sample was drawn into the tip, and discarded after 5 seconds. After washing 3× with 5 µl $H_2O$, glycopeptides were eluted with 10% acetonitrile. Before MALDI-MS, it was necessary to clean up the reaction mixture using a C18 ZipTip in order to eliminate the buffer (NaOAc) used in the reaction. The ZipTip flowthrough, water wash and 10% acetonitrile elution were all spotted on the plate. The glycopeptide conjugates (in the 10% elution fraction) were readily observed in the MALDI-MS, and neutral and acidic sugars ionized more evenly in the positive mode as compared to unmodified glycans.

While the glycan-peptide conjugation reaction is simple, the free peptide is particularly unstable. Specifically, the peptide's hydroxylamine group readily reacts with any aldehydes or ketones present, thus preventing it from conjugating to the glycans. Other labeling reagents (i.e. APTS, ANTS, AMAC, etc.) have been used but the analysis of unmodified glycans, separated into neutral and acidic fractions, was the method of choice for these studies.

MALDI-MS Analysis Optimization of Unmodified Glycans

Neutral and acidic sugars require different treatment when being analyzed by MALDI-MS. In particular, neutral sugars ionize well in the positive ion mode, while the ionization of acidic sugars is optimal using the negative ion mode. To be able to analyze the low abundance glycans present in a mixture glycoforms or different glycoproteins, a matrix of matrices containing more than 96 possible recipe combinations was generated. This study was designed to optimize the MALDI-MS analysis for the highest sensitivity, spot morphology, reduced peak splitting, reduced fragmentation and linear response as a function of concentration.

As a starting point, the matrix for glycans (DHB) was utilized in combination with spermine (20 mg/ml DHB in acetonitrile and 25 mM spermine in water in a 1:1 ratio.). This recipe resulted in detection limits of 1 pmol and 10 pmol for neutrals and acidic glycan respectively. Significant peak splitting with multiple sodium and potassium ions were observed. Also, this matrix crystallized as long needle-shaped crystals, which makes it difficult to achieve reproducible quantification of glycans present in a sample and eliminates the possibility for the automation of data acquisition.

Figure 20A:
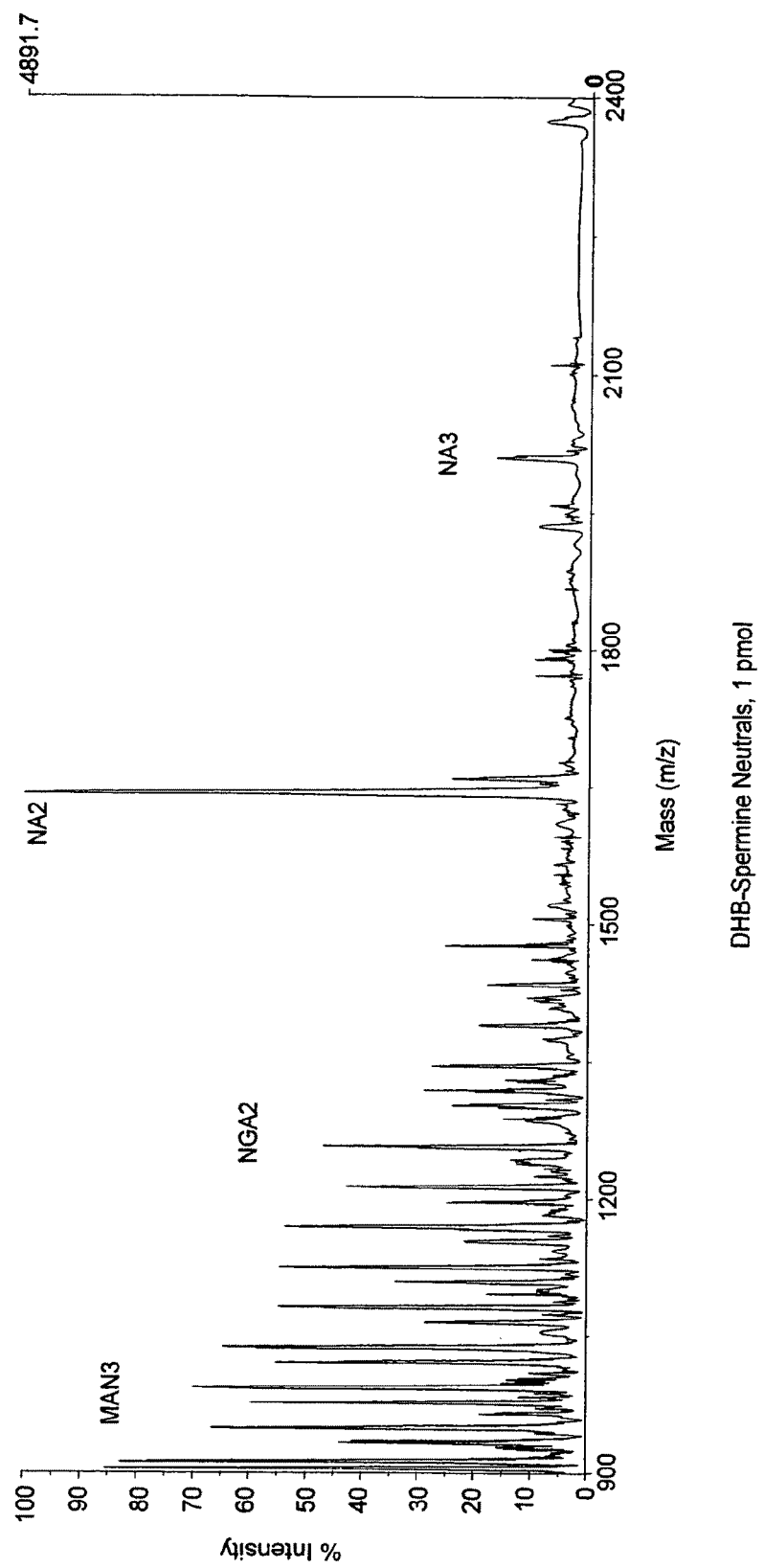
FIG. 20 provides a MALDI spectra of glycans before (A) and after (B) applying new recipe with optimized conditions.
Figure 20B:
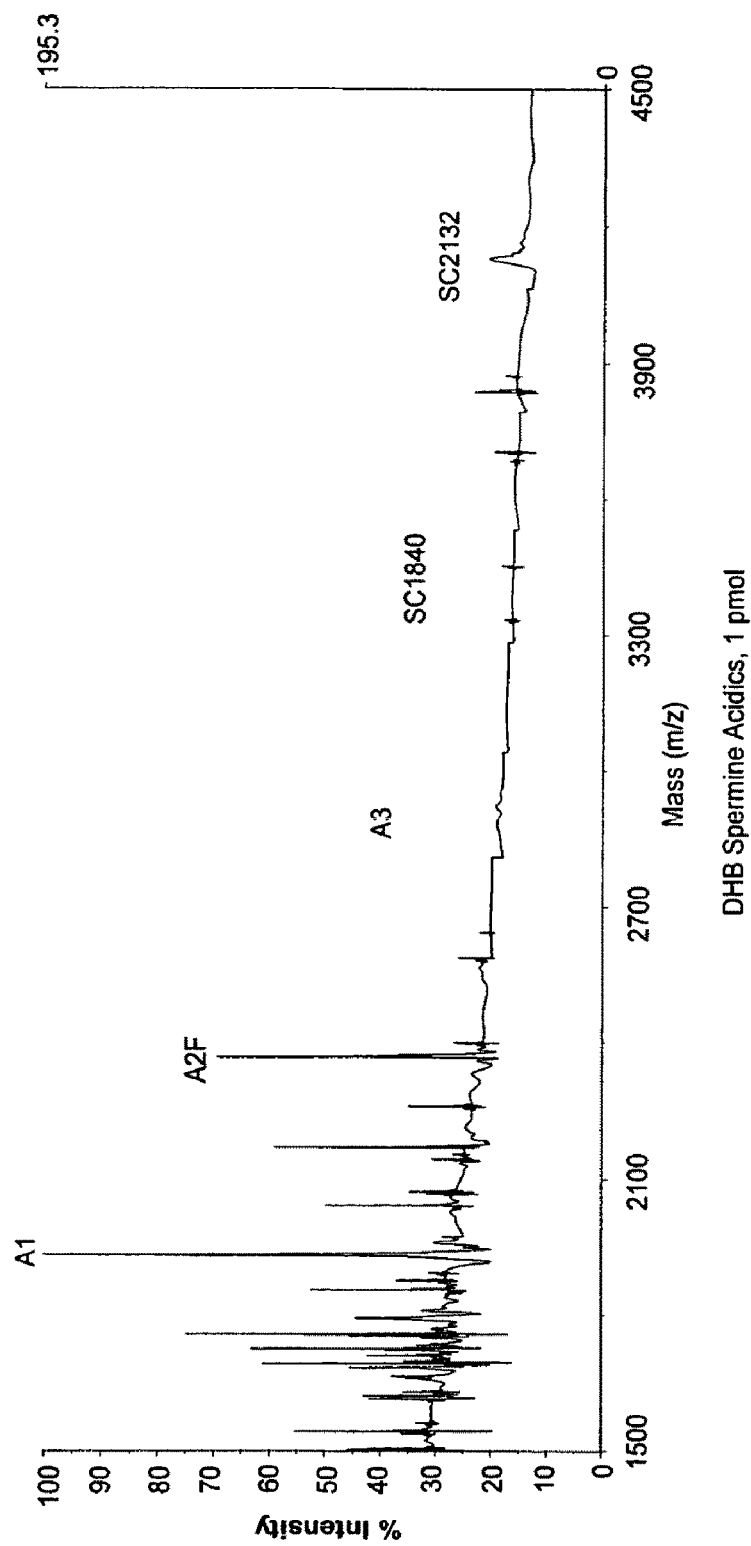
Figure 20D:
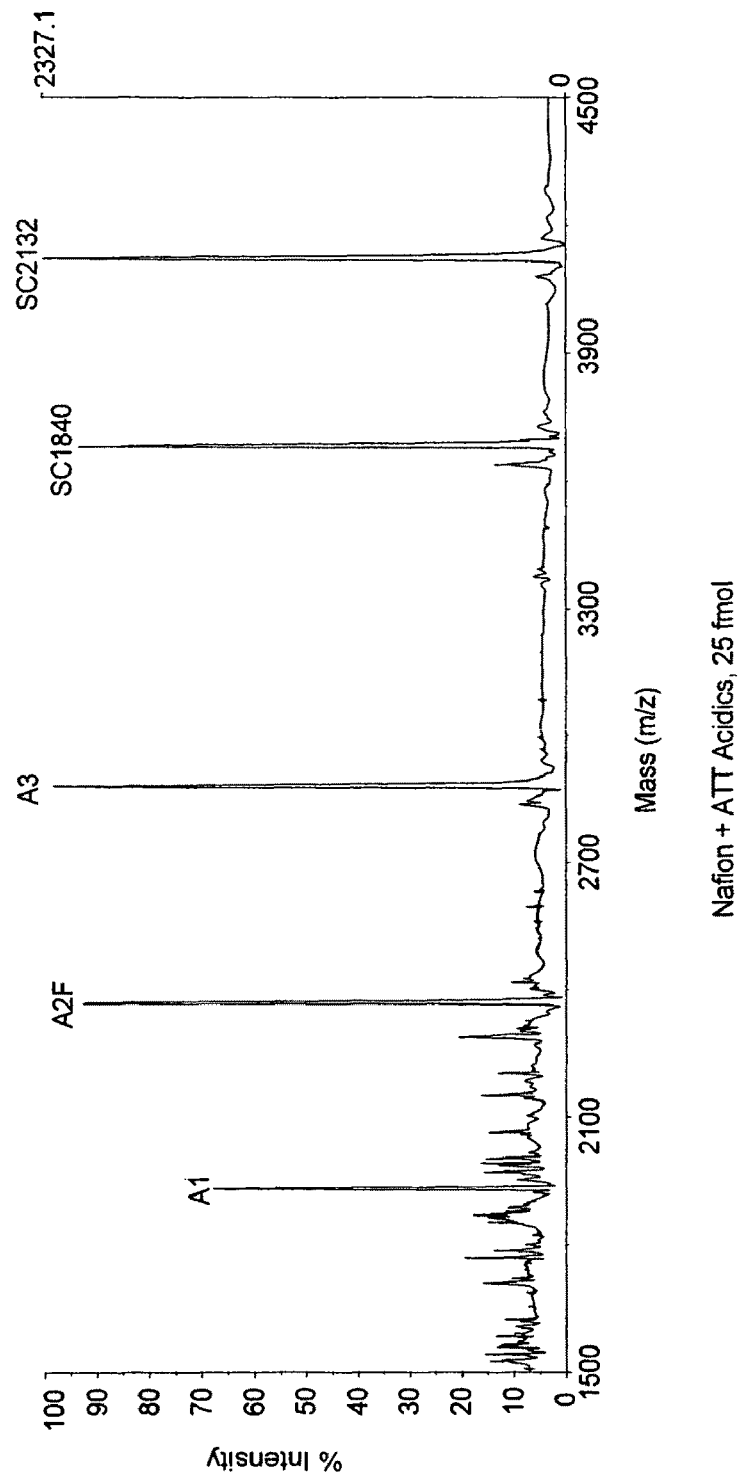

Some of the matrices and reagents used in this study were: caffeic acid, dihydroxybenzoic acid (DHB), spermine, 1-hydroxyisoquinoline (HIQ), 6-aza-2-thiothymine (ATT), 2,4,6-trihydroxyacetophenone (THAP), NAFION® (a perfluorinated ion-exchange compound), 6-hydroxypicolinic acid, 3-hydroxypicolinic, 5-methoxysalicylic acid (5-MSA), ammonium citrate, ammonium tartrate, sodium chloride, ammonium resins, etc. These reagents were used in combination with different solvents such as methanol, ethanol, acetonitrile and water. The matrix of matrices study resulted in new recipes of 2,5-dihydroxybenzoic acid (5 mg/ml) and 5-methoxysalicylic acid (0.25 mg/ml) in acetonitrile for neutrals and 6-aza-thiothymine (10 mg/ml in Ethanol) spotted on NAFION® (a perfluorinated ion-exchange compound) coating for acidic glycans. These matrices displayed the best detection limits for a mixture of carbohydrates to our knowledge: 25 fmol and 5 fmol for neutrals and acidic glycans respectively (FIG. 20). The new matrices also showed minimum peak splitting, highly uniform signal intensity, spot morphology and no detectable fragmentation.

Figure 21A:
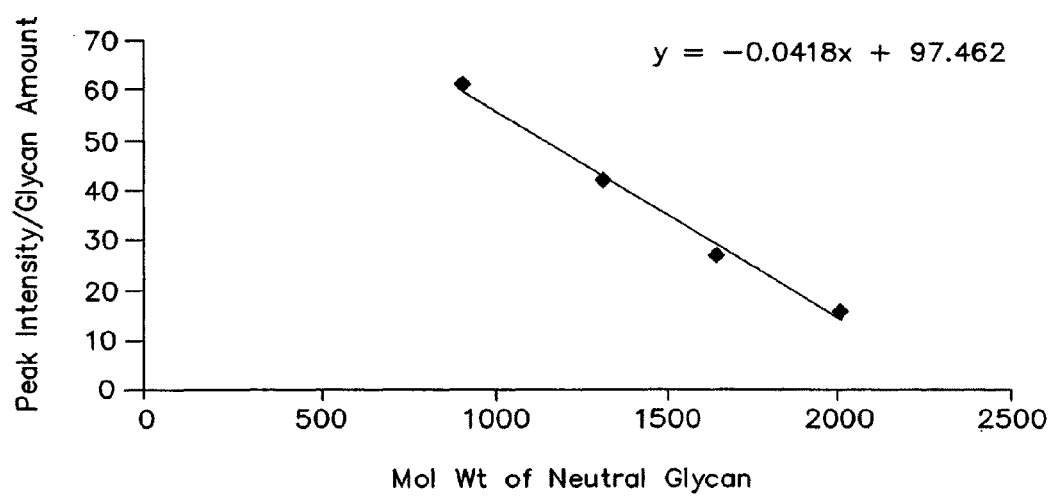
FIG. 21 provides results from glycan quantification using optimized matrix recipe for MALDI-MS FIG. 22 provides a schematic of an example of a methodology for analysis.

A detailed study to correlate between signal intensity, concentration and molecular weight was also performed. The analysis covered the entire range of possible molecular weights for N-glycans (900-4200 Da). Linear response as a function of concentration was observed for different glycans. Taken together, MALDI analysis of glycans using these matrices can be used to quantify the amount of glycans present in a mixture (FIG. 21). In particular these data enable the quantification of glycans at the low fmole concentration range. Other methods known to those of ordinary skill in the relevant art can also be used to quantify glycans at a higher range of concentrations [Harvey, 1993]. For FIGS. 1 and 2, the assigned peaks and the labels correspond to glycan standards from Dextra Laboratories Ltd. (Reading, United Kingdom).

Figure 21B:
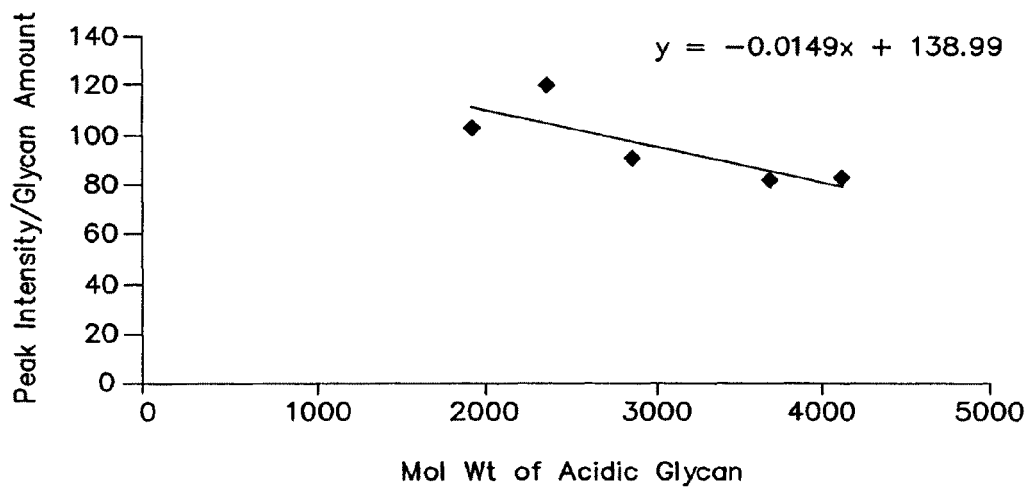

A potential concern in MALDI is that the ion yield of specific analyte in a mixture drops as the number of constituents increase. To evaluate this, the effect of the signal strength on the number of glycans present in a mixture was also evaluated for both matrices. Interestingly, there was very little change in the intensity of individual glycan signals even in the presence of other glycans, thus indicating that the ion yield of a specific constituent is not affected by the number of analytes present in the glycan mixture (FIG. 21B). This ensures that even in a complex mixture of glycans accurate amounts can be calculated using the signal intensity. Finally, the dynamic range of these matrices were in the low fmol range ensuring that changes in low abundant glycans can be accurately monitored by using these matrices.

To prepare the sample spots, three methods were used. For the crushed spot method, 1 μl of matrix was spotted on the stainless steel MALDI-MS sample plate and allowed to dry. After crushing the spot with a glass slide, 1 μl of matrix mixed 1:1 with sample was spotted on the seed crystals and allowed to dry. Alternatively, 1 μl of matrix was applied followed by 1 μl of sample, or vice versa. When resins were used in combination with the matrices, 1 μl of the resin was applied to the probe and allowed to dry before applying the sample in a 1:1 mixture with the matrix. All spectra were taken with the following instrument parameters: accelerating voltage 22000V, grid voltage 93%, guide wire 0.15% and extraction delay time of 150 nsec (unless otherwise noted). All N-glycans were detected in linear mode with delayed extraction and positive polarity for neutrals and negative polarity for acidics.

LC-MS, LC-MS/MS and Capillary Electrophoresis

Due to the limitations in isomass characterization using MALDI-MS, in some instances other techniques such as LC-MS (or MS/MS) and CE-LIF can be applied to further characterize the glycans released from the glycoprotein of interest. For LC-MS (or MS/MS), the reducing end of the carbohydrates is reduced using sodium borohydrate and the carbohydrates are separated in the using graphitized carbon column. The column is directly attached to an electrospray ionization mass spectrometer (ESI-MS) which allows the detection and characterization of the carbohydrates as they elute from the column. Although the use of exoglycosidases is often added to this LC-MS analysis, MS/MS fragmentation is also used for further linkage characterization of the carbohydrates based on the fragmentation pattern.

Similarly, capillary electrophoresis-laser induced fluorescence (CE-LIF) can also used for the further separation and characterization of the glycans. In this case, the carbohydrates, are first derivatized, in some preferred embodiments, by a reductive amination, at their reducing end with a fluorescent molecule such as APTS, ANTS, AMAC, etc. The fluorescently-modified (or "labeled") carbohydrates are then separated by capillary electrophoresis and detected with high sensitivity via laser induced fluorescence. Similar to LC-MS, glycosidases can also used in combination with CE-LIF in order to get further structural linkage information on the carbohydrates.

Identifying Glycans Composition from MALDI-MS Data

In a MALDI-MS spectrum, the main information obtained is mass of the parent ion. With just this data, it was indeed possible to deduce the monosaccharide composition of each peak (number of hexNAc, hexose, fucose and sialic acid residues). Using available information of biosynthetic rules, as well as whether each glycan is charged or uncharged, the number of possible structures for each mass peak observed can be significantly limited. A spreadsheet to use as a lookup table for unknown peaks was created. In addition to unmodified masses, entries for permethylated masses were included as well as peptide-conjugated glycans, according to the following equations:

$$n = Hex\text{NAc} \quad h = \text{hexose} \quad f = \text{fucose} \quad s = \text{sialic acid}$$

$$MW\text{-}H_2O = 203.1 \quad\quad 162.1 \quad\quad 146.1 \quad\quad 291.3$$

Unmodified Glycans $$\text{mass} = 203.1n + 162.1h + 146.1f + 291.3s + 18$$

Permethylated Glycans $$\text{perm} = \text{mass} + 51 + 14[3(n+h) + 2f + 5s]$$

Peptide-Conjugated Glycans $$\text{peptide} = \text{mass} + 1527.1$$

Using this table, regardless of the analytical methods, mass spectrometry peaks can be associated with specific monosaccharide compositions. A table of sample entries was shown above in Table 6. Other methods known to the art can be used to determine the glycan identity from MS data (See, for example U.S. Pat. No. 5,607,859; U.S. Ser. No. 09/558,137; and WO 00/65521).

Computational Tools to Characterize Glycoprotein Mixture

Figure 22:
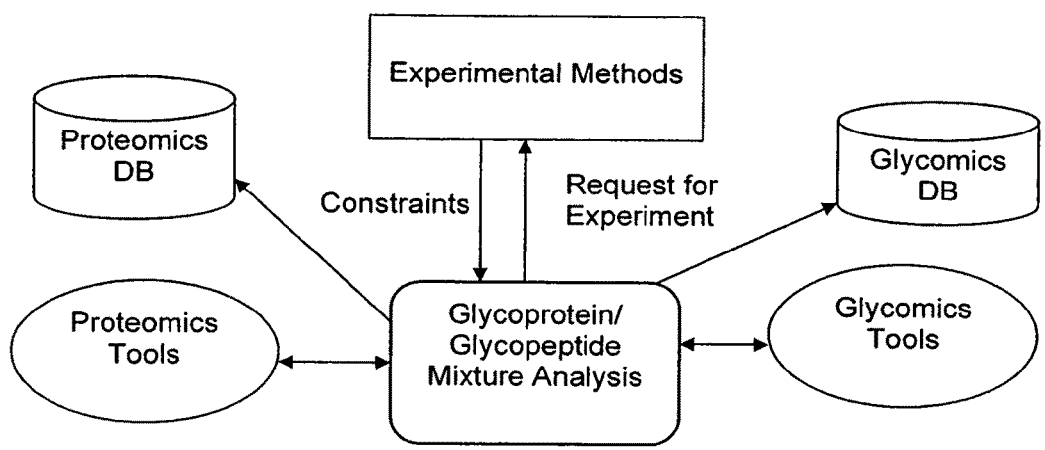
Figure 23:
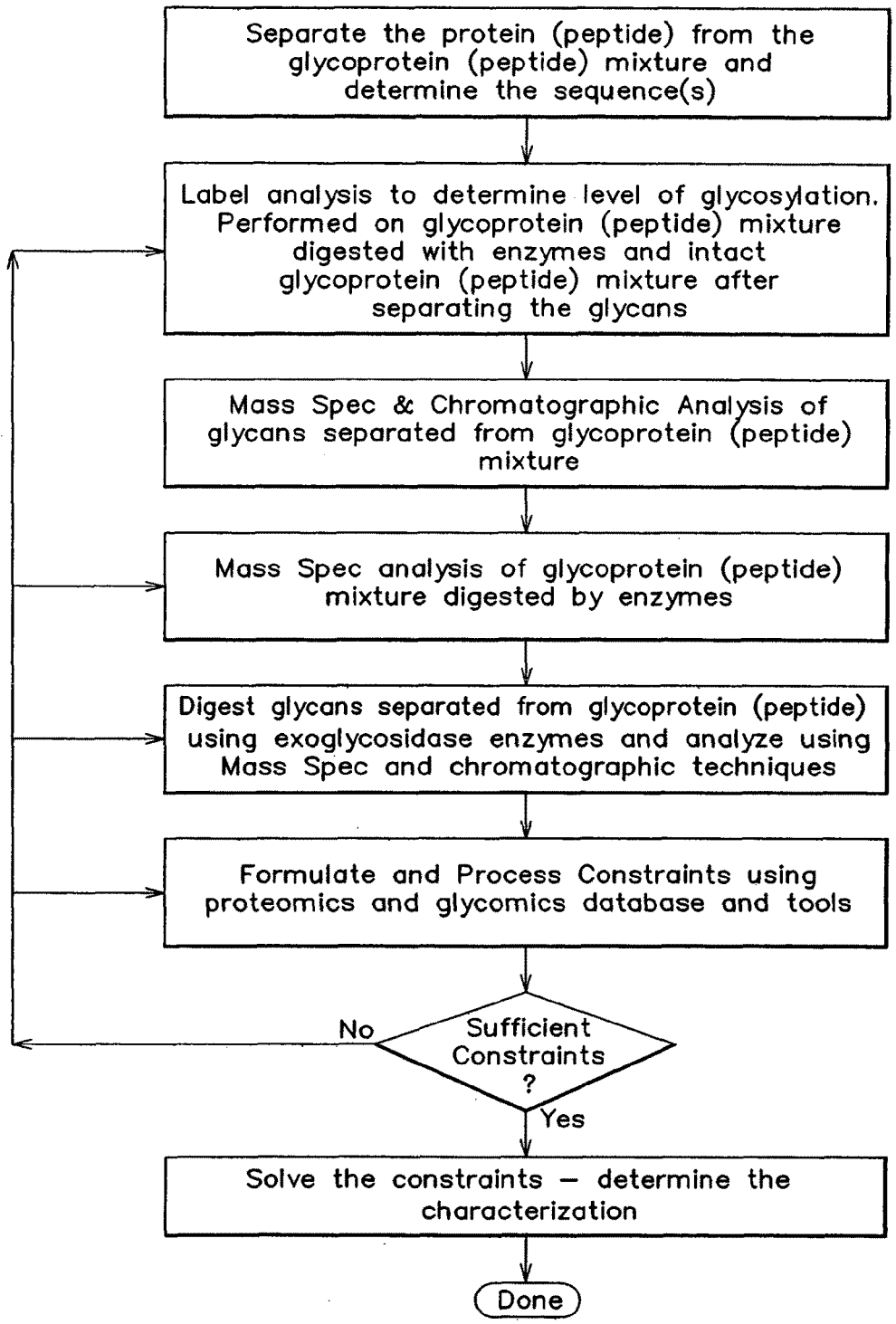
FIG. 23 provides a flowchart illustration of one example of a combined analytical-computational method for glycan analysis.

The diverse information gathered from the different experimental techniques are incorporated as constraints and used in combination with a panel of proteomics and glycomics based bioinformatics tools and databases for the efficient characterization (glycosylation site occupancy, quantification, glycan structure, etc.) of the glycoprotein mixture of interest (FIGS. 22 and 23). The following six steps provides one example of how, a known or unknown glycopeptide mixture can be characterized using the techniques described herein.

Step 1:
separate the glycans from the glycopeptides mixture. Isolated and sequence the resultant peptide(s). In the example, there was only one peptide chain and that was determined to be YCNISQKMMSRNLTKDR (SEQ ID NO: 1). This peptide has two possible N glycosylation sites: CNIS (SEQ ID NO: 2) and FNLT (SEQ ID NO: 3).

Step 2:
Digest the glycopeptide using trypsin followed by the cleavage of the glycans: one sample with $^{18}O$ labeling and another without labeling ($^{16}O$). Generate LC-MS spectra on both of the resultant samples. In this example, the following mass peaks were seen for the sample without labeling (289, 475, 476, 523, 855 and 856). With labeling the following mass peaks were seen (289, 475, 478, 523, 855, and 858).

By comparing the two spectra, the peptide fragments with mass 475 and 855 contain the glycosylation sites—both glycosylation sites are glycosylated. Based on a trypsin digest simulation of the peptide (YCNISQKMMSRNLTKDR) (SEQ ID NO: 1) (See, for example, us.expasy.org~tools/peptidecutter/) the different masses were assigned as the following: 289-DR; 475-NLTK (SEQ ID NO: 4); 523-MMSR (SEQ ID NO: 5); 855-YCNISQK (SEQ ID NO: 6).

During the deglycosylation step, the Asn residue is converted into an Asp residue which results in a total increase in molecular weight of 1 Da, thus explaining the appearance of the 476 and 856 peaks. The deglycosylation with concomitant $^{18}O$-labeling, results in an increase of 2 Da in the peptides that originally had a glycosylation site. This explains the appearance of the 478 and 858 peaks.

The quantitative measurement of the peaks via the methods described above reveals that the glycosylation site at NLTK (SEQ ID NO: 4) is 75% glycosylated. Similarly, the data for YCNISQK (SEQ ID NO: 6) reveals that it is 50% glycosylated. Similarly the undigested glycopeptide mixture is also cleaved of the glycans and label processed as described above. The resultant analysis shows that the entire mixture is 75% glycosylated.

Step 3:
The glycans are separated and the resultant glycans analyzed through MALDI-MS. In this example the resultant masses with Relative Abundance (Table 8) were:

TABLE 8

Masses and Relative Abundance

| Mass | Relative Abundance |
|------|--------------------|
| 1235 | 40 |
| 1397 | 44 |
| 1559 | 16 |

Thus, there are three different glycans in this glycopeptide mixture.

Step 4:
Digest the glycopeptide mixture with trypsin and analyze the resultant mixture through MALDI-MS. In this example the resultant masses are 289, 475, 523, 854, 1871, 2033 and 2089.

Based on comparing the MS results with the trypsin digest simulation of the peptide, the following observations are made. Fragment NLTK (SEQ ID NO: 4) is glycosylated with glycans with mass 1397 and 1559. Fragment YCNISQK (SEQ ID NO: 6) is glycosylated with glycan with mass 1235.

Thus there are six possible glycopeptide chains in the mixture.
  Chain A that is not glycosylated.
  Chain B in which the second Asn is glycosylated with Glycan-1397.
  Chain C in which the second Asn is glycosylated with Glycan-1559.
  Chain D in which the first Asn is glycosylated with Glycan 1235.
  Chain E in which the first Asn is glycosylated with 1235 and the second with 1397.
  Chain F in which the first Asn is glycosylated with 1235 and the second with 1559.

Step 5:
Generate equations based on the experimental results and/or other data.
  a, b, c, d, e and f are the relative abundances of the chains A, B, C, D, E and F respectively, and the following set of equations were generated based on the experimental results from steps 1 through 4.
  a+b+c+d+e+f=1 6 possible chains
  a+b+c=d+e+f 50% occupancy in first glycosylation site
  (a+d)*3=(b+c+e+f) 75% occupancy in second glycosylation site
  d+e+f=2.5*(c+t) Glycan 1235 to Glycan 1559
  b+e=2.75*(c+f) Glycan 1397 to Glycan 1559
  3*a=b+c+d+e+f 75% of glycopeptide chains are glycosylated Solving the equations, the results are:
a=0.25, b=0.25, c=d=0, e=0.3, f=0.2

Step 6:
The masses from step 3 can be resolved into potential glycan structures by using a glycan database lookup (www.functionalglycomics.org/glycomics/molecule/jsp/carbohydrate/searchByMw.jsp), and the exact structure of the carbohydrates were corroborated from the glycosidase digest analysis. By putting together the results in steps 1 to 6, the unknown glycoprotein mixture was determined to be (Tables 9 and 10):

TABLE 9

Glycan Identification

| Peptide | Glycan Site 1 | Glycan Site 2 | Relative Abundance |
|---------|---------------|---------------|--------------------|
| YCN$_1$ISQKMMSRN$_2$LTKDR (SEQ ID NO: 7) | None | None | .25 |
| YCN$_1$ISQKMMSRN$_2$LTKDR (SEQ ID NO: 7) | None | HEX$_6$HEXNAC$_2$ | .25 |
| YCN$_1$ISQKMMSRN$_2$LTKDR (SEQ ID NO: 7) | HEX$_5$HEXNAC$_2$ | HEX$_6$HEXNAC$_2$ | .3 |
| YCN$_1$ISQKMMSRN$_2$LTKDR (SEQ ID NO: 7) | HEX$_5$HEXNAC$_2$ | HEX$_7$HEXNAC$_2$ | .2 |

TABLE 10

Glycan Structure

| Glycan | Structure |
|---|---|
| HEX$_5$HEXNAC$_2$ | Man a1→6<br>　　　　Man a1→6<br>Man a1→3　　　　Man b1—4 GlcNAc b1—4 GlcNAc<br>　　　　　　　　→3<br>　　　　Man a1 |
| HEX$_6$HEXNAC$_2$ | Man a1→6<br>　　　　Man a1→3→6<br>Man a1　　　　　　Man b1—4 GlcNAc b1—4 GlcNAc<br>　　　　　　　　→3<br>Man a1—2 Man a1 |
| HEX$_7$HEXNAC$_2$ | Man a1—2 Man a1→6<br>　　　　　　　　Man a1→3→6<br>Man a1　　　　　　　　Man b1—4 GlcNAc b1—4 GlcNAc<br>　　　　　　　　　　→3<br>Man a1—2 Man a1 |

Analysis of Glycosylation of Glycoprotein Standards

As an example, the optimized procedures were performed using two known N-glycosylated protein standards with different properties, ribonuclease B (RNaseB), a glycoprotein that only contains high mannose structures, and ovalbumin, which contains both hybrid and complex glycan structures at one glycosylation site. The procedures described above were applied to samples (obtained from the Hamel laboratory, MIT Bioprocess Engineering Center, Cambridge, Mass.) produced under various conditions.

Determination and Quantification of Glycosylation Site Occupancy

Before protease cleavage, the glycoproteins are first denatured in the presence of urea, reduced with DTT and carboxymethylated with iodoacetamide. To remove the denaturing reagents, the samples are concentrated using a centrifugal concentrator (3,000 MWCO) followed by buffer exchanged into protease compatible buffer (50 mM ammonium bicarbonate, pH 8.5, for trypsin digest). The proteins are then cleaved by proteases followed by denaturation of proteases by boiling the sample in water and liophilization. Glycosylation site specific labeling is achieved by reacting the samples with PNGase F in the presence of $^{18}$O-water (FIG. 24). After desalting the glycosylated, unglycosylated, and $^{18}$O-labeled unglycosylated peptides through a C-18 solid phase extraction cartridge, these are used for LC-MS, LC-MS/MS, MALDI or MALDI-FTMS. For this study the $^{16}$O and $^{18}$O labeled samples were mixed in a 1:1 ratio before injection in order to facilitate the analysis. Other techniques for peptide sequencing can also be used at this point. The peptides were analyzed using a capillary LC-MS using a Vydac C-18 MS 5 μm (250×0.3 mm) column coupled to a Mariner Biospectrometry Workstation. The peptides generated from the protease cleavage were corroborated using the Swiss-Prot database (ribonuclease B, P00656 and ovalbumin, P01012).

Figure 25A:
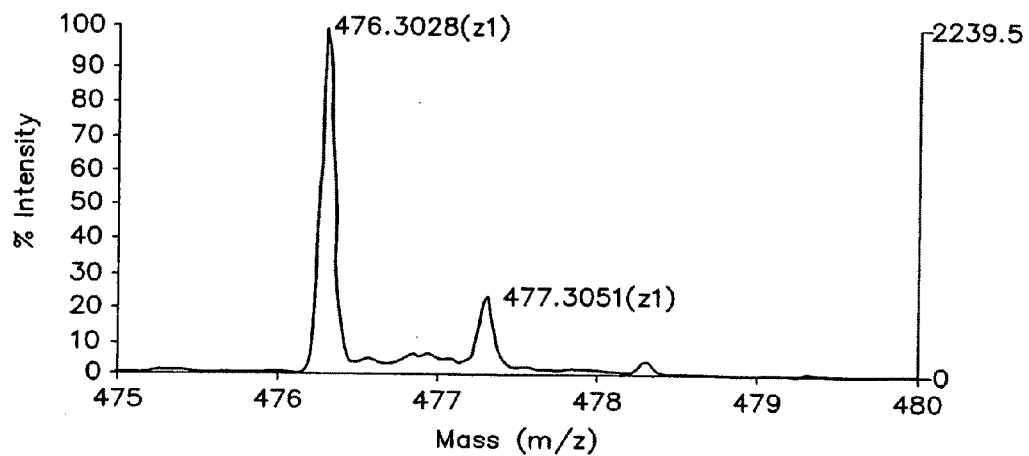
FIG. 25 provides results from glycan site occupancy analysis for ribonuclease B. MS data for peptide eluting at 7.8 minutes for unlabeled sample (A) and for the 16O/18O labeled 1:1 mixture (B). The expected [M+H]+ for the unlabeled peptide fragment is 476.29 Da.
Figure 25B:
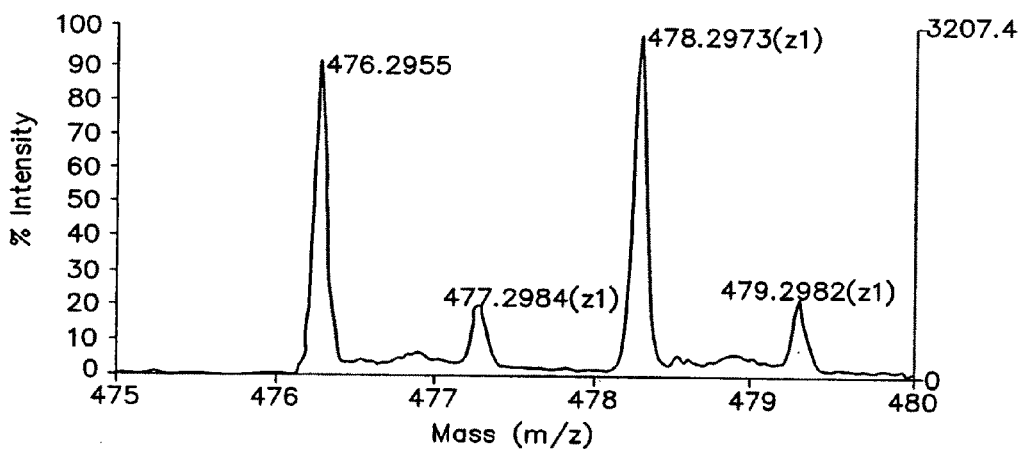

By studying the data obtained from the differentially labeled peptides after glycan cleavage, the specific glycosylation site can be easily determined. The introduction of the $^{18}$O at the glycosylation site is detected as a 2 Da increase for a specific peptide. This data facilitate the determination of the glycosylation site and its occupancy. As determined using the peptide mass calculator from the protein data bank (us.expasy.org/tools/peptide-mass.html), the tryptic digest of ribonuclease B should yield a peptide fragment with a [M+H]$^+$ of 475.29 Da containing the glycosylation site (NLTK) (SEQ ID NO: 4). Since the enzyme-mediated glycan cleavage generates an aspartic acid at the asparagine site, a peptide ion of [M+H]$^+$ of 476.29 Da for the unlabeled peptide and a 478.29 Da for the $^{18}$O-labeled peptide containing the glycosylation site was expected. As shown in FIG. 25, it was easy to identify the peptide fragment containing the glycosylation site in ribonuclease B by comparing the LC-MS data from the 1:1 mixture of $^{16}$O/$^{18}$O labeled peptides against the unlabeled sample. The presence of the +2 Da species in a 1:1 ratio in the $^{16}$O/$^{18}$O labeled mixture and the absence of species with [M+H]$^+$ of 475.29 Da indicates that this peptide contains a glycosylation site and that it is 100% occupied in both samples of the mixture. By analyzing the differences between the peptide masses in this batch to the peptide masses from the samples not exposed to glycan cleavage, a preliminary identification of the glycans was obtained. This was further validated and quantified by analyzing the glycans separately as described below.

Release and Purification of N-Glycans from Glycoprotein Standards

Several enzymatic and chemical methods were used to separate glycans from their protein cores. Of the chemical methods, hydrazinolysis provides the most efficient release of glycans [31]. However, this approach requires the sample to be very clean, with no residual salts, and the reaction does not proceed efficiently in air or water, making hydrazinolysis somewhat undesirable as a quick measure of quality control. N-glycanase F (PNGaseF) was chosen among enzymatic methods for the cleavage of N-linked glycans since the use of other enzymes results in loss of information such as fucosylation at the proximal GlcNAc.

For optimal enzyme activity proteins were unfolded, reduced and carboxymethylated prior to enzymatic digestion. Typically, the samples were denatured by heating in the presence of β-mercaptoethanol and/or SDS or by incubating at room temperature with urea, followed by reduction with DTT and carboxymethylation with iodoactic acid or iodoacetamide. To isolate the carbohydrates from the sample, the proteins were first precipitated with ethanol and the supernatant containing the glycans was then dried under vacuum and resuspended in water. Subsequent purification steps were required when detergents were used. Optimal results were obtained by using porous graphitic carbon columns. Neutral and charged carbohydrates were separated using these columns and eluted in mass spectrometry-compatible buffers. At this point, the most difficult component to get rid of was the detergent, which interferes with the types of analytical techniques that were used in this study.

Glycan Analysis

Figure 26:
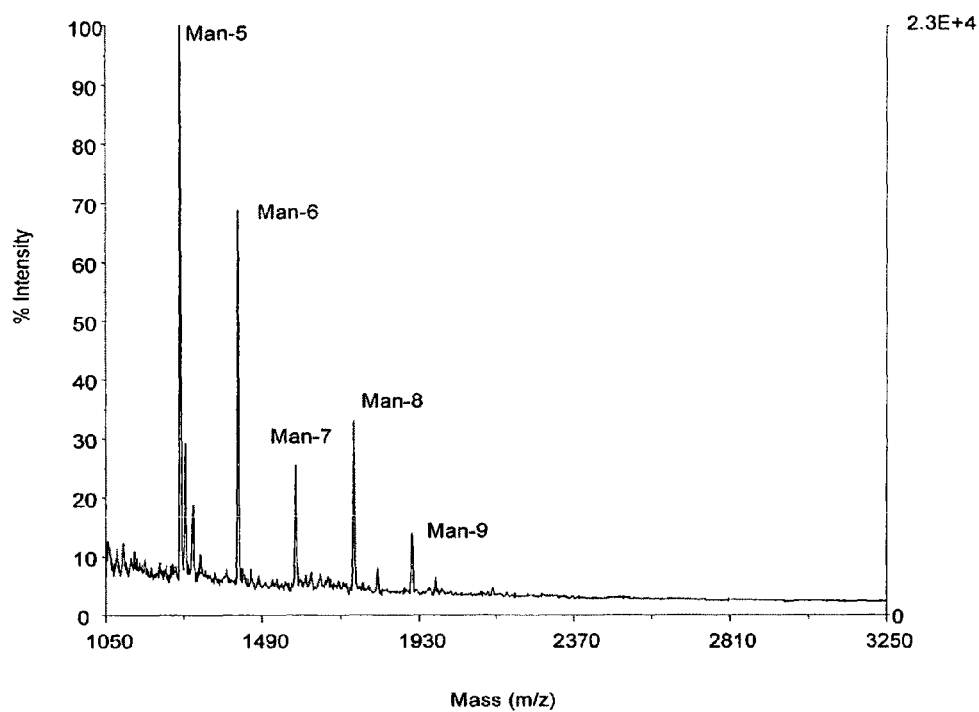
FIG. 26 provides MALDI-MS spectra of N-glycans from RNaseB with the expected high mannose structures.
Figure 27:
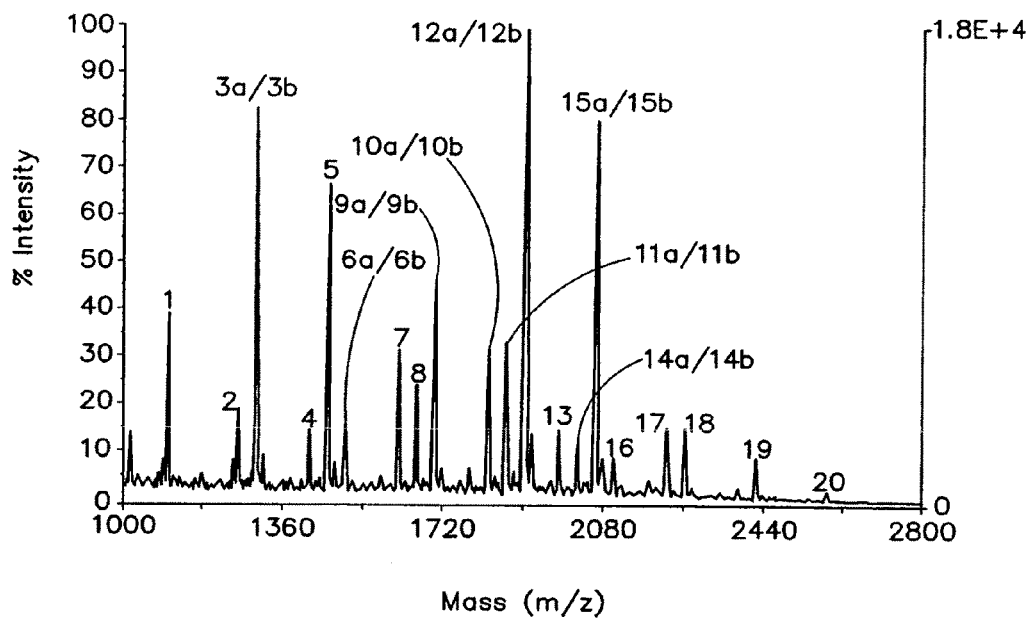
FIG. 27 provides results from MALDI-MS of N-glycans from ovalbumin. Each labeled peak corresponds to a previously reported structure listed below.

Different analytical techniques known in the art can be used for the glycan analysis methods. In this study MALDI-MS was used due to its simplicity and sensitivity (low femtomol after optimizations described above). The MALDI-MS protocol was optimized for the detection and quantification of low abundance carbohydrates (FIGS. 26 and 27). In particular, FIG. 27 shows the MALDI-MS spectrum of ovalbumin glycans. The observed peaks and their structures were found. The results are as shown above in Table 3.

RNAse B Computational Analysis

The information obtained from the previous analysis was analyzed using the computational platform that contains the proteomics and glycomics based bioinformatics tools and databases described herein.

The sequence of the protein backbone was determined from the proteomics database as follows:

```
                                              (SEQ ID NO: 8)
MALKSLVLLS LLVLVLLLVR VQPSLGKETA AAKFERQHMD

SSTSAASSSN YCNQMMKSRN₁ LTKDRCKPVN TFVHESLADV

QAVCSQKNVA CKNGQTNCYQ SYSTMSITDC RETGSSKYPN

CAYKTTQANK HIIVACEGNP YVPVHFDASV
```

The glycosylation site is at SNLT (SEQ ID NO: 9). It is 100% glycosylated and five different glycans were observed on analysis of the glycans via MALDI-MS. The results of the computational analysis showed that there were 5 different chains in the glycoprotein mixture as shown in Table 11 below:

TABLE 11

Results from the Computational Analysis

| Protein Sequence | Glycan | Relative Abundance |
|---|---|---|
| MALKSLVLLS LLVLVLLLVR VQPSLGKETA AAKFERQHMD SSTSAASSSN YCNQMMKSRN₁ LTKDRCKPVN TFVHESLADV QAVCSQKNVA CKNGQTNCYQ SYSTMSITDC RETGSSKYPN CAYKTTQANK HIIVACEGNP YVPVHFDASV (SEQ ID NO: 8) | $HEX_5H$ $EXNAC_2$ | .41 |
| MALKSLVLLS LLVLVLLLVR VQPSLGKETA AAKFERQHMD SSTSAASSSN YCNQMMKSRN₁ LTKDRCKPVN TFVHESLADV QAVCSQKNVA CKNGQTNCYQ SYSTMSITDC RETGSSKYPN CAYKTTQANK HIIVACEGNP YVPVHFDASV (SEQ ID NO: 8) | $HEX_6H$ $EXNAC_2$ | .29 |
| MALKSLVLLS LLVLVLLLVR VQPSLGKETA AAKFERQHMD SSTSAASSSN YCNQMMKSRN₁ LTKDRCKPVN TFVHESLADV QAVCSQKNVA CKNGQTNCYQ SYSTMSITDC RETGSSKYPN CAYKTTQANK HIIVACEGNP YVPVHFDASV (SEQ ID NO: 8) | $HEX_7H$ $EXNAC_2$ | .1 |

TABLE 11-continued

Results from the Computational Analysis

| Protein Sequence | Glycan | Relative Abundance |
|---|---|---|
| MALKSLVLLS LLVLVLLLVR VQPSLGKETA AAKFERQHMD SSTSAASSSN YCNQMMKSRN₁ LTKDRCKPVN TFVHESLADV QAVCSQKNVA CKNGQTNCYQ SYSTMSITDC RETGSSKYPN CAYKTTQANK HIIVACEGNP YVPVHFDASV (SEQ ID NO: 8) | $HEX_8H$ $EXNAC_2$ | .14 |
| MALKSLVLLS LLVLVLLLVR VQPSLGKETA AAKFERQHMD SSTSAASSSN YCNQMMKSRN₁ LTKDRCKPVN TFVHESLADV QAVCSQKNVA CKNGQTNCYQ SYSTMSITDC RETGSSKYPN CAYKTTQANK HIIVACEGNP YVFVHFDASV (SEQ ID NO: 8) | $HEX_9H$ $EXNAC_2$ | .06 |

MALDI-MS Analysis Of N-Glycans from Antibodies Produced in Applikon and Wave Reactors Two antibody samples produced by mouse-mouse hybridoma cells (Biokit S A, Barcelona, Spain) grown in an Applikon stirred tank reactor (STR) were analyzed, along with three samples produced in Wave reactors. The reactor conditions used are shown in Table 12.

TABLE 12

Reactor conditions used to produce antibody samples.

| Sample | Reactor Type | DO | pH | Other |
|---|---|---|---|---|
| 1 | Applikon STR | 50% | 7 | |
| 2 | Applikon STR | 90% | Not controlled | |
| 3 | Wave | Controlled | Not controlled | |
| 4 | Wave | Controlled | 7 | NaHCO₃ for pH control |
| 5 | Wave | Not controlled | 7 | Fresh media for pH control |

In the Applikon STR reactor, pH can be controlled automatically by the instrument, which dispenses $CO_2$, $NaHCO_3$ and $O_2$ as needed. In the Wave reactor, however, measurements must be taken manually and pH adjusted by hand. The pH in this reactor can be controlled by either adding fresh media as the cells grow, or adding $NaHCO_3$ for increased buffering capacity, and $CO_2$ as needed. The main difference between the reactor types is the mode of agitation. In the Applikon STR, a blade stirrer keeps the cell suspension in motion, while a sparger introduces oxygen to the system in a controlled manner. In the Wave reactor, a rocking motion generates waves that mix the components of the system and aids the transfer of oxygen and other gases into the system.

Figure 28:
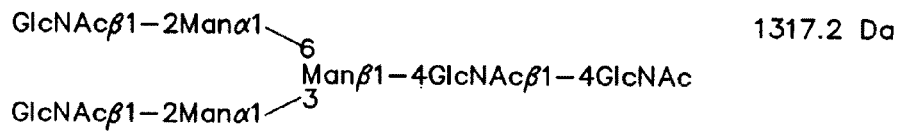
FIG. 28 provides structures and theoretical masses of N-glycans released from antibodies.
Figure 28:
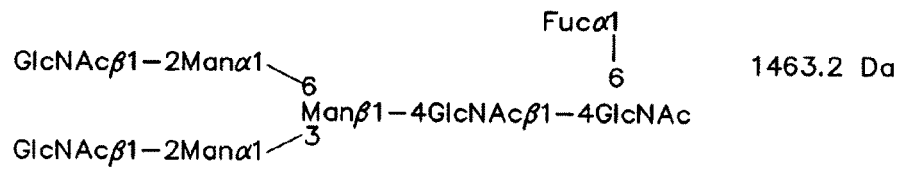
Figure 28:
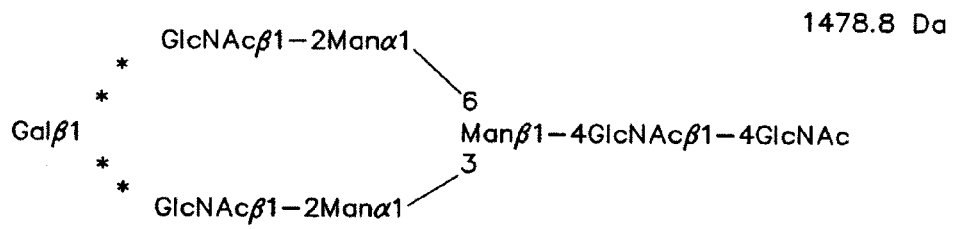
Figure 28:
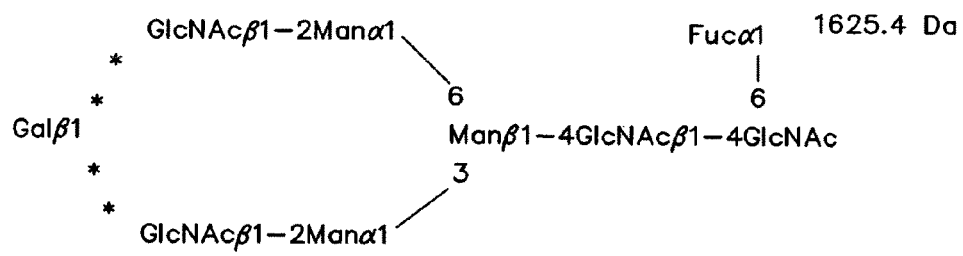
Figure 28:
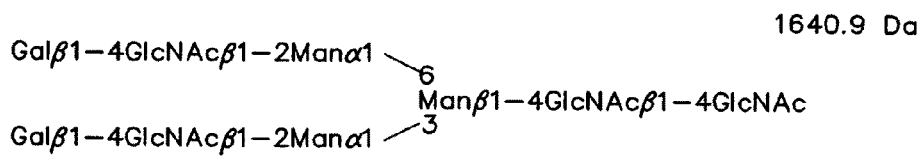
Figure 28:
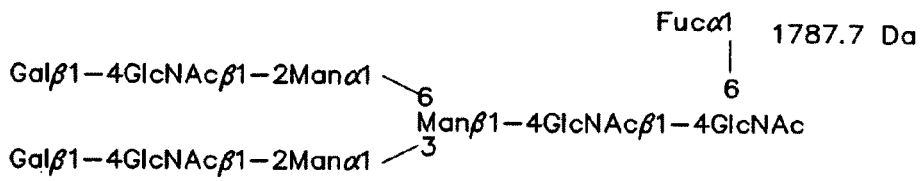

The purified antibodies were processed according to the optimized method described above. For each sample, 100 μg of protein was used as the starting material. Both positive and negative ion modes were used in the MALDI-MS to determine whether there were charged sugars present. No acidic glycans were observed from the analysis; which indicated neutral sugars were obtained from the antibodies. The MALDI-MS data of the five antibody samples produced using different conditions contained the same six glycans with molecular weights of 1317 Da, 1463 Da, 1478 Da, 1625 Da, 1641 Da and 1787 Da. The corresponding structures to these glycans were determined using the methods described above and are shown in FIG. 28 with their theoretical masses.

These results indicate that the production method did not alter the nature of the glycans present in the samples, rather, the quantities of some glycans were affected. Notably, samples prepared in the Wave reactor displayed a 40% decrease in 1625.4 Da glycan as well as 20% reductions in the 1787.7 Da glycan with respect to samples prepared in the Applikon reactor while the other glycans remained equal.

While the exact mechanisms for these changes are not known, it is interesting that the largest changes occurred due to reactor type, not reactor conditions such as pH, DO or media composition. Because the Applikon STR and the Wave reactors differ most in their method of agitation, reactor configuration is therefore the most likely source of glycan variation.

Differences in protein glycosylation have been linked to shear stress, such as by the stirring blade or the gas sparger in an STR reactor. However, the turbulence created in the Wave reactor also generates shear stress. One hypothesis for the shear stress effect is that cells must increase their overall protein production in response to membrane and/or cytoskeletal damage. As a consequence, the biosynthetic enzymes for glycosylation are diverted away from the protein of interest [27].

Although most observed parameters, including total antibody production, were similar in Applikon STR and Wave cultures, cells from the Wave reactor had slight increases in metabolic rates. Changes in cell metabolism may yield effects similar to those caused by shear stress, as all glycoproteins synthesized in the cell must compete for the same machinery in the ER and golgi.

Example 3

References

1. Hirschberg, C. B., Snider, M. D. (1987) Topography of glycosylation in the rough endoplasmic reticulum and Golgi apparatus. *Annu Rev Biochem* 56, 63-87.
2. Bause, E. (1983) Structural requirements of N-glycosylation of proteins. Studies with proline peptides as conformational probes. *Biochem J* 209, 331-6.
3. Marshall, R. D. (1972) Glycoproteins. *Annu Rev Biochem* 41, 673-702.
4. Dwek, R. A. (1996) Glycobiology: Toward Understanding the Function of Sugars. *Chem Rev* 96, 683-720.
5. O'Connor, S. E., Imperiali, B. (1996) Modulation of protein structure and function by asparagine-linked glycosylation. *Chem Biol* 3, 803-12.
6. Crocker, P. R., Varki, A. (2001) Siglecs in the immune system. *Immunology* 103, 137-45.
7. Helenius, A., Aebi, M. (2001) Intracellular functions of N-linked glycans. *Science* 291, 2364-9.
8. Imperiali, B., O'Connor, S. E. (1999) Effect of N-linked glycosylation on glycopeptide and glycoprotein structure. *Curr Opin Chem Biol* 3, 643-9.
9. Furukawa, K., Takamiya, K., Okada, M., Inoue, M., Fukumoto, S. (2001) Novel functions of complex carbohydrates elucidated by the mutant mice of glycosyltransferase genes. *Biochim Biophys Acta* 1525, 1-12.
10. Jaeken, J., Matthijs, G. (2001) Congenital disorders of glycosylation. *Annu Rev Genomics Hum Genet.* 2, 129-51.
11. Freeze, H. H., Aebi, M. (1999) Molecular basis of carbohydrate-deficient glycoprotein syndromes type I with normal phosphomannomutase activity. *Biochim Biophys Acta* 1455, 167-78.
12. Carchon, H., Van Schaftingen, E., Matthijs, G., Jaeken, J. (1999) Carbohydrate-deficient glycoprotein syndrome type IA (phosphomannomutase-deficiency). *Biochim Biophys Acta* 1455, 155-65.
13. Powell, L. D., Sgroi, D., Sjoberg, E. R., Stamenkovic, I., Varki, A. (1993) Natural ligands of the B cell adhesion molecule CD22 beta carry N-linked oligosaccharides with alpha-2,6-linked sialic acids that are required for recognition. *J Biol Chem* 268, 7019-27.
14. Sgroi, D., Varki, A., Braesch-Andersen, S., Stamenkovic, I. (1993) CD22, a B cell-specific immunoglobulin superfamily member, is a sialic acid-binding lectin. *J Biol Chem* 268, 7011-8.
15. Karlsson, K. A. (1998) Meaning and therapeutic potential of microbial recognition of host glycoconjugates. *Mol Microbiol* 29, 1-11.
16. Pritchett, T. J., Brossmer, R., Rose, U., Paulson, J. C. (1987) Recognition of monovalent sialosides by influenza virus H3 hemagglutinin. *Virology* 160, 502-6.
17. Sears, P., Wong, C. H. (1998) Enzyme action in glycoprotein synthesis. *Cell Mol Life Sci* 54, 223-52.
18. Varki, A. (1999) *Essentials of glycobiology*. Cold Spring Harbor Laboratory Press, Cold Spring Harbor, N.Y.
19. Parodi, A. J. (2000) Protein glucosylation and its role in protein folding. *Annu Rev Biochem* 69, 69-93.
20. Chang, G. D., Chen, C. J., Lin, C. Y., Chen, H. C., Chen, H. (2003) Improvement of glycosylation in insect cells with mammalian glycosyltransferases. *J Biotechnol* 102, 61-71.
21. Perlman, S., van den Hazel, B., Christiansen, J., Gram-Nielsen, S., Jeppesen, C. B., Andersen, K. V., Halkier, T., Okkels, S., Schambye, H. T. (2003) Glycosylation of an N-terminal extension prolongs the half-life and increases the in vivo activity of follicle stimulating hormone. *J Clin Endocrinol Metab* 88, 3227-35.
22. Darling, R. J., Kuchibhotla, U., Glaesner, W., Micanovic, R., Witcher, D. R., Beals, J. M. (2002) Glycosylation of erythropoietin affects receptor binding kinetics: role of electrostatic interactions. *Biochemistry* 41, 14524-31.
23. Krapp, S., Mimura, Y., Jefferis, R., Huber, R., Sondermann, P. (2003) Structural analysis of human IgG-Fc glycoforms reveals a correlation between glycosylation and structural integrity. *J Mol Biol* 325, 979-89.
24. Raju, T. S., Briggs, J. B., Borge, S. M., Jones, A. J. (2000) Species-specific variation in glycosylation of IgG: evidence for the species-specific sialylation and branch-specific galactosylation and importance for engineering recombinant glycoprotein therapeutics. *Glycobiology* 10, 477-86.
25. Kunkel, J. P., Jan, D. C., Butler, M., Jamieson, J. C. (2000) Comparisons of the glycosylation of a monoclonal antibody produced under nominally identical cell culture conditions in two different bioreactors. *Biotechnol Prog* 16, 462-70.
26. Zhang, F., Saarinen, M. A., Itle, L. J., Lang, S. C., Murhammer, D. W., Linhardt, R. J. (2002) The effect of dissolved oxygen (DO) concentration on the glycosylation of recombinant protein produced by the insect cell-baculovirus expression system. *Biotechnol Bioeng* 77, 219-24.
27. Senger, R. S., Karim, M. N. (2003) Effect of Shear Stress on Intrinsic CHO Culture State and Glycosylation of Recombinant Tissue-Type Plasminogen Activator Protein. *Biotechnol Prog* 19, 1199-209.
28. Muthing, J., Kemminer, S. E., Conradt, H. S., Sagi, D., Nimtz, M., Karst, U., Peter-Katalinic, J. (2003) Effects of buffering conditions and culture pH on production rates and glycosylation of clinical phase I anti-melanoma mouse IgG3 monoclonal antibody R24. *Biotechnol Bioeng* 83, 321-34.
29. Joao, H. C., Dwek, R. A. (1993) Effects of glycosylation on protein structure and dynamics in ribonuclease B and some of its individual glycoforms. *Eur J Biochem* 218, 239-44.
30. Harvey, D. J., Wing, D. R., Kuster, B., Wilson, I. B. (2000) Composition of N-linked carbohydrates from ovalbumin and co-purified glycoproteins. *J Am Soc Mass Spectrom* 11, 564-71.
31. Patel, T., Bruce, J., Merry, A., Bigge, C., Wormald, M., Jaques, A., Parekh, R. (1993) Use of hydrazine to release in intact and unreduced form both N- and O-linked oligosaccharides from glycoproteins. *Biochemistry* 32, 679-93.
32. Tarentino, A. L., Plummer, T. H., Jr., Maley, F. (1974) The release of intact oligosaccharides from specific glycoproteins by endo-beta-N-acetylglucosaminidase H. *J Biol Chem* 249, 818-24.
33. Tarentino, A. L., Maley, F. (1974) Purification and properties of an endo-beta-N-acetylglucosaminidase from *Streptomyces griseus*. *J Biol Chem* 249, 811-7.
34. Tarentino, A. L., Gomez, C. M., Plummer, T. H., Jr. (1985) Deglycosylation of asparagine-linked glycans by peptide: N-glycosidase F. *Biochemistry* 24, 4665-71.
35. Hu, G. F. (1995) Fluorophore-assisted carbohydrate electrophoresis technology and applications. *J Chromatogr A* 705, 89-103.
36. Rhomberg, A. J., Ernst, S., Sasisekharan, R., Biemann, K. (1998) Mass spectrometric and capillary electrophoretic investigation of the enzymatic degradation of heparin-like glycosaminoglycans. *Proc Natl Acad Sci USA* 95, 4176-81.

Example 4

Glycome Profiling

Sample Preparation and Carbohydrate Purification

Samples (usually 60 µl) from the different body fluids (serum, saliva, urine, tears, etc.) were processed in a similar manner as described below. Although in most cases the entire glycoproteome from the sample was analyzed, in some cases, the samples were further fractionated in order to analyze a "sub-glycome" from a specific body fluid. For example, a specific subset of proteins (such as antibodies, serum albumins, and other high abundance proteins) were removed from the original serum sample in order to analyze a more specific subset of glycoproteins in more detail. For fractionation, the sample proteome was divided into "high abundance" and "low abundance" using solid supports containing antibodies, proteins and synthetic molecules specific for the desired proteins to be removed or concentrated. For example, IgGs were removed using protein A agarose (Biorad), beads and serum albumin was removed using Affi-blue gel (Biorad). Other fractionations included the separation into acidic and basic proteome using cation and anion exchange chromatography or the separation between glycosylated and unglycosylated proteins using Con-A columns. The removal of specific proteins was quantified by western blots.

Proteins in the samples (either fractionated or unfractionated) were then denatured using a buffer containing 8M urea, 3.2 mM EDTA and 360 mM Tris, pH 8.6.[Papac, 1998]. Reduction and carboxymethylation of the sample proteome was then achieved using DTT and iodoacetamide respectively. Although iodoacetic acid is often used as the alkylating agent for the carboxymethylation, this one is not optimal when analyzing body fluids containing a wide range of glycoproteins since it generally causes precipitation of most proteins. After removal of denaturing, reducing and alkylating reagents, N-glycans were selectively released from the glycoproteins by incubation with PNGase F. The steps for protein denaturing, protein alkylation and glycan release were also performed with the proteins bound to a solid support as described below. The released carbohydrates were then purified from the proteins and separated into neutrals and acidic glycans in one step using a graphitized carbon columns. The glycan purification step was also performed in a high-throughput format by using columns in 96-well plates. This process was facilitated by the use of a TECAN robot. This protocol allowed the processing of more than 90 samples at the same time.

Fractionation of Serum Proteins

As an example, to remove serum albumin and IgGs, Affi-Blue Gel (Biorad, 200 µL) and Prot A (Biorad, 200 µL) were mixed in a 1:1 ratio and placed in a serum protein column. The column was washed with 1 mL of compatible serum protein binding buffer (20 mM phosphate, 100 mM NaCl, pH 7.2) using gravity flow. The column was placed in an empty 2 mL collection tube and centrifuged at 10,000 G for 20 seconds at 4° C. The flow was stopped during the sample preparation. Serum (60 µL) was mixed with compatible serum protein binding buffer (180 µL), and 200 µL of diluted serum was added to the top of the resin bed and allowed to mix with the column for 15 minutes. The column was then centrifuged at 10,000 G for 20 seconds at 4 C. Using the same collection tube, the column was washed with 200 µL of compatible serum protein binding buffer and centrifuged again at 10,000 G for 20 seconds at 4° C. For the removal of IgGs alone, only protein A agarose beads were used and the binding buffer was modified to 10 mM phosphate, 150 mM NaCl, pH 8.2.

To separate glycosylated (mainly high-mannose) from unglycosylated proteins, Concanavalin A-agarose beads (Vector Laboratories, Burlingame, Calif.) were used. To prepare the column, 3 ml ConA-agarose slurry was washed with ConA buffer (20 mM Tris, 1 mM $MgCl_2$, 1 mM $CaCl_2$, 500 mM NaCl, pH 7.4). Before loading, 500 µl of serum was mixed with 150 µl of 5×ConA buffer. After washing with 3 ml ConA buffer, glycoproteins were eluted with 2 ml of 500 mM α-methyl-mannoside and dialyzed against 10 mM phosphate pH 7.2 overnight at 4° C.

Analysis of IgG and Serum Albumin Depletion

Samples were prepared for SDS-Page electrophoresis by diluting 1:1 with 2× sample buffer (120 mM Tris base, 280 mM SDS, 20% Glycerol, 10% BME, 20 ng/ml BPB), boiled for 5 minutes, and 10 µl was loaded per lane in a 4-12% Bis-Tris precast gel (Invitrogen: NPO323BOX). Lane one contained 5 ul of a standard (BioRad: Precision All Blue Standard, 161-0373). The gel was run for 70 minutes at 200V. The gel was stained with SimplyBlue (Invitrogen:LC6060) according to the manufacturer. Imaging was performed on a Kodak Image Station 2000R. Another set of duplicate depleted samples were run as before and one gel was for SimplyBlue and the other was transferred to a 0.20 um nitrocellulose membrane (Invitrogen:LC2000) employing an X Cell Blot Module (Invitrogen:E19051) for 70 minutes at 30V. The membrane was then blocked overnight at 4° C. in 5% Blotto (Santa Cruz:sc-2325) and then probed with 1:1000 Protein A-hrp (Zymed:10-1023) for 1 hour at 4° C. and washed 4 times with washing buffer (1×TBS:200 mMTris base, 1.5M NaCl, pH7.5). The blot was developed with 4 ml of substrate (ECL plus Western Blotting Detection System: RPN2132) for 2 minutes and then exposed. The bands corresponding to the treatments were manually captured as ROI (region of interest) employing the Kodak 1D Image Analysis Software and the Mean Intensity was normalized to the controls.

Figure 29B:
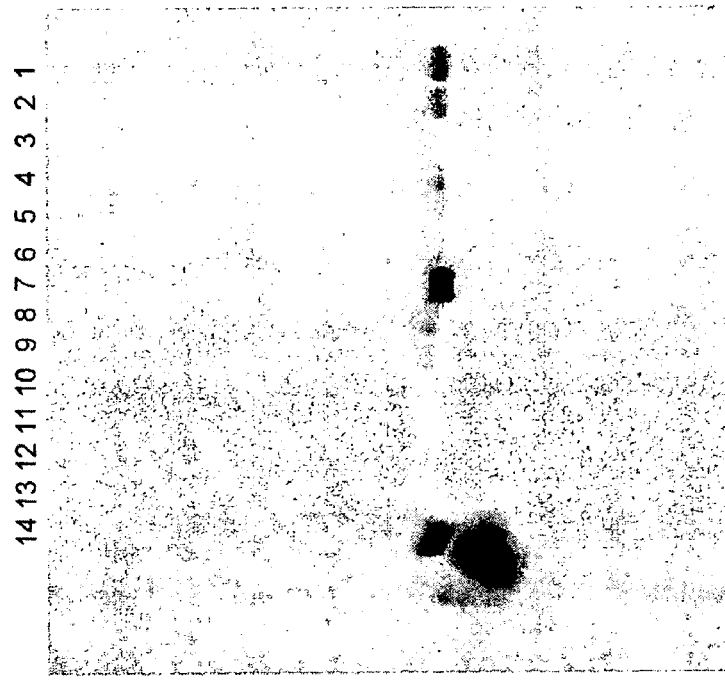
FIG. 29 shows the results from an analysis of depletion of serum albumin and IgGs from serum. A) SDS gel stained with Simply blue before (lane 7 and 14) and after removal of serum albumin and IgG using different conditions (lanes 1-6 and 8-13). B) Western blot (using protein A-HRP detection) used for quantifying the removal of IgGs. Lanes 7 and 14 are without depletion and 1-6 and 8-13 are using different conditions for the removal. C) Quantification of IgG removal.
Figure 29A:
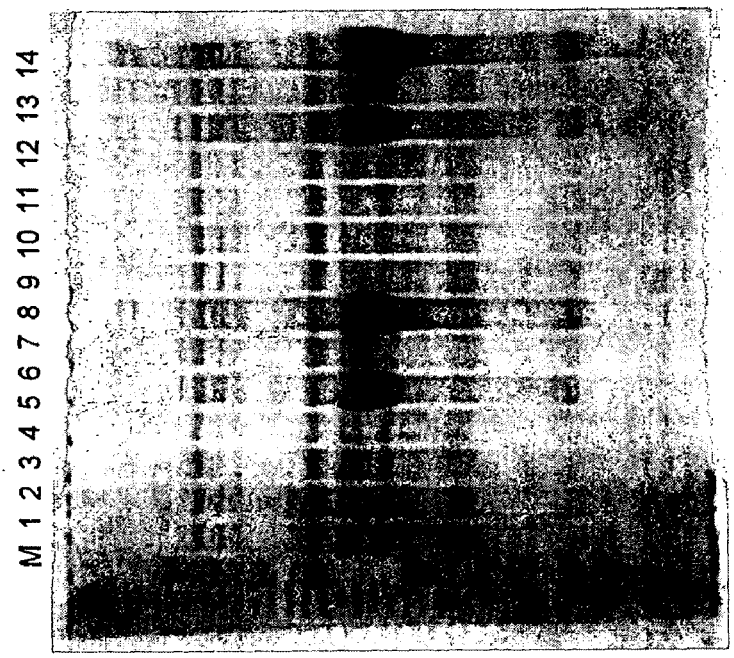
Figure 29C:
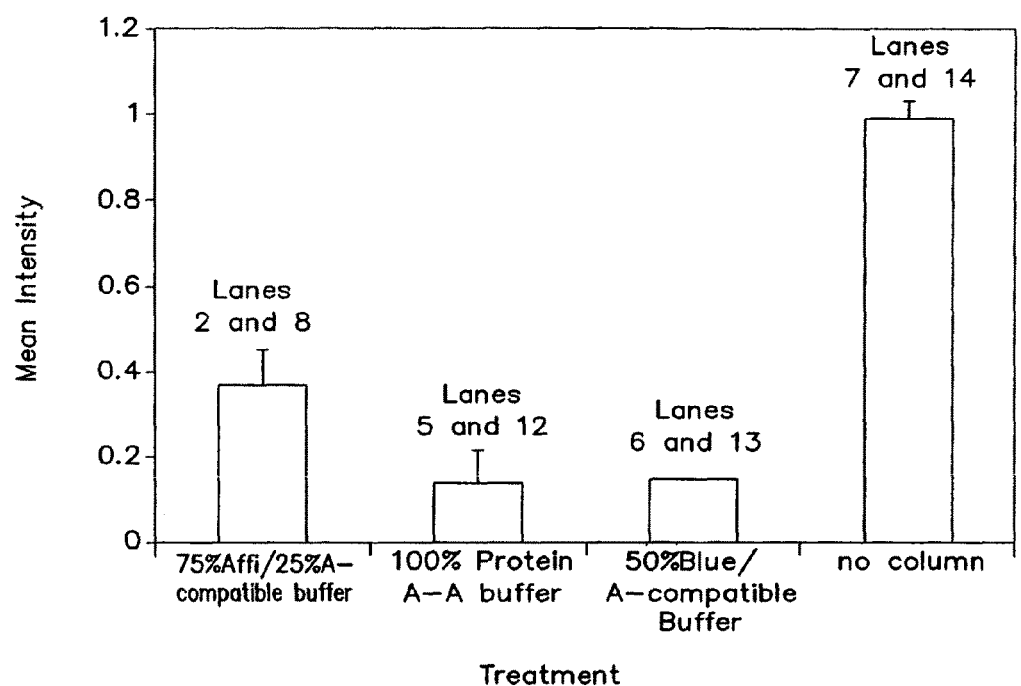

The same blot was then washed again and re-probed with 1:1000 Sheep Anti-human Albumin-hrp (Serotec:AHP102P) for 1 hour at 4° C. The blot was washed again, developed and imaged as before (FIG. 29).

Glycoblotting of Serum Samples

Protein samples were prepared for SDS-PAGE by diluting 1:1 with 2× denaturing buffer (40 µg/ml SDS, 20% glycerol, 30 µg/ml DTT and 10 µg/ml bromophenol blue in 125 mM Tris, pH 6.8) and boiling for 2 min. Pre-cast Nu-PAGE 10% Bis-Tris protein gels were obtained from Invitrogen (Carlsbad, Calif.). Each lane was loaded with a maximum of 10 µl of sample and run for 50 min at 200V. After electrophoresis was complete, the gel was stained with Invitrogen SafeStain (1 hour in staining solution, then washed overnight with water).

The GlycoTrack glycoprotein detection kit was obtained from Prozyme (formerly Glyko). All reagents except buffers were supplied with the kit. Two methods were attempted—either biotinylating glycoproteins after blotting (a) or before blotting (b). For both methods, samples were first diluted 1:1 with 200 mM sodium acetate buffer, pH 5.5. The membrane was blocked by incubating overnight at 4° C. with blocking reagent, then washed 3×10 minutes with TBS.

For method (a), samples were denatured with SDS sample buffer, and subjected to SDS-PAGE and blotting to nitrocellulose. After washing the membrane with PBS, the proteins were oxidized with 10 ml of 10 mM sodium periodate in the dark at room temperature for 20 minutes. The membrane was washed 3 times with PBS, and 2 µl of biotin-hydrazide reagent was added in 10 ml of 100 mM sodium acetate, 2 mg/ml EDTA for 60 minutes at room temperature. After 3 washes with TBS, the membrane was blocked overnight at 4° C. with blocking reagent. Before adding 5 µl of streptavidin-alkaline phosphatase (S-AP) conjugate, the membrane was washed again with TBS. The S-AP was allowed to incubate for 60 minutes at room temperature, and excess was washed off with TBS. To develop the blot, 50 µl of nitro blue tetrazolium (50 mg/ml) and 37.5 µl of 5-bromo-4-chloro-3-indolyl phosphate p-toluidine (50 mg/ml) were added in 10 ml TBS, 10 mg/ml $MgCl_2$. After 60 minutes, the blot was washed with distilled water and allowed to air dry.

Figure 30:
FIG. 30 shows the results of protein A separation of IgG from serum. (a) Glycoblot of Protein A flow-through (Lane 3) and elution (Lane 4). Lane 1 contains protein standards, while Lane 2 (negative control) contains human serum albumin (* marks where album would run on an SDS-PAGE gel). Only glycosylated proteins are observed in the glycoblot, so the albumin does not stain.

In method (b), 20 µl of sample was mixed with 10 µl of 10 mM periodate in 100 mM sodium acetate, 2 mg/ml EDTA and incubated in the dark at room temperature for 20 minutes. To destroy excess periodate 10 µl of a 12.5 mg/ml sodium bisulfite solution in 200 mM NaOAc, pH 5.5 was added for 5 minutes at room temperature. Biotinylation was performed by adding 5 µl of biotin amidocaproyl hydrazide solution in DMF. After incubating at room temperature for 60 minutes, the sample was mixed with SDS denaturing buffer and boiled for 2 minutes. Samples were run on SDS-PAGE gels and transferred to a nitrocellulose membrane (2 hrs, 30V). At this point, blocking and developing steps were identical to method (a) (FIG. 30).

Glycan Release Using Solid Supports: PNGaseF Digestion on PVDF Membrane

Glycans were also released using PVDF membranes as described by Papac, et. al. [Papac, 1998]. However, high abundance proteins were first removed before using this method since it resulted in low recoveries when processing entire body fluids. PVDF-coated wells in a 96-well plate were washed with 200 µl MeOH, 3×200 µl $H_2O$ and 200 µl RCM buffer (8M urea, 360 mM Tris, 3.2 mM EDTA, pH 8.3). The protein samples (50 µl) were then loaded in the wells along with 300 µl RCM buffer. After washing with wells two times with fresh RCM buffer, 500 µl of 0.1M DTT in RCM buffer was added for 1 hr at 37° C. To remove the excess DTT, the wells were washed three times with $H_2O$. For the carboxymethylation, 500 µl of 0.1M iodoacetic acid in RCM buffer was added for 30 minutes at 37° C. in the dark. The wells were washed again with water, then the membrane was blocked with 1 ml polyvinylpyrrolidone (360,000 AMW, 1% solution in $H_2O$) for 1 hr at room temperature. Before adding the PNGaseF, the wells were washed again with water. To release the glycans, 4 µl of PNGaseF was added in 300 µl of 50 mM Tris, pH 7.5 and incubated overnight at 37° C. Released glycans were pipetted from the wells and purified through a graphitized carbon column. Similar to protocols used for the purification of glycans after performing the cleavage in solution, the purification of glycans after their release using PVDF membranes was also performed in a high-throughput format using columns in 96-well plates. This process was facilitated by the use of a TECAN robot.

Glycome Analysis using Mass Spectrometry

Figure 31A:
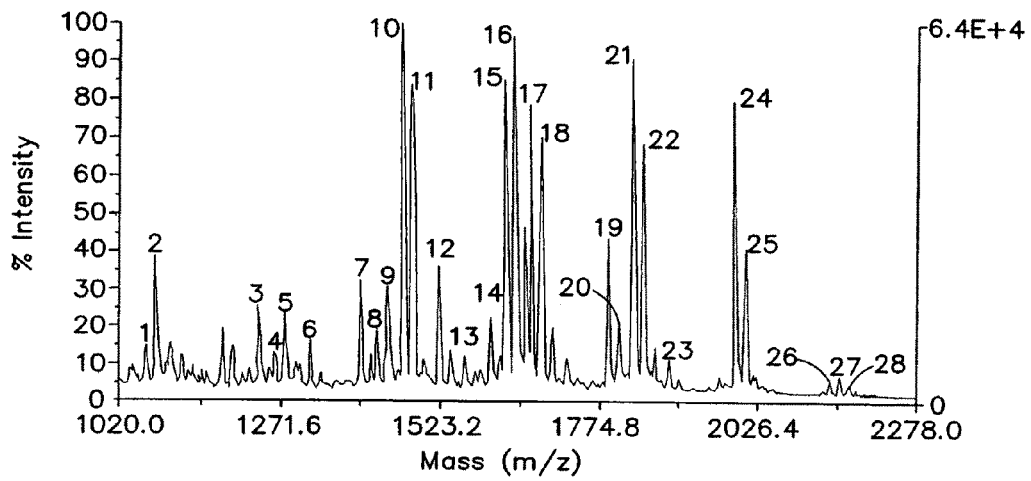
FIG. 31 shows the identification of serum N-glycans from MALDI-MS spectra. (a) shows neutral glycans, while (b) shows acidic glycans.
Figure 31B:
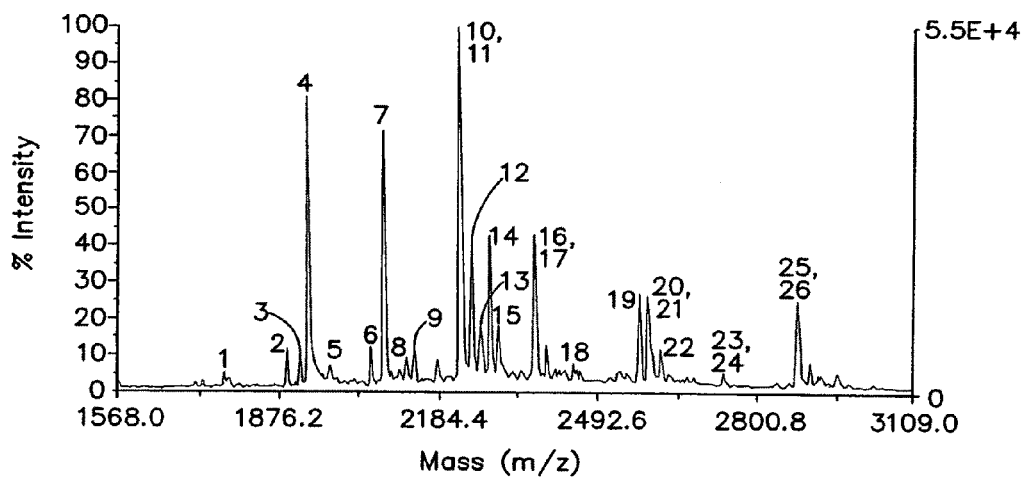

Glycan analysis using methods known to the art were used and applied to the total body fluid glycome analysis. Using the methods provided above were also able to analyze more than 90 samples. Optimized MALDI-MS methods which did not required additional labeling and purification steps and also displayed great reproducibility and sensitivity for the carbohydrate analysis was used. As shown in FIG. 31, total serum glycome profiles typically displayed between 25-30 neutral glycans as well as 25-30 acidic glycans.

Using the look-up table described previously, almost all the peaks in MALDI-MS serum profiles could be identified as glycans of known composition. Many of the unidentified peaks are sodium adducts. The composition and mass of each labeled peak are as listed above in Table 18. However, a few peaks in the acidic glycan spectrum correspond to more than one composition. This is more common in the higher mass range since there are a larger number of possible monosaccharide compositions.

Validation of Biomarker Structures

Figure 32A:
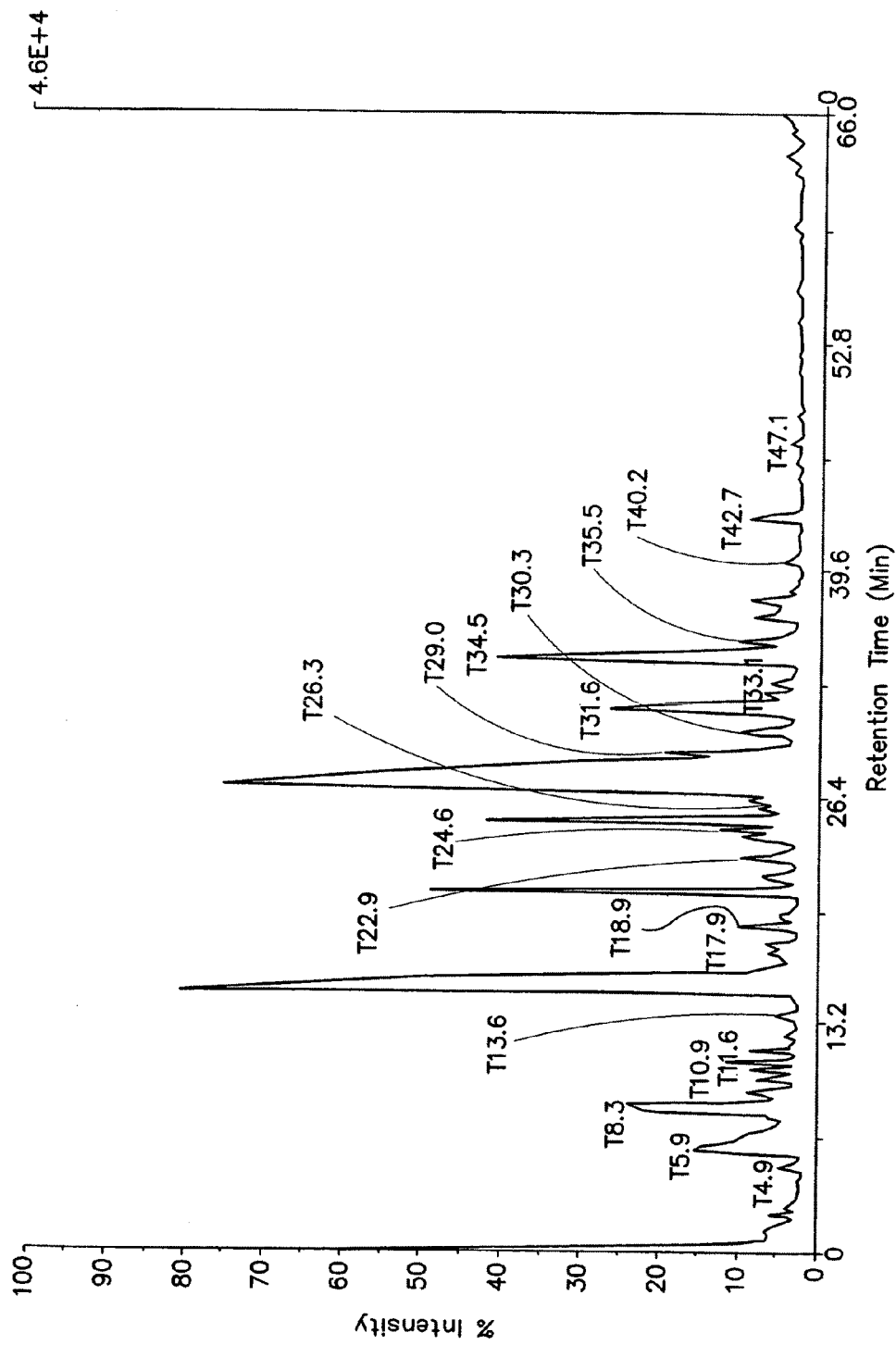
FIG. 32 provides the results from LC-MS (A) and CE-LIF (B) analysis of neutral glycome from serum.
Figure 32B:
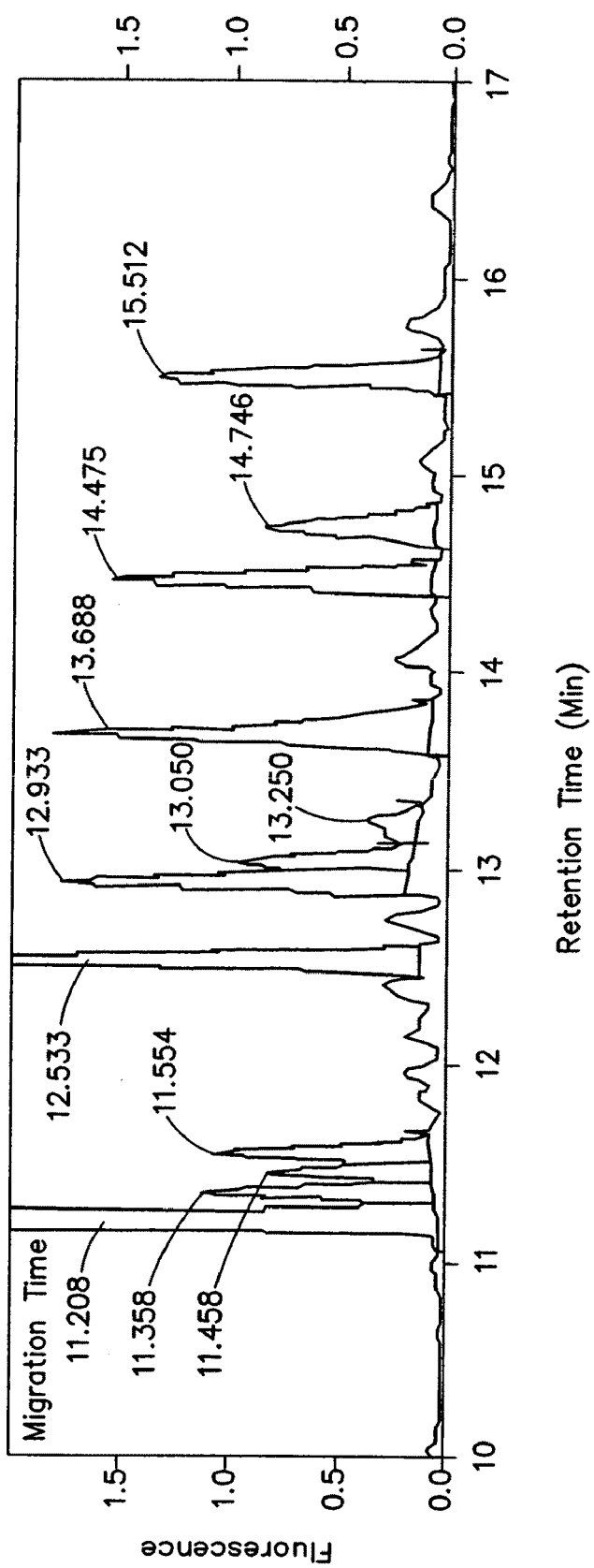

MALDI-MS analysis allows us to analyze the entire glycome profile in a sample and compare the changes in the glycome composition between samples in a rapid and efficient manner. Due to the limitations in isomass characterization, in some instances, other techniques known to the art can be used to further characterize and validate the biomarkers determined from the total profile found using MALDI-MS techniques. For example, liquid chromatography-mass spectrometry (LC-MS) and capillary electrophoresis-laser induced fluorescence (CE-LIF), are used in combination with a panel of exoglycosidases in order to obtain further linkage characterization of the carbohydrates (FIG. 32). After a specific pattern is established based on MALDI-MS results and the possible species are determined, matched samples displaying the differences in patterns are analyzed by these techniques in order to come up with defined structures of the biomarkers of interest. LC-MS/MS is also used to obtain linkage information based on the fragmentation patterns.

Other Body Fluids

Figure 33A:
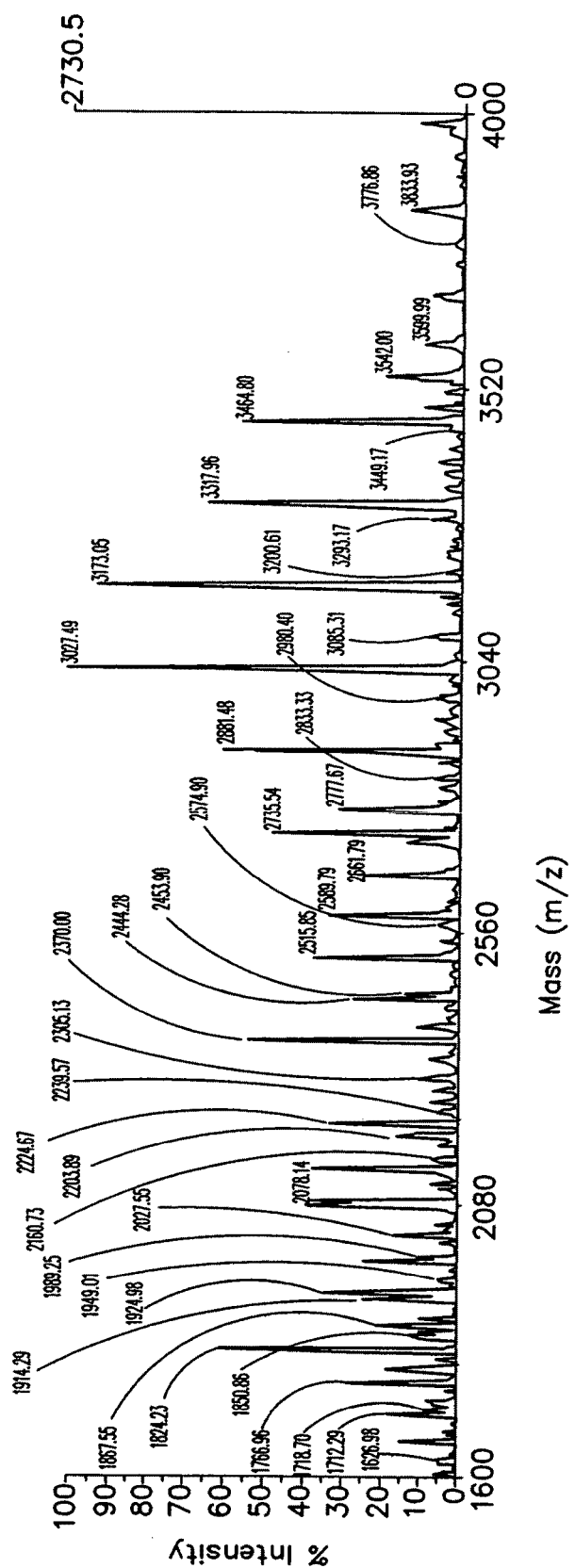
FIG. 33 provides the MALDI-MS acidic glycome profile of saliva (A) and urine (B).
Figure 33B:
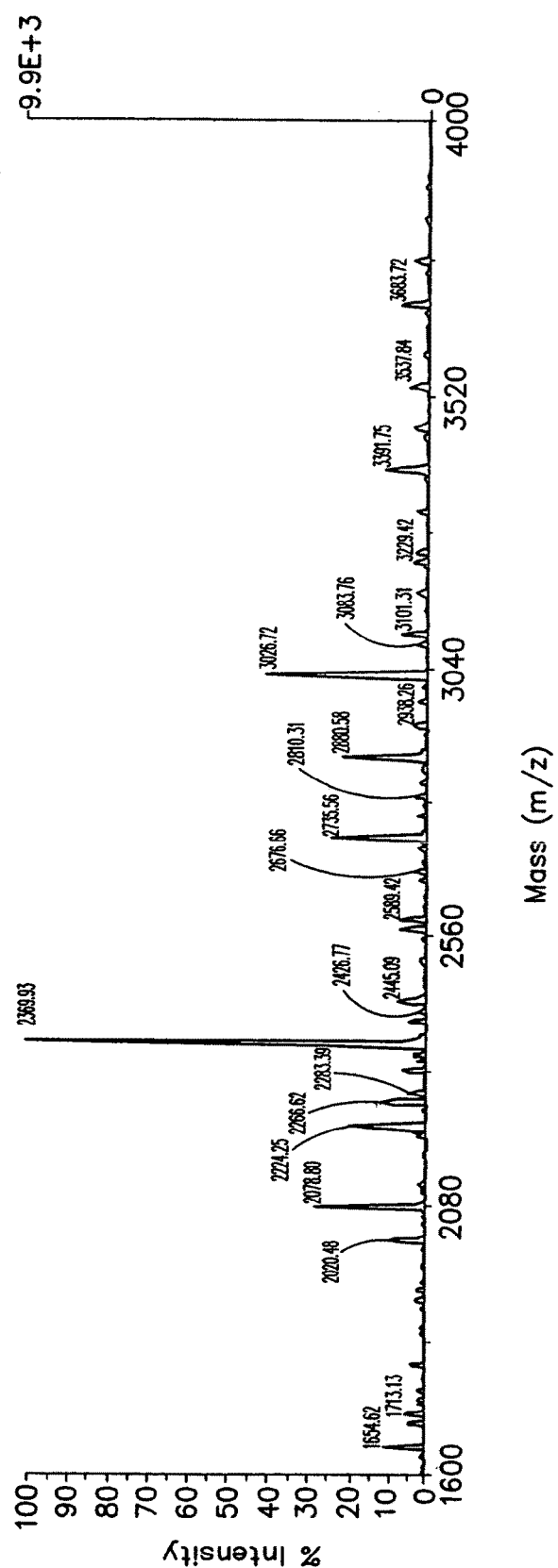

Similar to the serum glycome analysis, the entire glycome from other body fluids such to as saliva and urine have been studied (FIG. 33). For these cases, similar protocols employed for serum were used. In some instances, additional fractionations were also employed if a fraction of the glycome or glycoproteome was to be studied. The method showed to be equally, reproducible and sensitive for these other body fluids.

Glycome Analysis of Cell Surface Glycoproteins

The methods are also applied to the glycoprofiling of cell surfaces. All cell surface glycoproteins are cleaved using methods know to the art. Briefly, to harvest glycans using protease extraction, cells are washed 3× with PBS and incubated for 20-45 minutes with trypsin/EDTA (GibcoBRL) at 37° C. for protease extraction. The samples are centrifuged for 10 minutes at 3000×g to pellet the cells, and the supernatant containing glycopeptides is collected and processed using methods described herein.

Glycomic Pattern Analysis

The emerging field of clinical proteomics has set new avenues for the identification of potential cancer-related biomarkers. In particular, the recent introduction of proteomic pattern diagnostics[Petricoin III, 2002; Wulfkuhle, 2003; Conrads, 2003] provides a promising platform for the high-throughput discovery of new and important biomarkers. Since the alterations to the normal function of the glycosylation machinery have been increasingly recognized as a consistent indication of malignant transformations and tumorigenesis [Orntoft, 1999; Burchell, 2001; Brockhausen, 1999; Dennis, 1999] the final glycoproteins (specifically their carbohydrate moieties) can serve as sensitive and reliable biochemical markers to numerous diseases including cancer.

Some of the basic concepts from proteomic pattern diagnostics have been adapted and applied to total glycomic pattern analysis where the total profile of carbohydrates from body fluids or tissues can be examined in a rapid format. This approach provides an efficient overview of the total changes in carbohydrate composition of a tissue or body fluid as a result of pathological alterations and should be very reliable in sensing susceptible physiological changes to the body's natural homeostasis. This method not only serves as a fast diagnostic/prognostic tool but should also help to understand the function of specific carbohydrate modifications in some diseases. This method also provides a reliable system to efficiently monitor the effects of therapeutics.

Figure 34A:
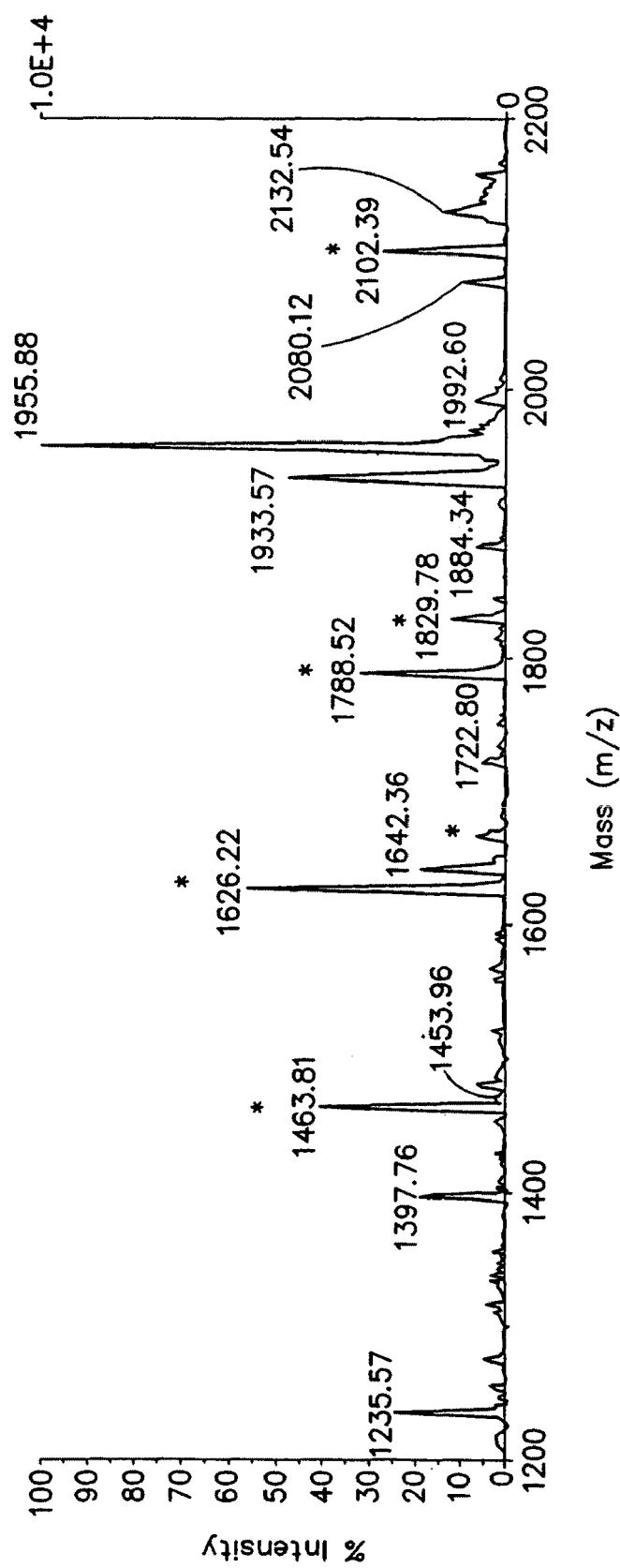
FIG. 34 provides quantitative neutral glycome profile for serum with normal (A) and low (B) IgG levels.
Figure 34B:
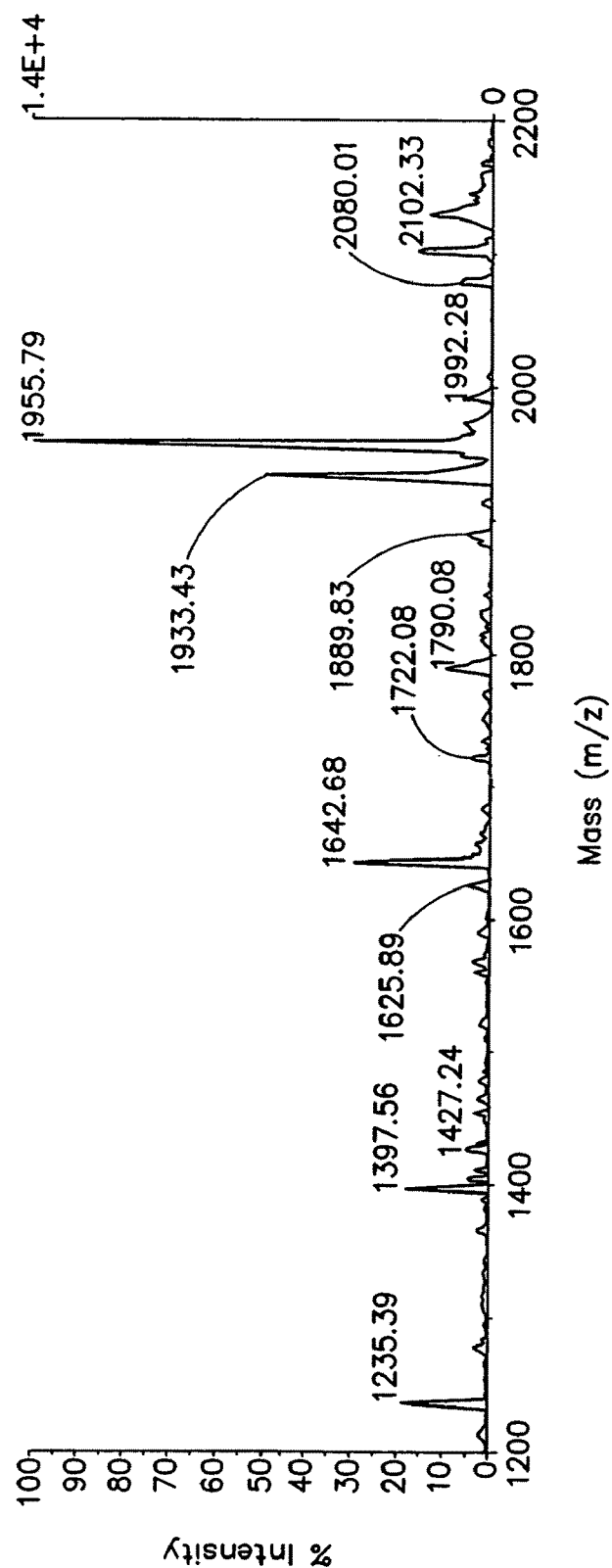

The optimization of the MALDI-MS analysis allows reliable reproducibility that enables the fast evaluation of alterations to the glycomic patterns and their subsequent association to pathological/physiological changes to a sample donor. The optimized detection limits for this method (low femtomol) allows the detection of low abundance species associated to diseases. Every signal in the pattern is rapidly correlated to the glycan identity and can be further validated using a panel of glycosydases and other techniques. This prevents the erroneous identification as it has sometimes been the case in the field of proteomic pattern diagnostics. The pattern alterations can be easily determined manually or more efficiently with the aid of bioinformatics tools (described below). In some cases the decreasing levels of circulating glycoproteins in serum are easily matched to the analyzed glycans. As shown in FIG. 34, the glycome profile from serum with low IgG levels, reflects the specific decrease in the respective IgG glycans with molecular weights of 1463, 1626, 1666, 1788, 1829, 2102, and 1844. These glycans have been previously shown to be attached to IgG molecules in serum [Butler, 2003].

Figure 35A:
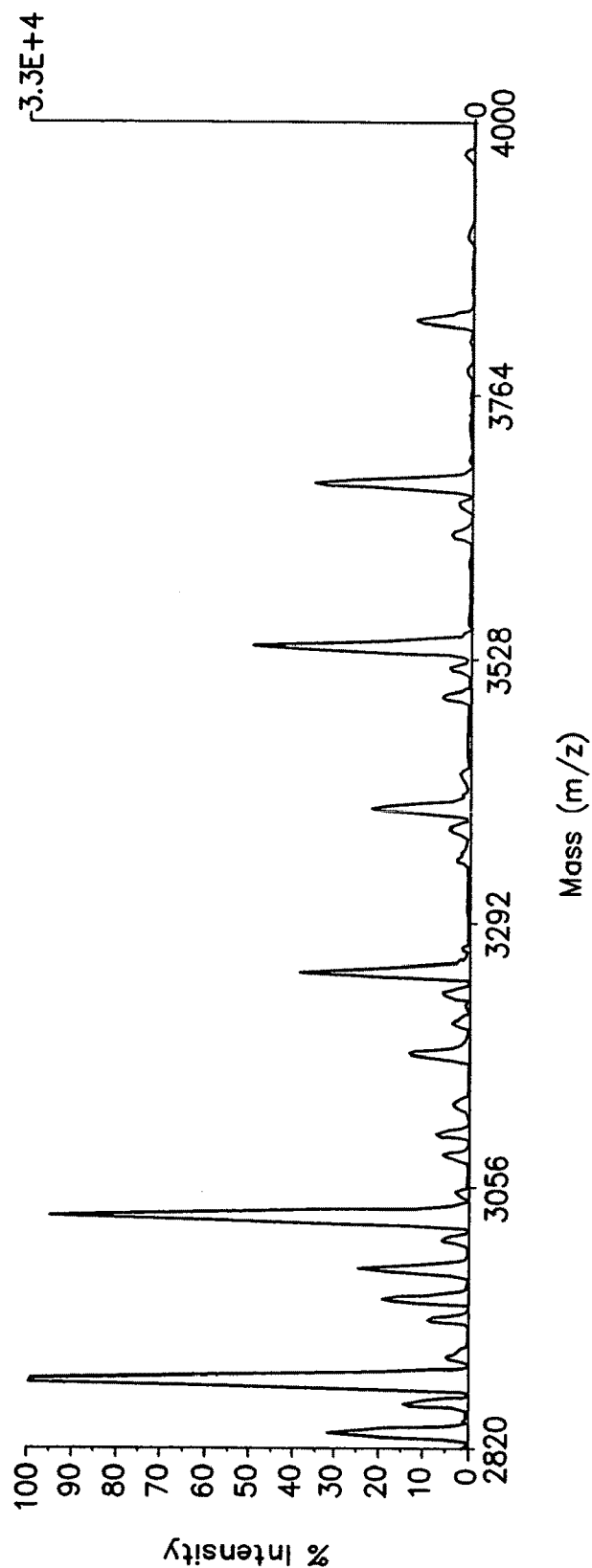
FIG. 35 provides alterations in serum glycomic patterns between matched healthy (A) and cancer (B) patients FIG. 36 provides a schematic representation of an example of the computational strategy for the analysis of glycoprofile patterns.
Figure 35B:
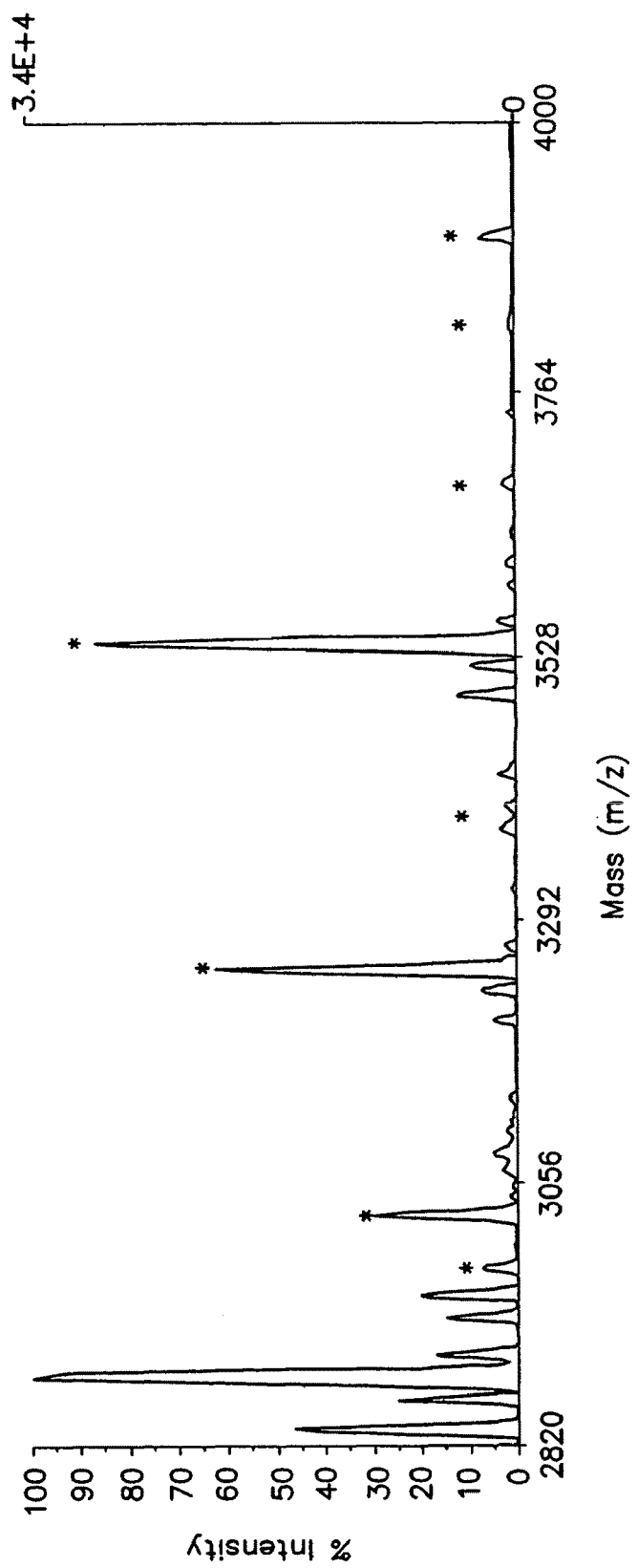

By applying the "glycomic pattern diagnostics" platform to different body fluids from patients with well-defined demographics, specific alterations in the glycomic pattern that can be correlated to the pathological state of the donor can be determined. For example, glycomic patterns have been associated to prostate cancer by studying the serum from prostate cancer patients (FIG. 35). Glycomic patterns from the saliva of patients with viral infections have also been established. Since every signal inside the pattern corresponds to specific glycans, the alteration of these patterns are easily determined and correlated with the expression levels of the carbohydrates, such as with the methods provided herein. The specific alterations in these glycan patterns are associated with a disease state. Therefore, the methods provided serve as a reliable platform for diagnosis, prognosis and monitoring the effects of therapeutics.

Computational Pattern Analysis of Glycoprofile

Figure 36:
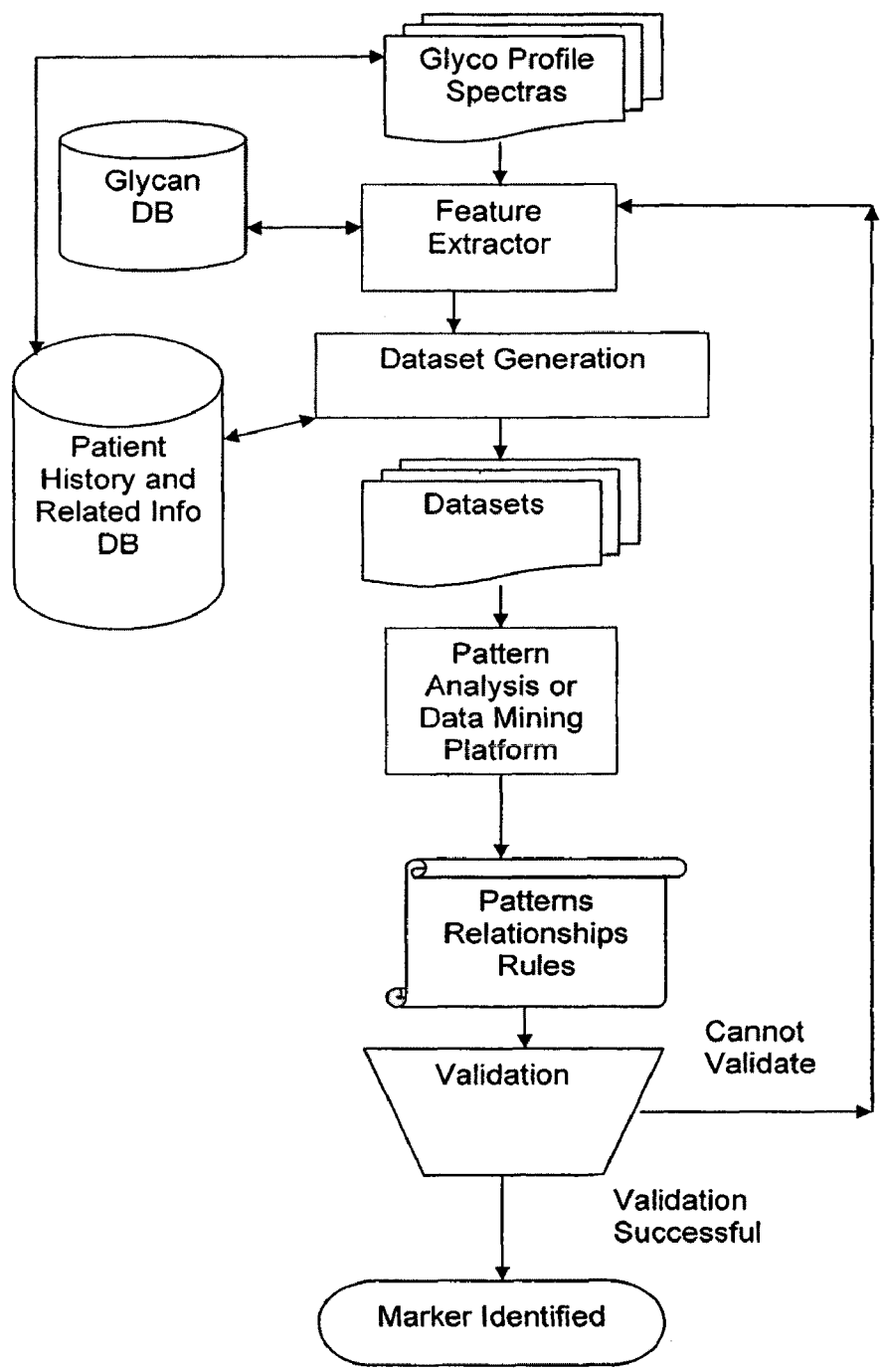

The following is an example of a computational approach for identifying glycan-based biomarkers for specific diseases using data from glycoprofiling. The different steps of the process are illustrated in the FIG. 36.

Using prostate cancer as an example, the goal is to identify glycan-based markers for individuals with prostate cancer. In this example, there are three possible categories of individuals—individuals with prostate cancer, benign prostatic hyperplasia (BPH) and individuals that are normal (healthy, non-diseased prostate).

Glycoprofiling data such as mass spectras are generated from samples from patients belonging to the different categories. Features are extracted from the glycoprofiling spectras. These features can be the presence or absence of one or more glycans in the profile, the relative amount of different glycans in the profile, combinations of different glycans found in the profile and other glycan-related properties. These glycans are identified in the glycoprofile spectra and can be corroborated with other methods, for instance, by using a Glycan database (www.functionalglycomics.org/glycomics/molecule/jsp/carbohydrate/carbMoleculeHome.j sp) and/or associated glycomics-based bioinformatics tools.

The appropriate patient population is selected for the study (based on their history in a patient database), such that the subjects chosen in the different categories of prostate cancer, BPH and normal have the same distribution when it comes to other properties such as age, ethnicity, behavioral factors etc. This ensures that the variation in the glycan profiles can be attributed to the disease condition rather than other factors. The glycan related features extracted for this population via the previous step is run through a dataset generator to create the datasets needed for pattern analysis [see Weiss, S. & Indurkhya, N. Predictive data mining—A practical guide, (Morgan Kaufmann, San Francisco, 1998)].

Different types of pattern analysis are performed to identify the patterns in this dataset [Weiss and Indurkhya, 1998]. Three examples of patterns, rules or relationships that can be identified are as follows:

Linear Discriminant: The pattern identified is in the form of weights ($w_{11}$, $w_{12}$, etc.) for the different glycan related features ($G_1$, $G_2$, etc.) as they are related to property or claw of interest (ProstateCancer, BPH or Normal).

$w_{11}G_1 + w_{12}G_2 + \ldots + w_{1m}G_m + w_1 = $ ProstateCancer
$w_{21}G_1 + w_{22}G_2 + \ldots + w_{2m}G_m = $ BPH Neural Network: The neural network identifies non linear relationships or patterns between the different features and the property or class of interest.

$net_j = \Sigma W_{ij} * f_i + C_j$
$d_j = 1/(1+e^{-net_j})$, where $d_j$ can be Prostate Cancer, BPH or Normal Decision Rules: The pattern identified is in the form of IF-THEN rules, for example (IF $G_{11}$ is present and $G_7$ is not present) or (IF $G_8$ is present and $G_9$ is present) THEN Class=Prostate Cancer (IF $G_1$ is present and $G_2$ is present and $G_3$ is not present) THEN Class=BPH Otherwise Class=Normal Once a pattern is identified using the decision set rules above, the patterns, rules or relationships are validated. The validation can be made based on variety of statistical methods that are used in biomarker validation as well as scientific methods to verify that the glycans found in the patterns do accurately reflect the disease state. If the patterns cannot be validated, the process described above can be repeated to look for other glycan-based patterns in the glycoprofiles.

Use of Human Glycome for the Profiling of Populations: Population-Tailored Treatments It is well documented that different people react differently to certain drugs. In many instances this might be a result of drug interference with other inherent molecular components. Also, the down-regulation of enzymes may prevent the metabolism of some drugs or their by-products. The recent emphasis in the development of new carbohydrate-based therapeutics will face major challenges (in comparison to protein-based drugs) due to less currently available glycomic information as well as less understanding of the field.

More information of all human molecular components will significantly facilitate the design and prescription of medications to specific populations. The efficient analysis of the entire glycome from body fluids not only serves as a reliable diagnosis/prognosis platform but should become very valuable for the profiling of populations. The generation of a human glycome databank from different ethnic groups, gender, ages, diseases, etc. will become of enormous value for current and future development and applications of drugs that might interfere with carbohydrate functions. For example, the overexpression of specific carbohydrates in a specific population will aid in the design or prescription of therapeutic antibodies (lectins, or other molecules) that might interfere with these molecules. This information will also aid in prospective studies for the selection of dosing, activity monitoring and efficacy endpoints.

References for Example 4

1. Petricoin III, E. F. et al. Use of proteomic patterns in serum to identify ovarian cancer. Lancet 359, 572-577 (2002).
2. Wulfkuhle, J. D., Liotta, L. A. & Petricoin III, E. F. Proteomic applications for the early detection of cancer. Nature Rev. Cancer 3, 267-275 (2003).
3. Conrads, T. P., Zhou, M., Petricoin III, E. F., Liotta, L. A. & Veenstra, T. D. Cancer diagnosis using proteomic patterns. Expert. Rev. Mol. Diagn. 3, 411-420 (2003).
4. Orntoft, T. F. & Vestergaard, E. M. Clinical aspects of altered glycosylation of glycoproteins in cancer. Electrophoresis 20, 362-371 (1999).
5. Burchell, J. M., Mungul, A., & Taylor-Papadimitriou, J. O-linked glycosylation in the mammary gland: changes that occur during malignancy. J. Mam. Gland Biol. Neoplasia 6, 355-364 (2001).
6. Brockhausen, I. Pathways of O-glycan biosynthesis in cancer cells. Biochim. Byophis. Acta 1473, 67-95 (1999).
7. Dennis, J. W., Granovsky, M. & Waren, C. E. Glycoprotein glycosylation and cancer progression. Biochim. Byophis. Acta 1473, 21-34 (1999).
8. Pierce, M., Buckhaults, P., Chen, L. & Fregien, N. Regulation of N-acetylglucosaminyltransferase V and Asn-linked oligosaccharide beta(1,6) branching by a growth factor signaling pathway and effects on cell adhesion and metastatic potential. Glycoconj. J. 14, 623-630 (1997).
9. Murata, K. et al. Expression of N-acetylglucosaminyltransferase V in colorectal cancer correlates with metastasis and poor prognosis. Clin. Cancer Res. 5, 1772-1777 (2000).
10. Yanagi, M., Aoyagi, Y., Suda, T., Mita, Y. & Asakura, H. N-Acetylglucosaminyltransferase V as a possible aid for the evaluation of tumor invasiveness in patients with hepatocellular carcinoma. J. Gastroenterol. Hepatol. 16, 1282-1289 (2001).
11. Ihara, S. et al. Prometastatic effect of N-acetylglucosaminyltransferase V is due to modification and stabilization of active matriptase by adding beta 1-6 GlcNAc branching. J. Biol. Chem. 277, 16960-16967 (2002).
12. Yousefi, S. et al. Increased UDP-GlcNAc:Gal beta 1-3GaLNAc-R (GlcNAc to GaLNAc) beta-1,6-N-acetylglucosaminyltransferase activity in metastatic murine tumor cell lines. Control of polylactosamine synthesis. J. Biol. Chem. 266, 1772-17782 (1991).
13. Shimodaira, K. et al. Carcinoma-associated expression of core 2 beta-1,6-N-acetylglucosaminyltransferase gene in human colorectal cancer: role of O-glycans in tumor progression. Cancer Res. 57, 5201-5206 (1997).
14. Machida, E., Nakayama, J., Amano, J. & Fukuda, M. Clinicopathological significance of core 2 beta-1,6-N-acetylglucosaminyltransferase messenger RNA expressed in the pulmonary adenocarcinoma determined by in situ hybridization. Cancer Res. 61, 2226-2231 (2001).
15. Vander, A. J., Sherman, J. H. & Luciano, D. S. Human physiology: the mechanisms of body function, Edn. 8th. (McGraw-Hill, Boston, Mass.; 2001).
16. Rohovec, J., Maschmeyer, T., Aime, S. & Peters, J. A. The structure of the sugar residue in glycated human serum albumin and its molecular recognition by phenylboronate. Chemistry 9, 2193-2199 (2003).
17. Bihoreau, N., Ramon, C., Lazard, M. & Schmitter, J. M. Combination of capillary electrophoresis and matrix-assisted laser desorption ionization mass spectrometry for glycosylation analysis of a human monoclonal anti-Rhesus (D) antibody. J Chromatogr B Biomed Sci Appl 697, 123-133 (1997).
18. Watt, G. M. et al. Site-specific glycosylation of an aglycosylated human IgG1-Fc antibody protein generates neoglycoproteins with enhanced function. Chem Biol 10, 807-814 (2003).
19. Papac, D. I., Briggs, J. B., Chin, E. T. & Jones, A. J. A high-throughput microscale method to release N-linked oligosaccharides from glycoproteins for matrix-assisted laser desorption/ionization time-of-flight mass spectrometric analysis. Glycobiology 8, 445-454 (1998).
20. Butler, M. et al. Detailed glycan analysis of serum glycoproteins of patients with congenital disorders of glycosylation indicates the specific defective glycan processing step and provides an insight into pathogenesis. Glycobiology 13, 601-622 (2003).

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method comprising steps of:
   providing a sample containing at least one acidic glycan;
   contacting the sample with a mass spectroscopy matrix comprising a perfluorinated ion exchange compound (NAFION®) and 6-aza-2-thiothymine (ATT); and
   detecting the at least one acidic glycan.

2. The method of claim 1, wherein the method comprises analyzing the purity of the sample containing at least one acidic glycan.

3. The method claim 1, wherein the method comprises analyzing the glycans of a sample of one or more cells, a tissue or body fluid from a subject, wherein the sample contains at least one acidic glycan.

4. A high-throughput method of claim 1, wherein more than one sample containing at least one acidic glycan is analyzed.

5. The method of claim 4, wherein the more than one sample containing at least one acidic glycan are contained in a 96-well plate.

6. The method of claim 4, wherein the more than one sample containing at least one acidic glycan are affixed to a membrane.

7. The method of claim 1, wherein the method comprises analyzing the total glycome of a sample of body fluid, wherein the sample of body fluid contains at least one acidic glycan, comprising:
   (a) analyzing the glycans of a sample of body fluid, and
   (b) comparing the results from (a) with a known pattern.

8. The method of claim 7, wherein the sample of body fluid is a sample of serum, plasma, blood, urine, saliva, sputum, tears, CSF, seminal fluid, feces, tissues or cells.

9. The method of claim 7, wherein the method is a method of diagnosis and the pattern is associated with a diseased state.

10. The method of claim 9, wherein the pattern associated with a diseased state is a pattern associated with cancer.

11. The method of claim 10, wherein the cancer is prostate cancer, melanoma, bladder cancer, breast cancer, lymphoma, ovarian cancer, lung cancer, colorectal cancer or head and neck cancer.

12. The method of claim 9, wherein pattern associated with a diseased state is a pattern associated with an immunological disorder.

13. The method of claim 9, wherein pattern associated with a diseased state is a pattern associated with a neurodegenerative disease.

14. The method of claim 13, wherein the neurodegenerative disease is a transmissible spongiform encephalopathy, Alzheimer's disease or neuropathy.

15. The method of claim 9, wherein pattern associated with a diseased state is a pattern associated with inflammation.

16. The method of claim 9, wherein pattern associated with a diseased state is a pattern associated with rheumatoid arthritis.

17. The method of claim 9, wherein pattern associated with a diseased state is a pattern associated with cystic fibrosis.

18. The method of claim 9, wherein pattern associated with a diseased state is a pattern associated with an infection.

19. The method of claim 18, wherein the infection is viral or bacterial.

20. The method of claim 7, wherein the method comprises monitoring prognosis and the known pattern is associated with the prognosis of a disease.

21. The method of claim 7, wherein the method comprises monitoring drug treatment and the known pattern is associated with the drug treatment.

22. The method of claim 1, wherein the method comprises generating the complete glycan profile of a sample of body fluid, wherein the body fluid contains at least one acidic glycan, comprising:
   (a) analyzing the glycans in the sample, and
   (b) identifying the complete glycan profile of the sample.

* * * * *

UNITED STATES PATENT AND TRADEMARK OFFICE
CERTIFICATE OF CORRECTION

PATENT NO.      : 8,000,904 B2
APPLICATION NO. : 12/574161
DATED           : August 16, 2011
INVENTOR(S)     : Pankaj Gandhe Page 1 of 1

It is certified that error appears in the above-identified patent and that said Letters Patent is hereby corrected as shown below:

Delete the paragraph titled 'GOVERNMENT SUPPORT' encompassing column 1, lines 15-18:

"Aspects of the invention may have been made using funding from National Institutes of Health Grant number GM57073. Accordingly, the Government may have rights in the invention."

and replace with:

--This invention was made with government support under Grant No. R01 GM057073 awarded by the National Institutes of Health. The government has certain rights in this invention.--

Signed and Sealed this
Twenty-third Day of October, 2012

David J. Kappos
*Director of the United States Patent and Trademark Office*